United States Patent [19]
Ohno et al.

[11] Patent Number: 4,822,804
[45] Date of Patent: * Apr. 18, 1989

[54] 5,6,7,-TRINOR-4,8-INTER-M-PHENYLENE 2-NOR $PGI_2$ DERIVATIVES AND ANTI-ULCER, ANTI-THROMBOTIC AND ANTI-HYPERTENSIVE PHARMACEUTICAL COMPOSITIONS CONTAINING THEM

[75] Inventors: Kiyotaka Ohno, Fujisawa; Hiroshi Nagase; Mamoru Ishikawa, both of Kamakura; Kazuhisa Matsumoto, Tsujidohigashikaigan Fujisawa; Shintaro Nishio, Ebina, all of Japan

[73] Assignee: Toray Industries, Inc., Tokyo, Japan

[*] Notice: The portion of the term of this patent subsequent to Jan. 14, 2003 has been disclaimed.

[21] Appl. No.: 102,391

[22] Filed: Sep. 29, 1987

Related U.S. Application Data

[63] Continuation-in-part of Ser. No. 96,273, Sep. 9, 1987, which is a continuation of Ser. No. 810,011, Dec. 12, 1985, abandoned, which is a continuation-in-part of Ser. No. 567,755, Jan. 1, 1984, Pat. No. 4,564,620, which is a continuation of Ser. No. 353,875, Mar. 2, 1982, abandoned.

[30] Foreign Application Priority Data

Mar. 3, 1981 [JP] Japan .................. 56-29357

[51] Int. Cl.$^4$ .................. A61K 31/34; A61K 31/557; C07D 307/93
[52] U.S. Cl. .................. 514/337; 514/444; 514/460; 514/468; 546/269; 549/60; 549/414; 549/415; 549/458
[58] Field of Search .................. 549/458, 414, 415, 60; 546/269; 514/337, 444, 460, 468

[56] References Cited

U.S. PATENT DOCUMENTS 4,301,164 11/1981 Ohno et al. .................. 549/458
4,564,620 1/1986 Ohno et al. .................. 549/458

Primary Examiner—Mary C. Lee
Assistant Examiner—Bernard I. Dentz
Attorney, Agent, or Firm—Austin R. Miller

[57] ABSTRACT

Pharmaceutically useful compounds are 5,6,7-trinor-4,8-inter-m-phenylene $PGI_2$ derivatives such as
5,6,7-trinor-4,8-inter-m-phenylene-2-nor-16,16-dimethyl $PGI_2$,
5,6,7-trinor-4,8-inter-m-phenylene-2-nor-17(S)-methyl $PGI_2$,
5,6,7-trinor-4,8-inter-m-phenylene-2-nor-17(R)-methyl $PGI_2$,
5,6,7-trinor-4,8-inter-m-phenylene-2-nor-16,16-dimethyl-ω-homo $PGI_2$,
5,6,7-trinor-4,8-inter-m-phenylene-2-nor-17(S)-methyl-ω-homo $PGI_2$,
5,6,7-trinor-4,8-inter-m-phenylene-2-nor-17(R)-methyl-ω-homo $PGI_2$,
5,6,7-trinor-4,8-inter-m-phenylene-2,17,18,19,20-pentanor-16,16-dimethyl-16-p ropoxy $PGI_2$,
5,6,7-trinor-4,8-inter-m-phenylene-2,18,19,20-tetranor-16,16-dimethyl-17-etho xy $PGI_2$,
5,6,7-trinor-4,8-inter-m-phenylene-2,18,19,20-tetranor-16,16-dimethyl-17-prop oxy $PGI_2$,
5,6,7-trinor-4,8-inter-m-phenylene-2,17,18,19,20-pentanor-16-phenoxy $PGI_2$ and methyl esters thereof.
5,6,7-trinor-4,8-inter-m-phenylene-2,17,18,19,20-pentanor-16,16-dimethyl-16 -phenoxy $PGI_2$ or its methyl ester, 5,6,7-trinor-4,8-inter-m-phenylene-2,17,18,19,20-pentanor-16-methyl-16-phenox y $PGI_2$ or its methyl ester.

They are useful in treatment of ulcers, thrombii and hypertension for example.

34 Claims, No Drawings

5,6,7,-TRINOR-4,8-INTER-M-PHENYLENE 2-NOR PGI$_2$ DERIVATIVES AND ANTI-ULCER, ANTI-THROMBOTIC AND ANTI-HYPERTENSIVE PHARMACEUTICAL COMPOSITIONS CONTAINING THEM

BACKGROUND OF THE INVENTION

This is a continuation-in-part of application Ser. No. 096,273, filed Sept. 9, 1987, itself a continuation of application Ser. No. 810,011, filed Dec. 12, 1985, now abandoned, itself a continuation in part of application Ser. No. 567,755 filed Jan. 1, 1984, now U.S. Pat. No. 4,564,620 itself a continuation application application Ser. No. 353,875, filed Mar. 2, 1982, now abandoned.

Prostaglandin I$_2$ (PGI$_2$, prostacyclene) is a compound discovered by J. R. Vane et al in 1976, biosynthesized from arachidoric acid via endo peroxide (PGH$_2$ or PGG$_2$) in the arterial wall, attracting attention as a substance having a strong platelet aggregation inhibiting activity and vasodilating activity.

(Refer to C & EN, Dec. 20, 1976, p 17 and S. Moncada, R. Gryglewski, S. Bunting, J. R. Vane, "Nature," 263,633 (1976)),

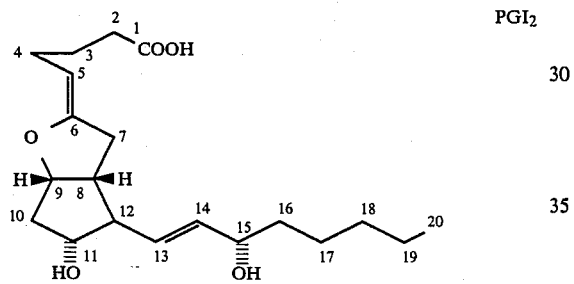

PGI$_2$

Because of the unstable exoenol ether structure, PGI$_2$ is very unstable even in a neutral aqueous solution, changing into 6-oxo PGF$_{1\alpha}$ having hardly any physiological activity. The instability of PGI$_2$ becomes a serious drawback when it is used as a medicinal compound. Further, PGI$_2$ is unstable inside an organism, having another drawback in that its physiological action has no continuity.

It is an object of this invention to overcome these disadvantages of PGI$_2$.

SUMMARY OF THE INVENTION

The above-mentioned object of the invention is achieved by a compound of the formula

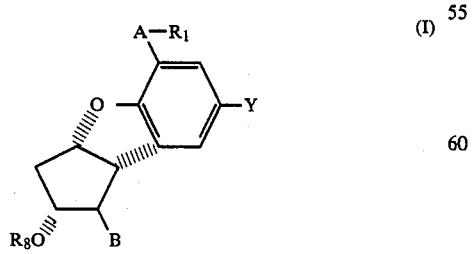

(I)

wherein

R$_1$ denotes a carboxyl group or a functional derivative thereof,

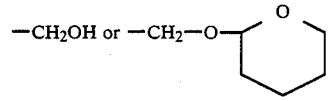

A denotes
 (i) —(CH$_2$)$_n$—, preferably —CH$_2$CH$_2$—,
 (ii) —CH=CH—CH$_2$—,
 (iii) —CH$_2$CH=CH— or
 (iv) —CH$_2$—O—CH$_2$—, wherein n is an integer of 1-3, Y denotes hydrogen, alkyl having 1-4 carbon atoms, chlorine, fluorine, bromine, formyl, methoxy or nitro, B denotes to all A and Y
 (i)

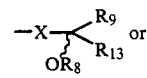

(ii)

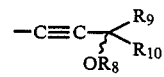

further, when A is (ii) —CH=CH—CH$_2$—, (iii) —CH$_2$CH=CH—, (iv) —CH$_2$—O—CH$_2$— or when Y is an alkyl group having 1-4 carbon atoms, chlorine, fluorine, bromine, formyl, methoxy or nitro, B further denotes
 (iii)
  (i)

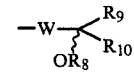

wherein
 R$_9$ denotes hydrogen or an alkyl group having 1-4 carbon atoms,
 R$_8$ denotes hydrogen, acyl having 1-12 carbon atoms, aroyl having 6-15 carbon atoms, tetrahydropyranyl, tetrahydrofuranyl, 1-ethoxy ethyl or t-butyl,
X denotes
 (i) —CH$_2$CH$_2$—,
 (ii) —CH=CH— (trans) or
 (iii) —C≡C—
R$_{10}$ denotes
 (i) straight chain alkyl having 4-10 carbon atoms, or
 (ii)

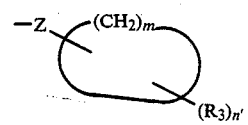

wherein Z denotes valence bond, or straight chain or branched alkylene which may be represented by C$_t$H$_{2t}$, wherein t denotes an integer of 1-5, further, m denotes an integer of 5-12, R$_3$ denotes hydrogen or alkyl having 1-5 carbon atoms, and n' denotes an integer of 1-3, or
(iii) —Z—Ar$_2$, wherein Z is the same as defined above, and Ar$_2$ denotes phenyl, α-naphthyl, β-naphthyl or at least one chlorine, bromine, fluorine, trifluoromethyl, alkyl having 1-4 carbon atoms, nitro, methoxy, phenyl or phenoxy-substituted phenyl, R$_{13}$ denotes
(i) branched alkyl having 5-10 carbon atoms, or
(ii) —C$_t$H$_{2t}$OR$_{14}$, wherein C$_t$H$_{2t}$ is the same as defined above, and R$_{14}$ denotes straight chain or branched alkyl having 1-5 carbon atoms,

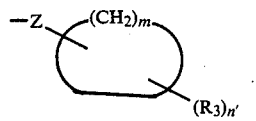

or —Z—Ar$_2$, wherein Z, m, R$_3$, n' and Ar$_2$ are the same as defined above, or
(iii)

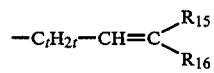

(wherein C$_t$H$_{2t}$ is the same as defined above, R$_{15}$ and R$_{16}$ denote hydrogen, methyl, ethyl, propyl or butyl group, W denotes
(i) —CH$_2$CH$_2$— or
(ii) —CH=CH— (trans)
and the general formula denotes d form, l form or dl form.)

DETAILED DESCRIPTION OF THE INVENTION

Hereinafter preferable R$_1$, A, B, R$_8$ and Y, and preferable combinations thereof are shown.
(a) The following groups (A), (B) and (C) are preferable R$_1$. In these groups (A) (i) and —COOCH$_3$ are the most preferable.
(A) COOR$_2$, wherein R$_2$ denotes
(i) hydrogen or a pharmacologically acceptable cation,
(ii) straight chain alkyl having 1-12 carbon atoms or branched alkyl having 3-12 carbon atoms,
(iii)

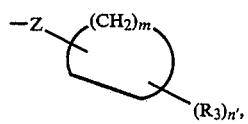

wherein Z, m, R$_3$ and n' are the same as defined above.
(iv) —(CH$_2$CH$_2$O)$_l$CH$_3$, wherein l is an integer of 1-5,
(v) —Z—Ar$_1$, wherein Z is the same as defined above, Ar$_1$ denotes phenyl, α-naphthyl, β-naphthyl, 2-pyridyl, 3-pyridyl, 4-pyridyl, α-furyl, β-furyl, α-thienyl, β-thienyl or substituted phenyl (wherein the substituent is at least one chlorine, bromine, fluorine, trifluoromethyl, alkyl having 1-4 carbon atoms, nitro, methoxy, phenyl, phenoxy,

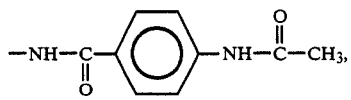

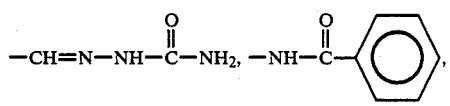

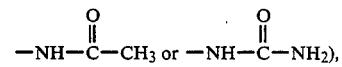

(vi) —C$_l$H$_{2l}$COOR$_3$
(vii) —CH$_2$C$_l$H$_{2l}$N(R$_3$)$_2$ (wherein l and R$_3$ are the same as defined above),
(viii)

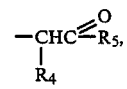

wherein R$_4$ denotes hydrogen or benzoyl and R$_5$ denotes phenyl, p-bromophenyl, p-biphenyl, p-benzamidophenyl or 2-naphthyl,
(ix) —C$_p$H$_{2p}$—B', wherein B' is

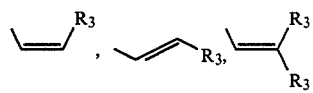

or —C≡C—R$_6$, wherein R$_3$ is the same as defined above, R$_6$ denotes straight chain or branched alkyl having 1-30 carbon atoms, and p is an integer of 1-5, or
(x)

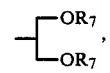

wherein R$_7$ denotes alkyl or acyl having 1-30 carbon atoms,
(B) —CH$_2$OH, and
(C)

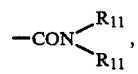

wherein R$_{11}$ denotes hydrogen, alkyl having 1-10 carbon atoms, cycloalkyl having 3-12 carbon atoms, phenyl, substituted phenyl, aralkyl having 7-12 carbon atoms or —SO$_2$R$_{12}$, wherein R$_{12}$ denotes alkyl having 1-12 carbon atoms, cycloalkyl having 3-12 carbon atoms, phenyl, substituted phenyl or aralkyl having 7-12 carbon atoms, two R$_{11}$ may be the same or different, however, when one denotes —SO$_2$R$_{12}$, the other is not —SO$_2$R$_{12}$.

(b) Preferable A is (i) —(CH$_2$)$_n$— or (iii) —CH$_2$CH=CH—, wherein n is an integer of 1-3. Highly preferable A is —CH$_2$CH$_2$—.

(c) When A is (i) —(CH$_2$)$_n$— or (iii) —CH$_2$CH=CH—, preferable B is (i)

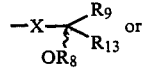

or (ii)

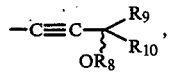

wherein n, X, R$_8$, R$_9$, R$_{10}$, and R$_{13}$ are the same as defined above. In this case, the following is more preferable: n is 2, R$_8$ and R$_9$ are both hydrogen.

(d) When A is (i) —(CH$_2$)$_n$— or (iii) —CH$_2$CH=CH— and B is (i)

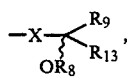

preferable X and R$_{13}$ are as follows:
X is (ii) —CH=CH— (trans) or (iii) —C≡C—,
R$_{13}$ is
(i) branched alkyl having 5-10 carbon atoms, or
(iii)

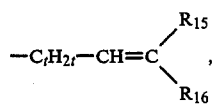

wherein n, t, R$_9$, R$_{15}$ and R$_{16}$ are the same as defined above. Preferably t is 3 or 4, R$_{15}$ is hydrogen or methyl and R$_{16}$ is methyl or ethyl.

In this case, preferable R$_8$ and Y are both hydrogen, and preferable n is 2.

(e) When A is (i) —(CH$_2$)$_n$ especially —(CH$_2$)$_2$— or (iii) —CH$_2$CH=CH— and B is (ii)

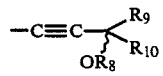

preferable R$_{10}$ is as follows: R$_{10}$ is
(i) straight chain alkyl having 4-10 carbon atoms, or
(ii)

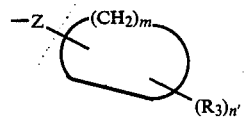

wherein n, n', m, R$_3$, R$_8$, R$_9$ and Z are the same as defined above.

Preferably n is 2, n' is 1 or 2, m is 5 or 6, R$_3$ is hydrogen, methyl or ethyl, and R$_8$ and R$_9$ are both hydrogen.

In this case, preferable Y is hydrogen.

(f) When A is (iii) —CH$_2$CH=CH—, the following group is also preferable as group B:

(iii)

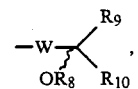

wherein R$_8$, R$_9$, R$_{10}$ and W are the same as defined above.

(g) Whe A is (iii) —CH$_2$CH=CH— and B is (iii)

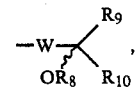

Preferable W and R$_{10}$ are as follows:
W is (ii) —CH=CH— (trans),
R$_{10}$ is (i) straight chain alkyl having 4-10 carbon atoms, or
(ii)

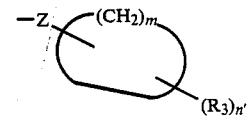

wherein m, n', R$_3$, R$_8$, R$_9$ and Z are the same as defined above. Preferably R$_8$ is hydrogen or acetyl (hydrogen is more preferable), Y is hydrogen, n' is 1 or 2, m is 5 or 6, R$_3$ is hydrogen, methyl, ethyl or propyl and R$_9$ is hydrogen.

(h) In the case of the above (b)-(g), it is more preferable to select R$_1$ as is shown in (a).

More specifically, when R$_2$ is a pharmacologically acceptable cation, such cation includes a metal cation, ammonium cation, amine cation or quaternary ammonium cation, and especially preferable metal cations are derived from alkaline metals, for example, lithium, sodium and potassium and alkaline earth metals, for example, magnesium and calcium.

It is needless to say that cations of metals, for example aluminium, zinc and iron are included in the present invention.

Pharmacologically acceptable protonated amines are derived from primary, secondary or tertiary amine. Examples of suitable amines include methyl amine, dimethyl amine, triethyl amine, ethyl amine, dibutyl amine, triisopropyl amine, N-methylhexyl amine, decyl amine, dodecyl amine, allyl amine, crotyl amine, cyclopentyl amine, dicyclohexyl amine, benzyl amine, dibenzyl amine, α-phenylethyl amine, β-phenylethyl amine, ethylene diamine, diethylene triamine and similar aliphatic, alicyclic and heterocyclic amines each containing up to about 18 carbon atoms, for example, 1-methyl piperidine, 4-ethyl morpholine, 1-isopropyl pyrrolidine, 2-methyl pyrrolidine, 4-dimethyl piperazine and 2-methyl piperidine, further, amines having water-soluble or hydrophilic groups, for example, mono- di- and tri-ethanol amines, ethyl diethyl amine, N-butyl ethanol amine, 2-amino-1-butanol, 2-amino-2-ethyl-1,3-propane diol, tris(hydroxymethyl)amino methane, N-phenyl ethanol amine, N-(p-tert-amyl phenyl) diethanol amine, galactamine, N-methyl glutamine, N-methyl glucosamine, ephedrine, phenyl ephrine, epinephrine and procaine, further, basic amino acid, especially, lysine and agrinine. As examples of R$_2$ which is a straight chain alkyl group having 1-12 carbon atoms, there may be cited methyl, ethyl, propyl, butyl, pentyl, hexyl, heptyl, octyl and dodecyl. Furthermore, as examples of $R_2$ which is a branched alkyl group having 3-12 carbon atoms, there may be cited isopropyl, sec-butyl, t-butyl, 2-methyl pentyl and 6-methyl heptyl.

And as examples of $R_2$ and $R_{10}$, either one or both of which may be represented by

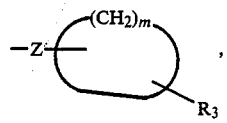

there may be cited, for example, cyclopentyl, cyclohexyl, cycloheptyl, cyclooctyl, cyclododecyl, cyclopentylmethyl, cyclohexylmethyl, cycloheptylmethyl, cyclododecylmethyl, cyclopentylethyl, cyclohexylethyl, cycloheptylethyl, cyclopentylpropyl, cyclohexylpropyl, cyclopentylbutyl, cyclohexylbutyl, cyclohexylpentyl, 2-methylcyclopentyl, 3-methylcyclopentyl, 2-methylcyclohexyl, 3-methylcyclohexyl, 4-methylcyclohexyl, 2-methylcycloheptyl, 3-methylcycloheptyl, 4-methylcycloheptyl, 4-methylcyclooctyl, 2-ethylcyclopentyl, 3-ethylcyclopentyl, 2-ethylcyclohexyl, 3-ethylcyclohexyl, 4-ethylcyclohexyl, 2-ethylcycloheptyl, 2-ethylcyclooctyl, 3-ethylcyclooctyl, 2-methylcyclopentylmethyl, 3-methylcyclopentylmethyl, 2-methylcyclohexylmethyl, 3-methylcyclohexylmethyl, 4-methylcyclohexylmethyl, 2-methylcycloheptylmethyl, 3-methylcycloheptylmethyl, 2-methylcyclooctylmethyl, 2-(2-methylcyclopentyl)ethyl, 2-(3-methylcyclopentyl)ethyl, 2-(2-methylcyclohexyl)ethyl, 2-(3-methylcyclohexyl)ethyl, 2-(4-methylcyclohexyl)ethyl, 2-(2-methylcycloheptyl)ethyl, 2-(2-methylcyclooctyl)ethyl, 3-(2-methylcyclopentyl)propyl, 3-(3-methylcyclopentyl)propyl, 3-(2-methylcyclohexyl)propyl, 3-(3-methylcyclohexyl)propyl, 3-(4-methylcyclohexyl)propyl, 5-(2-methylcyclopentyl)pentyl, 2-ethylcyclopentylmethyl, 3-ethylcyclopentylmethyl, 2-ethylcyclohexylmethyl, 3-ethylcyclohexylmethyl, 4-ethylcyclohexylmethyl, 2-ethylcycloheptylmethyl, 3-methylcycloheptylmethyl, 2-ethylcyclooctylmethyl, 2-(2-ethylcyclopentyl)ethyl, 2-(3-ethylcyclopentyl)ethyl, 2-(4-ethylcyclohexyl)ethyl, 2-(2-ethylcycloheptyl)ethyl, 2-(2-ethylcyclooctyl)ethyl, 3-(2-ethycyclopentyl)propyl, 3-(3-ethylcyclopentyl)propyl, 3-(2-ethylcyclohexyl)propyl, 3-(3-ethylcyclohexyl)propyl, 3-(4-ethylcyclohexyl)propyl, 5-(2-ethylcyclopentyl)pentyl and 5-(2-ethylcyclopentyl)pentyl.

When $R_2$ is $-(CH_2CH_2O)_lCH_3$, examples include 2-methoxyethyl, 2-(2-methoxyethoxy)ethyl and 2-[2-(methoxyethoxy)ethoxy]ethyl.

When $R_2$ is $-C_lH_{2l}COOR_3$, examples include carbomethoxymethyl group ($-CH_2COOCH_3$), (1-carbomethoxy)ethyl ($-\overset{CH_3}{\underset{|}{CH}}-COOCH_3$), carboethoxymethyl ($-CH_2COOC_2H_5$), carbopropoxymethyl ($-CH_2COOC_3H_7$), carbobutoxymethyl ($-CH_2COOC_4H_9$), 3-carbomethoxypropyl ($-(CH_2)_3COOCH_3$), carboethoxypropyl ($-(CH_2)_3COOC_2H_5$), $-(CH_2)_3COOC_3H_7$ and $-(CH_2)_3COOC_4H_9$. $R_3$ is methyl, ethyl, propyl, butyl and pentyl groups.

When $R_2$ is

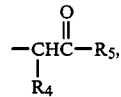

there may be cited, for example, phenacyl ($-CH_2\overset{O}{\underset{||}{C}}-\bigcirc$), 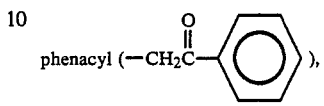

p-bromophenacyl ($-CH_2\overset{O}{\underset{||}{C}}-\bigcirc-Br$), 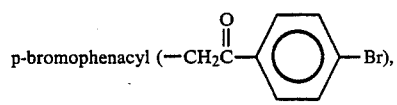

p-phenylphenacyl ($-CH_2\overset{O}{\underset{||}{C}}-\bigcirc-\bigcirc$), 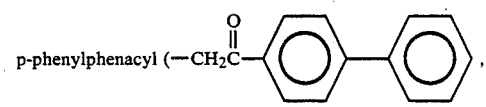

p-nitrophenacyl ($-CH_2\overset{O}{\underset{||}{C}}-\bigcirc-NO_2$), 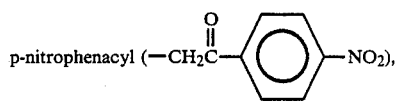

p-benzoylamino phenacyl ($-CH_2-\overset{O}{\underset{||}{C}}-\bigcirc-NH-\overset{O}{\underset{||}{C}}-\bigcirc$), 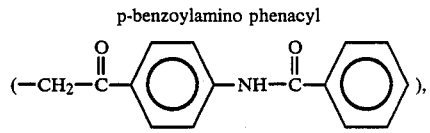

β-napthoylmethyl ($-CH_2-\overset{O}{\underset{||}{C}}-$ 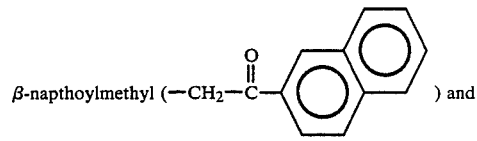 ) and dibenzoyl methyl 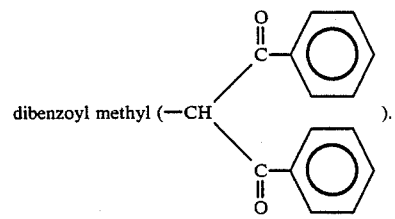.

As examples of the case when $R_2$ is $C_lH_{2l}-B'$, there may be cited $-CH_2-C\equiv C-CH_3$, $-CH_2-C\equiv C-C_2H_5$,

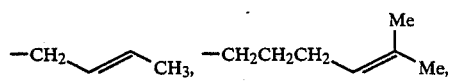

$-CH_2-C\equiv C-C_3H_7$ and $-CH_2-CH_2-C\equiv C-C_2H_5$. 

As specific examples when $R_2$ represents

there may be cited 1,3-dimethoxy-2-propyl ( 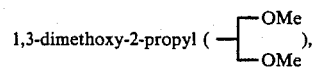 ), 1,3-diethoxy-2-propyl ( 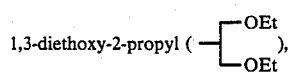 ), 1-methoxy-3-stearoyloxy-2-propyl ( 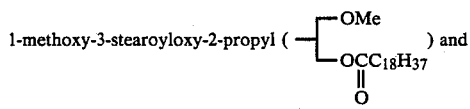 ) and 1,3-diacetoxy-2-propyl ( 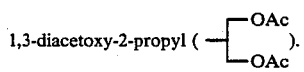 ).

As specific examples when $Ar_1$ is substituted phenyl group, there may be cited p-chlorophenyl, p-bromophenyl, p-fluorophenyl, m-chlorophenyl, m-fluorophenyl, 3,4-dichlorophenyl, p-(trifluoromethyl)phenyl, p-tolyl, 3,4-dimethylphenyl, p-anisyl, 3,4-dimethoxyphenyl, 4-phenoxyphenyl, p-benzoylaminophenyl, p-acetaminophenyl, p-carbamoylaminophenyl and p-nitrophenyl.

As specific examples of —z—$Ar_2$, there may be cited phenyl, p-chlorophenyl, p-bromophenyl, p-fluorophenyl, 3,4-dichlorophenyl, m-fluorophenyl, m-trifluoromethylphenyl, p-trifluoromethylphenyl, p-nitrophenyl, p-anisyl, 3,4-dimethoxyphenyl, p-tolyl, m-tolyl, o-tolyl, p-ethylphenyl, p-propylphenyl, p-butylphenyl, 3,4-dimethyl phenyl, 2,4-dimethylphenyl, 3-chloro-4-methylphenyl, 3-fluoro-4-methylphenyl, 4-biphenyl, p-phenoxyphenyl, p-phenoxy-3-chlorophenyl, benzyl, p-chlorobenzyl, m-chlorobenzoyl, p-methoxybenzyl, o-methoxybenzyl, p-methylbenzyl, p-ethylbenzyl, p-propylbenzyl, p-nitrobenzyl, 3,4-dichlorobenzyl, α-methylbenzyl, α,α'-dimethylbenzyl, phenethyl, p-chlorophenethyl, p-bromophenethyl, p-fluorophenethyl, m-chlorophenethyl, m-fluorophenethyl, o-chlorophenethyl, p-methyl phenethyl, p-methoxyphenethyl, 3,4-dimethoxyphenethyl, p-ethyl phenethyl, α-methylphenethyl, β-methylphenethyl, α,α'-dimethyl phenethyl, β,β'-dimethylphenethyl, 3-phenylpropyl, 3-(p-chloro phenyl)propyl, 3-(p-fluorophenyl)propyl, 3-(p-bromophenyl)propyl, 3-(m-chlorophenyl)propyl, 3-(3,4-dichlorophenyl)propyl, 3-(p-tolyl)propyl, 3-(p-ethylphenyl)propyl, 4-phenylbutyl, 4-(p-chlorophenyl)butyl, 4-(3,4-dichlorophenyl)butyl, 4-(p-tolyl)butyl and 5-phenylpentyl.

As examples when $R_{11}$ or $R_{12}$ denotes an alkyl group having 1–10 carbon atoms, specifically there may be cited methyl, ethyl, propyl, octyl and decyl. As examples when $R_{11}$ or $R_{12}$ denotes a cycloalkyl group having 3–12 carbon atoms, there may be cited cyclopropyl, cyclopentyl, cyclohexyl, cyclooctyl and cyclododecyl.

As examples when $R_{11}$ or $R_{12}$ denotes a substituted phenyl group, what is the same as the case wherein $A_{r2}$ denotes a substituted phenyl is illustrated. As examples when $R_{11}$ or $R_{12}$ denotes an aralkyl group having 7–12 carbon atoms, specifically there may be cited benzyl, phenethyl, 3-phenylpropyl, p-methylbenzyl, p-ethylbenzyl, p-propylbenzyl and 3,4-dimethylbenzyl.

As specific examples when $R_8$ denotes an acyl group having 1–12 carbon atoms, there may be cited acetyl, propionyl, butyroyl, octanoyl and dodecanoyl. As specific examples when $R_8$ denotes an aroyl group having 6–12 carbon atoms, there may be cited benzoyl, phenylacetyl, 3-phenylpropionyl, p-phenylbenzoyl, α-naphthoyl and β-nahthoyl.

As specific examples when $R_7$ denotes a straight chain alkyl group having 1–30 carbon atoms, there may be cited methyl, ethyl, propyl, butyl, pentyl, hexyl, octyl, hexadecanyl and octaeicosanyl. As specific examples when $R_7$ denotes an acyl group having 1–30 carbon atoms, there may be cited acetyl, octanoyl, palmitoyl, eicosanoyl and hexaeicosanoyl.

Specific examples when $R_9$ or Y denotes an alkyl groups having 1–4 carbon atoms include methyl, ethyl, propyl and butyl.

Specific examples when $R_{10}$ is straight chain alkyl having 4–10 carbon atoms include n-butyl, n-pentyl, n-hexyl, n-heptyl, n-octyl and n-decyl.

As specific examples when $R_{13}$ is branched alkyl having 5–10 carbon atoms, there may be cited 1,1-dimethylpentyl, 1-methylpentyl, 2-methylpentyl, 3-metylpentyl, 1,1-dimenthylhexyl, 2-methylhexyl and 1,1-dimethyl-2-methylhexyl.

As specific examples when $R_{14}$ denotes straight chain or branched alkyl having 1–5 carbon atoms, there may be cited methyl, ethyl, n-propyl, n-butyl, n-pentyl, isobutyl and 3-methylbutyl.

As specific examples of $C_tH_{2t}$, there may be cited methylene, ethylene, propylene, butylene, 1,1-dimethyl methylene, 1,1-dimethylethylene, 1,1-dimethylpropylene and 3-methylpropylene.

The compound represented by the aforesaid general formula (I) obtained according to the present invention is a $PGI_2$ derivative having a novel skeleton converting the structure of the exoenol ether part which is a characteristic structure of $PGI_2$ to an inter-m-phenylene type.

This compound is characterized in that drawbacks recognized in $PGI_2$ in general are sharply improved. Namely, the compound represented by the general formula (I) is very stable in an aqueous solution, in addition, its physiological action is very continuous even if it is inside an organism. Further, the compound represented by the general formula (I) has excellent properties in the aspect of having the multi-facet physiological activities possessed by $PGI_2$ in a more selective form, wherein lies its merit from the viewpoint of its utilization as a medicine.

The compound represented by the aforesaid general formula (I) obtained according to the present invention can be named in accordance with the nomenclature of prostaglandin and prostacyclene-analog proposed by N. A. Nelson et al. (N. A. Nelson, "J. Med. Chem.," 17, 911 (1974) and R. A. Johnson, D. R. Morton, N. A. Nelson, "Prostaglandins," 15, 737 (1974)). The most fundamental compound converting the exoenol ether structure part of $PGI_2$ to inter-m-phenylene is represented by the following formula, numbered as shown and named 5,6,7-trinor-4,8-inter-m-phenylene $PGI_2$.

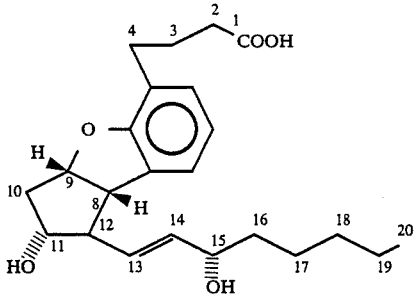

According to this nomenclature, the compound of the following formula included in the present invention is named 5,6,7-trinor-4,8-inter-m-phenylene-13,14-didehydro-16,17,18,19,20-pentanor-15-cyclohexyl PGI$_2$.

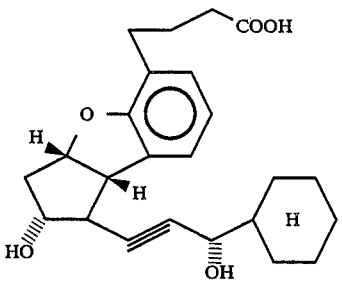

Further, when there is a substituent in a phenylene group to be inserted, there is no properly proposed nomenclature, however, by expanding the aforesaid nomenclature, it is named as follows. Namely, number of a phenylene group at a position bonding to 4-position is named 1' and said number at a position bonding to 8-position carbon is named 3'.

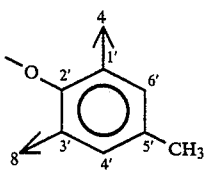

Thus, such compound is named 5,6,7-trinor-4-, 8-inter-(5'-methyl-m-phenylene) or 5,6,7-trinor-4,8-inter-(5'-methyl)-1',3'-phenylene). According to this nomenclature, the compound of the following formula included in the present invention

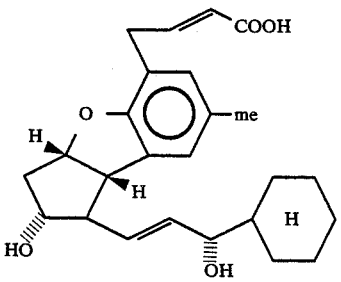

is named 5,6,7-trinor-4,8-inter-(5'-methyl-m-phenylene)-2,3-didehydro-16,17,18,19,20-pentanor-15-cyclohexyl PGI$_2$. This compound according to the formal nomenclature, is named after cyclopental[b]benzofuran ring as a substituent. According to this method, the name of this compound is

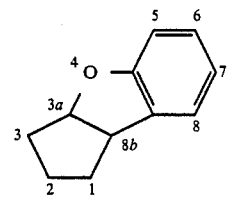

[1,2,3a,8b-tetrahydro-3a,8b-cis-2-endo-hydroxy-7-metyl-1-exo-(3-cyclohexyl-3-hydroxypyopen-1-yl)-5-cyclopenta[b]benzofuranyl-2,3-didehydrobutanoic acid. However, in this specification, the compound is named according to the aforesaid simple nomenclature excluding the synthetic intermediate.

When compounds included in the present invention are shown according to the aforesaid nomenclature, the following compounds may be cited.

5,6,7-trinor-4,8-inter-m-phenylene-16(S)-methyl PGI$_2$,
5,6,7-trinor-4,8-inter-m-phenylene-16(R)-methyl PGI$_2$,
5,6,7-trinor-4,8-inter-m-phenylene-16-methyl-ω-homo PGI$_2$,
5,6,7-trinor-4,8-inter-m-phenylene-17(S)-methyl-ω-homo PGI$_2$,
5,6,7-trinor-4,8-inter-m-phenylene-13,14-didehydro-16,17,18,19,20-pentanor-15-cyclohexyl PGI$_2$,
5,6,7-trinor-4,8-inter-m-phenylene-13,14-didehydro-ω-homo PGI$_2$,
5,6,7-trinor-4,8-inter-m-phenylene-2,3-didehydro-17(S)-methyl PGI$_2$,
5,6,7-trinor-4,8-inter-m-phenylene-2,3-didehydro-17(S)-methyl-ω-homo PGI$_2$,
5,6,7-trinor-4,8-inter-m-phenylene-2,3-didehydro-16,17,18,19,20-pentanor-15-cyclopentyl PGI$_2$,
5,6,7-trinor-4,8-inter-m-phenylene-2,3-didehydro-16,17,18,19,20-pentanor-15-cyclohexyl PGI$_2$, The following compounds are also advantageous.

5,6,7-trinor-4,8-inter-m-phenylene-16,16-dimethyl PGI$_2$,
5,6,7-trinor-4,8-inter-m-phenylene-16-methyl PGI$_2$,
5,6,7-trinor-4,8-inter-m-phenylene-16(S)-methyl-ω-homo PGI$_2$,
5,6,7-trinor-4,8-inter-m-phenylene-16(R)-methyl-ω-homo PGI$_2$,
5,6,7-trinor-4,8-inter-m-phenylene-17(S)-methyl PGI$_2$,
5,6,7-trinor-4,8-inter-m-phenylene-17(R)-methyl PGI$_2$,
5,6,7-trinor-4,8-inter-m-phenylene-17(R)-methylω-homo PGI$_2$,
5,6,7-trinor-4,8-inter-m-phenylene-13,14-didehydro PGI$_2$,
5,6,7-trinor-4,8-inter-m-phenylene-13,14-didehydro-17(S)-methyl PGI$_2$,
5,6,7-trinor-4,8-inter-m-phenylene-13,14-didehydro-17(R)-methyl PGI$_2$,
5,6,7-trinor-4,8-inter-m-phenylene-13,14-didehydro-17(S)-methyl-ω-homo PGI$_2$,
5,6,7-trinor-4,8-inter-m-phenylene-13,14-didehydro-17(R)-methyl-ω-homo PGI$_2$,
5,6,7-trinor-4,8-inter-m-phenylene-13,14-didehydro-16,17,18,19,20-pentanor-15-cyclopentyl PGI$_2$, 5,6,7-trinor-4,8-inter-m-phenylene-13,14-didehydro-16,17,18,19,20-pentanor-15-(2-methylcyclopentyl) PGI$_2$,
5,6,7-trinor-4,8-inter-m-phenylene-13,14-didehydro-16,17,18,19,20-pentanor-15-(3-methylcyclopentyl) PGI$_2$,
5,6,7-trinor-4,8-inter-m-phenylene-13,14-didehydro-16,17,18,19,20-pentanor-15-(2-methylcyclohexyl) PGI$_2$,
5,6,7-trinor-4,8-inter-m-phenylene-13,14-didehydro-16,17,18,19,20-pentanor-15-(3-methylcyclohexyl) PGI$_2$,
5,6,7-trinor-4,8-inter-m-phenylene-13,14-didehydro-16,17,18,19,20-pentanor-15-(4-methylcyclohexyl) PGI$_2$,
5,6,7-trinor-4,8-inter-m-phenylene-13,14-didehydro-16,17,18,19,20-pentanor-15-phenyl PGI$_2$,
5,6,7-trinor-4,8-inter-m-phenylene-13,14-didehydro-16,17,18,19,20-pentanor-15-(p-tolyl) PGI$_2$,
5,6,7-trinor-4,8-inter-m-phenylene-17,18,19,20-tetranor-16-phenoxy PGI$_2$,
5,6,7-trinor-4,8-inter-m-phenylene-18-oxa PGI$_2$,
5,6,7-trinor-4,8-inter-m-phenylene-2,3-didehydro PGI$_2$,
5,6,7-trinor-4,8-inter-m-phenylene-2,3-didehydro-ω-homo PGI$_2$,
5,6,7-trinor-4,8-inter-m-phenylene-2,3-didehydro-16,16-dimethyl PGI$_2$,
5,6,7-trinor-4,8-inter-m-phenylene-2,3-didehydro-17(R)-methyl PGI$_2$,
5,6,7-trinor-4,8-inter-m-phenylene-2,3-didehydro-17(R)-methyl-ω-homo PGI$_2$,
5,6,7-trinor-4,8-inter-m-phenylene-2,3-didehydro-16,17,18,19,20-pentanor-15-(14-methylhexyl) PGI$_2$,
5,6,7-trinor-4,8-inter-m-phenylene-2,3-didehydro-16,17,18,19,20-pentanor-15-phenyl PGI$_2$,
5,6,7-trinor-4,8-inter-m-phenylene-2,3-didehydro-17,18,19,20-tetranor-16-phenyl PGI$_2$,
5,6,7-trinor-4,8-inter-m-phenylene-2,3-didehydro-18,19,20-trinor-17-phenyl PGI$_2$,
5,6,7-trinor-4,8-inter-m-phenylene-2,3-didehydro-17,18,19,20-tetranor-16-phenoxy PGI$_2$,
5,6,7-trinor-4,8-inter-m-phenylene-2,3-didehydro-18-oxa PGI$_2$,
5,6,7-trinor-4,8-inter-m-phenylene-2,3,13,14-tetradehydro PGI$_2$
5,6,7-trinor-4,8-inter-m-phenylene-2,3,13,14-tetradehydro-16,17,18,19,20-pentanor-15-cyclohexyl PGI$_2$,
5,6,7-trinor-4,8-inter-m-phenylene-2,3,13,14-tetradehydro-16,17,18,19,20-pentanor-15-cyclopentyl PGI$_2$,
5,6,7-trinor-4,8-inter-m-phenylene-2,3,13,14-tetradehydro-16,17,18,19,20-pentanor-15-phenyl PGI$_2$,
and the corresponding methyl ester, ethyl ester, benzyl ester, phenyl ester, methoxy methyl ester, carbomethoxy methyl ester, phenacyl ester, 1,3-diacetoxy-2-propyl ester, phenethyl ester, amide, butyl amide, cyclohexyl amide, (N-methanesulfonyl) amide and morpholine amide may be cited.

Further, as compounds included in the present invention, the following compounds may be cited.
5,6,7-trinor-4,8-inter-m-phenylene-16,16-dimethyl-ω-homo PGI$_2$,
5,6,7-trinor-4,8-inter-m-phenylene-18-methyl PGI$_2$,
5,6,7-trinor-b 4,8-inter-m-phenylene-19-methyl PGI$_2$,
5,6,7-trinor-4,8-inter-m-phenylene-15-methyl-17(S)-methyl PGI$_2$,
5,6,7-trinor-4,8-inter-m-phenylene-13,14-didehydro-15-methyl PGI$_2$,
5,6,7-trinor-4,8-inter-m-phenylene-13,14-didehydro-16,16-dimethyl PGI$_2$,
5,6,7-trinor-4,8-inter-m-phenylene-13,14-didehydro-17,18,19,20-tetranor-16-cyclopentyl PGI$_2$,
5,6,7-trinor-4,8-inter-m-phenylene-2,3-didehydro-17,18,19,20-tetranor-16-cyclohexyl PGI$_2$,
5,6,7-trinor-4,8-inter-m-phenylene-13,14-didehydro-18,19,20-trinor-17-cyclopentyl PGI$_2$,
5,6,7-trinor-4,8-inter-m-phenylene-13,14-didehydro-18,19,20-trinor-17-cyclohexyl PGI$_2$,
5,6,7-trinor-4,8-inter-m-phenylene-13,14-didehydro-16,17,18,19,20-pentanor-15-(p-chlorophenyl) PGI$_2$,
5,6,7-trinor-4,8-inter-m-phenylene-13,14-didehydro-16,17,18,19,20-pentanor-15-(m-chlorophenyl) PGI$_2$,
5,6,7-trinor-4,8-inter-m-phenylene-13,14-didehydro-16,17,18,19,20-pentanor-15-(3,4-dichlorophenyl) PGI$_2$,
5,6,7-trinor-4,8-inter-m-phenylene-13,14-didehydro-16,17,18,19,20-pentanor-15-(p-methoxyphenyl) PGI$_2$,
5,6,7-trinor-4,8-inter-m-phenylene-13,14-didehydro-17,18,19,20-tetranor-16-phenyl PGI$_2$,
5,6,7-trinor-4,8-inter-m-phenylene-13,14-didehydro-17,18,19,20-tetranor-16-(p-chlorophenyl) PGI$_2$,
5,6,7-trinor-4,8-inter-m-phenylene-13,14-didehydro-17,18,19,20-tetranor-16-(m-chlorophenyl) PGI$_2$,
5,6,7-trinor-4,8-inter-m-phenylene-13,14-didehydro-17,18,19,20-tetranor-16-(p-tolyl) PGI$_2$,
5,6,7-trinor-4,8-inter-m-phenylene-13,14-didehydro-18,19,20-trinor-17-phenyl PGI$_2$,
5,6,7-trinor-4,8-inter-m-phenylene-13,14-didehydro-18,19,20-trinor-17-(p-chlorophenyl) PGI$_2$,
5,6,7-trinor-4,8-inter-m-phenylene-13,14-didehydro-18,19,20-trinor-17-(m-chlorophenyl) PGI$_2$,
5,6,7-trinor-4,8-inter-m-phenylene-13,14-didehydro-18,19,20-trinor-17-(3,4-dichlorophenyl) PGI$_2$,
5,6,7-trinor-4,8-inter-m-phenylene-13,14-didehydro-16,17,18,19,20-pentanor-15-(p-trifluoromethylphenyl) PGI$_2$,
5,6,7-trinor-4,8-inter-m-phenylene-13,14-didehydro-16,17,18,19,20-pentanor-15-(m-trifluoromethylphenyl) PGI$_2$,
5,6,7-trinor-4,8-inter-m-phenylene-13,14-didehydro-16,17,18,19,20-pentanor-15-(m-fluorophenyl) PGI$_2$,
5,6,7-trinor-4,8-inter-m-phenylene-13,14-didehydro-19,20-dinor-18-phenyl PGI$_2$,
5,6,7-trinor-4,8-inter-m-phenylene-17,18,19,20-tetranor-16-(m-chlorophenoxy) PGI$_2$,
5,6,7-trinor-4,8-inter-m-phenylene-17,18,19,20-tetranor-16-(p-chlorophenoxy) PGI$_2$,
5,6,7-trinor-4,8-inter-m-phenylene-17,18,19,20-tetranor-16-(p-trifluoromethylphenyl) PGI$_2$,
5,6,7-trinor-4,8-inter-m-phenylene-17,18,19,20-tetranor-16-(m-trifluoromethylphenyl) PGI$_2$,
5,6,7-trinor-4,8-inter-m-phenylene-17-oxa PGI$_2$,
5,6,7-trinor-4,8-inter-m-phenylene-16,17-dimethyl-18-oxa PGI$_2$,
5,6,7-trinor-4,8-inter-m-phenylene-17-oxa-ω-homo PGI$_2$,
5,6,7-trinor-4,8-inter-m-phenylene-17,18,19,20-tetranor-16-cyclohexyloxy PGI$_2$,
5,6,7-trinor-4,8-inter-m-phenylene-17,18,19,20-tetranor-cyclopentyloxy PGI$_2$,
5,6,7-trinor-4,8-inter-m-phenylene-2,3-didehydro-16,17,18,19,20-pentanor-15-cycloheptyl PGI$_2$,
5,6,7-trinor-4,8-inter-m-phenylene-2,3-didehydro-16,17,18,19,20-pentanor-15-cyclooctyl PGI$_2$,
5,6,7-trinor-4,8-inter-m-phenylene-2,3-didehydro-17,18,19,20-tetranor-16-cyclohexyl PGI$_2$, 5,6,7-trinor-4,8-inter-m-phenylene-2,3-didehydro-17,18,19,20-tetranor-16-cyclopentyl PGI$_2$,
5,6,7-trinor-4,8-inter-m-phenylene-2,3-didehydro-18,19,20-trinor-17-cyclohexyl PGI$_2$,
5,6,7-trinor-4,8-inter-m-phenylene-2,3-didehydro-16,17,18,19,20-pentanor-15-(p-tolyl) PGI$_2$,
5,6,7-trinor-4,8-inter-m-phenylene-2,3-didehydro-16,17,18,19,20-pentanor-15-(p-chlorophenyl) PGI$_2$,
5,6,7-trinor-4,8-inter-m-phenylene-2,3-didehydro-16,17,18,19,20-pentanor-15-(m-chlorophenyl) PGI$_2$,
5,6,7-trinor-4,8-inter-m-phenylene-2,3-didehydro-16,17,18,19,20-pentanor-15-(m-fluorophenyl) PGI$_2$,
5,6,7-trinor-4,8-inter-m-phenylene-2,3-didehydro-16,17,18,19,20-pentanor-15-(p-fluorophenyl) PGI$_2$,
5,6,7-trinor-4,8-inter-m-phenylene-2,3-didehydro-16,17,18,19,20-pentanor-15-(p-trifluoromethylphenyl) PGI$_2$,
5,6,7-trinor-4,8-inter-m-phenylene-2,3-didehydro-16,17,18,19,20-pentanor-15-(m-trifluoromethylphenyl) PGI$_2$,
5,6,7-trinor-4,8-inter-m-phenylene-2,3-didehydro-16,16-dimethyl-18-oxa PGI$_2$,
5,6,7-trinor-4,8-inter-m-phenylene-2,3-didehydro-17-oxa-ω-homo PGI$_2$,
5,6,7-trinor-4,8-inter-m-phenylene-2,3,13,14-tetradehydro-17,18,19,20-tetranor-16-phenyl PGI$_2$,
5,6,7-trinor-4,8-inter-m-phenylene-3,4-didehydro-PGI$_2$,
5,6,7-trinor-4,8-inter-m-phenylene-3,4-didehydro-16,17,18,19,20-pentanor-15-phenyl PGI$_2$,
5,6,7-trinor-4,8-inter-m-phenylene-3,4-didehydro-16,17,18,19,20-pentanor-15-cyclohexyl PGI$_2$,
5,6,7-trinor-4,8-inter-m-phenylene-3-oxa PGI$_2$,
5,6,7-trinor-4,8-inter-m-phenylene-3-oxa-16,17,18,19,20-pentanor-15-phenyl PGI$_2$,
5,6,7-trinor-4,8-inter-m-phenylene-3-oxa-16,17,18,19,20-pentanor-15-cyclohexyl PGI$_2$,
5,6,7-trinor-4,8-inter-m-phenylene-3-oxa-13,14-didehydro-16,17,18,19,20-pentanor-15-cyclohexyl PGI$_2$,
5,6,7-trinor-4,8-inter-m-phenylene-3-oxa-13,14-didehydro-16,17,18,19,20-pentanor-15-cyclopentyl PGI$_2$,
5,6,7-trinor-4,8-inter-m-phenylene-3-oxa-13,14-didehydro PGI$_2$,
5,6,7-trinor-4,8-inter-m-phenylene-3-oxa-13,14-didehydro-16,17,18,19,20-pentanor-15-phenyl PGI$_2$,
5,6,7-trinor-4,8-inter-m-phenylene-3-oxa-13,14-didehydro-16,17,18,19,20-pentanor-15-cyclohexyl PGI$_2$,
5,6,7-trinor-4,8-inter-m-phenylene-2,3-didehydro-13,14-dihydro-16,17,18,19,20-pentanor-15-phenyl PGI$_2$,
5,6,7-trinor-4,8-inter-m-phenylene-2,3-didehydro-13,14-dihydro-16,17,18,19,20-pentanor-15-cyclohexyl PGI$_2$,
5,6,7-trinor-4,8-inter-m-phenylene-2,3-didehydro-13,14-dihydro-17,18,19,20-tetranor-16-phenoxy PGI$_2$,
5,6,7-trinor-4,8-inter-m-phenylene-2,3-didehydro-13,14-dihydro-17(S)-methyl PGI$_2$,
5,6,7-trinor-4,8-inter-m-phenylene-2,3-didehydro-13,14-dihydro-17(R)-methyl PGI$_2$,
5,6,7-trinor-4,8-inter-m-phenylene-2,3-didehydro-13,14-dihydro-17(S)-methyl-ω-homo PGI$_2$,
5,6,7-trinor-4,8-inter-m-phenylene-2,3-didehydro-13,14-dihydro-17(R)-methyl-ω-homo PGI$_2$,
5,6,7-trinor-4,8-inter-(5'-methyl-m-phenylene)-16,17,18 19,20-pentanor-15-phenyl PGI$_2$,
5,6,7-trinor-4,8-inter-(5'-bromo-m-phenylene)-16,17,18,19,20-pentanor-15-cyclohexyl PGI$_2$,
5,6,7-trinor-4,8-inter-(5'-methyl-m-phenylene)-3-oxa PGI$_2$,
5,6,7-trinor-4,8-inter-(5'-methyl-m-phenylene)-13,14-didehydro-16,17,18,19,20-pentanor-15-cyclohexyl PGI$_2$,
5,6,7-trinor-4,8-inter-(5'-methyl-m-phenylene)-13,14-didehydro PGI$_2$,
5,6,7-trinor-4,8-inter-(5'-methyl-m-phenylene)-13,14-didehydro-17(S)-methyl PGI$_2$,
5,6,7-trinor-4,8-inter-(5'-methyl-m-phenylene)-13,14-didehydro-17(R)-methyl-ω-homo PGI$_2$,
5,6,7-trinor-4,8-inter-(5'-methyl-m-phenylene)-13,14-didehydro-16,17,18,19,20-pentanor-15-cyclohexyl PGI$_2$, and the corresponding methyl ester, ethyl ester, benzyl ester, phenyl ester, methoxy methyl ester, carbomethoxy methyl ester, phenacyl ester, 1,3-diacetoxy-2-propyl ester, phenethyl ester, amide, butyl amide, cyclohexyl amide, (N-methanesulfonyl) amide and morpholine a amide may be cited, however, such compounds are not limited thereto.

It has been discovered that especially advantageous potency is attained by the provision of the so-called "2-nor" compounds of this invention. In some cases the compounds are as much as one hundred times as potent as other compounds in respect of suppression of platelet aggregation, antihypertensive effects and treatment of stomach ulcers.

Representatives of compounds containing "2-nor":
5,6,7-trinor-4,8-inter-m-phenylene-2-nor-16,16-dimethyl PGI$_2$,
5,6,7-trinor-4,8-inter-m-phenylene-2-nor-17(S)-methyl PGI$_2$,
5,6,7-trinor-4,8-inter-m-phenylene-2-nor-17(R)-methyl PGI$_2$,
5,6,7-trinor-4,8-inter-m-phenylene-2-nor-17,17-dimethyl PGI$_2$,
5,6,7-trinor-4,8-inter-m-phenylene-2-nor-18,18-dimethyl PGI$_2$,
5,6,7-trinor-4,8-inter-m-phenylene-2-nor-16,16-dimethyl-ω-homo PGI$_2$,
5,6,7-trinor-4,8-inter-m-phenylene-2-nor-17(S)-methyl-ω-homo PGI$_2$,
5,6,7-trinor-4,8-inter-m-phenylene-2-nor-17(R)-methyl-ω-homo PGI$_2$,
5,6,7-trinor-4,8-inter-m-phenylene-2-nor-15(R)-methyl PGI$_2$,
5,6,7-trinor-4,8-inter-m-phenylene-2-nor-15(S)-methyl PGI$_2$,
5,6,7-trinor-4,8-inter-m-phenylene-2-nor-16,16-dimethyl-ω-dihomo PGI$_2$,
5,6,7-trinor-4,8-inter-m-phenylene-2-nor-16,16-dimetyl-ω-trihomo PGI$_2$,
5,6,7-trinor-4,8-inter-m-phenylene-2,17,18,19,20-pentanor-16-methyl PGI$_2$,
5,6,7-trinor-4,8-inter-m-phenylene-2,17,18,19,20-pentanor-16,16-dimethyl PGI$_2$, and the corresponding methyl ester, ethyl ester, propyl ester and benzyl ester.
5,6,7-trinor-4,8-inter-m-phenylene-2,17,18,19,20-pentanor-16-propoxy PGI$_2$,
5,6,7-trinor-4,8-inter-m-phenylene-2,18,19,20-tetranor-17-ethoxy PGI$_2$,
5,6,7-trinor-4,8-inter-m-phenylene-2,19,20-trinor-18-methoxy PGI$_2$,
5,6,7-trinor-4,8-inter-m-phenylene-2,17,18,19,20-pentanor-16,16-dimethyl-16-propoxy PGI$_2$,
5,6,7-trinor-4,8-inter-m-phenylene-2,18,19,20-tetranor-16,16-dimethyl-17-ethoxy PGI$_2$, 5,6,7-trinor-4,8-inter-m-phenylene-2,19,20-trinor-16,16-dimethyl-18-methoxy PGI$_2$,
5,6,7-trinor-4,8-inter-m-phenylene-2,17,18,19,20-pentanor-16-butoxy PGI$_2$,
5,6,7-trinor-4,8-inter-m-phenylene-2,17,18,19,20-pentanor-16-pentyloxy PGI$_2$,
5,6,7-trinor-4,8-inter-m-phenylene-2,17,18,19,20-pentanor-16-hexyloxy PGI$_2$,
5,6,7-trinor-4,8-inter-m-phenylene-2,18,19,20-tetranor-17-propoxy PGI$_2$,
5,6,7-trinor-4,8-inter-m-phenylene-2,18,19,20-tetranor-17-methoxy PGI$_2$,
5,6,7-trinor-4,8-inter-m-phenylene-2,18,19,20-tetranor-17-ethoxy PGI$_2$,
5,6,7-trinor-4,8-inter-m-phenylene-2,18,19,20-tetranor-17-butoxy PGI$_2$,
5,6,7-trinor-4,8-inter-m-phenylene-2,18,19,20-tetranor-17-pentyloxy PGI$_2$,
5,6,7-trinor-4,8-inter-m-phenylene-2,19,20-trinor-18-ethoxy PGI$_2$,
5,6,7-trinor-4,8-inter-m-phenylene-2,19,20-trinor-18-propoxy PGI$_2$,
5,6,7-trinor-4,8-inter-m-phenylene-2,17,18,19,20-pentanor-16,16-dimethyl-16-butoxy PGI$_2$,
5,6,7-trinor-4,8-inter-m-phenylene-2,18,19,20-tetranor-16,16-dimethyl-17-propoxy PGI$_2$,
5,6,7-trinor-4,8-inter-m-phenylene-2,18,19,20-tetranor-16,16-dimethyl-17-methoxy PGI$_2$,
5,6,7-trinor-4,8-inter-m-phenylene-2,18,19,20-tetranor-16,16-dimethyl-17-butoxy PGI$_2$,
5,6,7-trinor-4,8-inter-m-phenylene-2,19,20-trinor-16,16-dimethyl-18-ethoxy PGI$_2$,
5,6,7-trinor-4,8-inter-m-phenylene-2,19,20-trinor-16,16-dimethyl-18-propoxy PGI$_2$,
5,6,7-trinor-4,8-inter-m-phenylene-2,19,20-trinor-16,16-dimethyl-18-butoxy PGI$_2$,
5,6,7-trinor-4,8-inter-m-phenylene-2,17,18,19,20-pentanor-16-cyclopentyloxy PGI$_2$,
5,6,7-trinor-4,8-inter-m-phenylene-2,17,18,19,20-pentanor-16-cyclohexyloxy PGI$_2$,
5,6,7-trinor-4,8-inter-m-phenylene-2,17,18,19,20-pentanor-16-phenoxy PGI$_2$,
5,6,7-trinor-4,8-inter-m-phenylene-2,17,18,19,20-pentanor-16-(p-chlorophenoxy) PGI$_2$,
5,6,7-trinor-4,8-inter-m-phenylene-2,17,18,19,20-pentanor-16-(m-chlorophenoxy) PGI$_2$,
5,6,7-trinor-4,8-inter-m-phenylene-2,17,18,19,20-pentanor-16-(p-methylphenoxy) PGI$_2$,
5,6,7-trinor-4,8-inter-m-phenylene-2,17,18,19,20-pentanor-16-(p-methoxyphenoxy) PGI$_2$,
5,6,7-trinor-4,8-inter-m-phenylene-2,17,18,19,20-pentanor-16-(p-trifluoromethylphenoxy) PGI$_2$,
5,6,7-trinor-4,8-inter-m-phenylene-2,17,18,19,20-pentanor-16-(n-trifluoromethylphenoxy) PGI$_2$, and the corresponding methyl ester, ethyl ester, propyl ester and benzyl ester.
5,6,7-trinor-4,8-inter-m-phenylene-2-nor-13,14-didehydro-16,16-dimethyl PGI$_2$,
5,6,7-trinor-4,8-inter-m-phenylene-2-nor-13,14-didehydro-17(S)-methyl PGI$_2$,
5,6,7-trinor-4,8-inter-m-phenylene-2-nor-13,14-didehydro-17(R)-methyl PGI$_2$,
5,6,7-trinor-4,8-inter-m-phenylene-2-nor-13,14-didehydro-17,17-dimethyl PGI$_2$,
5,6,7-trinor-4,8-inter-m-phenylene-2-nor-13,14-didehydro-18,18-dimethyl PGI$_2$,
5,6,7-trinor-4,8-inter-m-phenylene-2-nor-13,14-didehydro-16,16-dimethyl-ω-homo PGI$_2$,
5,6,7-trinor-4,8-inter-m-phenylene-2-nor-13,14-didehydro-17(S)-methyl-ω-homo PGI$_2$,
5,6,7-trinor-4,8-inter-m-phenylene-2-nor-13,14-didehydro-17(R)-methyl-ω-homo PGI$_2$,
5,6,7-trinor-4,8-inter-m-phenylene-2-nor-13,14-didehydro-15(R)-methyl PGI$_2$,
5,6,7-trinor-4,8-inter-m-phenylene-2-nor-13,14-didehydro-15(S)-methyl PGI$_2$,
5,6,7-trinor-4,8-inter-m-phenylene-2-nor-13,14-didehydro-16,16-dimethyl-ω-dihomo PGI$_2$,
5,6,7-trinor-4,8-inter-m-phenylene-2-nor-13,14-didehydro-16,16-dimethyl-ω-trihomo PGI$_2$,
5,6,7-trinor-4,8-inter-m-phenylene-2,18,19,20-tetranor-13,14-didehydro PGI$_2$,
5,6,7-trinor-4,8-inter-m-phenylene-2,18,19,20-tetranor-13,14-didehydro-16-methyl PGI$_2$, and the corresponding methyl ester, ethyl ester, propyl ester and benzyl ester.
5,6,7-trinor-4,8-inter-m-phenylene-13,14-didehydro-2,17,18,19,20-pentanor-16-propoxy PGI$_2$,
5,6,7-trinor-4,8-inter-m-phenylene-13,14-didehydro-2,18,19,20-tetranor-17-ethoxy PGI$_2$,
5,6,7-trinor-4,8-inter-m-phenylene-13,14-didehydro-2,19,20-trinor-18-methoxy PGI$_2$,
5,6,7-trinor-4,8-inter-m-phenylene-13,14-didehydro-2,17,18,19,20-pentanor-16,16-dimethyl-16-propoxy PGI$_2$,
5,6,7-trinor-4,8-inter-m-phenylene-13,14-didehydro-2,18,19 20-tetranor-16,16-dimethyl-17-ethoxy PGI$_2$,
5,6,7-trinor-4,8-inter-m-phenylene-13,14-didehydro-2,19,20-trinor-16,16-dimethyl-18-methoxy PGI$_2$,
5,6,7-trinor-4,8-inter-m-phenylene-13,14-didehydro-2,17,18,19,20-pentanor-16-butoxy PGI$_2$,
5,6,7-trinor-4,8-inter-m-phenylene-13,14-didehydro-2,17,18,19,20-pentanor-16-pentyloxy PGI$_2$,
5,6,7-trinor-4,8-inter-m-phenylene-13,14-didehydro-2,17,18,19,20-pentanor-16-hexyloxy PGI$_2$,
5,6,7-trinor-4,8-inter-m-phenylene-13,14-didehydro-2,18,19,20-tetranor-17-propoxy PGI$_2$,
5,6,7-trinor-4,8-inter-m-phenylene-13,14-didehydro-2,18,19,20-tetranor-17-butoxy PGI$_2$,
5,6,7-trinor-4,8-inter-m-phenylene-13,14-didehydro-2,18,19,20-tetranor-17-pentyloxy PGI$_2$,
5,6,7-trinor-4,8-inter-m-phenylene-13,14-didehydro-2,19,20-trinor-18-ethoxy PGI$_2$,
5,6,7-trinor-4,8-inter-m-phenylene-13,14-didehydro-2,19,20-trinor-18-propoxy PGI$_2$,
5,6,7-trinor-4,8-inter-m-phenylene-13,14-didehydro-2,17,18,19,20-pentanor-16,16-dimethyl-16-butoxy PGI$_2$,
5,6,7-trinor-4,8-inter-m-phenylene-13,14-didehydro-2,18,19,20-tetranor-16,16-dimethyl-17-propoxy PGI$_2$,
5,6,7-trinor-4,8-inter-m-phenylene-13,14-didehydro-2,19,20-trinor-16,16-dimethyl-18-ethoxy PGI$_2$,
5,6,7-trinor-4,8-inter-m-phenylene-13,14-didehydro-2,19,20-trinor-16,16-dimethyl-18-propoxy PGI$_2$,
5,6,7-trinor-4,8-inter-m-phenylene-13,14-didehydro-2,19,20-trinor-16,16-dimethyl-18-butoxy PGI$_2$,
5,6,7-trinor-4,8-inter-m-phenylene-13,14-didehydro-2,17,18,19,20-pentanor-16-cyclopentyloxy PGI$_2$,
5,6,7-trinor-4,8-inter-m-phenylene-13,14-didehydro-2,17,18,19,20-pentanor-16-cyclohexyloxy PGI$_2$,
5,6,7-trinor-4,8-inter-m-phenylene-13,14-didehydro-2,17,18,19,20-pentanor-16-phenoxy PGI$_2$,
5,6,7-trinor-4,8-inter-m-phenylene-13,14-didehydro-2,17,18,19,20-pentanor-16-(p-chlorophenoxy) PGI$_2$,
5,6,7-trinor-4,8-inter-m-phenylene-13,14-didehydro-2,17,18,19,20-pentanor-16-(m-chlorophenoxy) PGI$_2$, 5,6,7-trinor-4,8-inter-m-phenylene-13,14didehydro-2,17,18,19,20-pentanor-16-(p-methylphenoxy) PGI$_2$,
5,6,7-trinor-4,8-inter-m-phenylene-2,17,18,19,20-pentanor-13,14-didehydro-16-(p-methoxyphenoxy) PGI$_2$,
5,6,7-trinor-4,8-inter-m-phenylene-13,14-didehydro-2,17,18,19,20-pentanor-16-(p-trifluoromethylphenoxy) PGI$_2$,
5,6,7-trinor-4,8-inter-m-phenylene-13,14-didehydro-2,17,18,19,20-pentanor-16-(m-trifluoromethylphenoxy) PGI$_2$, and the corresponding methyl ester, ethyl ester, propyl ester and benzyl ester.
5,6,7-trinor-4,8-inter-m-phenylene-13,14-dihydro-2-nor-16,16-dimethyl PGI$_2$,
5,6,7-trinor-4,8-inter-m-phenylene-13,14-dihydro-2-nor-17(S)-methyl PGI$_2$,
5,6,7-trinor-4,8-inter-m-phenylene-13,14-dihydro-2-nor-17(R)-methyl PGI$_2$,
5,6,7-trinor-4,8-inter-m-phenylene-13,14-dihydro-2-nor-17,17-dimethyl PGI$_2$,
5,6,7-trinor-4,8-inter-m-phenylene-13,14-dihydro-2-nor-18,18-dimethyl PGI$_2$,
5,6,7-trinor-4,8-inter-m-phenylene-13,14-dihydro-2-nor-16,16-dimethyl-ω-homo PGI$_2$,
5,6,7-trinor-4,8-inter-m-phenylene-13,14-dihydro-2-nor-17(S)-methyl-ω-homo PGI$_2$,
5,6,7-trinor-4,8-inter-m-phenylene-13,14-dihydro-2-nor-17(R)-methyl-ω-homo PGI$_2$,
5,6,7-trinor-4,8-inter-m-phenylene-13,14-dihydro-2-nor-15(R)-methyl PGI$_2$,
5,6,7-trinor-4,8-inter-m-phenylene-13,14-dihydro-2-nor-15(S)methyl PGI$_2$,
5,6,7-trinor-4,8-inter-m-phenylene-13,14-dihydro-2-nor-16,16-dimethyl-ω-dihomo PGI$_2$,
5,6,7-trinor-4,8-inter-m-phenylene-13,14-dihydro-2-nor-16,16-dimethyl-ω-trihomo PGI$_2$,
5,6,7-trinor-4,8-inter-m-phenylene-13,14-dihydro-2,18,19,20-tetranor PGI$_2$,
5,6,7-trinor-4,8-inter-m-phneylene-13,14-dihydro-2,18,19,20-tetranor-16-methyl PGI$_2$, and the corresponding methyl ester, ethyl ester, propyl ester and benzyl ester.
5,6,7-trinor-4,8-inter-m-phenylene-13,14-dihydro-2,17,18,19,20-pentanor-16-propoxy PGI$_2$,
5,6,7-trinor-4,8-inter-m-phenylene-13,14-dihydro-2,18,19,20-tetranor-17-ethoxy PGI$_2$,
5,6,7-trinor-4,8-inter-m-phenylene-13,14-dihydro PGI$_2$,
5,6,7-trinor-4,8-inter-m-phenylene-13,14-dihydro-2,17,18,19,20-pentanor-16,16-dimethyl-16-propoxy PGI$_2$,
5,6,7-trinor-4,8-inter-m-phenylene-13,14-dihydro-2,18,19,20-tetranor-16,16-dimethyl-17-ethoxy PGI$_2$,
5,6,7-trinor-4,8-inter-m-phenylene-13,14-dihydro-2,18,19,20-tetranor-16,16-dimethyl-17-butoxy PGI$_2$,
5,6,7-trinor-4,8-inter-m-phenylene-13,14-dihydro-2,19,20-trinor-16,16-dimethyl-18-methoxy PGI$_2$,
5,6,7-trinor-4,8-inter-m-phenylene-13,14-dihydro-2,17,18,19,20-pentanor-16-butoxy PGI$_2$,
5,6,7-trinor-4,8-inter-m-phenylene-13,14-dihydro-2,17,18,19,20-pentanor-16-pentyloxy PGI$_2$,
5,6,7-trinor-4,8-inter-m-phenylene-13,14-dihydro-2,17,18,19,20-pentanor-16-hexyloxy PGI$_2$,
5,6,7-trinor-4,8-inter-m-phenylene-13,14-dihydro-2,18,19,20-tetranor-17-propoxy PGI$_2$,
5,6,7-trinor-4,8-inter-m-phenylene-13,14-dihydro-2,18,19,20-tetranor-17-butoxy PGI$_2$,
5,6,7-trinor-4,8-inter-m-phenylene-13,14-dihydro-2,18,19,20-tetranor-17-pentyloxy PGI$_2$,
5,6,7-trinor-4,8-inter-m-phenylene-13,14-dihydro-2,19,20-trinor-18-ethoxy PGI$_2$,
5,6,7-trinor-4,8-inter-m-phenylene-13,14-dihydro-2,19,20-trinor-18-ethoxy PGI$_2$,
5,6,7-trinor-4,8-inter-m-phenylene-13,14-dihydro-2,19,20-trinor-18-propoxy PGI$_2$,
5,6,7-trinor-4,8-inter-m-phenylene-13,14-dihydro-2,17,18,19,20-pentanor-16,16-dimethyl-16-butoxy PGI$_2$,
5,6,7-trinor-4,8-inter-m-phenylene-13,14-dihydro-2,18,19,20-tetranor-16,16-dimethyl-17-propoxy PGI$_2$,
5,6,7-trinor-4,8-inter-m-phenylene-13,14-dihydro-2,19,20-trinor-16,16-dimethyl-18-ethoxy PGI$_2$,
5,6,7-trinor-4,8-inter-m-phenylene-13,14-dihydro-2,19,20-trinor-16,16-dimethyl-18-propoxy PGI$_2$,
5,6,7-trinor-4,8-inter-m-phenylene-13,14-dihydro-2,19,20-trinor-16,16-dimethyl-18-butoxy PGI$_2$,
5,6,7-trinor-4,8-inter-m-phenylene-13,14-dihydro-2,17,18,19,20-pentanor-16-cyclopentyloxy PGI$_2$,
5,6,7-trinor-4,8-inter-m-phenylene-13,14-dihydro-2,17,18,19,20-pentanor-16-cyclohexyloxy PGI$_2$,
5,6,7-trinor-4,8-inter-m-phenylene-13,14-dihydro-2,17,18,19,20-pentanor-16-phenoxy PGI$_2$,
5,6,7-trinor-4,8-inter-m-phenylene-13,14-dihydro-2,17,18,19,20-pentanor-16-(p-chlorophenoxy) PGI$_2$,
5,6,7-trinor-4,8-inter-m-phenylene-13,14-dihydro-2,17,18,19,20-pentanor-16-(m-chlorophenoxy) PGI$_2$,
5,6,7-trinor-4,8-inter-m-phenylene-13,14-dihydro-2,17,18,19,20-pentanor-16-(p-methylphenoxy) PGI$_2$,
5,6,7-trinor-4,8-inter-m-phenylene-13,14-dihydro-2,17,18,19,20-pentanor-16-(p-methoxyphenoxy) PGI$_2$,
5,6,7-trinor-4,8-inter-m-phenylene-13,14-dihydro-2,17,18,19,20-pentanor-16(p-trifluoromethylphenoxy) PGI$_2$,
5,6,7-trinor-4,8-inter-m-phenylene-13,14-dihydro-2,17,18,19,20-pentanor-16-(m-trifluoromethylphenoxy) PGI$_2$,
5,6,7-trinor-4,8-inter-m-phenylene-2,17,18,19,20-pentanor-16,16-dimethyl-16-phenoxy PGI$_2$,
5,6,7-trinor-4,8-inter-m-phenylene-2,17,18,19,20-pentanor-16,16-dimethyl-16-(p-chlorophenoxy) PGI$_2$,
5,6,7-trinor-4,8-inter-m-phenylene-2,17,18,19,20-pentanor-16,16-dimethyl-16-(o-chlorophenoxy) PGI$_2$,
5,6,7-trinor-4,8-inter-m-phenylene-2,17,18,19,20-pentanor-16,16-dimethyl-16-(m-chlorophenoxy) PGI$_2$,
5,6,7-trinor-4,8-inter-m-phenylene-2,17,18,19,20-pentanor-16,16-dimethyl-16-(2,4-dichlorophenoxy) PGI$_2$,
5,6,7-trinor-4,8-inter-m-phenylene-2,17,18,19,20-pentanor-16,16-dimethyl-16-(2,6-dichlorophenoxy) PGI$_2$,
5,6,7-trinor-4,8-inter-m-phenylene-2,17,18,19,20-pentanor-16,16-dimethyl-16-(m-fluorophenoxy) PGI$_2$,
5,6,7-trinor-4,8-inter-m-phenylene-2,17,18,19,20-pentanor-16,16-dimethyl-16-(m-trifluoromethylphenoxy) PGI$_2$,
5,6,7-trinor-4,8-inter-m-phenylene-2,17,18,19,20-pentanor-16,16-dimethyl-16-(p-nitrophenoxy) PGI$_2$,
5,6,7-trinor-4,8-inter-m-phenylene-2,17,18,19,20-pentanor-16,16-dimethyl-16-(p-methylphenoxy) PGI$_2$,
5,6,7-trinor-4,8-inter-m-phenylene-2,17,18,19,20-pentanor-16,16-dimethyl-16-(2-chloro-4-methoxyphenoxy) PGI$_2$,
5,6,7-trinor-4,8-inter-m-phenylene-2,17,18,19,20-pentanor-16,16-dimethyl-16-(p-bromophenoxy) PGI$_2$,
5,6,7-trinor-4,8-inter-m-phenylene-2,17,18,19,20-pentanor-16-methyl-16-phenoxy PGI$_2$, 5,6,7-trinor-4,8-inter-m-phenylene-2,17,18,19,20-pentanor-16-methyl-16-(p-chlorophenoxy) PGI$_2$, 5,6,7-trinor-4,8-inter-m-phenylene-2,17,18,19,20-pentanor-16-methyl-16-(o-chlorophenoxy) PGI$_2$, 5,6,7-trinor-4,8-inter-m-phenylene-2,17,18,19,20-pentanor-16-methyl-16-(m-chlorophenoxy) PGI$_2$, 5,6,7-trinor-4,8-inter-m-phenylene-2,17,18,19,20-pentanor-16-methyl-16-(2,4-dichlorophenoxy) PGI$_2$, 5,6,7-trinor-4,8-inter-m-phenylene-2,17,18,19,20-pentanor-16-methyl-16-(2,6-dichlorophenoxy) PGI$_2$, 5,6,7-trinor-4,8-inter-m-phenylene-2,17,18,19,20-pentanor-16-methyl-16-(2-chloro-4-methoxyphenoxy) PGI$_2$, 5,6,7-trinor-4,8-inter-m-phenylene-2,17,18,19,20-pentanor-16-methyl-16-(p-methylphenoxy) PGI$_2$, and methyl esters, ethyl esters, propyl esters and benzyl esters thereof.

3-decarboxy-3-hydroxymethyl-5,6,7-trinor-4,8-inter-m-phenylene-2,17,18,19,20-pentanor-16,16-dimethyl-16-phenoxy PGI$_2$, 3-decarboxy-3-hydroxymethyl-5,6,7-trinor-4,8-inter-m-phenylene-2,17,18,19,20-pentanor-16-methyl-16-phenoxy PGI$_2$, 5,6,7-trinor-4,8-inter-m-phenylene-13,14-dihydro-2,17,18,19,20-pentanor-16,16-dimethyl-16-phenoxy PGI$_2$, 5,6,7-trinor-4,8-inter-m-phenylene-13,14-dihydro-2,17,18,19,20-pentanor-16-methyl-16-phenoxy PGI$_2$.

Among the above "2-nor" compounds, the most preferable are as follows:

5,6,7-trinor-4,8-inter-m-phenylene-2,17,18,19,20-pentanor-16,16-dimethyl-16-phenoxy PGI$_2$ or its methyl ester, 5,6,7-trinor-4,8-inter-m-phenylene-2,17,18,19,20-pentanor-16-methyl-16-phenoxy PGI$_2$ or its methyl ester, 5,6,7-trinor-4,8-inter-m-phenylene-2-nor-16,16-dimethyl PGI$_2$ or its methyl ester, 5,6,7-trinor-4,8-inter-m-phenylene-2-nor-17(S)-methyl PGI$_2$ or its methyl ester, 5,6,7-trinor-4,8-inter-m-phenylene-2-nor-17(R)-methyl PGI$_2$ or its methyl ester, 5,6,7-trinor-4,8-inter-m-phenylene-2-nor-16,16-dimethyl-ω-homo PGI$_2$ or its methyl ester, 5,6,7-trinor-4,8-inter-m-phenylene-2-nor-17(S)-methyl-ω-homo PGI$_2$ or its methyl ester, 5,6,7-trinor-4,8-inter-m-phenylene-2-nor-17(R)-methyl-ω-homo PGI$_2$ or its methyl ester, 5,6,7-trinor-4,8-inter-m-phenylene-2,17,18,19,20-pentanor-16,16-dimethyl-16-propoxy PGI$_2$ or its methyl ester, 5,6,7-trinor-4,8-inter-m-phenylene-2,18,19,20-tetranor-16,16-dimethyl-17-ethoxy PGI$_2$ or its methyl ester, 5,6,7-trinor-4,8-inter-m-phenylene-2,18,19,20-tetranor-16,16-dimethyl-17-propoxy PGI$_2$ or its methyl ester, and 5,6,7-trinor-4,8-inter-m-phenylene-2,17,18,19,20-pentanor-16-phenoxy PGI$_2$ or its methyl ester.

The following "2-nor" compounds or their methyl esters are also preferable.

5,6,7-trinor-4,8-inter-m-phenylene-2-nor-17,17-dimethyl PGI$_2$, 5,6,7-trinor-4,8-inter-m-phenylene-2-nor-18,18-dimethyl PGI$_2$, 5,6,7-trinor-4,8-inter-m-phenylene-2,17,18,19,20-pentanor-16-methyl PGI$_2$, 5,6,7-trinor-4,8-inter-m-phenylene-2,17,18,19,20-pentanor-16-pentyloxy PGI$_2$, 5,6,7-trinor-4,8-inter-m-phenylene-2,18,19,20-tetranor-17-propoxy PGI$_2$, 5,6,7-trinor-4,8-inter-m-phenylene-2,18,19,20-tetranor-17-methoxy PGI$_2$, 5,6,7-trinor-4,8-inter-m-phenylene-2,18,19,20-tetranor-17-ethoxy PGI$_2$, 5,6,7-trinor-4,8-inter-m-phenylene-2,17,18,19,20-pentanor-16,16-dimethyl-16-butoxy PGI$_2$, 5,6,7-trinor-4,8-inter-m-phenylene-2,18,19,20-tetranor-16,16-dimethyl-17-methoxy PGI$_2$, 5,6,7-trinor-4,8-inter-m-phenylene-2,18,19,20-tetranor-16,16-dimethyl-17-butoxy PGI$_2$, 5,6,7-trinor-4,8-inter-m-phenylene-2,19,20-trinor-16,16-dimethyl-18-ethoxy PGI$_2$, 5,6,7-trinor-4,8-inter-m-phenylene-2,19,20-trinor-16,16-dimethyl-18-propoxy PGI$_2$, 5,6,7-trinor-4,8-inter-m-phenylene-2,19,20-trinor-16,16-dimethyl-18-butoxy PGI$_2$, ,6,7-inter-m-phenylene-2,17,18,19,20-pentanor-16-cyclopentyloxy PGI$_2$, 5,6,7-trinor-4,8-inter-m-phenylene-2,17,18,19,20-pentanor-16-cyclohexyloxy PGI$_2$, 5,6,7-trinor-4,8-inter-m-phenylene-2-nor-13,14-didehydro-16,16-dimethyl PGI$_2$, 5,6,7-trinor-4,8-inter-m-phenylene-13,14-didehydro-2,18,19,20-tetranor-16,16-dimethyl-17-ethoxy PGI$_2$, 5,6,7-trinor-4,8-inter-m-phenylene-13,14-didehydro-2,18,19,20-tetranor-16,16-dimethyl-17-propoxy PGI$_2$, 5,6,7-trinor-4,8-inter-m-phenylene-13,14-didehydro-2,17,18,19,20-pentanor-16-phenoxy PGI$_2$, 5,6,7-trinor-4,8-inter-m-phenylene-13,14-dihydro-2,18,19,20-tetranor-16,16-dimethyl-17-ethoxy PGI$_2$, 5,6,7-trinor-4,8-inter-m-phenylene-13,14-dihydro-2,18,19,20-tetranor-16,16-dimethyl-17-butoxy PGI$_2$, and 5,6,7-trinor-4,8-inter-m-phenylene-13,14-dihydro-2,18,19,20-tetranor-16,16-dimethyl-17-propoxy PGI$_2$.

The following "2-nor" compounds and their methyl esters are also useful.

5,6,7-trinor-4,8-inter-m-phenylene-2,17,18,19,20-pentanor-16,16-dimethyl PGI$_2$, 5,6,7-trinor-4,8-m-phenylene-2,19,20-trinor-16,16-dimethyl-18-methoxy PGI$_2$, 5,6,7-trinor-4,8-inter-m-phenylene-2,18,19,20-tetranor-17-butoxy PGI$_2$, 5,6,7-trinor-4,8-m-phenylene-2,18,19,20-tetranor-17-pentyloxy PGI$_2$, 5,6,7-trinor-4,8-inter-m-phenylene-2-nor-13,14-didehydro-17(S)-methyl PGI$_2$, 5,6,7-trinor-4,8-inter-m-phenylene-2-nor-13,14-didehydro-17(R)-methyl PGI$_2$, 5,6,7-trinor-4,8-inter-m-phenylene-2-nor-13,14-didehydro-17(S)-methyl-ω-homo PGI$_2$, 5,6,7-trinor-4,8-inter-m-phenylene-2-nor-13,14-didehydro-17(R)-methyl-ω-homo PGI$_2$, 5,6,7-trinor-4,8-inter-m-phenylene-2,18,19,20-tetranor-13,14-didehydro-16-methyl PGI$_2$, 5,6,7-trinor-4,8-inter-m-phenylene-13,14-didehydro-2,18,19,20-tetranor-17-ethoxy PGI$_2$, 5,6,7-trinor-4,8-inter-m-phenylene-13,14-didehydro-2,18,19,20-tetranor-17-propoxy PGI$_2$, 5,6,7-trinor-4,8-inter-m-phenylene-13,14-didehydro-2,18,19,20-tetranor-17-butoxy PGI$_2$, 5,6,7-trinor-4,8-inter-m-phenylene-13,14-didehydro-2,17,18,19,20-pentanor-16-cyclopentyloxy PGI$_2$, 5,6,7-trinor-4,8-inter-m-phenylene-13,14-didehydro-2,17,18,19,20-pentanor-16-cyclohexyloxy PGI$_2$, 5,6,7-trinor-4,8-inter-m-phenylene-13,14-dihydro-2-nor-16,16-dimethyl PGI$_2$,
5,6,7-trinor-4,8-inter-m-phenylene-13,14-dihydro-2-nor-17(S)-methyl PGI$_2$,
5,6,7-trinor-4,8-inter-m-phenylene-13,14-dihydro-2-nor-17(R)-methyl PGI$_2$,
5,6,7-trinor-4,8-inter-m-phenylene-13,14-dihydro-2-nor-17,17-dimethyl PGI$_2$,
5,6,7-trinor-4,8-inter-m-phenylene-13,14-dihydro-2-nor-16,16-dimethyl-ω-homo PGI$_2$,
5,6,7-trinor-4,8-inter-m-phenylene-13,14-dihydro-2-nor-17(S)-methyl-ω-homo PGI$_2$,
5,6,7-trinor-4,8-inter-m-phenylene-13,14-dihydro-2-nor-17(R)-methyl-ω-homo PGI$_2$,
5,6,7-trinor-4,8-inter-m-phenylene-13,14-dihydro-2,18,19,20-tetranor-17-ethoxy PGI$_2$,
5,6,7-trinor-4,8-inter-m-phenylene-13,14-dihydro-2,17,18,19,20-pentanor-16,16-dimethyl-16-propoxy PGI$_2$,
5,6,7-trinor-4,8-inter-m-phenylene-13,14-dihydro-2,17,18,19,20-pentanor-16-pentyloxy PGI$_2$,
5,6,7-trinor-4,8-inter-m-phenylene-13,14-dihydro-2,17,18,19,20-pentanor-16-hexyloxy PGI$_2$,
5,6,7-trinor-4,8-inter-m-phenylene-13,14-dihydro-2,18,19,20-tetranor-17-butoxy PGI$_2$,
5,6,7-trinor-4,8-inter-m-phenylene-13,14-dihydro-2,18,19,20-tetranor-17-pentyloxy PGI$_2$, and
5,6,7-trinor-4,8-inter-m-phenylene-13,14-dihydro-2,17,18,19,20-pentanor-16-phenoxy PGI$_2$.

The compounds of the present invention may be easily produced by the processes mentioned hereinbelow.

The compounds wherein A is —(CH$_2$)$_3$—, B is

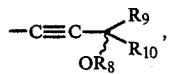

R$_1$ is COOH and R$_8$ is hydrogen are produced by the synthesizing processes shown in chart A.

chart A

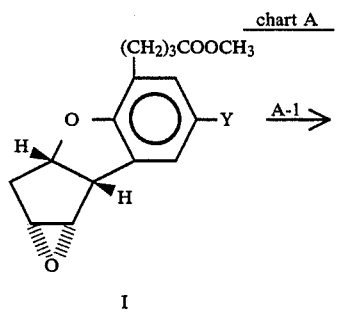

I

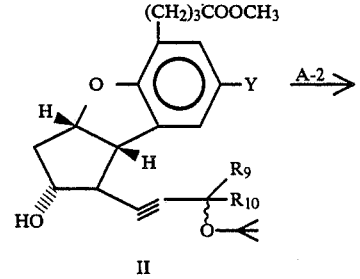

II

-continued
chart A

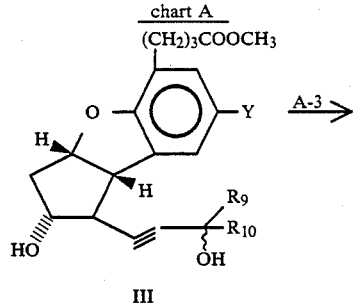

III

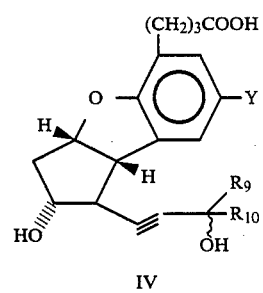

IV

The step A-1 is easily achieved by reacting an aluminium compound represented by the general formula

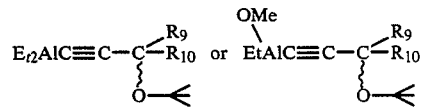

(wherein R$_9$ and R$_{10}$ are the same as defined above) with the compound I in a hydrocarbon solvent such as benzene, toluene and xylene. The reaction temperature ranges from −50° C. to 50° C., however, in a normal practice, a preferable result is obtained when the reaction temperature ranges from −20° C. to 30° C. The aluminium compound used in the reaction may be obtained by the reaction shown by formula (a) or (b).

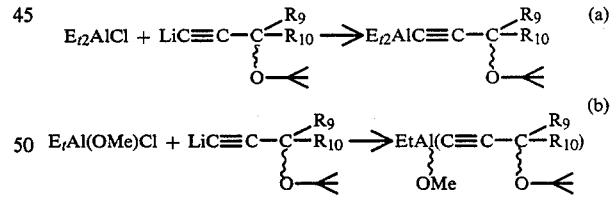

These aluminium compounds are normally not isolated, but generated per se in the system and used. An aluminium compound of a further complicated composition or a mixture of aluminium compounds may be generated in the system and used. Such aluminium compound is generated in the system by, for example, dissolving 1 equivalent of Et$_2$AlCl in toluene, adding 0.2–0.5 equivalent of MeOH to the resultant solution and subsequently adding thereto 1 equivalent of

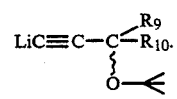

The step A-2 is a step of removing the protective group of alcohol (at 15-position). Normally, an acid is employed in this step and especially trifluoroacetic acid is preferably employed. A solvent may or may not be used, however, when it is used, a halogenated hydrocarbon such as methylene chloride is preferbly used. The reaction temperature ranges from −70° C. to 50° C., however, a sufficiently preferable result is obtained at a temperature ranging from −20° C. to 30° C. in an ordinary practice of the reaction.

The step A-3 is a step of hydrolyzing an ester.

For the hydrolysis of an ester, a base is preferably employed and for an ordinary practice, sodium hydroxide, potassium hydroxide, sodium carbonate and potassium carbonate are employed. As the solvent, aqueous methanol, aqueous ethanol, aqueous dioxane and aqueous dimethyl sulfoxide are employed, however, ordinarily, employment of aqueous methanol brings about a sufficiently preferable result.

The process for preparing the starting material I is shown in B.

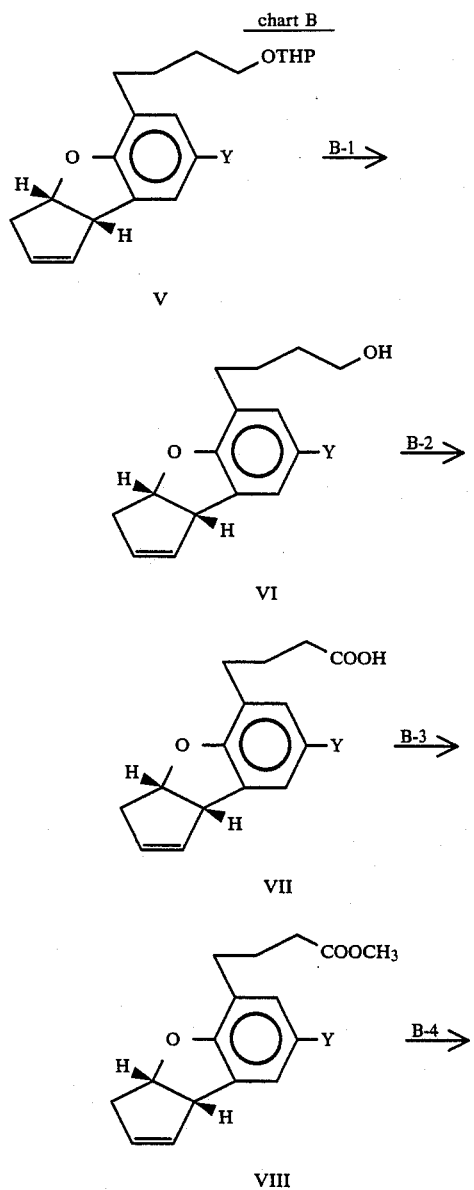

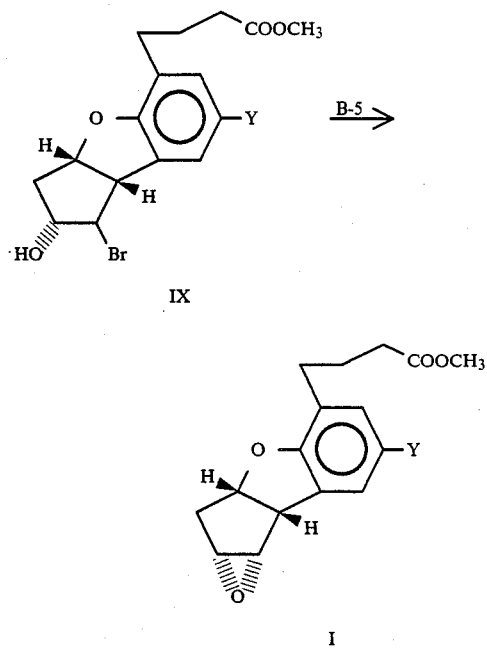

The step B-1 is a step of eliminating a tetrahydropyranyl group by an acid catalyst to obtain a hydroxy group. As this acid catalyst, a proper amount of hydrochloric acid, hydrobromic acid, acetic acid, p-toluenesulfonic acid or phosphoric acid may be added into a proper solvent, but the acid catalyst is not limited to these acids. As the solvent, mainly a water-containing solvent system such as acetonitrile-water, THF-acetic acid-water, acetic acid and water or methanol or ethanol is employed. For an ordinary practice, by heating the compound V in an acetic acid-water (2:1) mixture to 40° C., a preferable result is obtained.

The step B-2 is a step of oxidizing an alcohol, and as an oxidizing reagent, an ordinary oxidizing agent of an alcohol is employed, however, chromium trioxide and pyridinium dichromate ($Na_2Cr_2O_7PY$) are preferably employed, when chromium trioxide is employed, aqulous pyridine is preferable as solvent, and when pyridinium dichromate is employed dimethyl formamide is especially preferably employed as solvent, ordinarily, when pyridinium dichromate is employed in dimethyl formamide, a preferable result is obtained.

The reaction temperature ranges from −40° C. to 100° C., however, ordinarily a preferable reaction rate is obtained at the reaction temperature ranging from 0° C. to 50° C.

The step B-3 is a methyl esterification step, which is easily achieved ordinarily by bringing the compound VII into contact with the ether solvent of diazomethane.

The step B-4 is practiced by dissolving the compound VIII in a dimethyl sulfoxide-water solvent system and treating with N-bromosuccinimide (NBS).

The step B-5 is a step of treating bromohydrin IX with a base to convert the fomer to epoxide. Ordinarily, suffices it to treat the compound IX in an anhydrous methanol with potassium carbonate employed as the base.

A process for preparing the compound V wherein Y is hydrogen was made public by an already filed patent application the inventors of which were the present inventors (Japanese Patent Application No. 111709/1979), however, even when Y is not hydrogen, by using what has a substituent Y at the para-position as a starting phenol compounds, said compound V is prepared via a similar step.

A compound wherein A is —(CH$_2$)$_3$—, B is

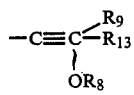

R$_1$ is COOH and R$_8$ is hydrogen, is synthesized by steps similar to chart A.

A compound wherein A is —CH$_2$O—CH$_2$—, B is

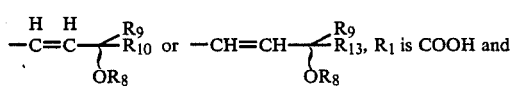, R$_1$ is COOH and

R$_8$ is hydrogen is also synthesized by steps similar to chart A. However, in this case, the necessary starting compound XIV is prepared by steps shown in chart C.

chart C

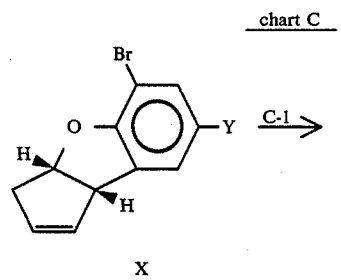

X

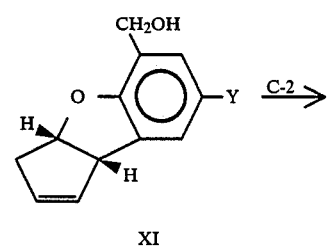

XI

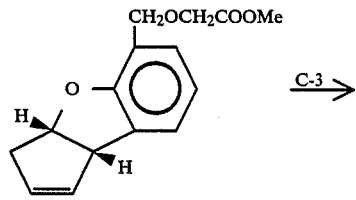

XII

-continued
chart C

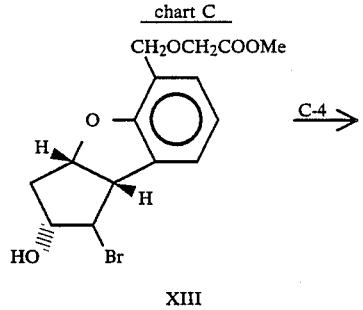

XIII

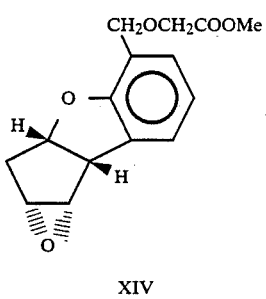

XIV

The step C-1 is a step of substituting bromine of the compound X to a hydroxy methyl group. For this end, the compound X is treated with a base to make the former the corresponding phenyl anion and subsequently anhydrous formalin may be reacted therewith.

As the base ordinarily, butyl lithium, phenyl lithium, cyclohexyl magnesium bromide and isopropyl magnesium bromide are employed, however, said base is not limited thereto.

Ordinarily, when phenyl lithium is employed and the reaction is carried out in tetrahydrofuran at a temperature ranging from $-40°$ C. to $20°$ C., a preferable result is obtained.

The step C-2 is a step of carbomethoxy methyl etherification of a hydroxy group of the compound XI. For this end, the compound XI is at first reacted with sodium hydride to make the corresponding alkoxy anion and subsequently methyl bromoacetate is added thereto and reacted therewith.

The step C-3 is carried out in the same manner as in the step B-4 and the step C-4 is carried out in the same manner as in the step B-5.

A compound wherein A is (i) —(CH$_2$)$_3$— or (iv) —CH$_2$—O—CH$_2$—, R$_8$ and R$_9$ are hydrogen, X is —CH=CH— (trans) and R$_{13}$ is either branched alkyl having 5-10 carbon atoms or

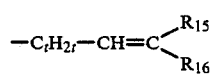

is prepared by steps shown in chart D.

chart D

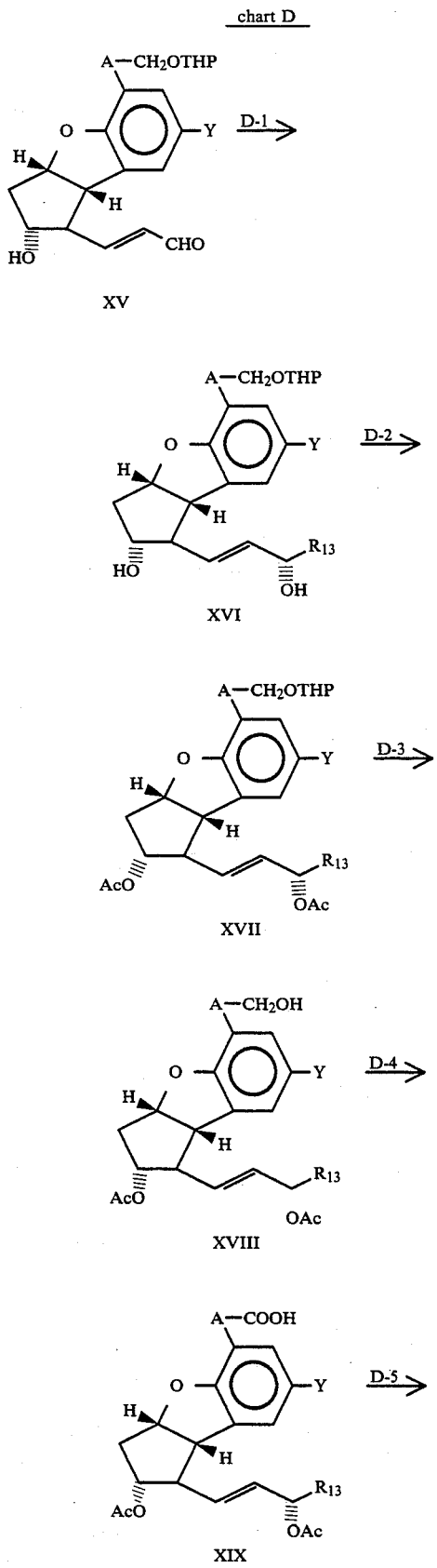

-continued
chart D

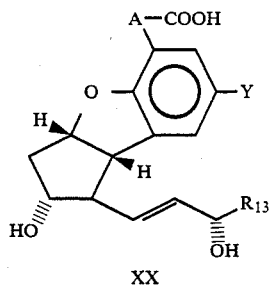

The step D-1 is an alkylating step, which is practiced by reacting $R_{13}MgCl$ or $R_{13}MgBr$ with the compound XV. As said $R_{13}MgCl$ and $M_{13}MgBr$, there may be cited 2-(2-methyl)hexylmagnesium chloride, 2-(2-methyl)heptyl magnesium chloride, 2-methylpentyl magnesium chloride, 2(R)methylpentyl magnesium chloride, 2(S)-methylpentyl magnesium chloride, 2-methylhexyl magnesium chloride, 2-(R)-methylhexyl magnesium chloride, 2(S)-methylhexyl magnesium chloride, 3-methylpentyl magnesium chloride, 2-methylpentyl magnesium bromide, 6-methyl-5-heptenyl magnesium bromide and 2-pentenyl magnesium chloride, however, it goes without saying that said $R_{13}MgCl$ and $R_{13}MgBr$ are not limited to these compounds. The practice of the reaction is very easy, ordinarily, the compound XV is dissolved in a solvent and an equimolar amount of excess amount of a THE or ether solution of the aforesaid Grignard reagent may be added dropwise thereto at a temperature ranging from $-70°$ to $50°$ C.

As the solvent, a solvent of the ether series such as tetrahydrofuran, ether and dimethoxy ethane is preferably employable.

The step D-2 is a step of acetylating a free hydroxyl group, which is ordinarily practiced by reacting the compound XVI with acetic anhydride in pyridine.

The step D-3 is practiced in the same manner as in the step B-1.

The step D-4 is practiced, using the oxidizing agent described in connection with the step B-2 under the same conditions as in the step B-2. The step D-5 is a hydrolyzing step of an ester, and basically is practiced, using the same base as in the step A-3 under the same conditions as in the step A-3.

A compound wherein A is (i) $-(CH_2)_3-$ or $-(CH_2)_2-$ or (iv) $-CH_2-O-CH_2-$, $R_9$ is hydrogen, X is $-CH=CH-$ (trans), $R_{13}$ is $-C_tH_{2t}OR_{14}$ and $C_tH_{2t}$ is not an alkylene group having 2 carbon atoms in the main chain, empoying $LiC_tH_{2t}OR_{14}$ or $ClMgC_tH_{2t}OR_{14}$ instead of the alkylating agent employed in the step D-1 as an alkylating agent, is prepared by practicing the steps D-2, 3, 4 and 5 in this order thereafter. When $C_tH_{2t}$ is an alkylene group having 2 carbon atoms in the main chain, said compound is prepared by steps shown in E.

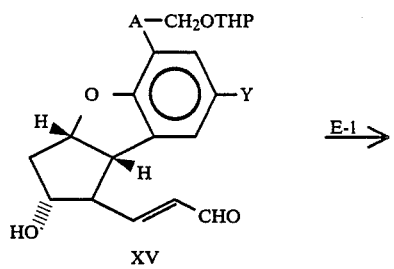
XV
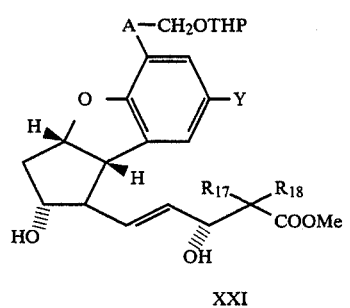
XXI
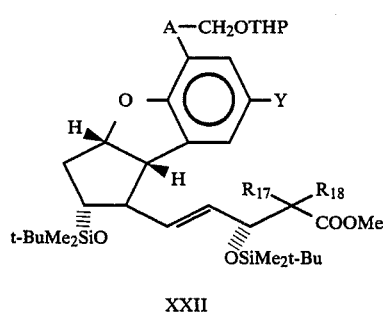
XXII
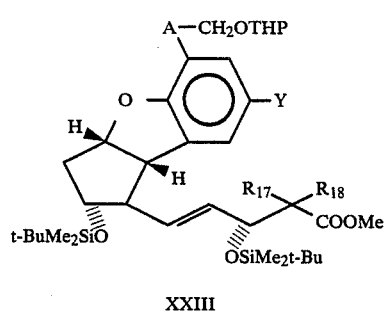
XXIII
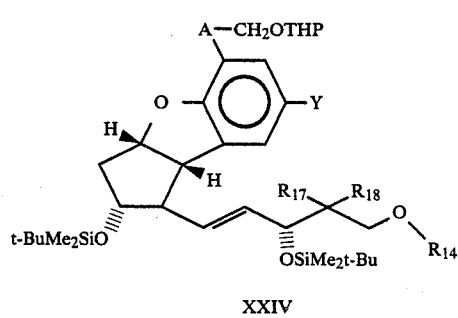
XXIV
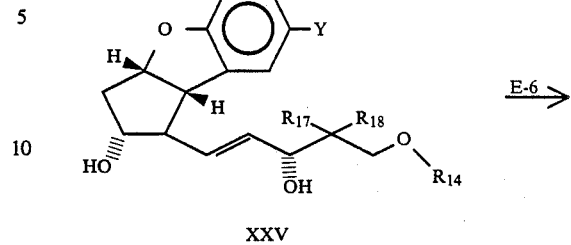
XXV
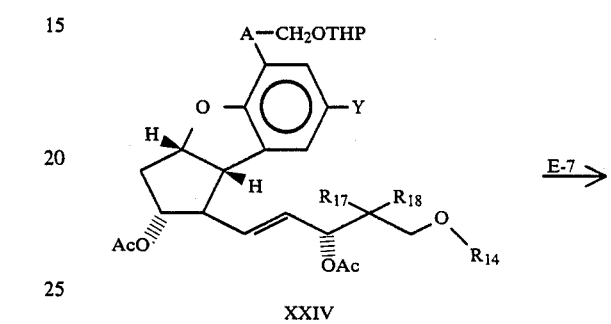
XXIV
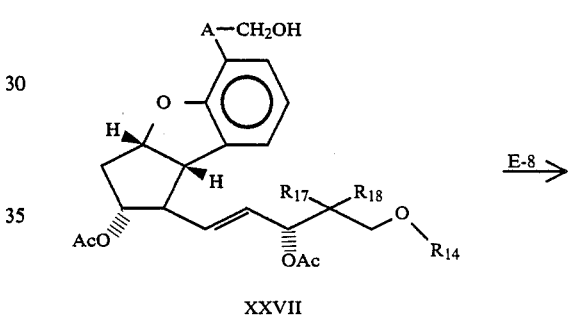
XXVII
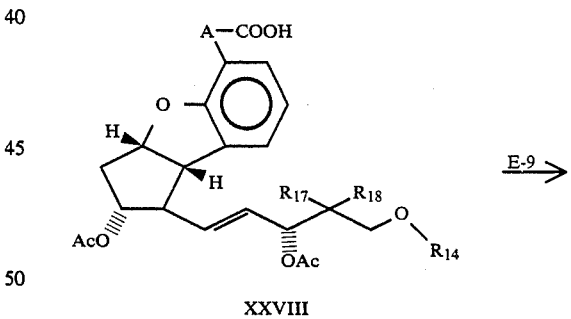
XXVIII
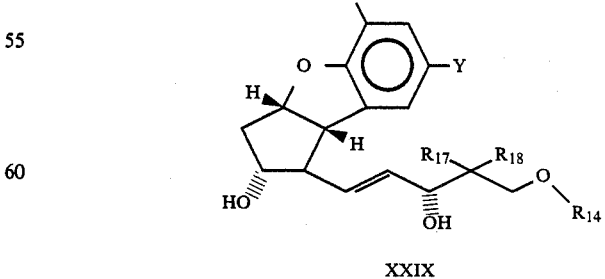
XXIX
The step E-1 is a so-called aldol condensation step, which may be practiced by treating the compound XV with

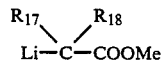

(wherein $R_{17}$ denotes hydrogen, methyl and ethyl, and $R_{18}$ denotes hydrogen, methyl and ethyl) at a temperature ranging from $-80°$ C. to $0°$ C. As a solvent, for an ordinary practice, tetrahydrofuran is preferably employed, however, the solvent is not limited thereto.

The step E-2 is a step of converting free hydroxy group, to dimethyl t-butyl silyl ether, which is ordinarily achieved by adding imidazole as a catalyst to a dimethyl formamide solution of the compound XXI and subsequently adding to the resultant mixture, dimethyl t-butyl silyl chloride (and reacting the mixture). The reaction temperature is ordinarily ranging from $0°$ to $50°$ C. and a preferable reaction rate is obtained at such temperature.

The step E-3 is a step of reducing a methoxy carbonyl group to a hydroxymethyl group and is practiced using a reducing agent ordinarily employed for this purpose. As the reducing agent, ordinarily lithium aluminium hydride and diisobutyl aluminium hydride are employed, however, for an ordinary practice, lithium aluminium hydride is economical and preferably employed. In case lithium aluminium hydride is employed as the reducing agent, it is preferable that a solvent of the ether system such as ether and tetrahydrofuran is employed and in case diisobutyl aluminium hydride is employed as the reducing agent, hydrocarbon such as benzene and toluene is preferably employed as the solvent.

The step E-4 is a step of alkylating a free hydroxy group, and as an alkylating agent, ordinarily what is known as an alkylating agent of an alcohol is utilized. For an ordinary practice, the compound XXIII may be converted to the corresponding alkoxy anion with sodium hydride and subsequently $R_{14}I$ (wherein $R_{14}$ is the same as defined above, however, when the step E is applied, Z is not to be valence bond) may be acted thereon. As a solvent, tetrahydrofuran, dimethylformamide, dimethylsulfoxide and dimethoxyethane are preferably employed. The reaction temperature is preferably within the range of $0°$-$80°$ C.

The step E-5 is a step of removing a dimethyl t-butyl silyl group which is a protective group of an alcohol, which is ordinarily achieved by treating XXIV with tetraalkyl ammonium fluoride. As said tetraalkyl ammonium fluoride, anything will do, however, ordinarily suffices it to use easily available tetrabutyl ammonium fluoride.

As a reaction solvent, tetrahydrofuran, dimethoxyethane and dimethyl formamide are preferably employed.

The step E-6 is practiced in the same manner as in the step D-2. The step E-7 is practiced in the same manner as in the step D-3. The step E-9 is practiced in the same manner as in the step D-5.

A compound wherein A is (i) $-(CH_2)_3-$ or (iv) $-CH_2-O-CH_2-$, both $R_8$ and $R_9$ are hydrogen, X is $-CH=CH-$ (trans), $R_{13}$ is $-C_tH_{2t}OR_{14}$ and the number of the main chain carbon atoms of $-C_tH_{2t}$ is 2, further, $R_{14}$ is

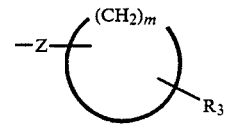

or $-Z-A_{r2}$ and Z denotes valence bond, is produced by tosylating or halogenating the compound XXIII instead of the step E-4 of E, thereafter, acting alkoxy anion or pheoxy anion or substituted phenoxy anion obtained by treating $R_{14}OH$ with sodium hydride or potassium hydride on said compound to introduce the same to the compound XXIV and subsequently practicing the steps E-5 to E-9 in the same manner.

A compound wherein A is $-CH_2-CH=CH-$, $R_1$ is COOH and $R_8$ is hydrogen is produced by the synthetic processes shown in F.

The step F-1 is a step of introducing a phenylseleno group to the $\alpha$-position of a methoxy carbonyl group. This step is practiced by treating the compound XXX with diisopropylamido lithium to generate an anion at the $\alpha$-position of a methoxy carbonyl group and subsequently adding diphenyl diselenide or phenyl selenyl bromide to the anion.

chart F

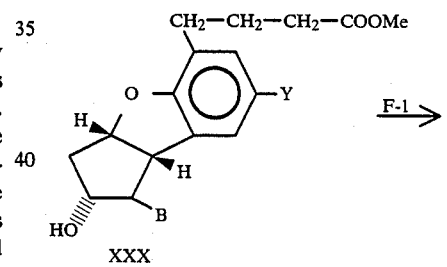

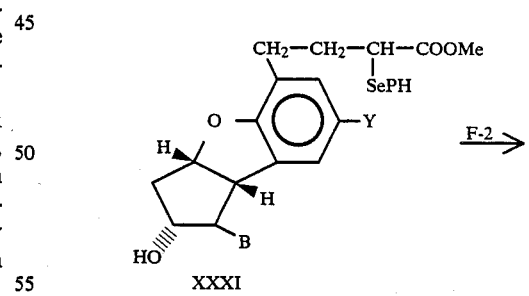

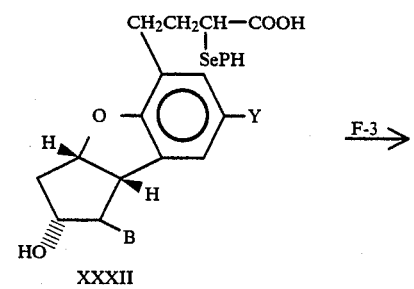

-continued
chart F

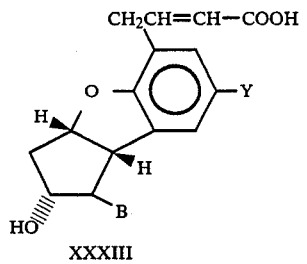

XXXIII

For producing anion at the α-position of a methoxy carbonyl group, ordinarily diisopropyl amido lithium is used in a solvent of the ethers such as tetrahydrofuran and dimethoxy ethane at a temperature ranging from −80° to C. to 50° C. A reaction after adding diphenyl diselenide is achieved by allowing the reaction mixture to stand at a temperatue ranging from −78° C. to 30° C. or stirring the reaction mixture at the same temperature for 10–120 minutes.

The step F-2 is a step of hydrolyzing an ester and is practiced in the same manner as in the step A-3.

The step F-3 contains a step of oxidizing selen of the compound XXXII to selenoxide and a step of producing olefin by eliminating phenylseleninic acid by heating, however, since elimination of phenylseleninic acid easily takes place at room temperature, the selenoxide of the compound XXXI does not isolated and the compound XXXIII is obtained.

For oxidizing a phenyl seleno group, a sufficiently preferable result is ordinarily obtained when hydrogen peroxide is employed.

A compound wherein A is —CH=CH—CH$_2$—, R$_1$ is COOH and R$_8$ is hydrogen may be produced by steps shown in chart G.

The step G-1 is practiced in the same manner a in the step F-3.

The step G-2 is practiced in a similar manner as in the step A-3. In this alkaline hydrolysis step, $\Delta^{2,3}$ double bond is easily isomerized to $\Delta^{3,4}$ double bond.

chart G

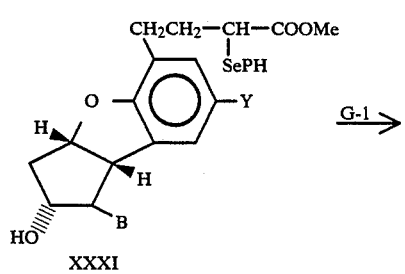

XXXI

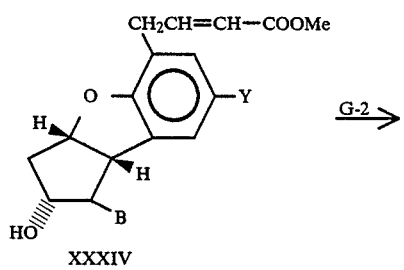

XXXIV

-continued
chart G

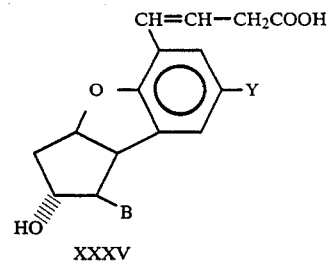

XXXV

Of the compound of the general formula (I) a compound wherein R$_1$ is —COOR$_2$ and R$_2$ is not hydrogen or cation, namely, R$_2$ is an ester residue, is produced by esterification (when the corresponding R$_2$ is a hydrogen carboxylic acid). As the esterification process, various processes are known, however, a process of using diazoalkane, a process of treating a silver salt or tertiary amine salt of a caboxylic acid with active halide and a mixed acid anhydride method are especially preferably employed for producing the compound of the present invention.

In a process employing diazoalkane, this object may be easily achieved by bringing a carboxylic acid into contact with diazoalkane in a solvent. As such diazoalkane, diazomethane, diazoethane, diazopropane and diazodecane may be cited, however, the diazoalkane is of course not limited thereto. The second process is ordinarily practiced by reacting the silver salt or tertinary amine salt of a carboxylic acid in an aprotic polar solvent such as dimethyl formamide or acetonitrile. As examples of said active halide, there may be cited benzyl chloride, benzyl bromide, p-bromo benzyl bromide p-methoxy benzyl bromide, p-bromo benzyl bromide phenacyl bromide, p-nitrophenacyl bromide and α-benzoyl phenacyl bromide, however, it goes without saying that such active halide is not limited thereto. The third process of a mixed acid anhydride is the broadest in its applicable scope and the greater part of the ester compounds of the present invention is produced by this process. This process comprises at first treating ethyl chlorocarbonate, pivaloyl chloride or p-toluenesulfonl chloride with a carboxylate to produce a mixed acid anhydride, adding thereto an excess amount of an alcohol R$_2$OH (wherein R$_2$ is the same as defined above, but not being hydrogen or cation) and heating the resultant mixture. Specific examples of said alcohol include methanol, ethanol, propanol, butanol, octanol, decanol, isopropanol, 2-ethylhexanol, benzyl alcohol, p-bromobenzyl alcohol, phenethyl alcohol, cyclopentyl alcohol, cyclopentylmethyl alcohol, 2-methoxy ethanol, 2-(2-methoxyethoxy) ethanol, hydroxy acetic acid methyl ester, lactic acid ethyl ester γ-hydroxybutyric acid methyl ester, 2-butyne-1-ol, 2-pentyne-1-ol, 1,3-di-(O)-methyl glycerine, 1,3-diacetyl glycerine, phenol, p-bromophenol, p-fluorophenol, m-chlorophenol, m-fluorophenol, 3,4-dichlorophenol, p-(trifluoromethyl)-phenol, p-methylphenol, 3,4-dimethylphenol, p-methoxyphenyl, 4-phenoxyphenol and p-benzoylamino-phenol, but said alcohol is not limited thereto.

Of the compounds represented by the general formula (I), a compound wherein R$_1$

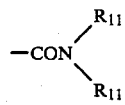

(wherein $R_{11}$ is the same as defined above, two $R_{11}$ may be the same or different, however, $R_{11}$ is not $-SO_2R_{12}$) is obtained by a step H-1 amidizing a compound represented by the general formula wherein $R_1$ is COOH.

chart H

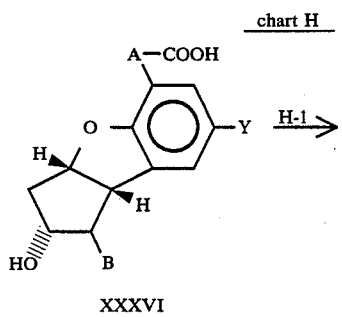

XXXVI

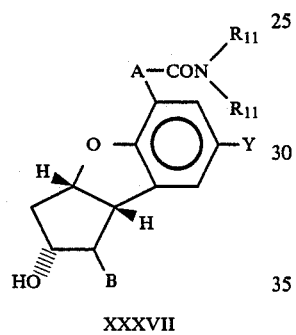

XXXVII

The step H-1 is a step converting a carboxylic acid to the corresponding amide, which is ordinarily achieved by treating a tertiary amine with a carboxylic acid of the compound represented by the general formula XXXVI to make a tertiary ammonium salt of a carboxylic acid, subsequently reacting it with ethyl chlorocarbonate or p-toluenesulfonic acid chloride to make a mixed acid anhydride, adding thereto an amine of

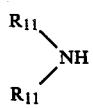

and heating the resultant mixture. Specific examples of aid amine include ammonia, N-methylamine, N-ethylamine, N-butylamine, N,N-dimethylamine, N,N-diethylamine, aniline, p-bromoaniline, cyclohexylamine, cyclopentylamine, N-benzylamine, phenethyl amine, morpholine and piperidine, however, said amine is not limited thereto.

Of the compounds represented by the general formula (I), a compound wherein $R_1$ is

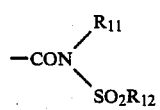

and $R_8$ is hydrogen, is produced by a step shown in chart I.

chart I

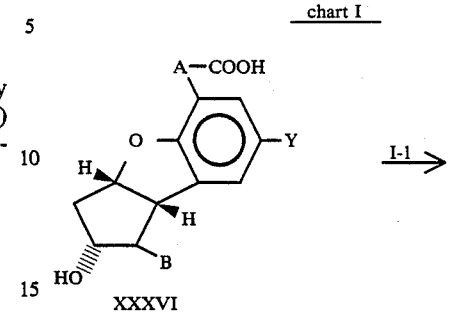

XXXVI

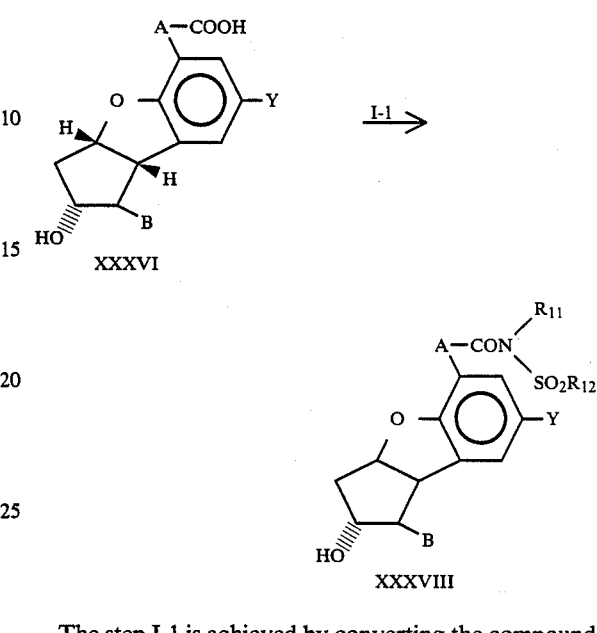

XXXVIII

The step I-1 is achieved by converting the compound (XXXVI) to a mixed acid anhydride, thereafter, reacting therewith a lithium sulfoneamide reagent represented by

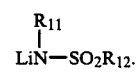

A compound wherein A is $-(CH_2)_n-$, Y is hydrogen, alkyl having 1–4 carbon atoms or methoxy and X is $-CH_2CH_2-$, is obtained by hydrogenating a compound wherei the corresponding X is $-CH=CH-$. Hydrogenation ordinarily employs palladium black, palladium on carbon, palladium on barium sulfate and Raney nickel as catalysts and a preferable result is obtained ordinarily under atmospheric pressure.

Another compound of the present invention wherein X is $-CH_2-CH_2-$, is obtained by employing, instead of the compound of the general formula XV, a compound represented by the general formula XXXIX

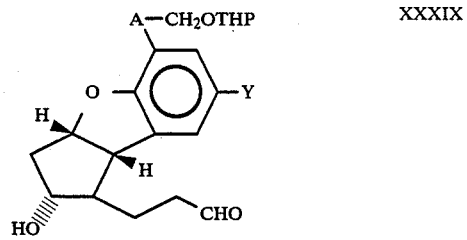

XXXIX and then practicing the steps shown in chart D.

A compound wherein $R_1$ is $CH_2OH$, is obtained by reducing a compound represented by the general formula XL or XLI with lithium aluminium hydride or alkaline hydrolysis of the compound of the general formula XVIII.

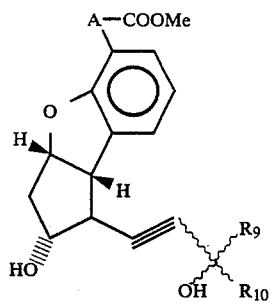

XL

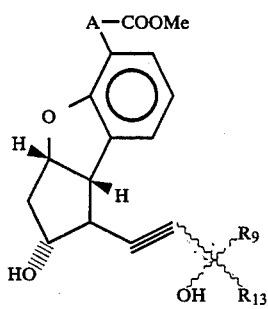

XLI

A compound wherein $R_9$ is an alkyl group having 1–4 carbon atoms, X is —CH=CH— and $R_1$ is —COOH, is synthesized by steps shown in J.

The step J-1 is a step of converting alkyl alcohol to α, β-unsaturated ketone, wherein ordinarily active manganese dioxide is employed as an oxidizing agent and said alcohol may be reacted in dichloromethane as a solvent.

The step J-2 is a step of trialkyl silylating a hydroxyl group. In the general formula XLV, $R_{17}$ denotes a straight chain or branched alkyl group having 1–10 carbon atoms and three $R_{17}$ may be the same or different. As specific examples of $R_{17}$, there may be cited methyl, ethyl, propyl, butyl, octyl, isopropyl, t-butyl and 2-ethylhexyl, but $R_{17}$ is not limited thereto.

chart J

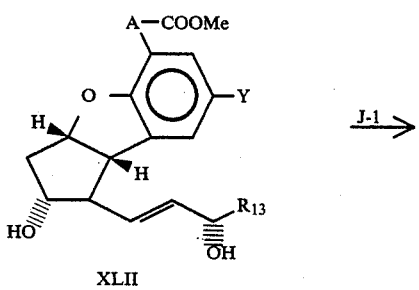

XLII

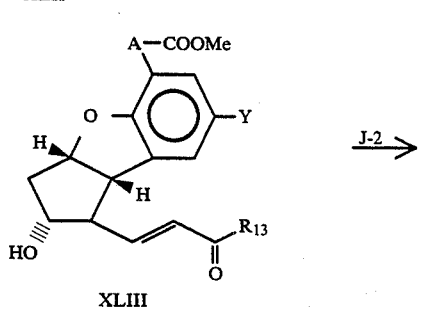

XLIII

-continued
chart J

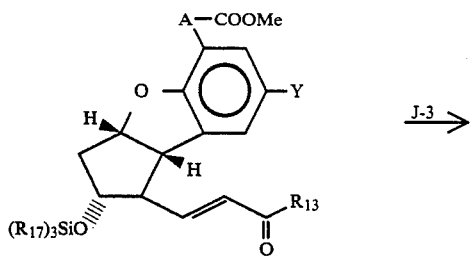

XLIV

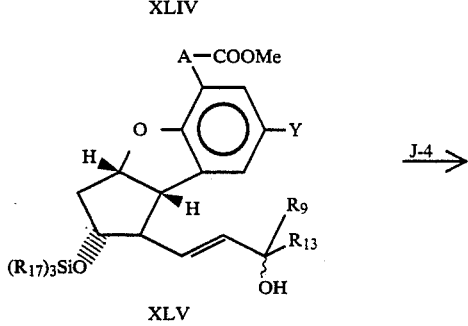

XLV

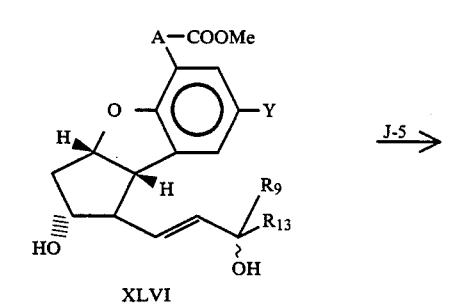

XLVI

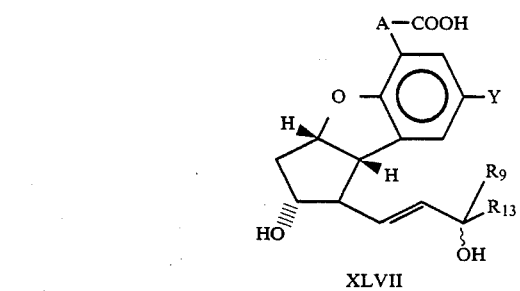

XLVII

For silylating a hydroxy group, general methods described in, for example, "Protective Groups in Organic Chemistry," compiled and written by J. F. W. McOmie, p 103–104, Plenum Press (London and New York) 1973) and literatures cited therein, are applicable.

Ordinarily trimethyl silylation or t-butyl dimethyl silylation is most simply used. For trimethyl silylation, trimethyl chlorosilane in the presence of a tertiary amine base such as pyridine and triethyl amine or a mixture of hexamethyldisilazane and trimethyl chlorosilane can be used. For t-butyl dimethyl silylation, ordinarily a method of using imidazole as a base is preferable.

Other general trialkyl silylation may react the corresponding trialkyl silyl chloride in the presence of a base such as pyridine and triethyl amine.

The step J-3 is achieved by treating XLIV with a Grignard reagent such as $R_9MgCl$, $R_9MgBr$ or $R_9MgI$ (wherein $R_9$ is the same as defined above) in ether or tetrahydrofuran. In this case, the Grignard reagent is used in an amount within the range of 0.8–1.5 mol equivalent based on the compound XLIV. Ordinarily, the product XLV is not isolated, but is used as a material of the step J-4.

The step J-4 is a step of removing a trialkyl silyl group which is a protective group of a hydrokyl group, which is ordinarily achieved by dissolving the trialkyl silyl group in an acidic aqueous solvent and heating the resulting solution.

Examples of said acidic aqueous solvent, is, inclusive acetic acid-water, acetic acid-tetrahydrofuran-water. acetic acid-ethanol water and ethanol-0.01N hydrochloric acid mixtures.

Ordinarily, the object is achieved when the trialkyl silyl group is allowed to stand in a solvent composed of an ethanol/water (10:1) mixture added with a drop of acetic acid at a temperature ranging from 0° C. to 50° C. for 0.5–5 hours. Further, as another method, a tetraalkyl ammonium fluoride may be acted on the compound XLV.

Ordinarily, when tetrabutyl ammonium fluoride is employed as said tetraalkyl ammonium fluoride, a sufficiently preferable result may be obtained.

The step J-5 is a step of alkaline hydrolysis and practiced in similar manner to the step A-3.

A compound represented by general formula (I) wherein A is —$(CH_2)_2$—, B is

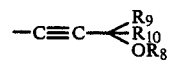

and $R_1$ is COOH and $R_8$ is hydrogen is easy to produce by applying a starting material wherein corresponding A is —$(CH_2)_2$— to processes $A_1$ to $A_3$.

A compound represented by general formula (I):

chart K

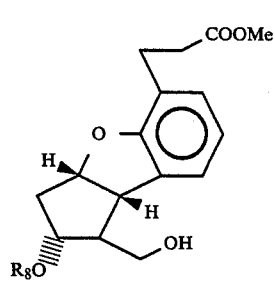

XLVIII

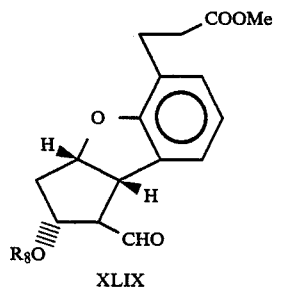

XLIX

-continued
chart K

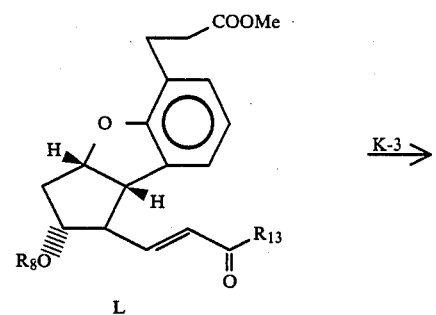

L

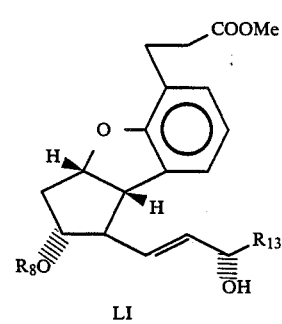

LI

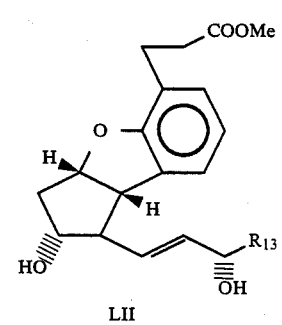

LII

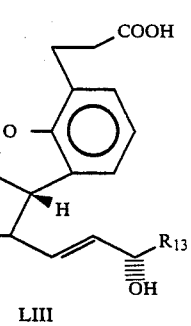

LIII wherein A is —$(CH_2)_2$—, Y is hydrogen, $R_1$ is a carboxylic or carbomethoxy group, $R_8$ is hydrogen, acyl or aroyl, B is (i), and $R_9$ is hydrogen is produced by chart K.

$R_8$ of the compounds XLVIII, XLIX, L and LI represented by K is acyl or aroyl.

K-1 is a so-called alcohol to aldehyde oxidation step. Various oxidizing agents are useful for it. Generally preferable thereamong are anhydrous chromic acid-pyridine complex (Collins' reagent), dimethylsulfoxide-dicyclohexylcarbodiimide, dimethylsulfide-chlorine, N-bromosuccinimide-dimethylsulfide, and so forth.

Step K-2 is practiced to condense aldehyde XLIX with dimethylphosphonate represented by general formula

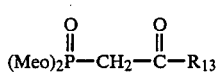

(wherein $R_{13}$ is the same as defined above). Usually the dimethylphosphonate is converted into a salt by a metal hydride (sodium potassium and other hydrides) in any of etheric solvents such as tetrahydrofuran and dimethoxyethane, and aldehyde XLIX is added thereto. Reaction temperature is selected out of $-30°$ to $100°$ C. Room temperature is however used preferentially. The dimethylphosphonate used therein can be synthesized by the reaction scheme represented by:

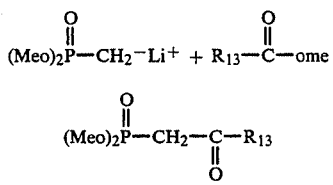

(Refer to E. J. Corey S, J. Am. Chem. Soc., 88, 5654 (1966).)

In step K-3, $\alpha,\beta$-unsaturated ketone is converted into a allylalcohol corresponding thereto. Reducing agents are generally used for this conversion. They should however be capable of reducing only the ketone groups, not the ester groups in compound L. Generally preferable thereamong are metal hydrides, trialcoxyaluminum compounds and dialkylaluminum compounds. Cited thereamong may be zinc boron hydride ($Zn(BH_4)_2$), sodium boron hydride with cerium trichloride; lithiumaluminum hydride with $\alpha$, $\alpha'$-binaphthol, diisobuthyl-(2,6-dimethylphenoxy)aluminum, triisopropoxyaluminum and so forth. However, they are not limited thereto. Preferable thereamong for normal reduction is sodium boron hydride-cerium trichloride reagent. In the process, etheric solvents such as ether, tetrahydrofuran and dimethoxyethane should preferably be used. Therein reaction temperature is selected out of $-110°$ to $80°$ C. However, generally preferable thereamong are $-78°$ C. to room temperature. The compound obtained by the step K-3 is generally a mixture of 15-$\alpha$ isomer (LI) and 15-$\beta$ isomer. It can be used in step K-4 without being separated.

Step K-4 is an ester exchange step of $R_8$ groups by means of methanol. It is easily done by dissolving compound LI (and its mixture with 15-$\beta$ isomer) in methanol, adding an appropriate base and leaving the resultant mixture at $-30°$ to $100°$ C. Generally preferably among bases are anhydrous sodium carbonate, potassium carbonate, sodium methoxide and potassium methoxide. Those as well as methanol used therein are required to be anhydrous for achieving the high yields of LII. The compound obtained therein is a mixture of 15-$\alpha$ isomer (LII) and its 15-$\beta$ isomer. They are separable by column chromatography (generally, separation should be preferably performed with silica gel; ethyl acetate-cyclohexane mixture solvent as developer).

Step K-5 is practised to hydrolyze methylester LII. It is easily done by dissolving compound LII in methanol or ethanol, adding an aqueous solution of more than one equivalent of a base, and causing the resultant mixture react at $-30°$ to $100°$ C. Preferably used among bases should be sodium and potassium hydroxides and carbonates. However, they are of course not limited thereto.

The 15-$\beta$ isomer of LII is obtainable by subjecting 15-$\beta$, an isomer of the LII produced by step K-4, to step K-5.

The processes for producing starting material XLVIII are described in Referential Examples 82 to 89.

Needless to say, a compound represented by general formula (I) wherein A is $-(CH_2)_2-$, Y is hydrogen, $R_8$ is hydrogen and $R_1$ is $-COOR_2$ ($R_1$, $R_2$: the same as defined above) and that wherein A is $-(CH_2)_2-$, Y and $R_8$ are hydrogen and $R_1$ is

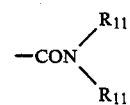

($R_{11}$: the same as defined above) can be synthesized by the aforesaid processes with LIII used as starting material.

A compound represented by general formula (I) wherein A is $-(CH_2)_2-$, Y is hydrogen, $R_1$ is $-CH_2OH$ and $R_8$ is hydrogen is producible by the reduction of a compound wherein corresponding $R_1$ is $-COOMe$ with a reducing agent. Satisfactorily-preferable results are obtainable when such reagents as lithium aluminum hydride and diisobutylaluminum hydride are used in etheric solvents such as ether, tetrahydrofuran and dimethoxyethane for the reduction.

A compound represented by general formula (I) wherein A is $-(CH_2)_2-$, Y is hydrogen, $R_1$ is $-COOH$ or $-COOR_2$ ($R_2$ is the same as defined above but not included among olefine and acetylene functional groups and the groups containing halogen atoms) and $R_8$ is hydrogen, acyl or aroyl, B is

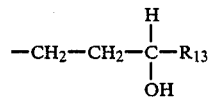

($R_{13}$ is the same as defined above but not included among the materials $R_{13}$ wherein $R_{13}$ is

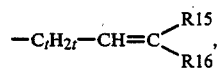

wherein the same is $-C_tH_{2t}OR_{14}$ and $R_{14}$ is $Z-Ar_2$ of which bromine or a nitro group is substituted for the $Ar_2$) is producible by hydrogen addition reaction to a compound wherein corresponding B is

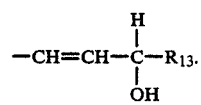

Generally used for this addition are such catalysts as metallic palladium and palladium on carbon as well as Raney nickel.

The methods of production mentioned so far are practiced in the same manner in the production of anyone of d form, l form or dl form, however, especially upon producing the d form or l form, it is possible to produce the same in accordance with the earlier mentioned method of production from the corresponding optically active starting material.

For example, the step described in chart K may be utilized for obtaining the compound LII or LIII in the form of any one of d-isomer, l-isomer or racemate. To obtain d-isomer or l-isomer, an optically active compound corresponding to the starting material of the general formula XLVIII may be used.

An optically active isomer of the compound of the general formula XLVIII may be obtained by following the procedure of the Reference Examples 98, 99 and 85, after conducting the optical resolution in accordance with Reference Example 97.

The compound represented by the general formula (I) obtained in accordance with the present invention has a strong platelet aggregation inhibiting activity and blood pressure lowering activity besides a strong gastric mucous membrane protecting action and a gastric juice secretion inhibiting activity. More particularly, blood collected from man or an anesthetized rabbit was prevented from coagulation with a 1/10 volume of 3.8% sodium citrate solution and centrifuged for 10 minutes, at 200 xg, the resultant platelet rich plasma was aggregated with arachidonic acid, adenosine-2-phosphoric acid (ADP) and collagen as aggregating agents according to Born's method ("Nature," 1962, 194, 927) using aggregometer. The anti-aggregatory effect by the pretreatment with the compounds (6), (9), (19), (48), (49), (55) and (97) of the present invention, was a comparable or stronger anti-aggregatory effect with or than that of prostaglandin $E_1$.

Under anesthesia with pentobarbital, the arterial pressure of rats was measured and the solutions of the compounds (6), (9), (19), (48), (49), (55) and (97) of the present invention were injected through a catheter into a vein. The blood pressure reducing activity of the compounds was 1-2 times that of prostglandin $E_1$, but with more prolonged duration.

As for the protecting action of the gastric mucous membrane, tests on the gastric mucous membrane lesion due to alcohol in a rat, acccording to Robert's method ("Gastroenterology," 1979, 77, 433), proved that the compounds (19), (76) and (97) of the present invention had the activity of 0.3–1 times that of prostaglandin $E_2$, i.e. 10–30 μg/kg administered orally strongly inhibited the lesion.

The result of the gastric juice secretion inhibiting effect according to Shay's method ("Gastroenterology," 1954, 26, 906), by subcutaneous injection of the compounds (19), (76), (60), (65) and (97) of the present invention shows the effective dose of 0.3–1 mg/kg, which is 0.1–0.3 times of the dose of prostaglandin $E_2$, in inhibiting the gastric juice The compounds of the present invention, especially the compounds (6), (9), (19), (48), (49), (55) and (97) do not exhibit the diarrhoea inducing actions recognized in prostaglandin $E_1$ and $E_2$ up to the dose of 3 mg/kg by subcutaneous administration in a rat.

A compound represented by general formula (I) wherein A is —$(CH_2)_2$— shows stronger platelet aggregation inhibiting and cytoprotective activities than that wherein A is —$(CH_2)_3$—. (See Tables 1 and 2.)

TABLE 1

| Human Platelet Aggregation Inhibiting Activity (aggregating agent ADP) | | | |
|---|---|---|---|
| A = —$(CH_2)_2$— | ID50 (ng/ml) | A = —$(CH_2)_3$— | ID50 (ng/ml) |
| 5,6,7-trinor-4,8-inter-m-phenylene-2-nor-16-methyl $PGI_2$ | 11 | 5,6,7-trinor-4,8-inter-m-phenylene-16-methyl $PGI_2$ | 31 |
| 5,6,7-trinor-4,8-inter-m-phenylene-2-nor-17(S)—methyl $PGI_2$ | 0.6 | 5,6,7-trinor-4,8-inter-m-phenylene-17(S)—methyl $PGI_2$ | 5 |
| 5,6,7-trinor-4,8-inter-m-phenylene-2-nor-17-oxa $PGI_2$ | 48 | 5,6,7-trinor-4,8-inter-m-phenylene-17-oxa $PGI_2$ | 490 |

TABLE 2

| Rat Cell Protecting Action | | | |
|---|---|---|---|
| A = —$(CH_2)_2$— | ED50 (g/kg) | A = —$(CH_2)_3$— | ED50 (g/kg) |
| 5,6,7-trinor-4,8-inter-m-phenylene-2-nor-16,16-dimethyl $PGI_2$ | 2.3 | 5,6,7-trinor-4,8-inter-m-phenylene-16,16-dimethyl $PGI_2$ | 49 |
| 5,6,7-trinor-4,8-inter-m-phenylene-2,17,18,19,20-pentanor-16-phenoxy $PGI_2$ | 4.6 | 5,6,7-trinor-4,8-inter-m-phenylene-17,18,19,20-tetranor-16-phenoxy $PGI_2$ | 127 |
| 5,6,7-trinor-4,8-inter-m-phenylene-2-nor-16-methyl $PGI_2$ | 0.46 | 5,6,7-trinor-4,8-inter-m-phenylene-16-methyl $PGI_2$ | 11.5 |
| 5,6,7-trinor-4,8-inter-m-phenylene-2-nor-17(S)—methyl $PGI_2$ | 0.86 | 5,6,7-trinor-4,8-inter-m-phenylene-17(S)—methyl $PGI_2$ | 3.5 |

The following experiments were carried out to demonstrate that the compounds of the above captioned application show greatly improved properties over the compounds of our prior U.S. Pat. No. 4,301,164 to Obno et al.

General Pharmacological Evaluation Procedures
Platelet Aggregation Inhibiting Activity Blood was collected from healthy volunteers using a disposable syringe containing 3.8% sodium citrate from the saphnous vein. The blood was centrifuged for 10 minutes at 160×g. The resultant supernatant liquid was used as platelet rich plasma (PRP). Aggregation was induced by 10 μm ADP (Adenosine diphosphate). The inhibition rate was calculated against a control aggregation of 100%.

ED$_{50}$ (effective dose 50) is defined as the dosage required to produce a response in 50% of the subjects to whom the compound is given.

Blood Pressure Measurement

Under pentobarbital anesthesia (50 mg/kg s.c.), a catheter was inserted into the carotid artery. The blood pressure was measured via a pressure transducer on a polygraph.

Gastric Acid Secretion Inhibition

Under urethane anesthesia (1,.25 g/kg s.c.), a catheter was introduced through the oesophagus into the stomach according to the method of Ghosh and Schild (Br. J. Pharmacol. 13, 54–61, 1958). Gastric juice was drawn through a catheter inserted in a duodenal incision and its pH was continuously measured using a pH meter. Carbamylcholine, administered by intravenous injection through the femoral vein, was used for stimulation of acid output. The effect of the drug was expressed in terms of inhibition percent against a control pH. The drug was injected intravenously prior to the stimulating agent.

Gastric Cytoprotection

Gastric cytoprotection was measured according to the method of Robert et al (Gastroenterol 77, 433-443, 1979). The rats fasted overnight and were given a necrotizing agent (0.2N NaOH 1 ml/rat (Method A) or Absolute EtOH (Method B)) and killed one hour later for the examination of gastric lesions. The test drug was administered 30 minutes before the necrotizing agent. The length of the lesion was measured and expressed in terms of the ulcer index. The effect of the drug was expressed in terms of the inhibition rate against the ulcer index of a control animal.

Accordingly, in application as medicines of the compounds of the present invention, an anti-ulcer agent, an anti-thrombotic agents, and a blood pressure reducing agent are conceivable, further, an anti-asthma medicine is conceivable based on the action of relaxing the bronchial smooth muscle. In application as an anti-thrombotic agent, application to extracorporeal circulation, treatment of Buerger's disease, prevention and treatment of muocardinal infarction and angina prectoris, prevention and treatment of cerebral infarction, prevention TIA and treatment of diabetic thrombosis are conceivable.

More particularly, for example, in an object of treating gastric ulcer, 0.01-100 mg/man is administered 1-3 times a day orally, subcutaneously, intramuscularlly or intra-rectally.

Further, the application as an anti-thrombotic agent or a blood pressure reducing agent is expectative. More particularly, for example, when treatment of Buerger's disease, by intraveneous injection of 0.001-100 ng/kg/min, when used as an anti-thrombotic agent, by orally administering 0.01-50 mg/man 1-3 times a day, and when used as a blood pressure reducing agent, by orally administering 0.01-5.0 mg/man 1-3 times a day.

The compounds of the present invention may be orally administered in the form of a solid material containing an additives such as starch, lactose, sucrose, a kind of clay and a taste curing agent. Or these can be administered parenterally in the form of a sterile solution, or these can contain other solute such as sodium chloride or glucose in an amount sufficient to make the solution isotonic.

Because the compound of the present invention has stable chemical structure, it has no difficulty in making a medicine and it can be applied in a broad range of administration routes such as the aforementioned medicine for oral administration, various kinds of injections and suppositories. Hereinbelow, the present invention will be explained by reference to examples.

Referential Example 1

3,5-cis-bis(2,6-dibromophenoxy)cyclopentene

To a nitrogen-substituted 500 ml flask, 5.6 g (0.117 mol) of sodium hydride in mineral oil dispersion was added and the sodium hydride was washed with n-hexane to remove mineral oils. To the flask, 100 ml of 1,2-dimethoxyethane was added and while the resulting mixture was being stirred at 0° C., 29.4 g (0.117 mol) of 2,6-dibromophenol which had been dissolved in 150 ml of 1,2-dimethoxyethane was slowly added thereto. When foaming calmed down, 280 mg (1.06 mmol, 2 mol % based on 3,5-dibromocyclopentene) of 18-crown-6 and 12 g (0.053 mol) of 3,5-dibromocyclopentene were added. The obtained mixture was stirred at room temperature for 3 days. The reaction mixture was filtered to give a solid substance, which was washed with 20 ml of water 3 times.

Further, the solid substance was dissolved in 1.5 liters of chloroform, the resulting mixture was dried over magnesium sulfate and concentrated to obtain 22.6 g (75%) of roughly pure white solid, which was 3,5-cis-bis(2,6-dibromophenoxy)cyclopentene, white needle-crystals, mp 205.0°–206.0° C.

Elemental analysis: Calculated for $C_{17}H_{12}Br_4O_2$ C: 35.95, H: 2.13; Found C: 35.86, H: 2.19, ($C_{17}H_{12}Br_4O_2$, mw 567.93); MS (m/e) 572, 571, 570, 569, 568, 567, 566, 565, 564 (M+); IR (KBr disk) $\nu cm^{-1}$: 1550, 960, 740; NMR (CDCl$_3$) δppm: 2.90 (dt, 1H), 3.12 (dt, 1H), 5.10 (dd, 2H) 6.31 (s, 2H), 6.83 (t, 2H), 7.52 (d, 4H).

Referential Example 2

3,5-cis-bis(2,6-dibromophenoxy)cyclopentene

To a solution of 227.6 g of 2,6-dibromophenol in 350 ml of ethanol was added a solution of 59 g of potassium hydroxide in 390 ml of ethanol.

The resulting mixture was stirred for 10 minutes and thereafter concentrated under reduced pressure.

The obtained crystals were dissolved in 1.2 liter of anhydrous DME, 2.2 g of 18-crown-6 was added and the resulting mixture was stirred.

Subsequently, 36.8 g of cyclopentadiene was dissolved in methylene chloride which had been cooled to −50° C., while the obtained solution was being stirred, a solution of 68.8 g of bromine in 10 ml of metylene chloride was added thereto dropwise, further, 15 g of sodium hydrogen carbonate was added and the obtained mixture was stirred for 10 minutes.

This reaction mixture was added to the above-prepared DME solution of a potassium salt of 2,6-dibromophenol and the resulting mixture was stirred at room temperature for 2 days. The separated crystals were filted and the obtained crystals were washed 3 times with water, once with ether and once with petroleum ether, thereafter, when the washed crystals were dried under reduced pressure, 95.3 g of a roughly pure product was obtained. Further, when the aforesaid motor liquid was concentrated, the separated crystals were washed 2 times with water, once with ether and 2 times with petroleum ether and dried to give 22.9 g of a roughly pure product. The total yield was 118.2 g, mp 205°-206° C.

IR (KBr) $v$cm$^{-1}$: 1550, 1470, 820, 750; NMR (CDCl$_3$) δ: 2.90 (1H, dt, J=16.0 Hz, 8.0 Hz), 3.12 (1H, dt, J=16.0 Hz, 8.0 Hz), 5.10 (2H, dd, J=8.0 Hz 7.0 Hz), 6.31 (2H, s), 6.83 (2H, t, J=8.0 Hz), 7.52 (4H, d, J=8.0 Hz). Elemental analysis: Calculated for C$_{17}$H$_{12}$Br$_4$O$_2$ C: 35.95, H: 2.13; Found C: 35.86, H: 2.19.

In a similar manner, when 2,6-dibromo-p-chlorophenol was employed instead of 2,6-dibromophenol, 3,5-cis-bis(2,6-dibromo-4-chlorophenoxy)cyclopentene is obtained.

Referential Example 3

3,5-cis(2,4,6-tribromophenoxy)cyclopentene

To a solution of 193 g of 2,4,6-tribromophenol in 600 ml of ethanol was added dropwise a solution of 45 g of potassium hydroxide in 250 ml of ethanol, the resulting solution was stirred for 10 minutes and thereafter concentrated under reduced pressure. Ethanol was added to the residue, the resulting mixture was again evaporated to dryness, and the obtained crystals were dried under reduced pressure. To a solution of 2,4,6-tribromophenol salt in 1200 ml of anhydrous DME, 2 g of 18-crown-6 was added and the resulting mixture was stirred at room temperature. Subsequently, a solution of 22.8 g of cyclopentadiene in methylene chloride was cooled to −50° C. and while the resulting solution was being stirred at −50° C., a solution of 42.4 g of bromine in 10 ml of methylene chloride was added dropwise thereto. This reaction mixture was added to the above-prepared DME solution of 2,4,6-tribromophenol potassium salt and the resulting mixture was stirred at room temperature for 2 days. The separated crystals were filtered, the obtained crystals were washed 3 times with water, once with ether and 2 times with pertroleum ether, and thereafter when they dried under reduced pressure, 109.6 g of roughly pure crystals was obtained. Further, when the aforesaid mother liquor was concentrated, the separated crystals were filtered and washed with petroleum ehter, 2 times with water, once with ether and 2 times with petroleum ether to yield 13.1 g of roughly pure crystals. The total yield was 123.4 g.

IR (KBr) $v$cm$^{-1}$: 1570, 1600, 1470, 805, 780.

In a similar manner, when instead of 2,4,6-tribromophenol, 2,4-dichloro-6-bromophenol is employed, 3,5-cis-bis(2,4-dichloro-6-bromophenoxy)cyclopentene is obtained, and, 2,6-dibromo-4-methoxyphenol is employed, 3,5-cis-bis(2,6-dibromo-4-methoxyphenyl)cyclopentene is obtained.

Referential Example 4

3,5-cis-bis(2,4-dibromophenoxy)cyclopentene

To a solution of 407 g of 2,4-dibromophenol in 400 ml of ethanol, was added a solution of 90.7 g of potassium hydroxide in 600 ml of ethanol, the resulting solution was stirred for 10 minutes and thereafter, concentrated under reduced pressure. Operations of dissolving the residue in DME and concentrating the resulting solution were repeated 2 times and thereafter, the obtained residue was well dried and under reduced pressure. The so obtained potassium salt of 2,4-dibromophenol was dissolved in 2000 ml of anhydrous DME, 4 g of 18-crown-6 was added and the resulting solution was stirred at room temperature.

Subsequently, 63 g of cyclopentadiene was dissolved in 80 ml of anhydrous methylene chloride, the resulting solution was cooled to −50° C. under argon atmosphere, and while it was being stirred, a solution of 37.9 g of bromine in 20 ml of methylene chloride was added dropwise thereto. To the reaction solution 10 g of sodium hydrogen carbonate was added and thereafter, the mixture was stirred for 10 minutes. This reaction mixture was added to the aboveprepared DME solution of the potassium salt of 2,4-dibromophenol, and the resulting mixture was stirred at room temperature for 2 days.

Crystals separated from this reaction mixture were filtered, the obtained crystals were washed 3 times with water, once with ether and 2 times with petroleum ether and dried to yield 71.9 g of crystals. Further, when the aforesaid mother liquor was concentrated, the separated crystals were washed with petroleum ether, 2 times with water, once with ether and 2 times with petroleum ether thereafter, when they were dired, 159.1 g of crystals was obtained. The total yiled was 231 g.

IR (KBr) $v$cm$^{-1}$: 1575, 1600, 1470, 805, 780.

In a similar manner, when phenol is employed instead of 2,4- dibromophenol, 3,5-cis-bisphenoxycyclopenten is obtained.

Referential Example 5

3,5-cis-bis(2,6-dibromo-4-methylphenoxy)cyclopentene

To a solution of 176 g of 2,6-dibromo-p-cresol in 210 ml of ethanol was added a solution of 43 g of potassium hydroxide in 280 ml of ethanol, the resulting solution was stirred fro 10 minutes and thereafter concentrated. The residue was dissolved in 900 ml of anhydrous DMS, 155 g of 18-crown-6 was added, and the resulting solution was stirred at room temperature.

Subsequently, the solution of 27 g of cyclopentadiene in 50 ml of methylene chloride had been cooledto −50° C. and while the resulting solution was being stirred, the solution of 50.5 g of bromine in 10 ml of methylene chloride was added dropwise thereto, 5 g of sodium hydrogen carbonate was added to the resulting solution and the resulting mixture was stirred for 10 minutes. This reaction mixture was added to the above-prepared DME solution of the potassium salt of 2,6-dibromo-p-cresol, and the resulting mixture was stirred at room temperature for 2 days. The separated crystals were filtered, the obtained crystals were washed 2 times with water, once with ether and 2 times with petroleum ether, thereafter, when they were dried under reduced pressue, 165.8 g of a roughly pure product was obtained. Further, the aforesaid mother liquor was concentrated, the separated crystals were washed 2 times with water, once with ether and 2 times with petroleum ether and thereafter, when they were dried under reduced pressure, 22.5 of a roughly pure product was obtained. The total yiled was 188.3 g.

IR (KBr) $v$cm$^{-1}$: 1590, 850, 800, 745. NMR (CDCl$_3$) δ: 2.38 (6H, s), 2.80 (1H, dd, J=14.0 Hz), 5.0 Hz), 3.10 (1H, dd, J=14.0 Hz, 7.0 Hz), 5.08 (2H, dd, J=5.0 Hz, 7.0 Hz), 6.32 (2H, s), 7.36 (4H, s).

Referential Example 6

3,5-cis-bis(o-bromophenoxy)cyclopentene

In a similar manner as in Referential Example 2, when o-bromophenol was employed instead of 2,6-dibromophenol, 6.0 g of 3,5-cis-bis(o-bromophenoxy)cyclopentene, mp 138°-138.5° C. was obtained from 6.2 g of 3,5-cis-dibromocyclopentene.

IR (KBr) $\nu$cm$^{-1}$: 1585, 1570, 1165, 992, 790. NMR (CDCl$_3$) $\delta$: 2.21 (1H, dd, J=14.0 Hz, 5.0 Hz), 3.08 (1H, dd, J=14.0 Hz, 7.0 Hz), 5.20 (2H, dd, J=7.0 Hz, 5.0 Hz), 6.30 (2H, s), 6.80–7.50 (8H, m). Calculated for C$_{17}$H$_{14}$O$_2$Br$_2$ C: 49.66, H: 3.68; Found C: 49.76, H: 3.56.

Referential Example 7

3a,8b-cis-dihydro-3H-5-bromo-cyclopenta[b]benzofuran

In an argon-substituted 50 ml flask, 515 mg (0.906 mmol) of 3,5-cis-bis(2,6-dibromophenoxy)cyclopentene was placed, which was dissolved in 11 ml of anhydrous tetrahydrofuran, and the resulting solution was cooled to −78° C. To the solution 0.72 ml (1.44 mmol) of n-butyl lithium (about 2.0M) was added dropwise in about 15 minutes, and the resulting solution was stirred at −10° C. for about 3 hours. To the reaction mixture 5 ml of a saturated aqueous solution of ammonium chloride was added and the resulting solution was extracted with ether (30 ml×3 times). The organic layer was dried over anhydrous magnesium sulfate and concentrated. When the concentrate was purified by column chromato-graphy (silica gel 7 g, developing solvent: cyclohexane/ethyl acetate 97:3), 98.6 mg (0.416 mmol, 45.9%) of a colorless oily substance was obtained.

TLC: Rf=0.6 (cyclohexane:ethyl acetate 97:3). IR (liquid film method) $\nu$cm$^{-1}$: 3060, 2950, 1600, 1585, 945, 750. NMR (CDCl$_3$) $\delta$ppm: 2.9 (m, 2H) 4.8 (m, 1H), 5.54 (m, 1H), 5.66 (m, 2H), 6.70 (t, 1H), 7.2 (m, 2H). MS (m/e): 238, 236 (M+), 209, 211, 128

Thereafter, in a similar manner, when 3,5-cis-bis(2-bromo-6-chlorophenoxy)cyclopentene is employed instead of 3,5-cis-bis(2,6-dibromophenoxy)cyclopentene, 3a,8b-cis-dihydro-3H-5-chlorocyclopenta[b]benzofuran is obtained.

Referential Example 8

3a,8b-cis-dihydro-3H-5-bromo-cyclopenta[b]benzofuran

To a stirred suspension of 87.1 g of 2,5-cis-bs(2,6-dibromophenoxy)cyclopentene in 300 ml of anhydrous THF at 40° C. was added 140 ml of cyclohexylmagnesiumbromide (2.18N) dropwise, and the resulting solution was stirred for 30 minutes. The temperature of this reaction mixture was allowed to cool to room temperature, 0.58 g of cuprous iodide was added and the resulting mixture was further stirred for 30 minutes. Precipitates existing in the reaction mixture was filtered, the filtrate was concentrated, and the residue was dissolved in cyclohexane. The resulting solution was washed with a 5% aqueous solution of sodium hydroxide, dried and thereafter concentrated to yield 60 g of an oily substance. When this only substance was distilled (bp 60° C./10$^{-3}$ mm Hg) on a molecular distillation apparatus, 20 g of crude crystals was obtained.

The spectrum data were the same as those of Referential Example 7.

Referential Example 9

3a,8b-cis-dihydro-3H-cyclopenta[b]benzofuran

In a similar manner as in Referential Example 7, instead of 3,5-cis-bis(2,6-dibromophenoxy)cyclopentene, 6.0 g of 3,5-cis-bis(o-bromophenoxy)cyclopentene was employed to give 1.84 g of the subject compound.

IR (neat) $\nu$cm$^{-1}$: 3060, 1602, 1585. NMR (CDCl$_3$) $\delta$: 2.80 (1H, dd, J=2.2, 0.5 Hz), 2.82 (1H, dd, J=5.2, 0.5 Hz), 4.35 (1H, d, J=7.8 Hz), 5.43 (1H, ddd, J=7.8, 5.2, 2.2 Hz), 5.71 (2H, s), 6.95 (4H, m).

Mass: 158 (M+).

Referential Example 10

3a,8b-cis-dihydro-3H-5,7-dibromo-cyclopenta[b]benzofuran

In a similar manner as in Referential Example 7, instead of 3,5-cis-bis(2,6-dibromophenoxy)cyclopentene, 50 g of 3,5-cis-bis(2,4,6-tribromophenoxy)cyclopentene was employed to give 10 g of 3a,8b-cis-dihydro-3H-5,7-dibromo-cyclopenta[b]benzofuran (mp 110°-112° C.).

IR (KBr) $\nu$cm$^{-1}$: 3070, 2980, 2920, 1595, 1570, 865, 830, 740, 720. NMR (CDCl$_3$) $\delta$: 2.90 (2H, m), 4.48 (1H, m), 5.60 (1H, m) 5.80 (2H, m), 7.25 (1H, d, J=2.0 Hz), 7.40 (1H, d, J=2.0 Hz). Mass: 314 (M+), 316 (M+2), 318 (M+4).

Referential Example 11

3a,8b-cis-dihydro-3H-7-bromo-cyclopenta[b]benzofuran

Under argon atmosphere, 2.0 g of 3,5-cis-bis(2,4-dibromophenoxy)cyclopentene was dissolved in 4 ml of 1,2-dimethoxyethane, 3, 8 ml of an ether solution (1.5M) of phenyllithium was added, and the resulting mixture was stirred at 40° C. for 3 hours and at 70° C. for 12 hours.

The temperature was allowed to cool to room temperature, 5 ml of a saturated aqueous solution of ammonium chloride was added to the reaction solution, the resulting solution was extracted with ether (20 ml×3) and the extracted liquid was washed with 10 ml of a 5% aqueous solution of sodium hydroxide and 10 ml of saturated brine and dried. After concentration. 1.8 g of an oily substance thus obtained was purified by column chromatography (silica gel; cyclohexane: chloroform (3:1)) to give 540 mg of the subject compound.

IR (CHCl$_3$) $\nu$cm$^{-1}$: 3060, 1602, 1583. NMR (CDCl$_3$) $\delta$ppm: 2.81 (2H, m), 4.36 (1H, d, J=8.0), 5.48 (1H, ddd, J=2,6, 5.2 7.8), 5.76 (2H, m), 6.62 (1H, d, J=8.0), 7.19 (1H, dd, J=8.0, 2.0), 7.30 (1H, d, J=2.0). Mass: 236 (M+), 238 (M+2)

Referential Example 12

3a,8b-cis-dihydro-3H-5-bromo-7-methylcyclopenta[b]benzofuran

Under argon atmosphere, 13.45 g of 3,5-cis-bis(2,6-dibromo-4-methylphenoxy)cyclopentene was placed in a 300 ml flask and dissolved in 100 ml of tetrahydrofuran, which was cooled to 40° C. To the resulting sultion, 55 ml of a tetrahydrofuran solution (0.83M) of cyclohexyl magnesium bromide was added dropwise over 45 minutes, and the resulting solution was stirred for 1 hour, 449 mg of cuprous iodide was added, the temperature was allowed to cool to room temperature, and the resulting mixture was stirred for 40 minutes. The reaction mixture was added to 100 ml of a vigrously stirred saturated aqueous solution of ammonium chloride, the resulting solution was extracted with ether (100 ml and 20 ml×3), the extracted liquid was washed with a 5% aqueous solution of sodium hydroxide (20 ml×3) and saturated brine (20 ml) and dried. After concentration, the obtained oily substance was purified by column chromatography (silica gel 300 g; cyclohexane/methylene chloride 100:1→20:1) to obtain 4.45 g (78%) of a white solid. When it was recrystallized from a cyclohexane—petroleum ether mixed solvent, 4.1 g of colorless needless (mp 182°–184° C.) was obtained.

IR (KBr) $v cm^{-1}$: 1605, 1585, 940, 780, 740, 710. NMR (CDCl$_3$) δ: 2.22 (3H, s), 2.84 (2H, m), 4.38 (1H, d, J=8.0 Hz), 5.48 (1H, dt, J=8.0, 4.0 Hz), 5.72 (2H, m), 6.90 (1H, s), 7.03 (1H, s). Mass: 250 (M+), 252 (M+2).

In a similar manner, when instead of 3,5-cis-bis(2,6-dibromo-4-methylphenoxy)cyclopentene, 3,5-cis-bis(2-bromo-6-chloro-4-methylphenoxy)cyclopentene is employed, 3a,8b-cis-dihydro-3H-5-chloro-7-methylcyclopenta[b]benzofuran is obtained, and when 3,5-cis-bis-(2-bromo-4-methylcyclopenta[b]benzofuran) is employed, 3,8b-cis-dihydro-3H-7-methylbenzofuran is obtained.

Referential Example 13

3a,8b-cis-dihydro-3H-5-bromo-7-chlorocyclopenta[b]benzofuran

In a similar manner as in Referential Example 7, instead of 3,5-cis-bis-(2,6-dibromophenoxy)cyclopentene, 1.10 g of 3,5-cis-bis(2,6-dibromo-4-chlorophenoxy)cyclopentene was employed to obtain 211 mg of the subject compound.

IR (CHCl$_3$) $v cm^{-1}$: 3060, 1605. Mass: 270 (M+), 272 (M+2), 274 (M+4).

In a similar manner, instead of 3,5-cis-bis(2,6-dibromo-4-chlorophenoxy)cyclopentene, when 3,5-cis-bis(2-bromo-4-chlorophenoxy)cyclopentene is employed, 3a,8b-cis-dihydro-3H-7-chlorocyclopenta[b]benzofuran is obtaned, and when 3,5-cis-bis(2-bromo-4,6-dichlorophenoxy)cyclopentene is employed, 3a,8b-cis-dihydro-3H-5,7-dichlorocyclopenta[b]benzofuran is obtained.

Referential Example 14

3a,8b-cis-dihydro-3H-5-(4-tetrahydropyranyloxy-n-butyl)cyclopenta[b]benzofuran

To a solution of 150 mg (0.632 mmol) of 3a,8b-cis-dihydro-3H-5-bromocyclopenta[b]benzofuran in 7 ml of THF, was added dropwise at −78° C. 0.32 ml of n-butyl lithium (2.0M). After stirring the resulting solution for 15 minutes, 215 mg (0.758 mmol, 1.2 equiv.) of 4-iodobutyl-tetrahydropyranyl ether was added thereto, and the resulting mixture was stirred at −78° C. for 2 hours and at −12° C. for 2 hours, 5 ml of saturated brine was added and the mixture was extracted with 50 ml of ether. After drying, it was concentrated to obtain 230 mg of an oily crude product, which was purified by high-speed liquid chromatography to obtain 171 mg (86.2%) of the subject compound as an oily substance.

IR (liquid film method) $v cm^{-1}$: 3400, 2920, 1590, 748. NMR (CDCl$_3$) δppm: 1.3–2.0 (m, 10H), 2.58 (t, 2H), 2.84 (m, 2H), 3.4 (m, 2H), 3.8 (m, 2H), 4.37 (d, 1H), 4.56 (s, 1H), 5.44 (m, 1H), 5.74 (s, 2H), 6.7–7.1 (m, 3H). MS (m/e): 314 (M+), 230, 214, 171.

Referential Example 15

1,2,3a,8b-cis-tetrahydro-5-(4-tetrahydropyranyloxy-n-butyl)-1-exo-bromo-2-endo-hydroxy-cyclopenta[b]benzofuran To a solution of 720 mg (2.3 mmol) of 3a,8b-cis-dihydro-3H-5-(4-tetrahydropyranyloxy-n-butyl)-cyclopenta[b]benzofuran in a mixture of 20 ml of dimethyl sulfoxide/water (18/1) and 3 ml of THF, 573 mg (3.2 mmol, 1.4 equiv.) of N-bromosuccinimide was added, followed by stirring for 1.5 hours at 0°–5° C. 5 ml of saturated aqueous solution of sodium hydrogen carbonate was added thereto and the resultant mixture was extracted with 200 ml of ether, dried and concentrated. The resulting crude substance was purified by column chromatography to yield 459 mg of the captioned compound.

Referential Example 16

1,2,3a,8b-cis-tetrahydro-5-(4-tetrahydropyranyloxy-n-butyl)-1,2-syn-epoxy-3H-cyclopenta[b]benzofuran To a solution of 450 mg (1.09 mmol) of 1,2,3a,8b-cis-tetrahydro-5-(4-tetrahydropyranyloxy-n-butyl)-1-exo-bromo-2-endo-hydroxy-cyclopenta[b]benzofuran in 5 ml of methanol was added 322 mg of potassium carbonate and the mixture was stirred at 0° C. for 1.5 hours, methanol was distilled off under a reduced pressure therefrom, the remaining mixture was extracted with 20 ml of ether, dried and thereafter, concentrated. By column chromatography, 320 mg (0.97 mmol, 89%) of the subject compound was obtained.

IR (neat) $v cm^{-1}$: 3030, 2920, 1590, 1470, 1220, 1130, 965, 840, 745. NMR (CDCl$_3$) δppm: 1.4–1.8 (m, 10H) 2.2 (dd, 1H), 2.5 (m, 3H), 3.5 (m, 2H), 3.64 (bs, 2H), 3.7 (m, 2H), 3.84 (d, 1H), 4.56 (bs, 1H), 5.3 (t, 1H), 6.7–7.3 (m 3H). MS (m/e): 330 (M+), 246, 227.

Referential Example 17

1,2,3a,8b-cis-tetrahydro-5-(4-tetrahydropyranyloxy-n-butyl)-1-exo-(2-formylvinyl)-2-endo-hydroxy-3H-cyclopenta[b]benzofuran To a solution of 315 mg (0.95 mmol) of 1,2,3a,8b-cis-tetrahydro-5-(4-tetrahydropyranyloxy-n-butyl)-1,2-syn-epoxy-cyclopenta[b]benzofuran in 2 ml of THF at −78° C. was added solution of separately synthesized 1,3-bis(-methylthio) allyl anion (2.4 mmol) in THF.

The resulting solution was stirred for 2 hours, and 1 ml of methanol and 3 ml of a saturated aqueous solution of ammonium chloride was added and extracted with 100 ml of ether. The ether extract was dried over anhydrous sodium sulfate and concentrated.

2.7 g (10 mmol) of mercuric chloride, 1.6 g (1.6 mmol) of calcium carbonate, 12 ml of acetonitrile, 3 ml of water and 2 ml of THF, was added to the resulting oily substance and the resulting mixture was heated to 40° C. under argon atmosphere, which was stirred with heating overnight, the reaction solution was filtered, and the precipitate was washed with 50 ml of ether, the ether layer was washed with 10 ml of saturated brine, dried and thereafter purified by column chromatography to obtain 151 mg (41% of the subject compound and 187 mg (51%) of the position isomer.

IR (neat) $v cm^{-1}$: 3600–3300, 2930, 1687, 1635, 1590, 750. NMR (CDCl$_3$) δppm: 1.5–1.8 (m, 10H) 2.1 (m, 1H), 2.6 (m, 1H), 2.6 (t, 2H), 2.83 (q, 1H), 3.1 (bs, 1H), 3.4 (m, 2H), 3.62 (t, 1H), 3.8 (m, 2H), 4.1 (m, 1H), 4.56 (m, 1H) 5.2 (m, 1H), 6.24 (dd, 1H), 6.7–7.1 (m, 4H), 9.6 (d, 1H). MS (m/e): 386 (M+), 302, 284.

Referential Example 18

3a,8b-cis-dihydro-3H-5-(4-tetrahydropyranyloxy-n-butyl)-7-methylcyclopenta[b]benzofuran To a solution of 507 mg (2.02 mmol) of 3a,8b-cis-dihydro-5-bromo-7-methylcyclopenta[b]benzofuran in 0.6 ml of THF at −20° C. under argon atmosphere, 2.15 ml (0.963M ether solution, 2.06 mmol) of phenyl lithium was added dropwise. After 1 hour a solution of 601 mg (2.11 mmol) of 4-iodobutyl tetrahydropyranyl ether in 2 ml of THF was added, and the resulting solution was stirred for 3 hours. Further, it was stirred for a time in which the temperature was allowed to raise to 15° C., thereafter, the reaction solution was added to 3 ml of a saturated aqueous solution of ammonium chloride, the solution was extracted from the water layer with ether (5 ml×5), the organic layer was dried and thereafter concentrated to obtain 904 mg of an oily substance, after it was purified by column chromatography (Merck Lobar Column B, cyclohexane:ethyl acetate 3:1), 537 mg (81%) of 2 in an oily state was obtained.

IR (neat) $\nu cm^{-1}$: 3060, 3010, 2930, 2860, 1610, 1210, 1080, 760, 720. NMR (CDCl$_3$) δ: 1.64 (10H m), 2.24 (3H, s), 2.54 (2H, m), 2.78 (2H, m), 3.44 (2H, m), 3.80 (2H, m), 4.31 (1H, d, J=8.0 Hz), 4.56 (1H, m), 5.41 (1H, m) 5.72 (2H, m) 6.73 (1H, s), 6.83 (1H, s). Mass (m/e): 328 (M+).

Referential Example 19

3a,8b,-cis-dihydro-3H-5-(4-tetrahydropyranyloxy-n-butyl)-7-bromocyclopenta[b]benzofuran In a similar manner as in Referential Example 18, 500 mg of 3a,8b-cis-dihydro-3H-5,7-dibromocyclopenta[b]benzofuran was employed instead of 3a,8b-cis-dihydro-3H-5-bromo-7-methylcyclopenta[b]benzofuran to obtain 200 mg of 3a,8b-cis-dihydro-3H-5-(4-tetrahydropyranyloxy-n-butyl)-7-bromocyclopenta[b]benzofuran.

IR (neat) $\nu cm^{-1}$: 3060, 2930, 1610, 760.

In a similar manner, when 3a,8b,-cis-dihydro-3H-5-bromo-7-chlorocyclopenta[b]benzofuran is employed instead of 3a,8b-cis-dihydro-3H-5,7-dihydrocyclopenta[b]benzofuran, 3a,6-cis-dihydro-3H-5-(4-tetrahydropyranyloxy-n-butyl)-7-chlorocyclopenta[b]benzofuran is obtained.

Referential Example 20

3a,8b,-cis-dihydro-3H-5-(4-hydroxy-n-butyl)-7-bromocycropenta[b]benzofuran

To a solution of 260 mg of 3a,8b-cis-dihydro-3H-5-(4-tetrahydropyranyloxy-n-butyl)-7-bromocyclopenta[b]benzofuran in 2 ml of acetonitrile and 2 ml of THF, was added at 0° C. 2 ml of 1/10N hydrochloric acid, and the resulting solution was stirred at room temperature for 14 hours, triethyl amine and a saturated aqueous solution of sodium hydrogen carbonate was added, and the resulting mixture was extracted with ether 3 times. The combined ether layer were washed with saturated brine, dried and concentrated, to afford 348 mg of an oil substance. The oily substance was purified by column chromatography [(silica gel: cyclohexane:ethyl acetate (7:3)] to yield 140 mg of a pure product.

IR (neat) $\nu cm^{-1}$: 3600–2300, 1590, 1050, 750. Mass (m/e): 308, 310 (M+).

In a similar manner, when instead of 3a,8b-cis-dihydro-3H-5-(4-tetrahydropyranyloxy-n-butyl)-7-bromocyclopenta[b]benzofuran, 3a,8b-cis-dihydro-3H-5-(4-tetrahydropyranyloxy-n-butyl)-7-methylcyclopenta[b]benzofuran is employed, 3a,8b-cis-dihydro-3H-5-(4-hydroxy-n-butyl)-7-methylcyclopenta[b]benzofuran is obtained, and 3a,8b-cis-dihydro-3H-5-(4-tetra-n-hydroxyphrayloxy-n-butyl)-7-chlorocyclopenta[b]benzofuran is employed, 3a,8b-cis-dihydro-3H-5-(4-hydroxy-n-butyl)-7-chlorocyclopenta[b]benzofuran is obtained.

Referential Example 21

3a,8b-cis-dihydro-3H-5-(3-carboxy-n-propyl)-7-bromocyclopenta[b]benzofuran

To a solution of 330 mg of 3a,8b-dihydro-3H-5-(4-hydroxy-n-butyl)-7-bromocyclopenta[b]benzofuran in 7.5 ml of DMF was added 1.9 g of pyridinium dichromate, and the resulting mixture was stirred at room temperature for 14 hours. Water was added and the mixture was extracted with ether 5 times, the combined ether layers were washed with saturated brine, dried and concentrated to give 340 mg of an oil substance. The oily substance was purified by column chromatography [silica gel (which had been treated with acetic acid); ethyl acetate:cyclohexane (1:1)] to afford 260 mg of a carboxylic acid.

IR (neat) $\nu cm^{-1}$: 3600–2300, 1705, 1605, 1580, 1190, 1000, 830, 710. NMR (CDCl$_3$) δ: 1.94 (2H, quintet, J=7.0 Hz), 2.37 (2H, t, J=7.0 Hz), 2.62 (2H, t, J=7.0 Hz), 2.80 (2H, m), 4.38 (1H, d, J=7.0 Hz), 5.42 (1H, m), 5.64 (2H, m), 7.03 (1H, d, J=1.5 Hz), 7.16 (1H, d, J=1.5 Hz). Mass (m/e): 322, 324 (M+).

In a similar manner, instead of 3a,8b-cis-dihydro-3H-5-(4-hydroxy-n-butyl)-7-bromocyclopenta[b]benzofuran, when 3a,8b-cis-dihydro-3H-5-(4-hydroxy-n-butyl)-7-chlorocyclopenta[b]benzofuran is employed, 3a,8b-cis-dihydro-3H-5-(3-carboxy-n-propyl)-7-chlorocyclopenta[b]benzofuran is obtained, and when 3a,8b-cis-dihydro-3H-5-(4-hydroxy-n-butyl)-7-methylcyclopenta[b]benzofuran is employed, 3a,8b-cis-dihydro-3H-5-(3-carboxy-n-propyl)-7-methylcyclopenta[b]benzofuran is obtained.

Referential Example 22

3a,8b-cis-dihydro-3H-5-(3-carbomethoxy-n-propyl)-7-bromocyclopenta[b]benzofuran

To a solution of 100 mg of 3a,8b-cis-dihydro-3H-5-(3-carboxy-n-propyl)-7-bromocyclopenta[b]benzofuran in 2 ml of ethyl acetate was added ether solution of a large excess of diazomethane. The resulting solution was well stirred, allowed to stand for 5 minutes and concentrated to afford 102 mg of a roughly pure methyl ester.

IR (neat) $\nu cm^{-1}$: 1738, 1605, 1580, 1190, 1000, 830, 710. NMR (CDCl$_3$) δ: 1.90 (2H, quintet, J=7.0 Hz), 2.30 (2H, t, J=7.0 Hz), 2.55 (2H, t, J=7.0 Hz), 2.80 (2H, m), 3.66 (3H, s), 4.35 (1H, m), 5.45 (1H, m), 5.65 (2H, m), 7.03 (1H, d, J=2.0 Hz), 7.16 (1H, d, J=2.0 Hz). Mass (m/e): 336, 338 (M+).

Thereafter, in a similar manner, instead of 3a,8b-cis-dihydro-3H-5-(3-carboxy-n-propyl)-7-bromocyclopenta[b]benzofuran, when 3a,8b-cis-dihydro-3H-5-(3-carboxy-n-propyl)-7-chlorocyclopenta[b]benzofuran is employed, 3a,8b-cis-dihydro-3H-5-(3-carbomethoxy-n-propyl)-7-chlorocyclopenta[b]benzofuran is obtained, and when 3a,8b-cis-dihydro-3H-5-(3-carboxy-n-propyl)-7-methylcyclopenta[b]benzofuran is employed 3a,8b-cis-dihydro-3H-5-(3-carbomethoxy-n-propyl)-7-methylcyclopenta[b]benzofuran is obtained.

Referential Example 23

3a,8b-cis-dihydro-3H-5-(3-carboethoxy-n-propyl)-7-bromocyclopenta[b]benzofuran

In a similar manner as in Referential Example 22, but by using diazoethane instead of diazomethane, 102 mg of 3a,8b-cis-dihydro-3H-5-(3-carboethoxy-n-propyl)-7-bromocyclopenta[b]benzofuran was obtained from 100 mg of 3a,8b-cis-dihydro-3H-5-(3-carboxy-n-propyl)-7-bromocyclopenta[b]benzofuran.

IR (neat) $v$cm$^{-1}$: 1738, 1605, 1580, 1190, 1000, 830, 710 Mass (m/e): 350, 352 (M+).

Thereafter, in a similar manner, instead of 3a,8b-cis-dihydro-3H-5-(3-carboxy-n-propyl)-7-bromoocyclopenta[b]benzofuran, when 3a,8b-cis-dihydro-3H-5-(3-carboxy-n-propyl)-7-chlorocyclopenta[b]benzofuran is employed, 3a,8b-cis-dihydro-3H-5-(3-carboethoxy-n-propyl)-7-chlorocyclopenta[b]benzofuran is obtained, and when 3a,8b-cis-dihydro-3H-5-(3-carboxy-n-propyl)-7-methylcyclopenta[b]benzofuran is employed, 3a,8b-cis-dihydro-3H-5-(3-carboethoxy-n-propyl)-7-methylcycloopenta[b]benzofuran is obtained.

Referential Example 24

3a,8b-cis-dihydro-3H-5-(3-carbobenzyloxy-n-propyl)-7-bromocyclopenta[b]benzofuran To an ice-cooled solution of 150 mg of 3a,8b-cis-dihydro-3H-5-(3-carboxy-n-propyl)-7-bromocyclopenta[b]benzofuran in 5 ml of DMF, was added 0.05 ml of triethyl amine and 0.05 ml of benzyl bromide, and the resulting solution was stirred at room temperature for 14 hours. Ether was added, and the resulting mixture was washed with water and brine, dried and concentrated to afford 200 mg of an oily substance. The oily substance was purified by column chromatography [silica gel; cyclohexane:ethyl acetate(9.5:0.5) to give 160 mg of a pure product.

IR (neat) $v$cm$^{-1}$: 1738, 1605, 1585, 1190, 1000, 830, 710. Mass (m/e): 412, 414 (M+).

Thereafter, in a similar manner, instead of 3a,8b-cis-dihydro-3H-5-(3-carboxy-n-propyl)-7-methylcyclopenta[b]benzofuran, when 3a,8b-cis-dihydro-3H-5-(3-carboxy-n-propyl)-7-chlorocyclopenta[b]benzofuran is employed, 3a,8b-cis-dihydro-3H-5-(3-carbobenzyloxy-n-propyl)-7-chlorocyclopenta[b]benzofuran is obtained, and when 3a,8b-cis-dihydro-3H-5-(3-carboxy-n-propyl)-7-methylcyclopenta[b]benzofuran is employed, 3a,8b-cis-dihydro-3H-5-(3-carbobenzyloxy-n-propyl)-7-methylcyclopenta[b]benzofuran is obtained.

Referential Example 25

3a,8b-cis-dihydro-3H-7-bromo-5-hydroxymethylcyclopenta[b]benzofuran

To a solution of 1.38 g (4.37 mmol) of 3a,8b-cis-dihydro-3H-5,7-dibromocyclopenta[b]benzofuran in 5 ml of tetrahydrofuran under argon atmosphere was added a solution of 10.0 ml (0.76M, 7.6 mmol, 1.7 equiv.) of cyclohexyl magnesium bromide in THF, and the resulting mixture was stirred at 40° C. for 2 hours. This solution was slowly added dropwise to a tetrahydrofuran solution of formaldehyde (which had been prepared from 21 g of para-formaldehyde) which had been cooled to −70° C. After the resulting solution was stirred at −78° C. for 30 minutes, white solids adhered to the vessel wall were smashed, 100 ml of water was added to the reaction solution, and the mixture was extracted with ethyl acetate (20 ml×5) and the extracts were dried over anhydrous sodium sulfate. After concentration, 150 mg of an oily crude product obtained was purified by column chromatography to give 913 mg (3.42 mmol, 78.2%) of a white solid. Recrystallization of the solid from 5 ml of cyclohexane petroleum ether (3:2) mixture afforded 800 mg of needles (mp 98°–102° C.).

IR (KBr) $v$cm$^{-1}$: 3300, 2980, 2930, 1180, 1010, 995, 945, 870, 830, 760, 710. NMR (CDCl$_3$) δ: 2.16 (1H, s), 2.78 (2H, m), 4.34 (1H, d, J=8.0 Hz), 4.57 (2H, s) 5.49 (1H, m), 5.63 (2H, m), 7.22 (2H, s). Mass (m/e): 266 (M+), 268.

Thereafter, in a similar manner, instead of 3a,8b-cis-dihydro-3H-5,7-dibromocyclopenta[b]benzofuran, when 3a,8b-cis-dihydro-3H-5-bromo-7-chlorocyclopenta[b]benzofuran is employed, 3a,8b-cis-dihydro-3H-7-chloro-5-hydroxymethylcyclopenta[b]benzofuran is obtained, and when 3a,8b-cis-dihydro-3H-5-bromo-7-methylcyclopenta[b]benzofuran is employed, 3a,8b-cis-dihydro-3H-5-hydroxymethyl-7-methylcyclopenta[b]benzofuran is obtained.

Referential Example 26

Methyl 3a,8b-cis-dihydro-3H-7-bromo-5-cyclopenta[b]benzofuranylmethyloxyacetate

To a suspension of 49.4 mg (2.06 mmol) of sodium hydride in 1 ml of dimethoxyethane, at 0° C. under argon atmosphere was added dropwise a solution of 256 mg (0.598 mmol) of 3a,8b-cis-dihydro-3H-7-bromo-5-hydroxymethyl-cyclopenta[b]benzofuran in 3 ml of DME and the resulting solution was stirred at 0° C. for 30 minutes. This solution was added to a solution of 456 mg (2.98 mmol) of methyl α-bromoacetate in 1 ml of a dimethoxyethane which had been cooled to −78° C. in advance, the temperature was raised to 0° C. and the resulting solution was stirred for 6 hours. 2 ml of a saturated aqueous solution of ammonium chloride was slowly added at 0° C., the resulting solution was extracted with ether (10 ml×3) and the extracts were dried over anhydrous sodium sulfate. 361 mg of an oily substance obtained after concentration was purified by column chromatography Merck Co.,'s Lobar Column, cyclohexane—ethyl acetate 4:1) to obtain 290.6 mg (0.957 mmol, 89.5%) of a white solid. Recrystallization from a cyclohexane—ethyl acetate mixture afforded 250 mg of needles (mp 81.5°–82.5° C.).

IR (KBr) $v$cm$^{-1}$: 2960, 2910, 1760, 1600, 1455, 1440, 1220, 1190, 1120, 995, 980, 940, 900, 870, 830, 760, 720. NMR (CDCl$_3$) δ: 2.80 (2H, m), 3.76 (3H, s), 4.13 (2H, s), 4.36 (1H, d, J=8.0 Hz), 4.55 (1H, d, J=12.0 Hz), 4.57 (1H, d, J=12.0 Hz), 5.50 (1H, m), 5.76 (2H, m), 7.29 (2H, m). Mass (m/e): 338, 340 (M+).

Thereafter, in a similar manner, instead of 3a,8b-cis-dihydro-3H-7-bromo-5-hyroxymethylcyclopenta[b]benzofuran, when 3a,8b-cis-dihydro-3H-7-chloro-5-hydroxymethyl-cyclopenta[b]benzofuran is employed, methyl 3a,8b-cis-dihydro-3H-7-chloro-5-cyclopenta[b]benzofuranylmethyl-oxyacetate is obtained, and when 3a,8b-cis-dihydro-3H-7-methyl-5-hydroxymethylcyclopenta[b]benzofuran is employed, methyl 3a,8b-cis-dihydro-3H-7-methyl-5-cyclopenta[b]benzofuranyl-methyl-oxyacetate is obtained.

Referential Example 27

Methyl 3a,8b-cis-dihydro-3H-7-bromo-5-cyclopenta[b]benzofuranylmethyloxyacetate

To a suspension of 49.4 mg (2.06 mmol) of sodium hydride 1 ml of dimethoxy ethane at 0° C. under argon atmosphere to which was added dropwise solution of 256 mg (0.958 mmol) of 3a,8b-cis-dihydro-3H-7-bromo-5-hydroxymethylcyclopenta[b]benzofuran in 3 ml of dimethoxyethane and the resulting solution was stirred at 0° C. for 30 minutes. This solution was added to a solution of 456 mg (2.98 mmol) of methyl α-bromoacetate in 1 ml of dimethoxyethane which had been cooled to −78° C., the temperature was raised to 0° C. and the resulting solution was stirred for 6 hours. Two ml of a saturated aqueous solution of ammonium chloride was slowly added at 0° C., the solution was extracted with ether (10 ml×3) and the extracts were dried over anhydrous sodium sulfate. After concentration, 361 mg of an oily substance obtained was purified by column chromatography (Merck Co.'s Lobar Column, cyclohexane-ethyl acetate 4:1) to give 290.6 mg (0.857 mmol, 89.5%) of a white solid 2. This solid was recrystallized from a cyclohexane—ethyl acetate mixture to yield 250 mg of needles (mp 81.5°-82.5° C.).

IR (KBr) $\nu cm^{-1}$: 2960, 2910, 1760, 1600, 1455, 1440, 1220, 1190, 1120, 995, 980, 940, 900, 870, 830, 760, 720. NMR (CDCl$_3$) δ: 2.80 (2H, m), 3.76 (3H, s), 4.13 (2H, s), 4.36 (1H, d, J=8.0 Hz), 4.55 (1H, d, J=12.0 Hz), 4.57 (1H, d, J=12.0 Hz), 5.50 (1H, m), 5.76(2H, m) 7.29 (2H, m). Mass (M/e): 338, 340 (M+).

Thereafter, in a similar manner, instead of 3a,8b-cis-dihydro-3H-7-bromo-3-hydroxymethylcyclopenta[b]benzofuran, when 3a,8b-cis-dihydro-3H-7-chloro-5-hydroxymethylcyclopenta[b]benzofuran is employed, methyl 3a,8b-cis-dihydro-3H-7-chloro-5-cyclopenta[b]benzofuranylmethyloxyacetate is obtained, and when 3a,8b-cis-dihydro-3H-7-methyl-5-hydroxymethylcyclopenta[b]benzofuran is employed, methyl 3a,8b-cis-dihydro-3H-7-methyl-5-cyclopenta[b]benzofuranylmethyloxy-acetate is obtained.

Referential Example 28

Ethyl 3a,8b-cis-dihydro-3H-7-bromo-5-cyclopenta[b]benzofuranylmethyloxyacetate

In a similar manner as in Referential Example 27, when ethylbromoacetate was employed instead of methyl α-bromoacetate, from 250 mg of 3a,8b-cis-dihydro-3H-7-bromo-5-hydroxymethylcyclopenta[b]benzofuran, 250 mg of an ester body was obtained.

IR (neat) $\nu cm^{-1}$: 2960, 2915, 1760, 1600, 1455, 1220, 1190, 995, 980, 940, 900, 870, 760. Mass (m/e): 352, 354 (M+).

Thereafter, in a similar manner, instead of 3a,8b-cis-dihydro-3H-7-bromo-5-hydroxymethylcyclopenta[b]benzofuran, when 3a,8b-cis-dihydro-3H-7-chloro-5-hydroxymethylcyclopenta[b]benzofuran is employed, ethyl 3a,8b-cis-dihydro-3H-7-chloro-5-cyclopenta[b]benzofuranylmethyloxyacetate is obtained, and when 3a,8b-cis-dihydro-3H-7-methyl-5-cyclopenta[b]benzofuran is employed, ethyl 3a,8b-cis-dihydro-3H-7-methyl-5-cyclopenta[b]benzofuranylmethyloxyacetate is obtained.

Referential Example 29

Benzyl 3a,8b-cis-dihydro-3H-7-bromo-5-cyclopenta[b]benzofuranylmethyloxyacetate

In a similar manner as in Referential Example 27, when benzyl α-bromoacetate was employed instead of methyl α-bromoacetate, from 250 mg of 3a,8b-cis-dihydro-3H-7-bromo-5-hydroxymethylcyclopenta[b]benzofuran, 260 mg of the subject compound was obtained.

IR (neat) $\nu cm^{-1}$: 2960, 2910, 1760, 1600, 1455, 1220, 1190, 995, 980, 830, 720. Mass (m/e): 414, 416 (M+).

Thereafter, in a similar manner, instead of 3a,8b-cis-dihydro-3H-7-bromo-5-hydroxymethylcyclopenta[b]benzofuran, when 3a,8b-cis-dihydro-3H-7-chloro-5-hydroxymethylcyclopenta[b]benzofuran is employed, 3a,8b-cis-dihydro-3H-7-chloro-cyclopenta[b]benzofuranylmethyloxyacetate is obtained, and when 3a,8b-cis-dihydro-3H-7-methyl-5-hydroxymethylcyclopenta[b]benzofuran is employed, benzyl 3a,8b-cis-dihydro-3H-7-methyl-5-cyclopenta[b]benzofuranylmethyloxy-acetate is obtained.

Referential Example 30

5-(3a,8b-cis-dihydro-3H-7-bromocyclopenta[b]benzofuranylmethyloxy)acetic acid

In a similar mannner as in Referential Example 27, when sodium α-bromoacetate was employed instead of methyl α-bromoacetate, from 250 mg of 5-(3a,8b-cis-dihydro-3H-7-bromo-5-hydroxymethylcyclopenta[b]benzofuran, 250 mg of 5-(3a,8b-cis-dihydro-3H-7-bromo-cyclopenta[b]benzofuranylmethyloxy)acetic acid was obtained.

IR (neat) $\nu cm^{-1}$: 3600-2300, 1710, 1600, 1190, 1120, 995, 940, 830, 750. Mass (m/e): 324, 326 (M+).

Thereafter, in a similar manner, instead of 3a,8b-cis-dihydro-3H-7-bromo-5-hydroxymethylcyclopenta[b]benzofuran, when 3a,8b-cis-dihydro-3H-7-chloro-5-hydroxymethylcyclopenta[b]benzofuran is employed, 5-(3a,8b-cis-dihydro-3H-7-chlorocyclopenta[b]benzofuranyl)methyloxyacetic acid is obtained, and when 3a,8b-cis-dihydro-3H-7-methyl-5-hydroxymethylcyclopenta[b]benzofuran is employed, 3a,8b-dihydro-3H-7-methyl-5-cyclopenta[b]benzofuranylmethyloxyacetic acid is obtained.

Referential Example 31

3a,8b-cis-dihydro-3H-7-bromo-5-(2-hydroxyethyloxy)-methylcyclopenta[b]benzofuran To a suspension of 200 mg of lithium aluminium hydride in 5 ml of anhydrous THF, at 0° C. under argon atmosphere was added a solution of 200 mg of methyl 3a,8b-cis-dihydro-3H-7-bromo-5-cyclopenta[b]benzofuranylmethoxyacetate in 5 ml of anhydrous THF and the resulting mixture was stirred at room temperature for 2 hours. Ethyl acetate and a saturated aqueous solution of sodium potassium tartarate was added and the produced precipitate was filtered. The filtrate was dried and thereafter concentrated to give 200 mg of an oily substance. This oily substance was purified by column chromatography [silica gel; cyclohexane:ethyl acetate (1:7)] to yield 150 mg of the alcohol.

IR (neat) $\nu cm^{-1}$: 3400, 1600, 1190, 1120, 1010, 995, 830, 730. Mass (m/e): 310, 312 (M+).

Thereafter, in a similar manner, instead of methyl 3a,8b-cis-dihydro-3H-7-bromocyclopenta[b]benzofuranylmethoxyacetate, when methyl 3a,8b-cis-dihydro-3H-7-chloro-5-cyclopenta[b]benzofuranylmethoxyacete is employed, 3a,8b-cis-dihydro-3H-7-chloro-5-(2-hydroxyethyloxy)methylcyclopenta[b]benzofuran is obtained, and when methyl 3a,8b-cis-dihydro-3H-7-methyl-5-cyclopenta[b]benzofuranylmethoxyacetate is employed, 3a,8b-cis-dihydro-3H-7-methyl-5-(2-hydroxyethyloxy)methylcyclopenta[b]benzofuran was obtained.

Referential Example 32

3a,8b-cis-dihydro-3H-7-bromo-5-(2-tetrahydropyranyloxyethyloxy)methylcyclopenta[b]benzofuran To a solution of 500 mg of 3a,8b-cis-dihydro-3H-7-bromo-5-hydroxyethyloxymethylcyclopenta[b]benzofuran in 2.5 ml of methylene chloride, was added 400 mg of dihydropyran. 0.25 ml of a solution of 1.8 g of p-toluenesulfonic acid in 50 ml of THF dried with a molecular sieve was added to the above mentioned solution under ice cold conditions, and the resulting mixture was stirred at room temperature for 10 minutes.

Pyridine was added and the resulting mixture was stirred for 30 minutes, thereafter, washed with 50% brine and saturated brine and dried and concentrated to give 600 mg of an oily substance.

This oily substance was purified by column chromatography (silica gel; ethyl acetate:cyclohexane (4:1)) to yield 500 mg of an oily substance.

IR (neat) $vcm^{-1}$: 1590, 1440, 1340, 1065, 1010, 855, 810, 748. Mass (m/e): 394, 396 (M+).

Thereafter, in a similar manner, instead of 3a,8b-cis-dihydro-3H-7-bromo-5-(2-hydroxyethyloxy)methylcyclopenta[b]benzofuran, when 3a,8b-cis-dihydro-3H-7-chloro-5-(2-hydroxyethyloxy)methylcyclopenta[b]benzofuran is employed, 3a,8b-cis-dihydro-3H-7-chloro-5-(2-tetrahydropyranyloxyethyloxy)methyloxycyclopenta[b]benzofuran is obtained, and when 3a,8b-cis-dihydro-3H-7-methyl-5-(2-hydroxyethyloxy)methylcyclopenta[b]benzofuran is employed, 3a,8b-cis-dihydro-3H-7-methyl-5-(2-tetrahydropyranyloxyethyloxy)-methyl-cyclopenta[b]benzofuran is obtained.

Referential Example 33

Methyl 1,2,3a,8b-cis-tetrahydro-7-bromo-1,2-syn-epoxy-5-cyclopenta[b]benzofuranylmethyloxyacetate To a solution of 274 mg (0.809 mmol) of methyl 3a,8b-cis-dihydro-3H-7-bromocyclopenta[b]benzofuranylmethyloxyacetate in 5 ml of a dimethyl sulfoxide—water (19:1) mixture and 0.9 ml of tetrahydrofuran was added, 218 mg (1.11 mmol, 1.5 equiv.) of imide N-bromosuccinate and the resulting mixture was stirred at room temperature for 3.5 hours, subsequently, 330 mg (2.39 mmol, 3.0 equiv.) of potassium carbonate and 8 ml of methanol and 8 ml of water were added to make the resulting mixture homogeneous, which was further stirred for 15 hours. After the solvent was distilled off under reduced pressure, 4 ml of saturated brine was added and the mixture was extracted with ethyl acetate (20 ml×5) and the extract were dried over anhydrous sodium sulfate. After concentration 461 mg of an oily substance obtained was purified by column chromatography (Merck Co.'s Lobar Column: cyclohexane-ethyl acetate(1:2)) to give 185 mg of crude crystals. This crude crystals were recrystallized from an ethyl acetate—cyclohexane mixture to yield 150 mg of needles (mp 100°–102° C.).

IR (KBr) $vcm^{-1}$: 3050, 3950, 1760, 1600, 1455, 1190, 1140, 975, 970, 840, 760, 710. NMR (CDCl$_3$) δ: 2.25 (1H, ddd, J=0.5 Hz, 7.0 Hz, 16.0 Hz), 2.45 (1H, d, J=16.0 Hz), 3.68 (3H, m), 3.73 (3H, s), 4.09 (2H, s), 4.50 (1H, d, J=12.0 Hz), 4.52 (1H, d J=12.0 Hz), 5.30 (1H, t, J=7.0 Hz), 7.31 (1H, d, J=2.0 Hz), 7.34 (1H, d, J=2.0 Hz). Mass (m/e): 354, 356 (M+).

Thereafter, in a similar manner, instead of methyl 3a,8b-cis-dihydro-3H-7-bromo-5-cyclopenta[b]benzofuranylmethyloxyacetate, when methyl 3a,8b-cis-dihydro-3H-7-chloro-5-cyclopenta[b]benzofuranylmethyloxyacetate is employed, methyl 1,2,3a,8b-cis-tetrahydro-7-chloro-1,2-syn-epoxy-5-cyclopenta[b]benzofuranylmethyloxyacetate is obtained, and when methyl 3a,8b-cis-dihydro-3H-7-methyl-5-cyclopenta[b]benzofuranylmethyloxyacetate is employed, methyl 1,2,3a,8b-cis-tetrahydro-7-methyl-1,2-syn-epoxy-5-cyclopenta[b]benzofuranylmethyloxyacetate is obtained.

Referential Example 34

Ethyl 1,2,3a,8b-cis-tetrahydro-7-bromo-1,2-syn-epoxy-5-cyclopenta[b]benzofuranylmethyloxyacetate In a similar manner as in Referential Example 33, when 250 mg of ethyl 3a,8b-cis-dihydro-3H-7-bromo-5-cyclopenta[b]benzofuranylmethoxyacetate was employed instead of methyl 3a,8b-cis-dihydro-3H-7-bromo-5-cyclopenta[b]benzofuranylmethoxyacetate, 150 mg of ethyl 1,2,3a,8b-cis-tetrahydro-7-bromo-1,2-syn-epoxy-5-cyclopenta[b]benzofuranylmethyloxyacetate was obtained.

IR (neat) $vcm^{-1}$: 3050, 2950, 1760, 1600, 1455, 1190, 1140, 975, 870, 840, 760, 710. Mass (m/e): 368, 370 (M+).

Thereafter, in a similar manner, instead of ethyl 3a,8b-cis-dihydro-3H-7-bromo-5-cyclopenta[b]benzofuranylmethoxyacetate, when ethyl 3a,8b-cis-dihydro-3H-7-chloro-5-cyclopenta[b]benzofuranylmethyloxyacete is employed, ethyl 1,2,3a,8b-cis-tetrahydro-7-chloro-1,2-syn-epoxy-5-cyclopenta[b]benzofuranylmethyloxyacetate is obtained, and when ethyl 3a,8b-cis-dihydro-3H-7-methyl-5-cyclopenta[b]benzofuranylmethyloxyacetate is employed, ethyl 1,2,3a,8b-cis-tetrahydro-7-methyl-1,2-syn-epoxy-5-cyclopenta[b]benzofuranylmethyloxyacetate is obtained.

Referential Example 35

Benzyl 1,2,3a,8b-cis-tetrahydro-7-bromo-1,2-syn-epoxy-5-cyclopenta[b]benzofuranylmethyloxyacetate In a similar manner as in Referential Example 33, when 250 mg of benzyl 3a,8b-cis-dihydro-3H-7-bromo-5-cyclopenta[b]benzofuranylmethoxyacetate was employed instead of methyl 3a,8b-cis-dihydro-3H-7-bromo-5-cyclopenta[b]benzofuranylmethoxyacetate, 250 mg of benzyl 1,2,3a,8b-cis-tetrahydro-7-bromo-1,2-syn-epoxy-5-cyclopenta[b]benzofuranylmethyloxyacetate was obtained.

IR (neat) $vcm^{-1}$: 3050, 2950, 1760, 1600, 1190, 975, 870, 845, 760, 710. Mass (m/e): 430, 432 (M+).

Thereafter, in the same manner, instead of benzyl 3a,8b-cis-dihydro-3H-7-bromo-5-cyclopenta[b]benzofuranylmethyloxyacetate, when benzyl 3a,8b-cisdihydro-3H-7-chloro-5-cyclopenta[b]benzofuranylmethoxyacetate is employed, benzyl 1,2,3a,8b-cis-tetrahydro-7-chloro-1,2-syn-epoxy-5-cyclopenta[b]benzofuranylmethyloxyacetate is obtained, and when benzyl 3a,8b-cis-dihydro-3H-7-methyl-5-cyclopenta[b]benzofuranylmethyloxyacetate is employed, benzyl 1,2,3a,8b-cis-tetrahydro-7-methyl-1,2-syn-epoxy-5-cyclopenta[b]benzofuranylmethyloxyacetate is obtained.

Referential Example 36

1,2,3a,8b-cis-tetrahydro-7-bromo-1,2-syn-epoxy-5-hydroxyethoxymethylcyclopenta[b]benzofuran In the same manner as in Referential Example 33, when 200 mg of 3a,8b-cis-dihydro-3H-7-bromo-5hydroxyethyloxymethylcyclopenta[b]benzofuran is employed instead of methyl 3a,8b-cis-dihydro-3H-7-bromo-5-cyclopenta[b]benzofuranylmethyloxyacetate, 150 mg of 1,2,3a,8b-cis-tetrahydro-7-bromo-1,2-syn-epoxy-5-hydroxyethyloxymethylcyclopenta[b]benzofuran is obtained.

IR (neat) νcm$^{-1}$: 3400, 1600, 1190, 1120, 1010, 995, 850, 830, 730. Mass (m/e): 326, 328 (M+).

Thereafter, in a similar manner, instead of 3a,8b-cis-dihydro-3H-7-bromo-5-hydroxyethyloxymethylcyclopenta[b]benzofuran, when 3a,8b-cis-dihydro-3H-7-chloro-5-hydroxyethyloxymethylcyclopenta[b]benzofuran is employed, 1,2,3a,8b-cis-tetrahydro-7-chloro-1,2-syn-epoxy-5-hydroxyethyloxymethylcyclopenta[b]benzofuran is obtained, and when 3a,8b-cis-dihydro-3H-7-methyl-5-hydroxyethyloxymethylcyclopenta[b]benzofuran is employed, 1,2,3a,8b-cis-tetrahydro-7-methyl-1,2-syn-epoxy-5-hydroxyethyloxymethylcyclopenta[b]benzofuran is obtained.

Referential Example 37

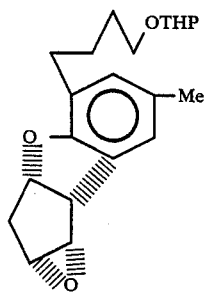

1,2,3a,8b-cis-tetrahydro-5-(4-tetrahydropyranyloxy-n-butyl)-7-methyl-1,2-syn-epoxycyclopenta[b]benzofuran To a solution of 9.13 g (27.8 mmol) of 3a,8b-cis-dihydro-3H-5-(4-tetrahydropyranyloxy-n-butyl)-7-methylcyclopenta[b]benzofuran in 230 ml of a dimethyl sulfoxide-water (18:1) mixture was added 40 ml of THF and 26.7 g (150 mmol, 5.4 equiv.) of imide N-bromosuccinate, and the resulting mixture was stirred at 0°–5° C. for 1 hour.

After confirming the loss of the starting material by TLC, 100 ml of methanol and 70 ml of water and 41.0 g (297 mmol, 10.7 equiv.) of potassium carbonate were added, and the resulting mixture was stirred at room temperature for 2.5 hours. After distilling off the solvent at a temperature less than 50° C., 100 ml of saturated brine was added and the mixture was extracted with 250 ml (50 ml×5) of ether, the combined organic layers were washed with 50 ml of saturated brine. After distilling off the solvent, when the resulting residue was purified by column chromatography (Merck silica gel, Art 7734 500 g, cyclohexane: ethyl acetate 50:1→3:1), 8.08 g of an oily substance was obtained.

IR (neat) νcm$^{-1}$: 3020, 2930, 2860, 1610, 1475, 1215, 1200, 1140, 1120, 1035, 870, 850, 780, 740. NMR (CDCl$_3$) δ: 1.64 (10H, m), 1.98 (1H, ddd, J=15.0 Hz, 3.0 Hz, 2.0 Hz), 2.28 (3H, s), 2.55 (2H, m), 2.62 (1H, dd, J=1.50 Hz, 8.0 Hz), 3.45 (2H, m), 3.52 (1H, t, J=2.0 Hz), 3.69 (1H, d, J=2.0 Hz), 3.82 (2H, m), 4.11 (1H, d, J=8.0 Hz), 4.58 (1H, m), 4.99 (1H, dt, J=8.0 Hz, 3.0 Hz), 6.82 (1H, s), 6.90 (1H, s). Mass (m/e): 344 (M+).

Referential Example 38

1,2,3a,8b-cis-tetrahydro-5-(4-tetrahydropyranyloxy-n-butyl)-7-bormo-1,2-syn-epoxycyclopenta[b]benzofuran In a similar manner as in Referential Example 37, from 1 g of 3a,8b-cis-dihydro-3H-5-(4-tetrahydropyranyloxy-n-butyl)-7-bromocyclopenta[b]benzofuran, 800 mg of 1,2,3a,8b-cis-tetrahydro-3H-5-(4-tetrahydropyranyloxy-n-butyl)-7-bromo-1,2-syn-epoxycyclopenta[a]benzofuran was obtained.

IR (neat) νcm$^{-1}$: 1605, 1590, 1195, 1035, 845, 735, 755. NMR (CDCl$_3$) δ: 1.4~1.8 (10H, m), 2.50 (3H, m), 3.40 (2H, m), 3.64 (4H, m), 3.80 (2H, m) 4.60 (1H, m), 5.34 (1H, t, J=8.0 Hz), 7.12 (1H, d, J=2.0 Hz), 7.21 (1H, d, J=2.0 Hz). Mass (m/e): 408, 410 (M$^{30}$).

Thereafter, in a similar manner, when 3a,8b-cis-dihydro-3H-5-(4-tetrahydropyranyloxy-n-butyl)-7-chlorocyclopenta[b]benzofuran is employed instead of 3a,8b-cis-dihydro-3H-5-(tetrahydropyranyloxy-butyl)-7-bromocyclopenta[b]benzofuran, 1,2,3a,8b-cis-tetrahydro-5-(4-tetrahydropyranyloxy-n-butyl)-7-chloro-1,2-syn-epoxycyclopenta[b]benzofuran is obtained.

Referential Example 39

1,2,3a,8b-cis-tetrahydro-5-tetrahydropyranyloxyethyloxymethyl-7-bromo-1,2-syn-epoxycyclopenta[b]benzofuran In a similar manner as in Referential Example 37, from 1 g of 3a,8b-cis-dihydro-3H-5-tetrahydropyranyloxyethyloxymethyl-7-bromo-cyclopenta[b]benzofuran, 800 mg of the subject compound was obtained.

IR (neat) νcm$^{-1}$: 1605, 1590, 1195, 1035, 845, 735, 755. Mass (m/e): 410, 412 (M+).

Thereafter, in a similar manner, instead of 3a,8b-cis-dihydro-3-H-tetrahydropyranyloxyethyloxymethyl-7-bromocyclopenta[b]benzofuran, when 3a,8b-cis-dihydro-3H-5-tetrahydropyranyloxyethyloxymethyl-7-chlorocyclopenta[b]benzofuran is employed, 1,2,3a,8b-cis-tetrahydro-5-tetrahydropyranyloxyethyloxymethyl-7-chloro-1,2-syn-epoxycyclopenta[b]benzofuran is obtained, and when 3a,8b-cis-dihydro-3H-5-tetrahydropyranyloxyethyloxy-7-methylcyclopenta[b]benzofuran is employed, 1,2,3a,8b-cis-tetrahydro-5-tetrahydropyranyloxyethyloxymethyl-7-methyl-1,2-syn-epoxycyclopenta[b]benzofuran is obtained.

Referential Example 40

1,2,3a,8b-cis-tetrahydro-5-(4-hydroxy-n-butyl)-7-bromo-1,2-syn-epoxycyclopenta[b]benzofuran In a similar manner as in Referential Example 37, from 1 g of 3a,8b-cis-dihydro-3H-5-(4-hydroxy-n- butyl)-7-bromocyclopenta[b]benzofuran, 700 mg of the subject compound was obtained.

IR (neat) νcm⁻¹: 3400, 1600, 1190, 1010, 850, 730. NMR (CDCl₃) δ: 1.4~1.9 (5H, m), 2.22 (1H, dd, J=16.0 Hz, 6.6 Hz), 2.50 (3H, m) 3.40–4.00 (5H, m), 5.32 (1H, t, J=8.0 Hz), 7.10 (1H, d, J=2.0 Hz), 7.20 (1H, d, J=2.0 Hz). Mass (m/e): 324, 326 (M+).

Thereafter, in a similar manner, instead of 3a,8b-cis-dihydro-3H-5-(4-hydroxy-n-butyl)-7-bromocyclopenta[b]benzofuran, when 3a,8b-cis-dihydro-3H-5-(4-hydroxy-n-butyl)-7-chlorocyclopenta[b]benzofuran is employed, 1,2,3a,8b-cis-tetrahydro-5-(4-hydroxy-n-butyl)-7-chloro-1,2-syn-epoxycyclopenta[b]benzofuran is obtained, and when 3a,8b-cis-dihydro-3H-5-(4-hydroxy-n-butyl)-7-methylcyclopenta[b]benzofuran is employed, 1,2,3a,8b-cis-tetrahydro-5-(4-hydroxy-n-butyl)-7-methyl-1,2-syn-epoxycyclopenta[b]benzofuran is obtained.

Referential Example 41

1,2,3a,8b-cis-tetrahydro-5-(3-carbomethyoxy-n-propyl)-7-bromo-1,2-syn-epoxycyclopenta[b]benzofuran In a similar manner as in Referential Example 37, from 1 g of 3a,8b-cis-dihydro-3H-5-(3-carbomethoxy-n-propyl)-7-bromo-cyclopenta[b]benzofuran, 700 mg of the epoxide was obtained.

IR (neat) νcm⁻¹: 1738, 1605, 1580, 1190, 1000, 850, 710. Mass (m/e): 352, 354 (M+).

Thereafter, in a similar manner, instead of 3a,8b-cis-dihydro-3H-5-(3-carbomethoxy-n-propyl)-7-bromocyclopenta[b]benzofuran, when 3a,8b-cis-dihydro-3H-5-(3-carbomethoxy-n-propyl)-7-chlorocyclopenta[b]benzofuran is employed, 1,2,3a,8b-cis-tetrahydro-5-(3-carbomethoxy-n-propyl)-7-chloro-1,2-syn-epoxycyclopenta[b]benzofuran is obtained, and when 3a,8b-cis-dihydro-3H-5-(3-carbomethoxy-n-propyl)-7methyl cyclopenta[b]benzofuran is employed, 1,2,3a,8b-cis-tetrahydro-5-(3-carbomethoxy-n-propyl)-7-methyl-1,2-syn-epoxycyclopenta[b]benzofuran is obtained.

Referential Example 42

1,2,3a,8a-cis-tetrahydro-5-(3-carboethoxy-n-propyl)-7-bromo-1,2-syn-epoxycyclopenta[b]benzofuran In a similar manner as in Referential Example 37, from 1 g of 3a,8b-cis-dihydro-3H-5-(3-carboethoxy-n-propyl)-7-bromocyclopenta[b]benzofuran, 800 mg of the epoxide was obtained.

IR (neat) νcm⁻¹: 1738, 1605, 1580, 1190, 1000, 850, 710. Mass (m/e): 366, 368 (M+).

Thereafter, in a similar manner, from 3a,8b-cis-dihydro-3H-5-(3-carboethoxy-n-propyl)-7-chlorocyclopenta[b]benzofuran, 1,2,3a,8b-cis-tetrahydro-5-(3-carboethoxy-n-propyl)-7-chloro-1,2-syn-epoxycyclopenta[b]benzofuran is obtained, and from 3a,8b-cis-dihydro-3H-5-(3-carboethoxy-n-propyl)-7-methylcyclopenta[b]benzofuran, 1,2,3a,8b-cis-tetrahydro-5-(3-carboethoxy-n-propyl)-7-methyl-1,2-syn-epoxycyclopenta[b]benzofuran is obtained.

Referential Example 43

1,2,3a,8b-cis-tetrahydro-5-(3-carbobenzyloxy-n-propyl)-7-bromo-1,2-syn-epoxycyclopenta[b]benzofuran In a similar manner as in Referential Example 37, from 1 g of 3a,8b-cis-dihydro-3H-5-(3-carbobenzyloxy-n-propyl)-7-bromocyclopenta[b]benzofuran, 700 mg of the epoxide was obtained.

IR (neat) νcm⁻¹: 1739, 1609, 1580, 1190, 1000, 890, 710. Mass (m/e): 428, 430 (M+).

Thereafter, in a similar manner, from 3a,8b-cis-dihydro-3H-5-(3-carbobenzyloxy-n-propyl)-7-chlorocyclopenta[b]benzofuran, 1,2,3a,8b-cis-tetrahydro-5-(3-carbobenzyloxy-n-propyl)-7-chloro-1,2-syn-epoxycyclopenta[b]benzofuran is obtained, and from 3a,8b-cis-dihydro-3H-5-(3-carbobenzyloxy-n-propyl)-7methylcyclopenta[b]benzofuran, 1,2,3a,8b-cis-tetrahydro-5-(3-carbobenzyloxy-n-propy)-7-methyl-1,2-synepoxycyclopenta[b]benzofuran is obtained.

Referential Example 44

1,2,3a,8b-cis-tetrahydro-5-(3-carboxy-n-propyl)-7-bromo-1,2-syn-epoxycyclopenta[b]benzofuran To a solution of 250 mg of 3a,8b-cis-dihydro-3H-5-(3-carboxy-n-propyl)-7-bromocyclopenta[b]benzofuran in 5 ml of a DMSO-Water (19:1) mixture and 0.5 ml of THF, was added 218 mg of NBS and the resulting mixture was stirred at room temperature for 3.5 hours. To the mixture were added 330 mg of potassium carbonate, 8 ml of methanol and 8 ml of water and the resulting mixture was further stirred for 15 hours. The reaction mixture was concentrated, water was added and the PH value of the mixture was adjusted to 3-4 with 1N hydrochloric acid under ice cold conditions and the mixture was extracted 3 times with ethyl acetate. The combined organic layer was washed with water and saturated brine, dried and thereafter, when it was concentrated, 460 mg of an oily substance was obtained. When this oily substance was purified by column chromatography (silica gel (which had been treated with acetic acid): ethyl acetate:cyclohexane (2:1), 170 mg of the subject compound was obtained. IR (neat) νcm⁻¹: 3600–2300, 1705, 1605, 1585, 1190, 1000, 850, 710. NMR (CDCl₃) δ: 1.95 (2H, m), 2.30 (2H, t, J=7.0 Hz), 2.55 (2H, t, J=7.0 Hz), 2.10–2.60 (2H, m), 3.66 (2H, s), 3.72 (1H, m), 5.25 (1H, t, J=7.0 Hz), 7.07 (1H, d, J=1.5 Hz), 7.25 (1H, d, J=1.5 Hz). Mass (m/e): 338, 340 (M+).

Thereafter, in a similar manner, when 3a,8b-cis-dihydro-3H-5-(3-carboxy-n-propyl)-7-chlorocyclopenta[b]benzofuran is employed, 1,2,3a,8b-cis-tetrahydro-5-(3-carboxy-n-propyl)-7-chloro-1,2-syn-epoxycyclopenta[b]benzofuran is obtained, and when 3a,8b-cis-dihydro-3H-5-(3-carboxy-n-propyl)-7-methylcyclopenta[b]benzofuran is employed, 1,2,3a,8b-cis-tetrahydro-5-(3-carboxy-n-propyl)-7-methyl-1,2-syn-epoxycyclopenta[b]benzofuran is obtained.

Referential Example 45

1,2,3a,8b-cis-tetrahydro-7-bromo-1,2-syn-epoxy-5-cyclopenta[b]benzofuranylmethyloxyacetic acid In a similar manner as in Referential Example 44, from 250 mg of 5-(3a,8b-cis-dihydro-3-H-7-bromocyclopenta[b]benzofuranylmethoxy) acetic acid, 150 mg of the subject compound was obtained.

IR (neat) νcm⁻¹: 3600–2300, 1705, 1605, 1585, 1190, 1140, 1050, 1000, 845, 710. Mass (m/e): 340, 342 (M+).

Thereafter, in a similar manner, from 3a,8b-cis-dihydro-3H-7-chloro-5-cyclopenta[b]benzofuranylmethyloxyacetic acid, 1,2,3a,8b-cis-tetrahydro-7-chloro-1,2-syn-epoxy-5-cyclopenta[b]benzofuranyl methyloxyacetic acid was obtained, and from 3a,8b-cis-dihydro-3H-7-methyl-5-cyclopenta[b]benzofuranylmethyloxyacetic acid, 1,2,3a,8b-cis-tetrahydro-7-methyl-1,2-synepoxycyclopenta[b]benzofuranylmethyloxy acetic acid was obtained.

Referential Example 46

Methyl 1,2,3a,8b-cis-tetrahydro-1,2-syn-epoxycyclopenta[b-]benzofuranylmethyloxyacetate

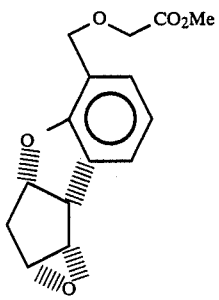

To a solution of 247 mg (0.695 mmol) of methyl 1,2,3a,8b-cis-tetrahydro-7-bromo-1,2-syn-epoxy-5-cyclopenta[b]benzofuranylmethoxyacetate and 205 mg (2.45 mmol) of sodium acetate in 30 ml of methanol was added 147 mg of 5% palladium-barium sulfate, and the resulting mixture was vigorously stirred at room temperature under hydrogen atmosphere for 1.5 hours. Palladiuim was removed by filtration, methanol was distilled off under reduced pressure, 5 ml of saturated brine and 5 ml of a saturated aqueous solution of sodium bicarbonate was added, and the mixture was extracted with ethyl acetate (10 ml×5). The combined extracts were dried over anhydrous sodium sulfate. After concentration, when 200 mg of an oil substance obtained was purified by column chromatography (Merck Co.'s Lobar Column; cyclohexane-ethyl acetate 1:2), 183 mg of a white solid was obtained. This solid was recrystalized from a cyclohexane-ether mixture to yield 150 mg of the subject compound as needles (mp 60°-62° C.).

IR (KBr) $\nu cm^{-1}$: 3020, 2950, 1750, 1600, 1260, 1120, 1030, 1000, 970, 860, 845, 780, 755. NMR (CDCl₃) δ: 2.29 (1H, dd, J=15.0 Hz, 7.0 Hz), 2.50 (1H, d, J=16.0 Hz), 3.72 (3H, m), 3.74 (3H, s), 4.10 (2H, s), 4.59 (1H, t, J=12.0 Hz), 4.62 (1H, d, J=12.0 Hz), 5.35 (1H, t, J=7.0 Hz), 6.87 (1H, dd, J=8.0 Hz, 6.0 Hz), 7.23 (1H, d, J=6.0 Hz), 7.24 (1H, d, J=8.0 Hz). Mass (m/e): 276 (M+).

Referential Example 47

Ethyl 1,2,3a,8b-cis-tetrahydro-1,2-syn-epoxycyclopenta[b-]benzofuranylmethyloxyacetate In a similar manner as in Referential Example 46, from 250 mg of ethyl 3a,8b-cis-tetrahydro-7-bromo-1,2-syn-epoxy-5-cyclopenta[b]benzofuranylmethoxyacetate, 153 mg of the debrominated compound was obtained.

IR (neat) $\nu cm^{-1}$: 3020, 2950, 1760, 1600, 1260, 1030, 970, 845, 860, 780. Mass (m/e): 290 (M+).

Referential Example 48

Benzyl 1,2,3a,8b-cis-tetrahydro-1,2-syn-epoxycyclopenta[b-]benzofuranylmethyloxyacetate In a similar manner as in Referential Example 46, from 250 mg of benzyl 1,2,3a,8b-cis-tetrahydro-7-bromo-1,2-syn-epoxycyclopenta[b]benzofuranylmethoxyacetate, 120 mg of the debrominated compound was obtained.

IR (neat) $\nu cm^{-1}$: 3020, 2950, 1760, 1600, 1260, 1120, 1030, 970, 845, 780. Mass (m/e): 352 (M+).

Referential Example 49

1,2,3a,8b-cis-tetrahydro-1,2-syn-epoxy-5-hydroxyethyloxymethylcyclopenta[b]benzofuran In a similar manner as in Referential Example 46, from 250 mg of 1,2,3a,8b-cis-tetrahydro-7-bromo-1,2-syn-epoxy-5-hydroxyethyloxymethylcyclopenta[b]benzofuran, 150 mg of the debrominated compound was obtained.

IR (neat) $\nu cm^{-1}$: 3400, 1600, 1190, 1120, 1010, 995 850, 830, 730. Mass (m/e): 248 (M+).

Referential Example 50

1,2,3a,8b-cis-tetrahydro-5-tetrahydropyranyloxyethyloxymethyl-1,2-syn-epoxycyclopenta[b]benzofuran In a similar manner as in Referential Example 46, from 250 mg of 1,2,3a,8b-cis-tetrahydro-5-tetrahydropyranyloxyethyloxymethyl-7-bromo-1,2-syn-epoxycyclopenta[b]benzofuran, 120 mg of the debrominated compound was obtained.

IR (neat) $\nu cm^{-1}$: 1605, 1590, 1195, 1035, 845, 735, 755. Mass (m/e): 332 (M+).

Referential Example 51

1,2,3a,8b-cis-tetrahydro-5-(3-carbomethoxy-n-propyl)-1,2-syn-epoxycyclopenta[b]benzofuran In a similar manner as in Referential Example 46, from 250 mg of 1,2,3a,8b-cis-tetrahydro-5-(3-carbomethoxy-n-propy)-7-bromo-1,2-syn-epoxycyclopenta[b-]benzofuran, 140 mg of the debrominated compound was obtained.

IR (neat) $\nu cm^{-1}$: 1738, 1605, 1580, 1190, 1000, 850, 710. NMR (CDCl₃) δ: 1.60 (2H, m) 1.90 (2H, t, J=7.0 Hz), 2.00–2.70 (4H, m), 3.62 (3H, s), 3.68 (2H, s), 3.77 (1H, d, J=8.0 Hz), 5.20 (1H, t, J=7.0 Hz), 6.80 (1H, t, J=7.0 Hz), 7.04 (1H, dd, J=7.0 Hz, 1.5 Hz), 7.14 (1H, dd, J=7.0 Hz, 1.5 Hz). Mass (m/e): 274 (M+).

Referential Example 52

1,2,3a,8b-cis-tetrahydro-5-(3-carboethoxy-n-propyl)-1,2-syn-epoxycyclopenta[b]benzofuran In a similar manner as in Referential Example 46, from 250 mg of 1,2,3a,8b-cis-tetrahydro-5-(3-carboethoxy-n-propyl)-7-bromo-1,2-syn-epoxycyclopenta[b-]benzofuran, 160 mg of the debrominated compound was obtained.

IR (neat) $\nu cm^{-1}$: 1738, 1605, 1580, 1000, 850, 710. Mass (m/e): 288 (M+).

Referential Example 53

1,2,3a,8b-cis-tetrahydro-5-(3-carbobenzyloxy-n-propyl)-1,2-syn-epoxycyclopenta[b]benzofuran In a similar manner as in Referental Example 46, from 250 mg of 1,2,3a,8b-cis-tetrahydro-5-(3-carbobenzyloxy-n-propyl)-7-bromo-1,2-syn-epoxycyclopenta[b-]benzofuran, 100 mg of the debrominated compound was obtained.

IR (neat) $\nu cm^{-1}$: 1738, 1605, 1580, 1000, 850, 710. Mass (m/e): 350 (M+).

Referential Example 54

1,2,3a,8b-cis-tetrahydro-5-(4-hydroxy-n-butyl)-1,2-syn-epoxycyclopenta[b]benzofuran In a similar manner as in Referential Example 46, from 250 mg of 1,2,3a,8b-cis-tetrahydro-5-(4-hydroxy-n-butyl)-7-bromo-1,2-syn-epoxy-cyclopenta[b]benzofuran, 160 mg of the debrominated compound was obtained.

IR (neat) $v cm^{-1}$: 3400, 1600, 1190, 1010, 850, 730. Mass (m/e): 246 (M+).

Referential Example 55

1,2,3a,8b-cis-tetrahydro-5-(4-tetrahydropyranyloxy-n-butyl)-1,2-syn-epoxycyclopenta[b]benzofuran In a similar manner as in Referential Example 46, from 250 mg of 1,2,3a,8-cis-tetrahydro-5-(4-tetrahydropyranyloxy-n-butyl)-7-bromo-1,2-syn-epoxycyclopenta[b]benzofuran, 150 mg of the debrominated compound was obtained.

IR (neat) $v cm^{-1}$: 3030, 2920, 2850, 1590, 1470, 1445, 1220, 1180, 1130, 1110, 1065, 1025, 965, 840, 745. NMR (CDCl$_3$) δ: 1.40–1.80 (10H, m), 2.20 (1H, dd, J=160 Hz, 6.6 Hz), 2.50 (3H, m), 3.50 (2H, m), 3.64 (2H, m), 3.70 (2H, m), 3.84 (1H, m), 4.56 (1H, s), 5.30 (1H, t, J=8.0 Hz), 6.70–7.30 (3H, m). Mass (m/e): 330 (M+).

Referential Example 56

1,2,3a,8b-cis-tetrahydro-5-(3-carboxy-n-propyl)-1,2-syn-epoxycyclopenta[b]benzofuran To a solution of 250 mg of 1,2,3a,8b-cis-tetrahydro-3H-5-(3-carboxy-n-propyl)-7-bromo-1,2-syn-epoxycyclopenta[b]benzofuran in 30 ml of methanol, were added 205 mg of sodium acetate and 147 mg of 5% palladium-barium sulfate, and the resulting mixture was stirred at room temperature under H$_2$ atmosphere for 1.5 hours. Palladium was filtered, the filtrate was concentrated, water was added, and the pH of the mixture was adjusted to 3-4 with 0.5M hydrochloric acid under ice cold conditions. The mixture was extracted 3 times with ethyl acetate and the combined organic layer was washed with water and saturated brine, dried, and thereafter concentrated to give 180 mg of an oily substance. This oily substance was purified by column chromatography (silica gel (which had been treated with acetic acid); cyclohexane:acetic acid (1:2)) to yield 150 mg of the pure carboxylic acid.

IR (neat) $v cm^{-1}$: 3600–2300, 1705, 1590, 1185, 850. NMR (CDCl$_3$) δ: 1.95 (2H, m), 2.30 (2H, t, J=7.0 Hz), 2.55 (2H, t, J=7.0 Hz), 2.10–2.60 (2H, m), 3.66 (2H, s), 3.72 (1H, m), 5.25 (1H, t, J=7.0 Hz), 6.78 (1H, t, J=7.0 Hz), 6.94 (1H, dd, J=7.0 Hz, 1.2 Hz), 7.20 (1H, dd, J=7.0 Hz, 1.2 Hz). Mass (m/e): 260 (M+).

Referential Example 57

5-(1,2,3a,8b-cis-tetrahydro-1,2-syn-epoxycyclopenta[b]benzofuranylmethoxy)acetic acid In a similar manner as in Referential Example 56, from 250 mg of 5-(1,2,3a,8b-cis-tetrahydro-7-bromo-1,2-syn-epoxycyclopenta[b]benzofuranylmethoxy)acetic acid, 160 mg of the debrominated compound was obtained.

IR (neat) $v cm^{-1}$: 3600–2300, 1705, 1590, 1185, 850. Mass (m/e): 262 (M+).

Referential Example 58

Preparation of 3a,8b-cis-dihydro-3H-5-carbomethoxycyclopenta[b]benzofuran

To a stirred solution of 3 g of 3a,8b-cis-dihydro-3H-5-bromo-cyclopenta[b]benzofuran in 60 ml of anhydrous THF, at −78° C. under argon atmosphere added dropwise 10.2 ml of n-butyl lithium (1.5N), and the resulting solution was stirred at −78° C. for 35 minutes, while carbon dioxide generated from dry ice was being passed thereinto. The temperature was gradually raised to −10° C., the solution was stirred at −10° C. for 1 hour. Solid ammonium chloride was added, the resulting mixture was stirred at room temperature for 5 minutes and thereafter THF was removed under reduced pressure. Benzene was added, the mixture was washed once with a saturated aqueous solution of sodium hydrogen carbonate and 2 times with water, thereafter, the pH value of the combined water layer was adjusted to 2 with 2N hydrochloric acid and the mixture was extracted 3 times with ethyl acetate. The combined ethyl acetate layers were washed with water and saturated brine, dried and thereafter concentrated to give 2.1 g of 3a,8b-cis-3H-5-carboxy-cyclopenta[b]benzofuran. This carboxylic acid was suspended in ethyl acetate, the suspension was methylated with an ether solution of diazomethane, which was concentrated to afford 2.2 g of a crude oily substance. This oily substance was purified by column chromatography (silica gel; ethyl acetate:cyclohexane (1:3)) to yield 1.9 g of 3a,8b-cis-dihydro-3H-5-carbomethoxy-cyclopenta[b]benzofuran (Yield 7.5%).

IR (neat) ν: 1720, 1605 cm$^{-1}$ NMR (CDCl$_3$) δ: 2.90 (2H, m) 3.89 (3H, s), 4.18 (1H, dd, J=8.0 Hz, 0.3 Hz), 5.60 (1H, dt, J=8.0 Hz, 4.0 Hz), 5.75 (2H, m), 6.84 (1H, t, J=8.0 Hz), 7.24 (1H, dd, J=8.0 Hz, 1.2 Hz), 7.70 (1H, dd, J=8.0 Hz, 1.2 Hz). Mass (m/e): 216 (M+).

Referential Example 59

Preparation of 3a,8b-cis-dihydro-3H-5-carbomenthyloxycyclopenta[b]benzofuran

To a suspension of 300 mg of 3a,8b-cis-dihydro-3H-5-carboxy-cyclopenta[b]benzofuran in 5 ml of anhydrous benzene was added 0.8 ml of oxalyl chloride and the resulting solution was stirred at 60° C. for 1 hour. The reaction mixture was concentrated and dried, the air was substituted by argon, the residue was dissolved in anhydrous pyridine, and 600 mg of 1-menthol was added and the mixture was stirred at 60° C. for 1.5 hours. The reaction solution was concentrated, ethyl acetate was added, the mixture was washed with a saturated aqueous solution of sodium hydrogen carbonate, water and saturated brine and concentrated. The obtained oily substance was purified by column chromatography (silica gel; ethyl acetate:cyclohexane (1:9)) to give 470 mg of 3a,8b-cis-dihydro-3H-5-carbomenthyloxy-cyclopenta[b]benzofuran was obtained (yield 90%).

IR (neat) ν: 1705, 1605, 1260, 1385, 1140, 1060, 1040, 1015 cm$^{-1}$.

Referential Example 60

Resolution of 3a,8b-cis-dihydro-3H-5-carbomentyloxycyclopenta[b-]benzofuran

When 300 mg of 3a,8b-cis-dihydro-3H-5-carbomenthyloxycyclopenta[b]benzofuran obtained in Referential Example 59 was separated and purified by column chromatography (silica gel; ethyl acetate:cyclohexane (0.5:9.5)), 73.7 mg of a less polar portion and 86.3 mg of a polar portion were obtained. Analytical data of the less polar portion:

IR (neat) $\nu$: 1705, 1605, 1260, 1285, 1140, 1060, 1040, 1015 cm$^{-1}$. NMR (CDCl$_3$) $\delta$: 0.78 (3H, d, J=8.0 Hz), 0.90 (6H, d, J=7.0 Hz), 1.4~1.9 (10H, m), 2.90 (1H, m), 4.40 (1H, d, J=8.0 Hz), 4.92 (1H, dt, J=11.0 Hz, 4.0 Hz), 5.70 (3H, m), 6.84 (1H, t, J=8.0 Hz), 7.34 (1H, dd, J=8.0 Hz, 1.2 Hz), 7.74 (1H, dd, J=8.0 Hz, 1.2 Hz). Mass (m/e): 340 (M+). $[\alpha]_D^{MeOH} = -116$.

Analytical data of the polar portion: IR (neat) $\nu$: 1705, 1603, 1260, 1285, 1138, 1058, 1040, 1015 cm$^{-1}$. NMR (CDCl$_3$) $\delta$: 0.80 (3H, d, J=6.5 Hz), 0.94 (6H, d, J=7.0 Hz) 1.4~1.9 (10H, m), 2.94 (1H, m), 4.38 (1H, d, J=8.0 Hz), 4.90 (1H, dt, J=10.0 Hz, 4.0 Hz), 5.70 (3H, m), 6.84 (1H, t, J=8.0 Hz), 7.34 (1H, dd, J=8.0 Hz, 1.2 Hz), 7.70 (1H, dd, J=8.0 Hz, 1.2 Hz). Mass (m/e): 340 (M+). $[\alpha]_D^{MeOH} = +11.5$.

Referential Example 61

Preparation of 3a,8b-cis-dihydro-3H-5-carboxy-cyclopenta[b]benzofuran (optical active compound)

63 mg of the compound ($[\alpha]_D^{MeOH} = -116$) resolved in Referential Example 60 was dissolved in 2 ml of methanol, 1 ml of 3N sodium hydroxide was added, and the resulting solution was stirred at 60° C. for 14 hours. The reaction mixture was concentrated, an ether-benzene (2:1) mixture was added and the mixture was extracted with water 3 times. The water layer was combined the pH of which was adjusted to 2 with 6N hydrochloric acid and extracted with ethyl acetate 3 times. The combined ethyl acetate layer was washed with water and saturated brine, dried and thereafter, concentrated to give 34.6 mg of the optically active carboxylic acid (mp 147°-148° C.).

IR (KBr) $\nu$: 3600-2400, 1690, 1605 cm$^{-1}$. Mass (m/e): 202 (M+). $[\alpha]_D^{MeOH} = -104$.

Under the similar conditions, when 76 mg of the compound whose $[\alpha]_D^{MeOH}$ was +11.5 was employed, 42 mg of the optically active carboxylic acid (mp 148°-150° C.) was obtained.

IR (KBr) $\nu$: 3600-2400, 1690, 1605 cm$^{-1}$. Mass (m/e): 202 (M+). $[\alpha]_D^{MeOH} = +105$.

Referential Example 62

Preparation of 3a,8b-cis-dihydro-3H-5-hydroxymethylcyclopenta[b-]benzofuran

To a solution of 300 mg of 3a,8b-cis-dihydro-3H-5-carbomethoxycyclopenta[b]benzofuran in 7 ml of anhydrous toluene at −78° C. was added, 0.298 ml of diisobutyl aluminium hydride and the resulting mixture was stirred at −78° C. for 3 hours. Methanol was added and the mixture was stirred at room temperature for 5 minutes, thereafter, 50% brine was added and the mixture was extracted with ether 3 times. The combined ether layer was washed with saturated brine and water, dried over magnesium sulfate and concentrated to give 300 mg of an oily substance. This oily substance was separated and purified by column chromatography (silica gel; ethyl acetate:cyclohexane (1:4)) to yield 230 mg of the alcohol (yield 88%).

IR (neat) $\nu$: 3245, 1598, 1000 cm$^{-1}$.

Referential Example 63

Preparation of 3a,8b-cis-dihydro-3H-5-formyl-cyclopenta[b]benzofuran

To a solution of 230 mg of 3a,8b-cis-dihydro-3H-5-hydroxymethylcyclopenta[b]benzofuran in 5 ml of methylene chloride was added 5 g of active manganese dioxide, and the resulting mixture was stirred at room temperature under argon atmosphere for 2 hours. The reaction mixture was passed through a short column made of silica gel to filter manganese dioxide, and the column washed well with methylene chloride. The combined methylene chloride solution was concentrated to give 210 mg of a roughly pure aldehyde (mp 59°-60° C.) (yield 91%).

IR (neat) $\nu$: 2730, 1680, 1605 cm$^{-1}$. NMR (CDCl$_3$) $\delta$: 2.90 (2H, m), 4.40 (1H, d, J=7.0 Hz), 5.70 (3H, m), 6.90 (1H, t, J=8.0 Hz), 7.41 (1H, dd, J=8.0 Hz, 1.2 Hz), 7.58 (1H, dd, J=8.0 Hz, 1.2 Hz), 10.10 (1H, s). Mass (m/e): 186 (M+).

Referential Example 64

Preparation of 3a,8b-cis-dihydro-3H-5-formyl-1,2-syn-epoxycyclopenta[b]benzofuran To an ice cooled solution of 100 mg of 3a,8b-cis-dihydro-3H-5-formyl-cyclopenta[b]benzofuran in 2.8 ml of a dimethyl sulfoxide-water (18:1) mixture and 0.42 ml of THF, was added, 180 mg of imide N-bromosuccinate and the resulting mixture was stirred for 4 hours. To the reaction mixture was added 300 mg of potassium carbonate and 0.5 ml of water, and the resulting mixture was stirred under ice cold conditions for 2 hours. Water was added to the reaction mixture, and the mixture was extracted with ether 5 times. The combined ether layer was washed with water, dried and concentrated to afford 130 mg of an oily substance. This oily substance was purified by column chromatography (silica gel; ethyl acetate:cyclohexane (1:1)) to give 105 mg of crude crystals. This crude crystals were recrystallized from a benzene-hexane mixture to yield 90 mg of a pure compound (mp 100°-101° C.).

IR (KBr) $\nu$: 2730, 1680, 1605, 845 cm$^{-1}$. NMR (CDCl$_3$) $\delta$: 2.30 (1H, dd, J=16.0 Hz, 7.0 Hz), 2.68 (1H, d, J=16.0 Hz) 3.82 (1H, d, J=8.0 Hz), 6.96 (1H, t, J=8.0 Hz), 7.50 (1H, dd, J=8.0 Hz, 1.2 Hz), 7.64 (1H, dd, J=8.0 Hz, 1.2 Hz), 10.18 (1H, s). Mass (m/e): 202 (M+).

Referential Example 65

Preparation of 1,2,3a,8b-cis-tetrahydro-5-(4-tetrahydropyranyloxy-1-hydroxy-n-butyl)-1,2-syn-epoxy-cyclopenta[b]benzofuran To a stirred solution of 10 mg of 1,2,3a,8b-cis-tetrahydro-5-formyl-1,2-syn-epoxy-cyclopenta[b]benzofuran in anhydrous THF was added at −60° C., a large excess of a THF solution of a Grignas reagent produced from 3-bromo-n-propyl-tetrahydropyranylether, and the resulting solution was stirred at −30° C. to −40° C. for 1.5 hours. Solid ammonium chloride was added, and the resulting mixture was stirred at −40° C. for 20 minutes, thereafter, water was added, and the mixture was extracted with ether 3 times, the extract was washed with saturated brine, dried and thereafter, concentrated. The obtained oily substance was purified by column chromatography (silica gel; ethyl acetate:cyclohexane (1:1)) to give 13 mg of a pure product.

IR (neat) ν: 3430, 1595, 1025, 845 cm⁻¹.

Preparation of 1,2,3a,8b-cis-tetrahydro-5-(4-tetrahydropyranyloxy-1-acetoxy-n-butyl)-1,2-syn-epoxy-cyclopenta[b]benzofuran 13 mg of 1,2,3a,8b-cis-tetrahydro-5-(4-tetrahydropyranyloxy-1-hydroxy-n-butyl)-1,2-syn-epoxycyclopenta[b]benzofuran was dissolved, in 1 ml of acetic anhydride and 0.5 ml of anhydrous pyridine, and the resulting solution was stirred at room temperature for 14 hours. The reaction solution was concentrated to dryness, the residue was dissolved in toluene and concentrated, and this operation was repeated. The obtained oily substance was refined by column chromatography (silica gel; ethyl acetate:cyclohexane (1:1)) to give 13 mg of a pure product.

IR (neat) ν: 1738, 1595, 1230, 1030, 845 cm⁻¹ NMR (CDCl₃) δ: 2.05 (3H, s), 3.68 (2H, s), 3.20–3.90 (5H, m), 4.58 (1H, m), 5.37 (1H, t, J=7.0 Hz), 5.93 (1H, J=7.0 Hz), 6.86 (1H, t, J=8.0 Hz) 7.20 (2H, m) Mass (m/e): 388 (M⁺)

Referential Example 67

Preparation of 1,2,3a,8b-cis-tetrahydro-5-(4-tetrahydropyranyloxy-n-butyl)-1,2-syn-epoxycyclopenta[b]benzofuran To a solution of 6 mg of 1,2,3a,8b-cis-tetrahydro-5-(4-tetrahydropyranyloxy-1-acetoxy-n-butyl)-1,2-syn-epoxycyclopenta [b]benzofuran in 0.5 ml of ethyl acetate was added, 15 mg of a 10% palladium-carbon was added, and the resulting mixture was stirred at room temperature under hydrogen atmosphere for 3 hours. The catalyst was filtered off and the filtrate was concentrated to afford 6 mg of an oily substance. This oily substance was separated and purified by column chromatography [silica gel; ethyl acetate:cyclohexane (1:2)] to give 3 mg of a pure product. The compound obtained herein was completely identical with the compound obtained in Referential Example 16 in IR, Mass and Rf value of TLC.

Referential Example 68

1,2,3a,8b-cis-tetrahydro-1-exo(1,3-bismethylthio-2-propenyl)-2-endo-hydroxy-7-methyl-5-(4-tetrahydropyranyloxy-n-butyl)cyclopenta[b]benzofuran

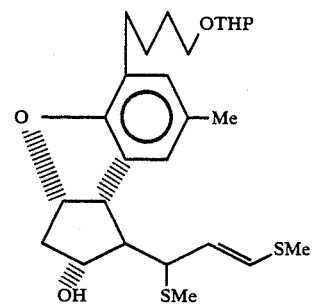

To a 170 ml of THF solution of 1,3-bismethylthio-1-propenyl lithium (0.16M, 27.2 ml, 1.45 equiv.) was added dropwise at −78° C. under argon atmosphere a solution of 6.43 g (18.7 mmol) of 1,2,3a,8b-cis-tetrahydro-7-methyl-5-(4-tetrahydropyranyloxybutyl)-1,2-syn-epoxycyclopenta[b]benzofuran in 40 ml of THF, and the resulting solution was stirred for 2 hours. The reaction solution was poured into 100 ml of a saturated aqueous solution of ammonium chloride, and products was extracted with ethyl acetate (20 ml×5) and the combined organic layers were dried. After concentration, the resulting 10.1 g of a crude products was purified by column chromatography (silica gel 400 g; cyclohexane:ethyl acetate 5:1→3:2) to afford 4.15 g (8.68 mmol, 46%) of polar 4 and 4.53 g (9.48 mmol, 51%) of the less plar position isomer, 2 kinds of oily substances.

NMR (CDCl₃) δ: 1.62 (m, 10H), 1.80–2.66 (m, 15H) (At 2.06, 2.14, 2.25, 2.29 and 2.31, five singlet could be confirmed), 3.22 (dd, J=8, 10 Hz, 1H), 3.53 (m, 2H), 3.80 (m, 2H), 4.14 (dd, J=6, 7 Hz, 1H), 4.20 (broad singlet, 1H), 4,56 (m, 1H), 5.06 (m, 1H), 5.32 (dd, J=15, 10 Hz, 1H), 6.17 (d, J=15 Hz, 1H), 6.77 (s, 1H), 6.88 (s, 1H). IR (neat): 3450 (3650–3150), 2970, 2930, 2860, 1600, 1475, 1435, 1215, 1200, 1140, 1120, 1075, 1030, 970, 865, 815, 740, 700. Mass spectrum: M⁺ 478.

In a similar manner of Referential Example 68

1,2,3a,8b-cis-tetrahydro-7-bromo-5-(4-tetrahydropyranyloxybutyl)-1,2-syn-epoxycyclopenta[b]benzofuran;

1,2,3a,8-cis-tetrahydro-7-chloro-5-(4-tetrahydropyranyloxybutyl)-1,2-syn-epoxycyclopenta[b]benzofuran, or 1,2,3a,8b-cis-tetrahydro-7-methoxy-5-(4-tetrahydropyranyloxybutyl)-1,2-syn-epoxycyclopenta[b]benzofuran is employed as the starting material to give 1,2,3a,8b-cis-tetrahydro-1-exo-(1,3-bismethylthio-2-propenyl)-2-endo-hydroxy-7-bromo-5-(4-tetrahydropyranyloxybutyl)cyclopenta[b]benzofuran;

1,2,3a,8b-cis-tetrahydro-1-exo-(1,3-bismethylthio-2-propenyl)-2-endo-hydroxy-7-chloro-5-(4-tetrahydropyranyloxybutyl)cyclopenta[b]benzofuran, or 1,2,3a,8b-cis-tetrahydro-1-exo-(1,3-bismethylthio-2-propenyl)-2-endo-hydroxy-7-methoxy-5-(4-tetrahydropyranyloxybutyl)cyclopenta[b]benzofuran.

Referential Example 69

1,2,3a,8b-cis-tetrahydro-1-exo-(2-formylethenyl)-3-endo-hydroxy-7-methyl-5-(4-tetrahydropyranyloxybutyl)cyclopenta[b]benzofuran

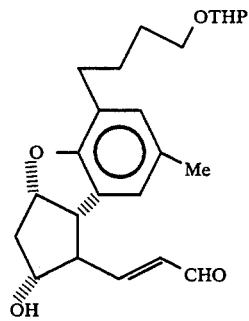

The mixture of 861 mg (5.05 mmol, 2.5 equiv.) of cupric chloride dihydrate, 2.00 g (20 mmol, 10 equiv.) of calcium carbonate and 5 ml of acetone was cooled to 0° C. To this suspension was added a solution of 954 mg (2.00 mmol) of 1,2,3a,8b -cis-tetrahydro-3H-1-exo-(1,3-bismethylthio-2-propenyl)-2-endo-hydroxy-7-methyl-5-(4-tetrahydropyranyloxy-n-butyl)cyclopenta[b]benzofuran in 6 ml of acetone and the resulting mixture was stirred at 0°-5° C. for 6 hours. After distilling off acetone, 50 ml of ether was added, the inorganic salt was filtered off, and the filtrate was washed with a saturated aqueous solution of ammonium chloride (1 ml×4) and dried. After concentration, 72.7 mg of the residue was purified by column chromatography (silica gel 70 g, cyclohexane:ethyl acetate 1:2→ethyl acetate) to afford to 528 mg (7.32 mmol, 66%) of 5 and 66 mg (0.21 mmol, 10%), of the aldehyde which a tetrahydropyranyl group of 5 was eliminated.

NMR (CDCl$_3$) δ: 1.63 (m, 10H), 2.64 (m, 1H), 2.22 (s, 3H), 2.54 (m, 3H), 2.74 (t, J=8, 1H), 3.08 (wide one-double line, 1H), 3.44 (m, 3H), 3.80 (m, 2H), 4.03 (m, 1H), 4.55 (m, 1H), 5.11 (q, J=7 Hz, 1H), 6.24 (dd, J=16, 8 Hz, 1H), 6.80 (m, 3H), 9.55 (d, J=8 Hz, 1H). IR (neat) νcm$^{-1}$: 3400 (3600-3100), 2930, 2860, 1680, 1640, 1475, 1220, 1200, 1130, 1070, 1030, 975, 860, 740. Mass spectrum: M+ 400.

In a similar manner of Referential Example 69, 1,2,3a,8b-cis-tetrahydro-1-exo-(1,3-bismethylthio-2-propenyl)-2-endo-hydroxy-7-bromo-5-(4-tetrahydropyranyloxybutyl)cyclopenta[b]benzofuran;

1,2,3a,8b-cis-tetrahydro-1-exo-(1,3-bismethylthio-2-propenyl)-2endo-hydroxy-7-chloro-5-(4-tetrahydropyranyloxybutyl)cyclopenta[b]benzofuran, or 1,2,3a,8b-cis-tetrahydro-1-exo-(1,3-bismethylthio-2-propenyl)-2endo-hydroxy-7-methoxy-5-(4-tetrahydropyranyloxybutyl)cyclopenta[b]benzofuran is employed as the starting material to give 1,2,3a,8b-cis-tetrahydro-1-exo-(2-formylethenyl)-3-endo-hydroxy-7-bromo-5-(4-tetrahydropyranyloxybutyl)cyclopenta[b]benzofuran;

1,2,3a,8b-cis-tetrahydro-1-exo-(2-formylethenyl)-3-endo-hydroxy-7-chloro-5-(4-tetrahydropyranyloxybutyl)cyclopenta[b]benzofuran, or 1,2,3a,8b-cis-tetrahydro-1-exo-(2-formaylethenyl)-3-endo-hydroxy-7-methoxy-5-(4-tetrahydropyranyloxybutyl)cyclopenta[b]benzofuran.

Referential Example 70

1-t-butyldimethylsiloxy-1-phenyl-2-propyne

To a solution of 5.0 g (37.9 mmol) of 1-phenyl-2-propyne-1-ol in 20 ml of dimethyl formamide were added 6.9 g (45.8 mmol) of t-butyl dimethylsilyl chloride and 6.2 g (91.1 mmol) of imidazole, and the resulting mixture was stirred at room temperature for 3 hours, 50 ml of water was added and the mixture was extracted with a pentane-ether (1:1) mixture (4×30 ml). The organic layer was washed with water (30 ml) and saturated brine, dried over anhydrous magnesium sulfate (30 mg) and thereafter concentrated. The residue was purified by column chromatography (silica gel 100 g, cyclohexane-ethyl acetate) and further distilled (dp 98° C./1 mm Hg) to give 5.7 g (24.7 mmol, 65%) of the subject compound.

IR (neat) νcm$^{-1}$: 3300, 3060, 3030, 2960, 2930, 2880, 2850, 2110, 1600, 1460, 1250, 1090, 1065, 840, 780, 695. GLC glass column: 3 mm×2 m, liq phase silicon: SE52; 2% Gaschrom: Q80/100; temp. column: 150° C.; injection: 200° C.; carrier gas: N$_2$ 60 ml/min; detector: FID; instrument: Shimadzu GC-5A; retention time 6.5 min.

Referential Example 71

6-methyl-5-heptene-1-ol

To a stirred suspension 77 g of isopropyltriphenylphosphonium iodide in 200 ml of anhydrous DMSO at −78° C. was added 57 ml of dimethyl-sulfinylcarbanion (prepared from 15 g of sodium hydride (55%) in mineral oil dispersion and 100 ml of anhydrous DMSO), and the resulting mixture was stirred at room temperature for 10 minutes. A solution of 6 g of 2-hydroxytetrahydropyran in 10 ml of anhydrous DMSO was added dropwise, and the resulting mixture was stirred at room temperature for 1 hour. Ice and water were added, and the mixture was extracted 3 times with n-hexane, the combined organic layers were washed with a 10% aqueous solution of sulfuric acid, a saturated aqueous solution of sodium hydrogen carbonate and water, thereafter dried and concentrated to give 10 g of an oily substance. This oily substance was distilled (bp 110° C./30 mmHg) to yield 5 g of a pure alcohol.

IR (neat) νcm$^{-1}$: 3400, 1160, 830. NMR (CDCl$_3$) δ: 1.60 (3H, s), 1.68 (3H, s), 2.00 (2H, q, J=7.0 Hz), 2.54 (1H, s), 3.60 (2H, t, J=6.0 Hz), 5.12 (1H, tq, J=7.0 Hz, 2.0 Hz). Mass (m/e): 128 (M+). Anal. Calcd for C$_8$H$_{16}$O C; 74.94, H; 12.58; Found C; 74.88, H; 12.52.

Referential Example 72

6-methyl-5-heptenyl tosylate

To an ice cooled solution of 5 g of 6-methyl-5-heptene-1-ol in 20 ml of anhydrous pyridine was added, 11.5 g of tosyl chloride and the resulting mixture was stirred under ice cold conditions for 2 hours. Ice was added and the mixture was extracted with n-hexane 3 times, the combined organic layers were washed 2 times with 2N hydrochloric acid, water and a saturated aqueous solution of copper sulfate, dried and thereafter, concentrated to give 11 g of roughly pure tosylate.

IR (neat) νcm$^{-1}$: 1595, 1440, 1355, 1175, 810. NMR (CDCl$_3$) δ: 1.56 (3H, s), 1.67 (3H, s), 1.96 (2H, q, J=7.0 Hz), 2.26 (3H, s), 4.04 (2H, t, J=6.0 Hz), 5.04 (1H, tq, J=8.0 Hz, 2.0 Hz), 7.36 (2H, d, J=8.0 Hz), 7.80 (2H, d, J=8.0 Hz). Mass (m/e): 282 (M+). Anal. Calcd for C$_{15}$H$_{22}$O$_3$S C; 63.83, H; 7.80 Found C; 63.78, H; 7.75.

Referential Example 73
6-methyl-5-heptenyl bromide

A solution of 11 g of 6-methyl-5-heptenyl tosylate in 100 ml of THF were added 10 ml of HMPA, 50 g of potassium bromide and 300 mg of 18-crown-6, and the resulting mixture was refluxed for 5 hours. After cooling, water was added, and the mixture was concentrated, the residue was extracted with pentane 3 times, the combined organic layers were washed with a saturated aqueous solution of sodium hydrogen carbonate water and saturated brine, dried and concentrated to give 8 g of an oily substance. This oily substance was distilled (bp 70° C./5 mm Hg) to yield 5.7 g of a pure bromide.

IR (neat $\nu cm^{-1}$: 1245, 840. NMR (CDCl$_3$) δ: 1.61 (3H, s), 1.70 (3H, s), 3.40 (2H, t, J=7.0 Hz), 5.10 (1H, tq, J=7.8 Hz, 2.0 Hz). Anal. Calcd for C$_8$H$_{15}$Br C; 50.00; H; 7.81 Found C; 49.98; H; 7.80.

Referential Example 74
2-methylpentyl bromide

To an ice cooled solution of 6 g of 2-methylpentyl alcohol in 30 ml of anhydrous pyridine was added 16 g of tosyl chloride, and the resulting mixture was stirred for 40 minutes. Ice was added under ice cold conditions, and the mixtures was extracted 3 times with n-hexane, the combined hexane layers were washed 2 times with 2N hydrochloric acid, once water and once a saturated aqueous solution of copper sulfate, dried and concentrated to afford 14 g of a roughly pure tosylate. To a stirred solution of the tosylate in 100 ml of THF were added 30 ml of HMPA, 50 g of potassium bromide and 5 g of 18-crown-6, the resulting mixture was refluxed for 14 hours. The reaction mixture was cooled, ice was added, and the mixture was extracted 3 times with pentane, the extract was washed 2 times with water and 2 times with saturated brine and thereafter concentrated to give 14 g of an oily substance. This oily substance was distilled (bp 54° C./30 mm Hg) to yield 6 g of a pure bromide.

NMR (CDCl$_3$) δ: 0.98 (3H, t, J=7.0 Hz), 1.02 (3H, d, J=6.8 Hz), 1.36 (4H, m), 1.80 (1H, octet J=6.8 Hz), 3.38 (2H, dd, J=5.0 Hz, 2.5 Hz) Mass (m/e): 166, 164 (M+), 123, 121. Anal. Calcd. for C$_6$H$_{13}$Br C; 43.64, H; 7.88 Found C; 43.51, H; 7.80.

Referential Example 75
l-citronelol-tetrahydropyranylether

To an ice cooled solution of 50 g of l-citronelol in 250 ml of anhydrous methylene chloride were added 40 g of dihydropyran and 25 ml of a THF solution of p-toluenesulfonic acid which was prepared by dissolving 1.8 g of p-toluenesulfonic acid in 50 ml of THF and drying the solution over a molecular sieve, and the resulting mixture was stirred under ice cold conditions for 10 minutes. Two ml of pyridine was added, the resulting solution was stirred at room temperature for 30 minutes, thereafter, washed with saturated brine:water (1:1) mixture and saturated brine, thereafter, dried and concentrated to give 76 g of a roughly pure ether body.

IR (neat) $\nu cm^{-1}$: 1670, 1140, 1120, 1080, 1030, 870, 820. NMR (CDCl$_3$) δ: 0.90 (3H, d, J=6.0 Hz), 1.00–1.90 (5H, m), 1.60 (3H, s), 1.68 (3H, s), 1.99 (2H, q, J=8.0 Hz), 3.50 (2H, m), 3.80 (2H, m), 4.57 (1H, m), 5.10 (1H, tq, J=8.0 Hz, 1.0 Hz). Mass (m/e): 240 (M+).

Referential Example 76
3(s)-methyl-6-tetrahydrofuranyloxyhexanal

Into a stirred solution of 35 g of l-citroneloltetrahydrofuranylether in 500 ml of methanol at −78° C. was passed a stream of ozone. After 2.5 hours, a nitrogen stream was vigorously bubbled through the solution for 1 hour to remove the excess ozone. Two hundred ml of dimethyl sulfide was added, the temperature was allowed to warm to room temperature over 1 hour, and resulting mixture was concentrated. The residue was dissolved in pentane, a small amount of ethyl acetate was added, and the mixture was washed with saturated brine, dried and thereafter concentrated to give 36 g of an oily substance. This oily substance was used in the following reaction without further purification.

IR (neat) $\nu cm^{-1}$: 1728, 1140, 1125, 1080, 1030, 870, 819. NMR (CDCl$_3$) δ: 0.94 (3H, d, J=5.0 Hz), 2.45 (2H, m), 1.20–2.00 (5H, m), 3.50 (2H, m), 3.80 (2H, m), 4.58 (1H, m), 10.00 (1H, t, J=2.0 Hz). Mass (m/e): 241 (M+).

Referential Example 77
3(s)-methyl-7-heptene-1-ol tetrahydropyranylether To a stirred solution of 30 g of methyltriphenylphosphonium bromide in 100 ml of anhydrous DMSO, under water cooled conditions was added 20 ml of dimethylsulfinylcarbanion (prepared from 6.6 g of sodium hydide (50% mineral oil dispersion) and 40 ml of anhydrous DMSO), the resulting solution was stirred for 10 minutes, thereafter, 10 g of 3(S)-methyl-6-tetrahydrofuranyloxyhexanal was added, and the resulting mixture was stirred at room temperature for 30 minutes. The reaction mixture was cooled with ice, and ice and water were added, and the mixture was extracted 3 times with n-pentane. The combined pentane layers were washed with water and saturated brine, dried and thereafter concentrated to afford 10 g of an oily substance. This oily substance was purified by column chromatography (silica gel; chloroform) to give 9 g of a pure product.

IR (neat) $\nu cm^{-1}$: 1640, 1120, 1075, 1030, 990, 905. NMR (CDCl$_3$) δ: 0.92 (3H, d, J=6.0 Hz), 1.10–1.90 (5H, m), 2.10 (2H, q, J=7.5 Hz), 3.50 (2H, m), 3.80 (2H, m), 4.60 (1H, m), 5.00 (2H, m), 5.80 (1H, m). Mass (m/e): 212 (M+).

Referential Example 78
3(s)-methyl-heptene-1-ol

To a solution of 3 g of 3(S)-methyl-7-heptene-1-ol tetrahydropyranylether in 84 ml of acetonitrile were added 42 ml of THF and 42 ml of ¼N hydrochloric acid, and the resulting solution was stirred at room temperature for 14 hours. Ether was added, and the mixture was shaken, the water layer was removed, the organic layer was washed with saturated aqueous solution of sodium hydrogen carbonate, dried and thereafter concentrated to give 3 g of an oily substance. This oily substance was purified by column chromatography (silica gel, 2% ethyl acetate-chloroform) to yield 1.5 g of the alcohol.

IR (neat) $\nu cm^{-1}$: 3330, 1640, 1050, 990, 910. NMR (CDCl$_3$) δ: 0.92 (3H, d, J=6.0 Hz), 1.10–2.00 (5H, m), 2.10 (2H, m), 3.67 (2H, t, J=8.0 Hz), 5.00 (2H, m), 5.80 (1H, m). Mass (m/e): 128 (M+).

Referential Example 79

3(S)-methylheptanol

To a solution of 8 g of 3(s)-methyl-7-heptene-1-ol in 50 ml of a 2% potassium hydroxide-methanol mixture was added 1 g of platinum oxide, and the resulting mixture was stirred at room temperature under hydrogen atmosphere for 3 hours. The reaction mixture was filtered, the filtrate was concentrated, the residue was treated with water and the mixture was extracted 3 times with ether. The combined ether layers were washed with water and saturated brine, dried and thereafter concentrated to give 7.9 g of the saturated alcohol in a roughly pure form.

IR (neat) $\nu$ cm$^{-1}$: 3300, 1120, 1055. NMR (CDCl$_3$) $\delta$: 0.90 (6H, m), 3,67 (2H, t, J=7.0 Hz), 1,00–2.90 (9H, m), 2,10 (2H, s). Mass (m/e): 130 (M+).

Referential Example 80

3(S)-methylheptanoic acid

To a solution of 1 g of 3(s)-methylheptanol in 3 ml of anhydrous DME was added 14 g of pyridinium dichromate, and the resulting mixture was stirred at room temperature for 14 hours. The reaction mixture was treated with water and the mixture was extracted 5 times with ether. The combined ether layers were washed with 2N hydrochloric acid, water and a saturated aqueous solution of copper sulfate and concentrated. The residue was dissolved in n-hexane, the solution was washed once with a saturated aqueous solution of sodium hydrogen carbonate and 6 times with water, the pH value of the water layer was adjusted to 2 with 2N hydrochloric acid and the layer was extracted with 5 times chloroform. The combined chloroform layer were washed with water, dried and thereafter concentrated to give 700 mg of the roughly pure carboxylic acid.

IR (neat) $\nu$ cm$^{-1}$: 3600–2300, 1710, 1100. NMR (CDCl$_3$) $\delta$: 0.90 (3H, t, J=7.0 Hz), 0.98 (3H, d, J=6.8 Hz), 1.10–1.60 (7H, m), 2.96 (2H, d, J=7.0 Hz). Mass (m/e): 144 (M+).

Referential Example 81

2(S)-methylhexyl chloride

To a solution 6 g of 3(s)-methylheptanoic acid in 100 ml of benzene under argon atmosphere were added 9.6 g of acetic acid, 0.9 ml of water and 20 g of lead tetraacetate, the resulting mixture was stirred at room temperature for 30 minutes, thereafter, 1.9 g of lithium chloride was added thereto under argon atmosphere, and the resulting mixture was stirred at 80° C. for 3 hours. The benzene layer was decanted, washed with diluted hydrochloric acid and an aqueous solution of sodium carbonate, dried and thereafter concentrated to give 8 g of an oily substance. This oily substance was purified by column chromatography (silica gel; hexane) to yield 34 g of the chloride.

NMR (CDCl$_3$) $\delta$: 0.90–1.10 (6H), 1.10–1.60 (6H), 1.60–2.00 (1H), 3,00–3.50 (2H). Mass (m/e): 134, 136.

EXAMPLE 1

5,6,7-trinor-4,8-inter-m-phenylene-13,14-didehydro PGI$_2$ methyl ester 15-t-butylether (1)

To a solution of 1.515 g (8.32 mmol) of 3-t-butyloxy-1-octyne in 5 ml of dry toluene at 0° C. under argon atmosphere, was slowly added 5 ml of a hexane solution of n-butyl lithium (1.54M, 7.7 mmol), and the resulting solution was stirred for 15 minutes.

To the solution was added 3.7 ml (7.25 mmol) of a toluene solution (1.96M) of a mixture of diethyl aluminium chloride and ethyl methoxy aluminium chloride (3:1), and the resulting solution was stirred at 0° C. for 1 hour. A solution of 302 mg (1.1 mmol) of methyl 4-(3a,8b-cis-dihydro-3H-1,2-syn-epoxycyclopenta[b-]benzofuran-5-yl)butanoate in 7 ml of dry toluene was added, and the resulting solution was stirred at room temperature for 1 hour in an ice bath and 30 ml of saturated brine was slowly added thereto. The resulting solution was extracted with 50 ml of ether and the ether layer was washed with saturated brine, dried over anhydrous sodium sulfate, thereafter, concentrated. After the excess 3-t-butyloxy-1-octyne was distilled off, the residue was purified by chromatography (Merck Lobar Column B; cyclohexane:ethyl acetate (2:1)) to give 160 mg (32%) of the subject compound and 140 mg (28%) of the position isomer.

Spectrum data of the subject compound:

IR (neat, $\nu$ cm$^{-1}$): 3450, 2950, 2855, 1220, 1740, 1595, 1450, 1370, 1255, 1195, 1035, 750. NMR (CDCl$_3$, $\delta$ ppm): 0.90 (t, 6 Hz, 3H), 1.26 (s, 9H), 1.2–1.7 (m, 6H), 1.8–2.45 (m, 9H), 2.60 (t, 7 Hz, 2H), 2.88 (td, 6 Hz, 2 Hz, 1H), 3.64 (s, 3H), 3.80 (dd, 8 Hz, 5 Hz, 1H), 4.02–4.22 (m, 2H), 5.26 (m, 1H), 6.79 (t, 7 Hz, 1H), 6.95 (dd, 7 Hz, 2 Hz, 1H), 7.14 (dd, 7 Hz, 2 Hz, 2 Hz, 1H). MS (m/e): 456, 382, 297, 279, 232, 201, 156, 144.

Spectrum data of the position isomer:

IR (neat, $\nu$ cm$^{-1}$): 3450, 2950, 2855, 2220, 1740, 1595, 1450, 1370, 1255, 1195, 1050, 750. NMR (CDCl$_3$, $\delta$ ppm): 0.88 (r, 6 Hz, 3H), 1.23 (s, 9H), 1.2–1.7 (m, 10H), 1.7–2.1 (m, 3H), 2.33 (t, 7 Hz, 2H), 2.42 (m, 1H), 2.60 (t, 7 Hz, 2H), 3.65 (s, 3H), 3.96 (t, 8 Hz, 1H), 4.10 (t, 6 Hz, 1H), 4.23 (t, 8 Hz, 1H), 5.18 (dd, 8 Hz, 5 Hz, 1H), 6.78 (t, 7 Hz, 1H), 6.99 (dd, 7 Hz, 2 Hz, 1H), 7.13 (dd, 7 Hz, 2 Hz, 1H). MS (m/e): 456 (M+) 400, 382, 325, 297, 201.

EXAMPLE 2

5,6,7-trinor-4,8-inter-m-phenylene-13,14-didehydro PGI$_2$ methyl ester (2)

To 185 mg (0.406 mmol) of 5,6,7-trinor-4,8-inter-m-phenylene-13,14-didehydro-PGI$_2$ methyl ester 15-t-butylether was added 1 ml of trifluoroacetic acid, and the resulting mixture was stirred for 2 hours in an ice bath. Trifluoroacetic acid was distilled off under reduced pressure and the residue was purified by chromatography (Lobar Column B, cyclohexane-ethyl acetate 1:2) to give 65 mg (0.163 mmol) of the subject compound.

IR (neat $\nu$ cm$^{-1}$): 3400, 2930, 2855, 2230, 1740, 1600, 1460, 1255, 1195, 1005, 865, 755. NMR (CDCl$_3$, $\delta$ ppm): 0.91 (t, 7 Hz, 3H), 1.2–2.5 (m, 14H), 2.30 (t, 7 Hz, 2H), 2.60 (t, 7 Hz, 2H), 2.84 (td, 6 Hz, 2 Hz, 1H), 3.65 (s, 3H), 3.80 (dd, 8 Hz, 5 Hz, 1H), 4.24 (q, 5 Hz, 1H), 4.40 (td, 6 Hz, 2 Hz, 1H), 5.13 (m, 1H), 6.79 (t, 7 Hz, 1H), 6.98 (dd, 7 Hz, 2 Hz, 1H), 7.14 (dd, 7 Hz, 2 Hz, 1H). MS (m/e): 400 (M+), 392, 232, 158.

The above mentioned procedure was followed except the use of 163 g (0.357 mmol) of the position isomer of (1), in place of (1) to give 88 mg (0.221 mmol, 62%) of the position isomer of the subject compond.

IR (neat, $\nu$ cm$^{-1}$): 3400, 2930, 2850, 2230, 1740, 1595, 1460, 1250, 1195 1005, 865, 755. NMR (CDCl$_3$, $\delta$ ppm): 0.88 (t, 6 Hz, 3H), 1.16–1.80 (m, 10H), 1.92 (m, 2H), 2.32 (t, 7 Hz, 2H), 2.41 (m, 1H), 2.59 (t, 7 Hz, 2H), 2.67 (x, 2H), 3.64 (s, 3H), 3.92 (t, 8 Hz, 1H), 4.21 (t, 8 Hz, 1 Hz), 4.30 (td, 6 Hz, 2 Hz, 1H), 5.16 (dd, 8 Hz, 5 Hz, 1H), 6.76 (t, 7 Hz, 1H), 6.98 (dd, 7 Hz, 2 Hz, 1H), 7.12 (dd, 7 Hz, 2 Hz, 1H). MS (m/e): 400 (M+), 325, 293, 233, 201.

EXAMPLE 3

5,6,7-trinor-4,8-inter-m-phenylene-13,14-didehydro-PGI$_2$ (3)

To a solution of 27.2 mg (0.0685 mmol) of 5,6,7-trinor-4,8-inter-m-phenylene-13,14-didehydro-PGI$_2$ methyl ester in 3 ml of MeOH was added 1 ml of an aqueous solution of 1N sodium hydroxide and the solution was stirred at room temperature for 2 hours. Methanol was distilled off and the residue was washed with 5 ml of an n-hexane:ether (2:1) mixture.

The residue was cooled with ice, 1N hydrochloric acid was added to adjust pH to 3 and the mixture was extracted with etyl acetate (3×10 ml). The organic layer was dried over sodium sulfate and concentrated to give 26.4 mg (0.0684 mmol, 100%) of the subject compound as an oily substance.

IR (neat, ν cm$^{-1}$): 3600–2500, 2930, 2850, 2230, 1710, 1595, 1450, 1250, 1190, 1030, 865, 745. NMR (CDCL$_3$, δ ppm): 0.90 (t, 6 Hz, 3H), 1.2–1.8 (m, 8H), 2.2–2.6 (m, 4H), 2.31 (t, 7 Hz, 2H), 2.62 (t, 7 Hz, 2H), 2.80 (td, 6 Hz, 2 Hz, 1H), 3.77 (dd, 8 Hz, 6 Hz, 1H). 4.11 (q, 6 Hz, 1H), 4.40 (td, 6 Hz, 2 Hz, 1H), 5.10 (b, 4H), 6.78 (t, 7 Hz, 1H), 6.97 (dd, 7 Hz, 1 Hz, 1H), 7.12 (dd, 7 Hz, 1 Hz, 1H). MS (m/e): 386 (M+), 368, 218, 158.

The above mentioned procedure was followed except the use of 56.4 mg (0.141 mmol) of the position isomer of (2) in place of (2) to give 51.4 mg (0.133 mmol, 94%) of the position isomer of the subject compound.

IR (neat, ν cm$^{-1}$): 3600–2500, 2930, 2850, 2230, 1710, 1595, 1450, 1250, 1190, 1000, 865, 750. NMR (CDCl$_3$, δ ppm): 0.89 (t, 6 Hz, 3H), 1.1–1.8 (m, 10H), 1.93 (q, 6 Hz, 2H), 2.30 (m, 1H), 2.35 (t, 7 Hz, 2H), 2.62 (t, 7 Hz, 2H), 3.92 (t, 8 Hz, 1H), 4.22 (t, 8 Hz, 1H), 4.30 (td, 6 Hz, 1 Hz, 1H), 5.17 (dd, 8 Hz, 5 Hz, 1H), 5.42 (bs, 3H), 6.77 (t, 7 Hz, 1H), 6.99 (dd, 7 Hz, 2 Hz, 1H), 7.14 (dd, 7 Hz, 2 Hz, 1H).

EXAMPLE 4

5,6,7-trinor-4,8-inter-m-phenylene-13,14-didehydro-20-methyl PGI$_2$ methyl ester 15-t-butylether (4)

The procedure of Example 1 was followed except the uses of 2.912 g (14.85 mmol) of 3-t-butyloxy-1-nonyne and 563 mg (2.055 mmol) of methyl 4-(3a,8b-cis-dihydro-3H-1,2-syn-epoxycyclopenta[b]benzofuran-5-yl)butanoate in place of 3-t-butyloxy-1-octyne and methyl 4-(3a,8b-cis-dihydro-3H-1,2-syne-poxycyclopenta[b]benzofuran-5-yl)butanoate to give 208 mg (0.441 mmol, 22%) of the subject compund and 210 mg (0.446 mmol, 22%) of the position isomer.

Sepctrum data of the subject cmpound:

IR (neat, ν cm$^{-1}$): 3450, 2930, 2855, 2230, 1745, 1595, 1450, 1370, 1255, 1195, 1040, 865, 750. NMR (CDCl$_3$, δ ppm): 0.89 (t, 6 Hz, 3H), 1.26 (s, 9H), 1.1–2.2 (m, 15H), 2.29 (t, 7 Hz, 2H), 2.59 (t, 7 Hz, 2H), 2.89 (td, 6 Hz, 2 Hz, 1H), 3.64 (s, 3H), 3.85 (dd, 8 Hz, 5 Hz, 1H), 4.12 (td, 6 Hz, 2 Hz, 1H), 4.25 (q, 5 Hz, 1H), 5.25 (m, 1H), 6.88 (t, 7 Hz, 1H), 6.96 (dd, 7 Hz, 2 Hz, 1H), 7.12 (dd, 2 Hz, 7 Hz, 1H). MS (m/e): 470 (M+), 396, 297, 279, 232, 158.

Spectrum data of the position isomer:

IR (neat, ν cm$^{-1}$): 3450, 2930, 2855, 2230, 1754, 1595, 1450, 1370, 1255, 1190, 1045, 1010, 865, 750. NMR (CDCl$_3$, δ ppm): 0.98 (t, 6 Hz, 3H), 1,23 (s, 9H), 1.1–1.7 (m, 12H), 1.8–2.1 (m, 3H), 2.32 (t, 7 Hz, 2H), 2.42 (m, 1H), 2.60 (t, 7 Hz, 2H), 3.65 (s, 3H), 3.95 (t, 8 Hz, 1H), 4.10 (td, 6 Hz, 1 Hz, 1H), 4.16 (t, 8 Hz, 1H), 5.18 (dd, 8 Hz, 5 Hz, 1H), 6.78 (t, 7 Hz, 1H), 6.98 (dd, 7 Hz, 2 Hz, 1H), 7.14 (dd, 7 Hz, 2 Hz, 1H). MS (m/e): 470 (M+), 414, 396, 297, 231, 201.

EXAMPLE 5

5,6,7-trinor-4,8-inter-m-phenylene-13,14-didehydro-20-methyl-PGI$_2$ methyl ester (5)

The procedure of Example 2 was followed except the use of 196 mg (0.416 mmol) of 5,6,7,-trinor-4,8-inter-m-phenylene-13,14-didehydro-20-methyl PGI$_2$ methyl ester 15-t-butylether in place of (1) to give 75 mg (0.180 mmol, 43%) of the subject compound.

IR (neat, ν cm$^{-1}$): 3400, 2930, 2850, 2225, 1740, 1595, 1450, 1250, 1190, 1030, 860, 750. NMR (CDCl$_3$, δ ppm): 0.90 (t, 6 Hz, 3H), 1.2–2.4 (m, 16H), 2.30 (t, 7 Hz, 2H) 2.60 (t, 7 Hz, 2H), 2.86 (td, 6 Hz, 2 Hz, 1H), 3.65 (s, 3H), 3.82 (dd, 8 Hz, 6 Hz, 1H) 4.25 (q, 6 Hz, 1H), 4.40 (td, 6 Hz, 2 Hz, 1H), 5.24 (m, 1H), 6.89 (t, 7 Hz, 1H), 6.97 (dd, 7 Hz, 2 Hz, 1H), 7.13 (dd, 7 Hz, 2 Hz, 1H). MS (m/e): 414 (M+), 396, 232, 158.

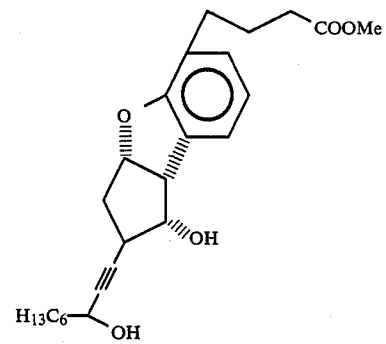

The above mentioned procedure was followed except the use of 168 mg (0.357 mmol) of the position isomer of (4) in place of (4) to give 88 mg (0.212 mmol, 59%) of the position isomer of the subject compound.

IR (neat, ν cm$^{-1}$): 3400, 2930, 2850, 2230, 1740, 1595, 1450, 1250, 1190, 1000, 860, 750. NMR (CDCl$_3$, δ ppm): 0.89 (t, 6 Hz, 3H), 1.1–1.8 (m, 12H0, 1.92 (m, 2H), 2.08 (bs, 2H), 2.34 (t, 7 Hz, 2H), 2.43 (m, 1H), 2.60 (t, 7 Hz, 2H), 3.65 (s, 3H), 3.95 (t, 8 Hz, 1H), 4.22 (t, 8 Hz, 1H), 4.32 (td, 6 Hz, 2 Hz 1H), 5.18 (dd, 8 Hz, 5 Hz, 1H), 6.78 (t, 7 Hz, 1H), 7.00 (dd. 7 Hz, 2 Hz, 1H), 7.14 (dd, 7 Hz, 2 Hz, 1H). MS (m/e): 414 (M+), 396, 375, 293, 233, 201.

EXAMPLE 6

5,6,7,-trinor-4,8-inter-m-phenylene-13,14-didehydro-20-methyl-PGI$_2$ (6)

The procedure of Example 3 was followed except the use of 55.5 mg (0.134 mmol) of 5,6,7-trinor-4,8-inter-m-phenylene-13,14-didehydro-20-methyl-PGI$_2$ methyl ester in place of (2) to give 47.0 mg (0.118 mmol 88%) of the subject compound.

IR (neat, ν cm$^{-1}$): 3600–2500, 2930, 2850, 1225, 1710, 1595, 1450, 1250, 1190, 1030, 860, 745. NMR (CDCl$_3$, δ ppm): 0.89 (t, 6 Hz, 3H), 1.1–2.2 (m, 14H), 2.31 (t, 7 Hz, 2H), 2.62 (t, 7 Hz, 2H), 2.82 (td, 6 Hz, 2 Hz, 1H), 3.88 (dd, 8 Hz, 6 Hz, 1H), 4.23 (q, 6 Hz, 1H), 4.39 (td, 6 Hz, 2 Hz, 1H), 4.64 (bs, 3H), 5.20 (m, 1H), 6.88 (t, 7 Hz, 1H), 6.96 (dd, 7 Hz, 2 Hz, 1H), 7.12 (dd, 7 Hz, 2 Hz, 1H). MS (M/e): 400 (M+), 218, 158.

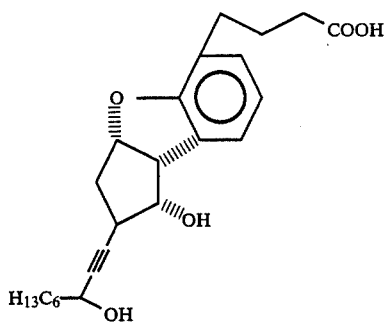

The above mentioned procedure was followed except the use of 64.7 mg (0.156 mmmol) of the position isomer of (5) in place of (5) to give 58 mg (0.145 mmol, 93%) of the position isomer of the subject compound.

IR (neat, ν cm$^{-1}$): 3600-2500, 2925, 2830, 2230, 1710, 1595, 1450, 1250, 1190, 1000, 865, 750. NMR (CDCl$_3$, δ ppm): 0.90 (t, 6 Hz, 3H), 1.1-1.8 (m, 12H), 1.98 (q, 7 Hz, 2H), 2.36 (t, 7 Hz, 2H), 2.40 (m, 1H), 2.62 (t, 7 Hz, 2H), 3.94 (t, 8 Hz, 1H), 4.22 (t, 8 Hz, 1H), 4.32 (td, 7 Hz, 2 Hz, 1H), 4.54 (bs, 3H), 5.16 (dd, 8 Hz, 5 Hz, 1H), 6.78 (t, 7 Hz, 1H), 7.00 (dd, 7 Hz, 2 Hz, 1H), 7.14 (dd, 7 Hz, 2 Hz, 1H). MS (m/e): 400 (M+), 311, 217, 201.

EXAMPLE 7

5,6,7-trinor-4,8-inter-m-phenylene-13,14-didehydro-15-cyclohexyl-16,17,18,19,20-pentanor PGI$_2$ methyl ester 15-t-butylether (7)

The procedure of Example 1 was followed except the use of 2.965 g (15.28 mmol) of 3-t-butyloxy-3-cyclohexyl-1-propyne and 552 mg (2.015 mmol) of methyl 4-(3a,8b-cis-dihydro-3H-1,2-syn-epoxy-cyclopenta[b]benzofuran-5-yl)butanoate in place of 3-t-butyloxy-1-octyne and methyl 4-(3a,8b-cis-dihydro-3H-1,2-syn-epoxy-cyclopenta[b]benzofuran-5-yl)butanoate to give 196 mg (0.419 mmol, 21%) of the subject compound and 210 mg (0.449 mmol, 22%) of the position isomer.

Spectrum data of the subject compound:
IR (neat, ν cm$^{-1}$): 3450, 2930, 2850, 1740, 1595, 1450, 1365, 1255, 1195, 1040, 1020, 865, 745. NMR (CDCl$_3$, δ ppm): 0.9-1.4 (m, 6H), 1.24 (s, 9H), 1.5-2.1 (m, 11H), 2.30 (t, 7 Hz, 2H), 2.59 (t, 7 Hz, 1H), 2.88 (td, 5 Hz, 2 Hz, 1H), 3.64 (s, 3H), 3.94 (m, 2H), 4.26 (q, 5 Hz, 1H), 5.30 (m, 1H), 6.79 (t, 7 Hz, 1H), 6.96 (dd, 7 Hz, 2 Hz, 1H), 7.12 (dd, 7 Hz, 2 Hz, 1H). MS (m/e): 468 (M+), 329, 299, 279, 154.

Spectrum data of the position isomer:
IR (neat, ν cm$^{-1}$): 3450, 2930, 2850, 1740, 1595, 1450, 1365, 1255, 1195, 1045, 1010, 865, 750. NMR (CDCl$_3$, δ ppm): 0.9-1.2 (m, 6H), 1.22 (s, 9H), 1.6-2.1 (m, 11H), 2.34 (t, 7 Hz, 2H), 2.43 (m, 1H), 2.61 (t, 7 Hz, 1H), 3.64 (s, 3H), 3.86 (dd, 6 Hz, 1 Hz, 1H), 3.97 (t, 8 Hz, 1H), 4.12 (m, 1H), 5.18 (dd, 8 Hz, 6 Hz, 1H), 6.79 (t, 7 Hz, 1H), 7.00 (dd, 7 Hz, 2 Hz, 1H), 7.14 (dd, 7 Hz, 2 Hz, 1H). MS (m/e): 468 (M+), 329, 297, 279, 201.

EXAMPLE 8

5,6,7,-trinor-4,8-inter-m-phenylene-13,14-didehydro-15-cyclohexyl-16,17,18,19,20-pentanor PGI$_2$ methyl ester (8)

The procedure of Example 2 was followed except the use of 193 mg (0.412 mmol) of 5,6,7-trinor-4,8-inter-m-phenylene-13,14-didehydro-15-cyclohexyl-16,17,18,19,20-pentanor PGI$_2$ methyl ester 15-t-butylether in place of (1) to give 99 mg (0.240 mmol, 58%) of the subject compound.

IR (neat, ν cm$^{-1}$): 3380, 2925, 2850, 2230, 1730, 1595, 1450, 1250, 1190, 1025, 865, 745. NMR (CDCl$_3$, δ ppm): 1.0-1.4 (m, 6H), 1.6-2.4 (m, 11H), 2.30 (t, 7 Hz, 2H), 2.59 (t, 7 Hz, 2H), 2.83 (td, 5 Hz, 2 Hz, 1H), 3.64 (s, 3H), 3.81 (dd, 8 Hz, 5 Hz, 1H), 4.18 (dd, 5 Hz, 2 Hz, 1H), 4.24 (q, 5 Hz, 1H), 5.24 (m, 1H), 6.79 (t, 7 Hz, 1H), 6.96 (dd, 7 Hz, 1 Hz, 1H), 7.14 (dd, 7 Hz, 1 Hz, 1H). MS (m/e): 412 (M+), 394, 232, 158.

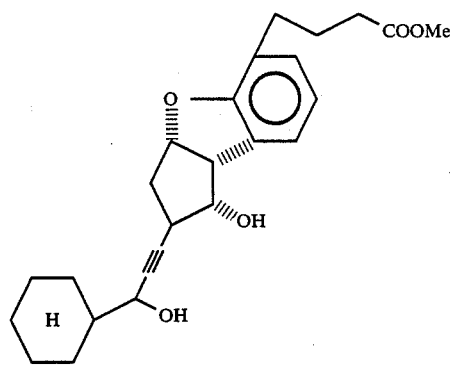

The above mentioned procedure was followed except the use of 162 mg (0.345 mmol) of the position isomer of (7), in place of (7) to give 68 mg (0.165 mmol, 48%) of the position isomer of the subject compound was obtained.

IR (neat, ν cm$^{-1}$): 3380, 2925, 2850, 2225, 1730, 1595, 1440, 1250, 1190, 1005, 860, 750. NMR (CDCl$_3$, δ ppm): 0.9-1.4 (m, 6H), 1.6-2.2 (m, 11H), 2.34 (t, 7 Hz, 2H), 2.43 (m, 1H), 2.59 (t, 7 Hz, 2H), 3.64 (s, 3H), 3.94 (t, 8 Hz, 1H), 4.11 (dd, 5 Hz, 1 Hz, 1H), 4.22 (t, 8 Hz, 1H), 5.17 (dd, 8 Hz, 5 Hz, 1H), 6.77 (t, 7 Hz, 1H), 6.97 (dd, 7 Hz, 2 Hz, 1H), 7.12 (dd, 7 Hz, 2 Hz, 1H). MS (m/e): 412 (M+), 396, 201, 176.

EXAMPLE 9

5,6,7,-trinor-4,8-inter-m-phenylene-13,14-didehydro-15-cyclohexyl-16,17,18,19,20-pentanor PGI$_2$ (9)

The procedure of Example 3 was followed except the use of 79.1 mg (0.192 mmol) of 5,6,7-trinor-4,8-inter-m-phenylene-13,14-didehydro-15-cyclohexyl-16,17,18,19,20-pentanor PGI$_2$ methyl ester, in place of (2) to give 61.5 mg (0.155 mmol, 81%) of the subject compound.

IR (neat, ν cm$^{-1}$): 3600-2500, 2930, 2850, 2225, 1705, 1595, 1450, 1260, 1190, 1080, 1020, 860, 740. NMR (CDCl$_3$, δ ppm): 0.8-1.5 (m, 6H), 1.5-2.2 (m, 9H), 2.31 (t, 7 Hz, 2H), 2.61 (t, 7 Hz, 2H), 2.80 (td, 5 Hz, 1 Hz, 1H), 3.79 (dd, 8 Hz, 5 Hz, 1H), 4.16 (dd, 6 Hz, 2 Hz, 1H), 4.22 (q, 5 Hz, 1H), 4.90 (bs, 3H), 5.18 (m, 1H), 6.78 (t, 7 Hz, 1H), 6.95 (dd, 7 Hz, 1 Hz, 1H), 7.12 (dd, 7 Hz, 1 Hz, 1H). MS (m/e): 398 (M+), 380, 297, 279, 218, 158.

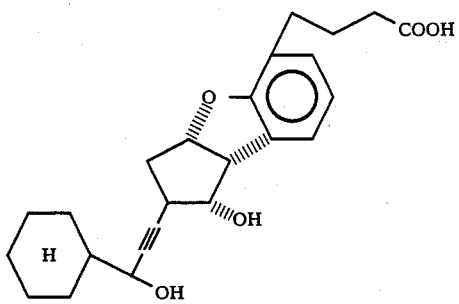

The above mentioned procedure was followed except the use of 49.9 mg (0.121 mmol) of the position isomer of (8), in place of (8) to give 43.7 mg (0.110 mmol, 91%) of the position isomer of the subject compound.

IR (neat, $\nu$ cm$^{-1}$): 3600–2500, 2925, 2850, 2225, 1705, 1595, 1450, 1250, 1190, 1090, 1000, 865, 750. NMR (CDCl$_3$, $\delta$ ppm): 0.8–1.5 (m, 6H), 1.5–2.2 (m, 9H), 2.36 (t, 7 Hz, 2H), 2.50 (m, 1H), 2.63 (t, 7 Hz, 2H), 3.95 (t, 8 Hz, 1H), 4.0–4.6 (m, 5H), 5.19 (dd, 8 Hz, 5 Hz, 1H), 6.78 (t, 7 Hz, 1H), 7.00 (dd, 7 Hz, 1 Hz, 1H), 7.14 (dd, 7 Hz, 1 Hz, 1H). MS (m/e): 398 (M$^+$), 380, 337, 297, 217, 201, 176.

EXAMPLES 10–18

The procedure of example 1 are followed except the uses of 3-t-butyloxy-3-(4-methylcyclohexyl)-1-propyne; 3-t-butyloxy-3-(3-methyl-cyclohexyl)-1-propyne; 3-t-butyloxy-3-(2,2-dimethyl-4-methylcyclohexyl)-1-propyne; 3-t-butyloxy-3-(2-methylcyclohexyl)-1-propyne; 3-t-butyloxy-3-cyclopentyl-1-propyne; 3-t-butyloxy-3-(2-methylcyclopentyl)-1-propyne; 3-t-butyloxy-4-cyclohexyl-1-butyne; 3-t-tutyloxy-4-cyclopentyl-1-butyne or 3-t-butyloxy-5-cyclohexyl-1-pentyne in place of 3-t-butyloxy-1-octyne and the procedure of Example 2 and 3 are followed successively except the uses of the resulting compounds to give 5,6,7-trinor-4,8-inter-m-phenylene-13,14-didehydro-16,17,18,19,20-pentanor-15-(4-methyl-cyclohexyl) PGI$_2$ (10), 5,6,7-trinor-4,8-inter-m-phenylene-13,14-didehydro-16,17,18,19,20-pentanor-15-(3-methylcyclohexyl) PGI$_2$ (11), 5,6,7-trinor-4,8-inter-m-phenylene-13,14-didehydro-16,17,18,19,20-pentanor-15-(2,2-dimethyl-4-methyl-cyclohexyl) PGI$_2$ (12), 5,6,7-trinor-4,8-inter-m-phenylene-13,14-didehydro-16,17,18,19,20-pentanor-15-(2-methylcyclohexyl) PGI$_2$ (13), 5,6,7-trinor-4,8-inter-m-phenylene-13,14-didehydro-16,17,18,19,20-pentanor-15-cyclopentyl PGI$_2$ (14), 5,6,7-trinor-4,8-inter-m-phenylene-13,14-didehydro-16,17,18,19,20-pentanor-15-(2-methylcyclopentyl) PGI$_2$ (15), 5,6,7-trinor-4,8-inter-m-phenylene-13,14-didehydro-17,18,19,20-tetranor-16-cyclohexyl PGI$_2$ (16), 5,6,7-trinor-4,8-inter-m-phenylene-13,14-didehydro-17,18,19,20-tetranor-16-cyclopentyl PGI$_2$ (17), or 5,6,7-trinor-4,8-inter-m-phenylene-13,14-didehydro-18,19,20-trinor-17-cyclohexyl PGI$_2$ (18). The infrared spectra and mass spectra of the compounds (10)–(18) are shown in Table 1.

TABLE 1

| Example | Compound | Mass spectrum (m/e, M$^+$) | Infrared spectrum cm$^{-1}$ |
|---|---|---|---|
| 10 | 10 | 412 | 3600–2500, 2930, 2850, 1705, 1595, 1450, 1262, 1190, 1080, 860, 740 |
| 11 | 11 | 412 | 3600–2500, 2930, 2852, 1705, 1595, 1452, 1260, 1192, 1080, 862, 740 |
| 12 | 12 | 440 | 3600–2500, 2932, 2850, 1704, 1595, 1448, 1260, 1190, 1082, 860, 742 |
| 13 | 13 | 412 | 1705, 1596, 1448, 1260, 1190, 1080, 860, 740 |
| 14 | 14 | 382 | 1705, 1596, 1450, 1265, 1190, 1080, 860, 740 |
| 15 | 15 | 398 | 1706, 1595, 1451, 1260, 1190, 1080, 860, 740 |
| 16 | 16 | 412 | 1705, 1596, 1450, 1260, 1190, 1080, 860, 740 |
| 17 | 17 | 398 | 1705, 1596, 1450, 860 |
| 18 | 18 | 426 | 1705, 1596, 1450, 860, 742 |

EXAMPLE 19

5,6,7-trinor-4,8-inter-m-phenylene-13,14-didehydro-15-phenyl-16,17,18,19,20-pentanor PGI$_2$ methyl ester (19)

To a solution of 4.461 g (19.36 mmol) of t-butyldimethylsiloxyphenyl-1-propyne in 10 ml of dry toluene at −50° C. under argon was added 11.5 ml (19.11 mmol) of a hexane solution (1.62M) of n-butyl lithium, and the resulting solution was stirred for 20 minutes. 8.5 ml (16.66 mmol) of a toluene solution (1.96M) of a diethylaluminium chloride:ethylmethoxyaluminium chloride (3:1) mixture was added, the resulting solution was stirred for 10 minutes, thereafter, the temperature was allowed to warm to 0° C. and stirring was carried out for 1 hour. A solution of 518 mg (1.89 mmol) of methyl 4-(3a,8b-cis-dihydro-3H-1,2-syn-epoxycylopenta[b]benzofuran-5-yl)butanoate in 6 ml of toluene was added, and the resulting solution was stirred at 60° C. for 12 hours.

Methanol (2 ml) and further 20 ml of saturated brine under ice cold conditions were added. The resulting solution was extracted with ether (200 ml), the ether layer was washed with saturated brine (3×30 ml), dried and thereafter concentrated.

The residue was purified by chromatography (Merck Lobar B, cyclohexane-ethyl acetate 5:2) to afford crude a 15-t-butyldimethylsilyl ether and the position isomer thereof. This silylether was dissolved in 5 ml of an acetic acid:water:THF (3:1:1) mixture and stirred at room temperature for 15 hours. The solvent was distilled off under a reduced pressure and the residue was purified by chromatography (Merck Lobar B, cyclohexane-ethyl acetate 1:3) to give 22.2 mg (0.0547 mmol, 29%) of the subject compound.

IR (neat, $\nu$ cm$^{-1}$): 3400, 3040, 2930, 2850, 2220, 1720, 1590, 1445, 1260, 1190, 1075, 1020, 735, 695. NMR (CDCl$_3$, $\delta$ ppm): 1.8–2.5 (m, 6H), 2.30 (t, 7 Hz, 2H), 2.60 (t, 7 Hz, 2H), 2.93 (dd, 5 Hz, 2 Hz, 1H), 3.64 (s, 3H), 3.87 (dd, 8 Hz, 5 Hz, 1H), 4.31 (q, 5 Hz, 1H), 5.26 (m, 1H), 5.51 (d, 2 Hz, 1H), 6.79 (t, 7 Hz, 1H), 6.97 (dd, 7 Hz, 2 Hz, 1H), 7.13 (dd, 7 Hz, 2 Hz, 1H), 7.30–7.70 (m, 5H). MR (m/e): 406 (M$^+$), 388, 232, 158, 131, 105.

The above mentioned procedure was followed to give 29.9 mg (0.0736 mmol, 3.9%) of the position isomer.

Spectrum data of the position isomer: IR (neat, $\nu$ cm$^{-1}$): 3380, 3020, 2930, 2850, 2225, 1730, 1590, 1445, 1240, 1190, 995, 750, 695. NMR (CDCl$_3$, δ ppm): 1.84–2.14 (m, 4H), 2.32 (t, 7 Hz, 2H), 2.43 (m, 1H), 2.59 (t, 7 Hz, 2H), 2.78 (bs, 2H), 3.64 (s, 3H), 3.90 (t, 8 Hz, 1H), 4.24 (t, 8 Hz, 1H), 5.15 (dd, 8 Hz, 5 Hz, 1H), 5.42 (s, 1H), 6.77 (t, 7 Hz, 1H), 6.98 (dd, 7 Hz, 1 Hz, 1H), 7.11 (dd, 7 Hz, 1 Hz, 1H), 7.12–7.65 (m, 5H).

MS (m/e): 406 (M+), 388, 200, 163, 144, 105.

EXAMPLE 20

5,6,7-trinor-4,8-inter-m-phenylene-13,14-didehydro-15-phenyl-16,17,18,19,20-pentanor-PGI$_2$ (20)

The procedure of Example 3 was followed except the use of 14.2 mg (0.0350 mmol) of 5,6,7-trinor-4,8-inter-m-phenylene-13,14-didehydro-15-phenyl-16,17,18,19,20-pentanor PGI$_2$ methyl ester in place of (2) to give 12.6 mg (0.0321 mmol, 92%) of the subject compound.

IR (neat, ν cm$^{-1}$): 3600–2500, 2925, 2850, 2220, 1700, 1595, 1450, 1240, 1190, 1075, 1025, 860, 745, 695. NMR (CDCl$_3$, δ ppm): 1.9–2.1 (m, 4H), 2.30 (t, 7 Hz, 2H), 2.52 (t, 7 Hz, 2H), 2.89 (td, 6 Hz, 2 Hz, 1H), 3.84 (dd, 8 Hz, 6 Hz, 1H), 4.25 (q, 6 Hz, 1H), 4.3 (bs, 3H), 5.23 (m, 1H), 5.49 (d, 2 Hz, 1H), 6.78 (t, 7 Hz, 1H), 6.96 (dd, 7 Hz, 2 Hz, 1H), 7.11 (dd, 7 Hz, 2 Hz, 1H), 7.30–7.70 (m, 5H). MS (m/e): 392 (M+), 374, 218, 158.

The above mentioned procedure was followed except the use of 27.5 mg (0.0677 mmol) of the position isomer of (19) in place of (19) to give 19.4 mg (0.0495 mmol, 73%) of the position isomer of the subject compound.

IR (neat, ν cm$^{-1}$): 3600–2500, 2920, 2850, 2225, 1700, 1590, 1450, 1240, 1190, 1100, 1040, 990, 850, 745, 695. NMR (CDCl$_3$, δ ppm): 1.8–2.15 (m, 4H), 2.34 (t, 7 Hz, 2H), 2.43 (m, 1H), 2.61 (t, 7 Hz, 2H), 3.91 (t, 8 Hz, 1H), 4.24 (t, 8 Hz, 1H), 4.53 (bs, 3H), 5.15 (dd, 8 Hz, 5 Hz, 1H), 5.41 (s, 1H), 6.76 (t, 7 Hz, 1H), 6.97 (dd, 7 Hz, 2 Hz, 1H), 7.10 (dd, 7 Hz, 2 Hz, 1H), 7.24–7.64 (m, 5H). MS (m/e): 392 (M+), 374, 170.

EXAMPLES 21–28

The procedure of Example 19 are followed except the uses of 3-(t-butyldimethylsiloxy)-3-(p-chlorophenyl)-1-propyne, 3-(t-butyldimethylsiloxy)-3-(m-chlorophenyl)-1-propyne, 3-(t-butyldimethylsiloxy)-3-(p-tolyl)-1-propyne, 3-(t-butyldimethylsiloxy)-3-(p-methoxyphenyl)-1-propyne, 3-(t-butyldimethylsiloxy)-3-(m-trifluoromethylphenyl)-1-propyne, 3-(t-butyldimethylsiloxy)-4-phenyl-1-butyne, 3-(t-butyldimethylsiloxy)-5-phenyl-1-pentyne, or 3-(t-butyldimethylsiloxy)-3-(β-naphthyl)-1-propyne in place of 3-t-butyldimethylsiloxy-3-phenyl-1-propyne, and the procedure of Example 20 is followed except the use of the each resulting compound to give 5,6,7-trinor-4,8-inter-m-phenylene-13,14-didehydro-16,17,18,19,20-pentanor-15-(p-chlorophenyl) PGI$_2$ (21), 5,6,7-trinor-4,8-inter-m-phenylene-13,14-didehydro-16,17,18,19,20-pentanor-15-(m-chlorophenyl) PGI$_2$ (22), 5,6,7-trinor-4,8-inter-m-phenylene-13,14-didehydro-16,17,18,19,20-pentanor-15-(p-tolyl) PGI$_2$ (23), 5,6,7-trinor-4,8-inter-m-phenylene-13,14-didehydro-16,17,18,19,20-pentanor-15-(p-methoxyphenyl) PGI$_2$ (24) 5,6,7-trinor-4,8-inter-m-phenylene-13,14-didehydro-16,17,18,19,20-pentanor-15-(m-trifluoromethylphenyl) PGI$_2$ (25), 5,6,7-trinor-4,8-inter-m-phenylene-13,14-didehydro-17,18,19,20-tetranor-16-phenyl PGI$_2$ (26), 5,6,7-trinor-4,8-inter-m-phenylene-13,14-didehydro-18,19,20-trinor-17-phenyl PGI$_2$ (27), or 5,6,7-trinor-4,8-inter-m-phenylene-13,14-didehydro-16,17,18,19,20-pentanor-15-(β-naphthyl) PGI$_2$ (28). The spectral data of the compounds (21)–(28) are shown in Table 2.

TABLE 2

| Example | Compound | Mass spectrum (m/e) | Infrared spectrum cm$^{-1}$ |
|---|---|---|---|
| 21 | 21 | 426, 428 | 3600–2500, 2925, 2850, 1700, 1595, 1400, 1240, 1190, 1075, 860 |
| 22 | 22 | 426, 428 | 1700, 1595, 1450, 1242, 1190, 1075, 860, 730 |
| 23 | 23 | 406 | 1700, 1595, 1450, 1242, 1190, 1075, 860, 815, 730 |
| 24 | 24 | 422 | 1700, 1598, 1455, 1240, 1190, 1075, 860 |
| 25 | 25 | 460 | |
| 26 | 26 | 406 | 1700, 1595, 1450, 1240, 1190, 1075, 1025, 860, 740, 695 |
| 27 | 27 | 420 | 1700, 1240, 1190, 860, 740, 695 |
| 28 | 28 | 442 | 1700, 1240, 1190 |

EXAMPLE 29–33

The procedure of Example 1 are followed except the uses of 3-t-butyloxy-5-methyl-1-octyne, 3-t-butyloxy-5-methyl-1-nonyne, 3-t-butyloxy-4,4-dimethyl-1-octyne, 3-t-butyloxy-4,4-dimethyl-1-nonyne, or 3-t-butyloxy-9-methyl-8-decene-1-yn in place of 3-t-butyloxy-1-octyne, and the procedures of Examples 2 and 3 are followed successively except the uses of the resulting compounds to give 5,6,7-trinor-4,8-inter-m-phenylene-13,14-didehydro-17-methyl PGI$_2$ (29), 5,6,7-trinor-4,8-inter-m-phenylene-13,14-didehydro-17-methyl-ω-homo PGI$_2$ (30), 5,6,7-trinor-4,8-inter-m-phenylene-13,14-didehydro-16,16-dimetyl PGI$_2$ (31), 5,6,7-trinor-4,8-inter-m-phenylene-13,14-didehydro-16,16-dimethyl-ω-homo PGI$_2$ (32), or 5,6,7-trinor-4,8-inter-m-phenylene-13,14-didehydro-20-isopropylidene PGI$_2$ (33). The spectral data of these compounds are shown in Table 3.

TABLE 3

| Example | Compound | Mass spectrum (m/e) | Infrared spectrum cm$^{-1}$ |
|---|---|---|---|
| 29 | 29 | 400 | 1710, 1595, 1450, 1250, 1190, 1030, 865, 745 |
| 30 | 30 | 414 | 1708, 1597, 1452, 1250, 1190, 1025 |
| 31 | 31 | 428 | 1710, 1595, 1450, 1250, 1190 |
| 32 | 32 | 442 | 1710, 1595, 1450, 1250, 1190 |
| 33 | 33 | 426 | 1705, 1595, 1450, 1250, 1190, 862, 740 |

EXAMPLE 34

2-decarboxy-2-tetrahydropyranyloxymethyl-5,6,7-trinor-4,8-inter-(5-bromo-1,3-phenylene)-16,16-dimethyl PGI$_2$ (34)

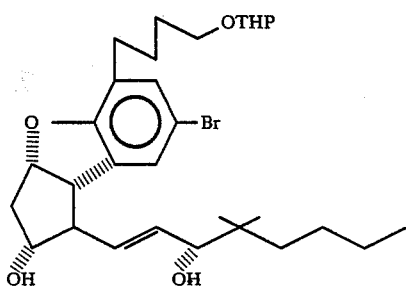

To a solution of 183 mg (0.394 mmol) of 1,2,3a,8b-cis-tetrahydro-7-bromo-1-exo-(2-formylethenyl)-2-endo-hydroxy-5-(4-tetrahydropyranyloxy-butyl)cyclopenta[b]benzofuran in 3 ml of THF −78° C. was added 1.9 ml (0.85M, 1.61 mmol, 4.1 equiv.) of a solution of 2-(2-methyl)hexylmagnesium chloride in THF, and the resulting solution was stirred for 30 minutes. After TLC analysis revealed completion, 2 ml of a saturated aqueous solution of ammonium chloride was added, and the mixture was extracted with ethyl acetate (10 ml×6). The organic layer was dried and thereafter concentrated to obtain 196 mg of an oily crude product. This crude product was purified by column chromatography (Merck Co.'s Lobar Column B; cyclohexane:ethyl acetate 1:3) to give 60 mg (27%) of the polar subject compound and 29 mg (13%) of a less polar 15-epimer.

IR (neat) $\nu$ cm$^{-1}$: 3400 (3650–3000), 2930, 2860, 1600, 1350, 1255, 1190, 1135, 1115, 1070, 1020, 965, 860, 745. NMR (CDCl$_3$ solution) δ ppm: 0.87 (s, 3H), 0.91 (s, 3H), 0.91 (t, J=6 Hz, 3H), 1.28 (m, 6H), 1.64 (m, 10H), 1.97 (m, 1H), 2.59 (m, 4H), 3.00 (broad s, 2H), 3.39 (m, 3H), 3.81 (m, 4H), 4.57 (m, 1H), 5.07 (m, 1H), 5.64 (m, 2H), 6.94 (s, 1H), 7.09 (s, 1H). Mass spectrum (m/e): M+ 564. Anal. Calcd. for C$_{30}$H$_{45}$O$_5$Br C: 63.71% H: 8.02% Br: 14.13%; Found C; 63.69% H; 8.03% Br; 14.11%.

EXAMPLE 35

2-decarboxy-2-tetrahydropyranyloxymethyl-5,6,7-trinor-4,8-inter-(5-bromo-1,3-phenylene)-16,16-dimethyl PGI$_2$ diacetate (35)

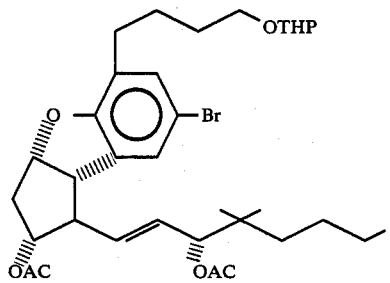

Under nitrogen atmosphere, to a solution of 132 mg (0.234 mmol) of 2-decarboxy-2-tetrahydropyranyloxymethyl-5,6,7-trinor-4,8-(5-bromo-1,3-phenylene)-16,16-dimethyl PGI$_2$ in 1 ml of pyridine was added acetic anhydride, and the resulting solution was stirred at room temperature for 15 hours. After TLC analysis revealed completion, the solution was concentrated to give 145 mg (0.223 mmol, 95.3%) of the subject compound as an oil.

NMR (CDCl$_3$ solution) δ ppm: 0.89 (m, 9H), 1.25 (m, 6H), 1.67 (m, 10H), 1.75 (s, 3H), 2.03 (m, 1H), 2.07 (s, 3H), 2.56 (m, 3H), 2.82 (m, 1H), 3.56 (m, 3H), 3.81 (m, 2H), 4.58 (m, 1H), 4.93 (q, J=6 Hz, 1H), 5.08 (m, 1H), 5.20 (m, 1H), 5.62 (m, 2H), 6.93 (s, 1H), 7.08 (s, 1H). IR (neat, $\nu$ cm$^{-1}$): 2930, 2860, 1735, 1450, 1365, 1235, 1130, 1120, 965, 900, 860, 750. Mass (m/e): 648 (M+), 650 (M+2). Anal. Calcd. for C$_{34}$H$_{49}$O$_7$Br C=62.86% H=7.60% Found C; 62.83% H; 7.59%.

EXAMPLE 36

2-decarboxy-2-hydroxymethyl-5,6,7-trinor-4,8-inter-(5-bromo-1,3-phenylene)-16,16-dimethyl PGI$_2$ 11(0), 15(0)-diacetate (36)

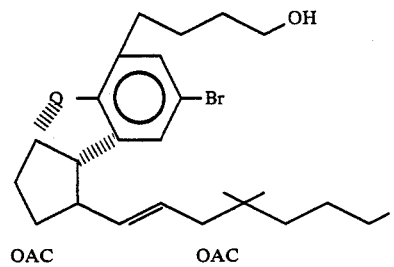

To a solution of 145 mg (0.223 mmol) of 2-decarboxy-2-tetrahydro-pyranyloxymethyl-5,6,7-trinor-4,8-inter-(5-bromo-1,3-phenylene)-16,16-dimethyl PGI$_2$ diacetate in 1 ml of THF and 2 ml of acetonitirile was added 1 m of 0.25N hydrochloric acid, and the resulting solution was stirred at room temperature for 7 hours. The reaction solution was cooled to 0° C., 3 ml of a saturated aqueous solution of sodium bicarbonate was added and the mixture was extracted with ethyl acetate (10 ml×5). The organic layer was dried over anhydrous Na$_2$SO$_4$, concentrated and 153 mg of an oily substance obtained was purified by column chromatography (Merck Co.'s Lobar Column; cyclohexane:ethly acetate 2:3) to give 101 mg (0.179 mmol, 80.2%) of 36 as an oil.

NMR (CDCl$_3$ solution) $\nu$ ppm: 0.89 (m, 9H), 1.25 (m, 6H), 1.64 (m, 4H), 1.74 (s, 3H), 2.03 (m, 1H), 2.07 (s, 3H), 2.12 (broad s, 1H), 2.55 (m, 3H), 2.80 (m, 1H), 3.61 (m, 3H), 4.93 (q, J=6 Hz, 1H), 5.07 (m, 1H), 5.20 (m, 1H), 5.60 (m, 2H), 6.92 (s, 1H), 7.07 (s, 1H).

IR (neat, $\nu$ cm$^{-1}$): 3450, (3650–3000), 2930, 2860, 1735, 1600, 1450, 1370, 1235, 1190, 1050, 1020, 970, 910, 860, 740. Mass (m/e): 564 (M+), 566 (M+2). Anal. Calcd. for C$_{29}$H$_{41}$O$_6$Br C=61.59% H=7.30% Found C; 61.55% H; 7.28%.

EXAMPLE 37

2-decarboxy-2-hydroxymethyl-5,6,7-trinor-4,8-inter-m-phenylene-16,16-dimethyl PGI$_2$ 11(0), 15(0)-diacetate (37)

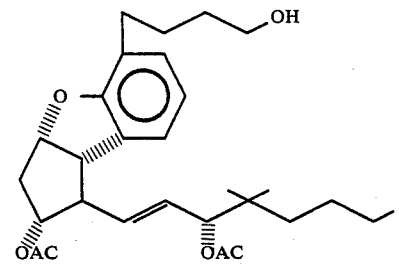

To a solution of 92 mg (0.162 mmol) of 2-decarboxy-2-hydroxymethyl-5,6,7-trinor-4,8-inter-(5-bromo-1,3-phenylene)-16,16-dimethyl-PGI$_2$ diacetate and 1 mg of 2,2'-azobisisobutyronitrile in 6 ml of benzene under argon atmosphere was added 300 mg (1.03 mmol, 6.4 equiv.) of tri-n-butyltin hydride, and the resulting mixture was stirred at 50° C. for 26 hours. To the mixture 1 ml of a saturated aqueous solution of sodium bicarbonate and 1 ml saturated brine were added and the mixture was extracted with ethyl acetate (10 ml×3). The organic layer was dried over anhydrous $Na_2SO_4$ and thereafter concentrated. When 343 mg of an oily substance obtained was purified by column chromatography (Merck Co.'s Lobar Column; cyclohexane:ethyl acetate 1:2), 69 mg (0.142 mmol, 87.6%) of 37 was obtained in an oily state.

NMR ($CDCl_3$ solution) δ ppm: 0.89 (m, 9H), 1.25 (m, 6H), 1.64 (m, 4H), 1.74 (s, 3H), 2.03 (m, 1H), 2.07 (s, 3H), 2.55 (m, 3H), 2.80 (m, 1H), 3,10 (broad s, 1H), 3.61 (m, 3H), 4.93 (q, J=6 Hz, 1H), 5.07 (m, 1H), 5.20 (m, 1H), 5.60 (m, 2H), 6.76 (dd, J=7, 8 Hz, 1H), 6.89 (d, J=7 Hz, 1H), 6.90 (d, J=8 Hz, 1H). IR (neat, ν $cm^{-1}$): 3450 (3650–3000), 2930, 2860, 1735, 1600, 1450, 1370, 1235, 1190, 1050, 1020, 970, 860, 760, 740. Mass (m/e): 486 ($M^+$). Anal. Calcd. for $C_{29}H_{42}O_6$ C=71.58% H=8.63% Found C; 71.56% H; 8.63%.

EXAMPLE 38

5,6,7-trinor-4,8-inter-m-phenylene-16,16-dimethyl $PGI_2$ diacetate (38)

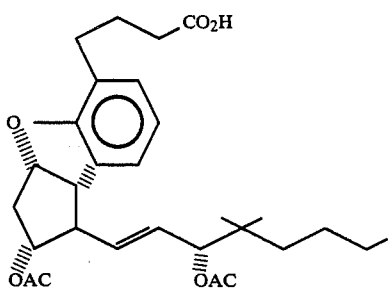

To a solution of 66.0 mg (0.136 mmol) of 2-decarboxy-2-hydroxymethyl-5,6,7-trinor-4,8-inter-m-phenylene-16,16-dimethyl $PGI_2$ diacetate in 1 ml of N,N-dimethylformamide was added 412 mg (1.10 mmol, 8.1 equiv.) of pyridinium dichromate, and the resulting mixture was stirred at room temperature for 7 hours.

Five ml of water was added and the mixture was extracted with ethyl acetate (10 ml×3), the organic layer was washed with saturated brine (1 ml×2) and dried over, anhydrous $Na_2SO_4$. After concentration, 194 mg of the obtained crude product was purified by column chromatography (Merck Co.'s Lobar Column cyclohexane: ACOEt 2:1) to give 64.0 mg (0.128 mmol, 94.1%) of 38.

NMR ($CDCl_3$ solution ) δ ppm: 0.89 (m, 9H), 1.25 (m, 6H), 1.74 (s, 3H), 1.99 (m, 1H), 2.08 (s, 3H), 2.10 (m, 2H), 2.39 (t, J=7 Hz, 2H), 2.60 (m, 3H), 2.82 (m, 1H), 3.60 (dd, J=6, 8 Hz, 1H), 4.95 (q, J=6 Hz, 1H), 5.09 (m, 1H), 5.22 (m, 1H), 5.62 (m, 2H), 6.76 (dd, J=7, 8 Hz, 1H), 6.89 (d, J=7 Hz, 1H), 6.90 (d, J=8 Hz, 1H). IR (neat, ν $cm^{-1}$): 3200 (3600–2300), 2960, 2930, 2860, 1735, 1710, 1600, 1450, 1370, 1235, 1190, 1020, 965, 860, 760, 740. Mass (m/e): 500 ($M^+$). Anal. Calcd. for $C_{29}H_{40}O_9$ C=69.58% H=8.05% Found C; 69.29% H; 7.82%.

EXAMPLE 39

5,6,7-trinor-4,8-inter-m-phenyelene-16,16-dimethyl $PGI_2$ (39)

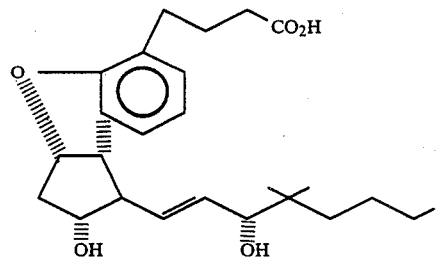

To a solution of 48.0 mg (0.96 mmol) of 5,6,7-trinol-4,8-inter-m-phenylene-16,16-dimethyl $PGI_2$ diacetate in 2 ml of methanol was added 0.5 ml (0.50 mmol, 5.2 equiv.) of 1N sodium hydroxide, and the resulting solution was stirred at room temperature for 24 hours. The solution was cooled to 0° C., 1N HCl was added slowly to adjust the pH of the reaction solution to 3, thereafter, the mixture was extracted with ethyl acetate (10 ml×5), and the organic layer was washed with saturated brine (1 ml×2) and thereafter dried over anhydrous $Na_2SO_4$. After evaporation of the solvent, 400 mg (0.096 mmol, 100%) of 39 was obtained.

NMR ($CDCl_3$ solution) δ ppm: 0.89 (m, 9H), 1.27 (m, 6H), 1.96 (m, 3H), 2.34 (m, 3H), 2.62 (m, 3H), 3,38 (t, J=9 Hz, 1H), 3.85 (m, 2H), 5.07 (non-dissociated quartet, J=8 Hz, 1H), 5.40 (broad singlet 3H), 5.63 (m, 2H), 6.74 (dd, J=8, 6 Hz, 1H), 6.94 (m, 2H). IR (neat, ν $cm^{-1}$): 3400 (3600–2220), 2960, 2930, 2860, 1710, 1600, 1450, 1250, 1190, 1070, 1020, 970, 910, 860, 765, 735. Mass (m/e): 416 ($M^+$). Anal. Calcd. for $C_{25}H_{36}O_5$ C=72.09% H=8.70% Found C; 71.98% H; 8.66%.

EXAMPLE 40

2-decarboxy-2-tetrahydropyranyloxymethyl-5,6,7-trinor-4,8-inter-m-phenylene-17-methyl $PGI_2$ (40, 41)

To a solution of 1 g of 1,2,3a,8b-cis-tetrahydro-5-(4-tetrahydropyranyloxymethyl)-1-exo-(2-formylethenyl)-2-endo-hydroxy cyclopenta(b)benzofuran in 20 ml of anhydrous THF cooled in ice bath was added dropwise 5 ml of 2-methylpentyl magnesium bromide (1N), and the resulting solution was stirred for 30 minutes. Ammonium chloride, methanol and water were added, and the mixture was extracted 3 times with ether. The combined ether layers were washed with water and saturated brine, dried and thereafter concentrated to afford 1.5 g of an oily substance. The oily substance was purified by column chromatography (silica gel; ethyl acetate) to give 196 mg of a less polar substance and 200 mg of a polar substance.

The less polar substance (17-α-methyl isomer) (40)

IR (neat) ν $cm^{-1}$: 3350, 1595, 970, 765, 745. NMR ($CDCl_3$) δ: 0.90 (6H, m), 3.40 (4H, m), 3.80 (4H, m) 4.20 (1H, m), 4.57 (1H, m), 5.10 (1H, m), 5.62 (2H, m), 6.72 (1H, t, J=7.0 Hz), 6.94 (1H, d, J=7.0 Hz), 6.96 (1H, d, J=7.0 Hz). Mass (m/e): 472, 454, 436.

The polar substance (17-β-methyl isomer) (41)

IR (neat, ν $cm^{-1}$): 3350, 1595, 970, 765, 745. NMR ($CDCl_3$) δ: 0.90 (6H, m), 3.40 (4H, m), 3.80 (4H, m), 4.20 (1H, m), 4.60 (1H, m), 5.10 (1H, m), 5.60 (2H, m), 6.72 (1H, t, J=7.0 Hz), 6.94 (1H, d, J=7.0 Hz), 6.96 (1H, d, J=7.0 Hz). Mass (m/e): 472, 454, 436. As $C_{29}H_{44}O_5$.

Anal. Calcd. for $C_{29}H_{44}O_5$ C=73.69% H=9.36% Found C; 73.61% H; 9.32%.

EXAMPLE 41

2-decarboxy-2-tetrahydropyranyloxymethyl-5,6,7-trinor-4,8-inter-m-phenylene-11,15-dideoxy-11,15-diacetoxy-17-α-methyl $PGI_2$ (42)

A solution of 170 mg of 2-decarboxy-2-tetrahydropyranyloxymethyl-5,6,7-trinor-4,8-inter-m-phenylene-17-α-methyl $PGI_2$ in 10 ml of acetic anhydride and 5 ml of anhydrous pyridine was stirred at room temperature for 2 hours. When the reaction solution was concentrated and the residue was treated azeotropically twice with toluence and once with benzene to give 200 mg of a nearly pure diacetate.

IR (neat, ν cm−): 1740, 1595, 1235, 970, 760, 750. NMR (CDCl$_3$) δ: 0.90 (5H, m), 1.72 (3H, s), 2.06 (3H, s), 2.60 (3H, s), 2.80 (1H, q, J=7.0 Hz), 3.20–4.00 (5H, m), 4.60 (1H, m), 4.92 (1H, m), 5.30 (2H, m), 5.60 (2H, m), 6.74 (1H, dd, J=8.0 Hz, 7.0 Hz), 6.96 (1H, d, J=8.0 Hz), 6.98 (1H, d, J=6.0 Hz) Mass (m/e): 556 (M+). Anal. Calcd. for $C_{33}H_{48}H_7$ C=71.19% H=8.69% Found C; 71.10% H; 8.60%.

EXAMPLE 42

2-decarboxy-2-tetrahydropyranyloxymethyl-5,6,7-trinor-4,8-inter-m-phenylene-11,15-dideoxy-11,15-diacetoxy-17-β-methyl $PGI_2$ (43)

The procedure of Example 41 was followed except the use of 180 mg of 2-decarboxy-2-tetrahydropyranyloxymethyl-5,6,7-trinol-4,8-inter-m-phenylene-17-methyl $PGI_2$ in place of (40) to give 200 mg of a diacetate.

IR (neat) ν cm−1: 1740, 1595, 1235, 970, 760, 750. NMR (CDCl$_3$) δ: 0.90 (6H, m), 1.73 (3H, s), 2.04 (3H, s), 2.60 (3H, s), 2.80 (1H, q, J=6.0 Hz), 3.20–4.00 (4H, m), 4.60 (1H, m), 4.92 (1H, m), 5.30 (2H, m), 5.60 (2H, m), 6.74 (1H, dd, J=8.0 Hz, 6.0 Hz), 6.96 (1H, d, J=6.0 Hz), 6.98 (1H, d, J=8.0 Hz). Mass (m/e): 556 (M+). Anal. Calcd. for $C_{33}H_{48}O_7$ C=71.19% H=8.69% Found C; 71.02% H; 8.58%.

EXAMPLE 43

2-decarboxy-2-hydroxymethyl-5,6,7-trinor-4,8-inter-m-phenylene-11,15-didehydroxy-11,15-diacetoxy-17-α-methyl $PGI_2$ (44)

To a solution of 200 mg of 2-decarboxy-2-tetrahydropyranyloxymethyl-5,6,7-trinor-4,8-inter-m-phenylene-11,15-didehydroxy-11,15-diacetoxy-17-α-methyl $PGI_2$ in 5.6 ml of acetonitrile were added ¼N hydrochloric acid and 2.6 ml of THF, and the resulting solution was stirred at room temperature for 4 hours. Water was added, and the mixture was extracted 3 times with ether, the combined ether layers were washed with water and saturated brine, dried and thereafter concentrated to afford 220 mg of an oily substance. The oily substance was purified by column chromatography (silica gel; ethyl acetate:cyclohexane (2:1)) to give 142 mg of the alcohol.

IR (neat) ν cm−1: 3450, 1740, 1595, 1240, 970, 760, 750. NMR (CDCl$_3$) δ: 0.90 (6H, m), 1.63 (3H, s), 2.06 (3H, m), 2.60 (3H, m), 2.80 (1H, q, J=6.0 Hz), 3.65 (3H, m), 4.92 (1H, m), 5.30 (2H, m), 5.60 (2H, m), 6.78 (1H, dd, J=10.0 Hz, 6.0 Hz), 6.93 (1H, d, J=6.0 Hz), 6.95 (1H, d, J=10.0 Hz). Mass (m/e): 472 (M+). Anal. Calcd. for $C_{28}H_{40}O_6$ C=71.16% H=8.53% Found C; 71.11% H; 8.48%.

EXAMPLE 44

2-decarboxy-2-hydroxymethyl-5,6,7-trinor-4,8-inter-m-phenylene-11,15-didehydroxy-11,15-diacetoxy-17-β-methyl $PGI_2$ (45)

The procedure of Example 43 was followed except the use of 180 mg of 2-decarboxy-2-tetrahydropyranyloxymethyl-5,6,7,-trinor-4,8-inter-m-phenylene-11,15-didehydroxy-11,15-diacetoxy-17-β-methyl $PGI_2$ in place of (42) to give 120 mg of the alcohol.

IR (neat) ν cm−1: 3450, 1740, 1595, 1240, 970, 760, 750. NMR (CDCl$_3$) δ: 0.92 (6H, m), 1.74 (3H, s), 2.05 (3H, s), 2.60 (3H, m), 2.80 (1H, q, J=6.0 Hz), 3.65 (3H, m), 4.92 (1H, m), 5.30 (2H, m), 5.60 (2H, m), 6.78 (1H, dd, J=10.0 Hz, 6.0 Hz), 6.93 (1H, d, J=6.0 Hz), 6.95 (1H, d, J=10.0 Hz). Mass (m/e): 472 (M+). Anal. Calcd. for $C_{28}H_{40}O_6$ C=71.16% H=8.53% Found C; 70.01% H; 8.41%.

EXAMPLE 45

5,6,7-trinor-4,8-inter-m-phenylene-11,15-dideoxy-11,15-diacetoxy-17-α-methyl $PGI_2$ (46)

To a solution of 129 mg of 2-decarboxy-2-hydroxymethyl-5,6,7-trinor-4,8-inter-m-phenylene-11,15-didehydroxy-11,15-diacetoxy-17-α-methyl $PGI_2$ in 3.3 ml of anhydrous DMF was added 820 mg of pyridinium dichromate, and the resulting mixture was stirred at room temperature for 16 hours. Water was added and the mixture was extracted 5 times with ether, the combined ether layers were washed with water and saturated brine, dried and thereafter concentrated to afford 140 mg of an oily substance. The oily substance was purified by column chromatography, to give 98.8 mg of the carboxylic acid.

IR (neat) ν cm−1: 3600–2300, 1740, 1710, 1595, 1240, 970, 760, 740. NMR (CDCl$_3$) δ: 0.87 (3H, t, J=5.0 Hz), 0.90 (3H, d, J=6.0 Hz), 1.72 (3H, s), 2.06 (3H, s), 2.40 (2H, t, J=8.0 Hz), 2.63 (2H, t, J=7.5 Hz), 2.84 (1H, l, J=6.0 Hz), 3.62 (1H, dd, J=10.0 Hz, 6.0 Hz), 4.92 (1H, q, J=6.0 Hz), 5.30 (2H, m), 5.60 (2H, m), 6.77 (1H, dd, J=8.0 Hz, 6.0 Hz), 6.95 (1H, d, J=6.0 Hz), 6.97 (1H, d, J=8.0 Hz). Mass (m/e): 486 (M+). Anal. Calcd. for $C_{28}H_{38}O_7$ C=69.11% H=7.87% Found C; 68.91% H; 7.69%.

EXAMPLE 46

5,6,7-trinor-4,8-inter-m-phenylene-11,15-dideoxy-11,15-diacetoxy-17-β-methyl $PGI_2$ (47)

The procedure of Example 45 was followed except the use of 100 mg of 2-decarboxy-2-hydroxymethyl-5,6,7-trinor-4,8-inter-m-phenylene-11,15-dideoxy-11,15-diacetoxy-17-β-methyl $PGI_2$ in place of (44) to give 85 mg of a carboxylic acid (47).

IR (neat) ν cm−1: 3600–2300, 1740, 1710, 1595, 1240, 970, 760, 740. NMR (CDCl$_3$) δ: 0.90 (6H, m), 1.72 (3H, s), 2.05 (3H, s), 2.40 (3H, t, J=7.0 Hz), 2.60 (3H, t, J=7.0 Hz), 2.85 (1H, t, J=6.0 Hz), 3.60 (1H, dd, J=10.0 Hz, 6.0 Hz), 4.82 (1H, q, J=6.0 Hz), 5.30 (2H, m), 5.60 (2H, m), 6.76 (1H, t, J=7.0 Hz), 6.98 (2H, t, J=7.0 Hz). Mass (m/e): 486 (M+). Anal. Calcd. for $C_{28}H_{38}O_7$ C=69.11% H=7.87% Found C; 68.97% H; 7.80%.

EXAMPLE 47

5,6,7-trinor-4,8-inter-m-phenylene-17-α-methyl PGI$_2$ (48)

To a solution of 88 mg of 5,6,7,-trinor-4,8-inter-m-phenylene-11,15-dideoxy-11,15-diacetoxy-17-α-methyl PGI$_2$ in 5 ml of methanol was added 1 ml of 1N sodium hydroxide, and the resoluting solution was stirred at room temperature for 2 hours. The reaction solution was concentrated, water was added, the pH of the mixture cooled in an ice bath was adjusted to 3 with 1N hydrochloric acid and the mixture was extracted 3 times with ethyl acetate. The combined organic layers were washed with water and saturated brine, dried and thereafter concentrated to give 68 mg of the pure diol.

IR (neat) ν cm$^{-1}$: 3600–2300, 1710, 1595, 970, 760, 740. NMR (CDCl$_3$) δ: 0.90 (6H, m), 3.37 (1H, t, J=8.0 Hz), 3.83 (1H, m), 4.16 (2H, m), 5.05 (1H, m), 5.60 (5H, m), 6.72 (1H, dd, J=8.0 Hz, 6.0 Hz), 6.92 (1H, d, J=6.0 Hz), 6.94 (1H, d, J=8.0 Hz). Mass (m/e): 402 (M+). Anal. Calcd. for C$_{24}$H$_{34}$O$_5$ C=71.61% H=8.51% Found C; 71.55% H; 8.48%.

EXAMPLE 48

5,6,7-trinor-4,8-inter-m-phenylene-17-β-methyl PGI$_2$ (49)

The procedure of Example 47 was followed except the use of 70 mg of 5,6,7-trinor-4,8-inter-m-phenylene-11,15-dideoxy-11,15-diacetoxy-17-β-methyl PGI$_2$ In place of (46) to give 57 mg of the diol (49).

IR (neat) ν cm$^{-1}$: 3600–2300, 1710, 1595, 970, 760, 740. NMR (CDCl$_3$) δ: 0.90 (6H, m), 2.33 (2H, t, J=7.0 Hz), 2.63 (2H, t, J=7.0 Hz), 3.36 (1H, t, J=8.0 Hz), 3.88 (1H, m), 4.17 (1H, m), 5.06 (1H, m), 5.53 (5H, m), 6.70 (1H, t, J=7.2 Hz), 6.95 (2H, m). Mass (m/e): 402 (M+). Anal. Calcd. for C$_{24}$H$_{34}$O$_5$ C=71.61% H=8.51% Found C; 71.52% H; 8.42%.

EXAMPLE 49

2-decarboxy-2-tetrahydropyranyloxymethyl-5,6,7-trinor-4,8-inter-m-phenylene-17-α-methyl-20-homo PGI$_2$ (50) (51)

To a solution of 2 g of 3a,8b-cis-tetrahydro-1H-5-(4-tetrahydropyranyloxymethyl)-1-β-(2-formylethenyl)-2-α-hydroxycyclopenta[b]benzofuran in 40 ml of anhydrous THF cooled in an ice bath was added dropwise 11 ml of 2(s)-methylhexyl magnesium chloride (0.9N), and the resulting solution was stirred for 30 minutes. Ammonium chloride, methanol and water were added, and the mixture was extracted 3 times with ether. The combined ether layers were washed with water and saturated brine, dried and thereafter concentrated to afford 3 g of an oily substance. The oily substance was purified by column chromatogaphy (silica gel; ethyl acetate) to give 400 mg a less polar substance and 203 mg of a polar substance.

The less polar substance (17-α-isomer, 50)

IR (neat) ν cm$^{-1}$: 3350, 1595, 970, 765, 745. NMR (CDCl$_3$) w: 0.85–1.10 (6H, m) 1.00–3.00 (25H), 3.00–4.00 (8H), 4.00–4.40 (1H), 4.40–5.00 (1H), 4.90–4.30 (1H), 5.40–5.80 (2H), 6.60–7.10 (3H). Mass (m/e): 486.

The polar substance (17-β-isomer, 51).

IR (neat) ν cm$^{-1}$: 3350, 1595, 970, 765, 745. NMR (CDCl$_3$) w: 0.70–1.10 (6H), 1.00–3.00 (25H), 3.00–4.40 (9H), 4.40–4.90 (1H), 4.90–5.40 (1H), 5.40–5.90 (2H), 6.40–7.20 (3H). Mass (m/e): 486.

EXAMPLE 50

2-decarboxy-2-tetrahydropyranyloxymethyl-5,6,7-trinor-4,8-inter-m-phenylene-11,15-dideoxy-11,15-diacetoxy-17-α-methyl-20-homo PGI$_2$ (52)

2-decarboxy-2-tetrahydropyranyloxymethyl-5,6,7-trinor-4,8-inter-m-phenylene-17-α-methyl-20-homo PGI$_2$ 320 mg was dissolved in 200 ml of acetic anhydride and 10 ml of anhydrous pyridine and the solution was stirred at room temperature for 2 hours. The reaction solution was concentrated and the resulting residue was azeotropically treated with toluene and benzene to give 390 mg of a nearly pure diacetate.

IR (neat) ν cm$^{-1}$: 1740, 1595, 1235, 970, 760, 750. NMR (CDCl$_3$) δ: 0.70–1.10 (9H), 1.00–3.00 (25H), 1.60–1.80 (3H), 1.90–2.20 (3H), 3.00–4.10 (4H), 4.40–5.00 (2H), 5.00–6.00 (4H), 6.50–7.10 (3H). Mass (m/e): 570 (M+).

EXAMPLE 51

2-decarboxy-2-hydroxymethyl-5,6,7-trinor-4,8-inter-m-phenylene-11,15-didehydro-11,15-diacetoxy-17-α-methyl-20-homo PGI$_2$ (53)

To a solution of 400 mg of 2-decarboxy-2-tetrahydropyranyloxymethyl-5,6,7-trinor-4,8-inter-m-phenylene-11,15-didehydroxy-11,15-diacetoxy-17-α-methyl-20-homo PGI$_2$ in 11.2 ml of acetonitrile were added 5.2 ml of ¼N hydrochloric acid and 5.2 ml of THF, and the resulting solution was stirred at room temperature for 4 hours. Water was added the mixture was extracted with ether 3 times, the combined ether layers were washed with water and saturated brine, dried and thereafter concentrated to afford 400 mg of an oily substance. The oily substance was purified by column chromatography (silica gel; ethyl acetate:cyclohexane (2:1)) to give 270 mg of the alcohol.

IR (neat) ν cm$^{-1}$: 3450, 1740, 1595, 1240, 970, 760, 750. NMR (CDCl$_3$) δ: 0.70–1.10 (6 Hz), 1.00–3.00 (19H), 1.60–1.80 (3H), 1.90–2.20 (3H), 3.50–3.90 (3H), 4.70–6.00 (5H), 6.70–7.10 (3H). Mass (m/e): 486 (M+).

EXAMPLE 52

5,6,7-trinor-4,8-inter-m-phenylene-11,15-dideoxy-11,15-diacetoxy-17-α-methyl-20-homo PGI$_2$ (54)

To a solution of 270 mg of 2-decarboxy-2-hydroxymethyl-5,6,7-trinor-4,8-inter-m-phenylene-11,15-didehydroxy-11,15-diacetoxy-17-α-methyl-20-homo PGI$_2$ in 3.3 ml of anhydrous DMF was added 1.6 g of pyridinium dichromate, and the resulting mixture was stirred at room temperature for 14 hours. Water was added, and the mixturer was extracted 5 times with ether, the combined ether layers were washed with water and saturated brine, dried and thereafter concentrated to give 270 mg of an oily substance. The oily substance was purified by column chromatography (silica gel (which had been treated with acetic acid) ethyl acetate:cyclohexane (1:2)) to yield 180 mg of a carboxylic acid.

IR (neat) ν cm$^{-1}$: 3600–2300, 1740, 1710, 1595, 1240, 970, 760, 740. NMR (CDCl$_3$) δ: 0.70–1.10 (6H), 1.10–3.00 (17H), 3.40–4,00 (1H), 4.60–6.00 (5H), 6.50–7.20 (3H). Mass (m/e): 500 (M+).

EXAMPLE 53

5,6,7-trinor-4,8-inter-m-phenylene-17-α-methyl-20-homo PGI$_2$ (55)

To a solution of 160 mg of 5,6,7-trinor-4,8-inter-m-phenylene-11,15-dideoxy-11,15-diacetoxy-17-α-methyl-20-homo PGI$_2$ in 10 ml of methanol was added 2 ml of 1N sodium hydroxide, and the resulting solution was stirred at room temperature for 2 hours. The reaction solution was concentrated, water was added, the pH of the mixture cooled in an ice bath was adjusted to 3 with 1N hydrochloric acid and the mixture was extracted 3 times with ethyl acetate. The combined organic layers were washed with water and saturated brine, dried and thereafter concentrated to give 130 mg of the pure diol.

IR (neat) ν cm$^{-1}$: 3600–2300, 1710, 1595, 970, 760, 740. NMR (CDCl$_3$) δ: 0.70–1.10 (9H), 1.00–3.00 (17H), 3.00–4.50 (4H), 4.80–5.90 (6H), 6.50–7.20 (3H). Mass (m/e): 416 (M$^+$).

EXAMMPLE 54

2-decarboxy-2-tetrahydropyranyloxymethyl-5,6,7-trinor-4,8-inter-m-phenylene-17,18,19,20-tetranor-16-phenoxy PGI$_2$ (56)

To a solution of 2 g of (phenoxymethyl)tri-n-butylstannane in 20 ml of anhydrous THF at −78° C. was added 3.3 ml of n-butyllithium (1.5N) and the resulting solution was stirred for 8 minutes, a solution of 700 mg of 3a,8b-cis-2,3,3a,8b-tetrahydro-1H-5-(4-tetrahydropyranyloxybutyl)-β-(2-formylethenyl)-2-α-hydroxycyclopenta[b]benzofuran in 4 ml of anhydrous THF was added dropwise. After stirring at −78° C. for 1 hour, methanol and solid ammonium chloride were added, the resulting mixture was stirred at −78° C. for 20 minutes and at room temperature for 20 minutes, thereafter, water was added and the mixture was extracted 3 times with ether. The combined ether layers were washed with saturated brine, dried and thereafter concentrated to give a crude oily substance. When this oily substance was purified by column chromatography (silica gel; ethyl acetate:cyclohexane (4:1)), 440 mg of the diol (15α) was obtained.

IR (neat) ν cm$^{-1}$: 3400, 1600, 1585, 970, 760. NMR (CDCl$_3$) δ: 3.45 (4H, m), 3.90 (6H, m), 4.58 (2H, m), 5.10 (1H, m), 5.80 (2H, m), 6.75 (1H, t, J=6.0 Hz), 6.96 (5H, m), 7.26 (2H, m). Mass (m/e): 494 (M$^+$). Anal. Calcd. for C$_{30}$H$_{38}$O$_6$ C=72.87% H=7.69% Found C; 72.80% H; 7.55%.

EXAMPLE 55

2-decarboxy-2-tetrahydropyranyloxymethyl-5,6,7-trinor-4,8-inter-m-phenylene-11,15-didehydroxy-11,15-diacetoxy-17,18,19,20-tetranor-16-phenoxy-PGI$_2$ (57)

To a solution of 420 mg of 2-decarboxy-2-tetrahydropyranyloxymethyl-5,6,7-trinor-4,8-inter-m-phenylene-17,18,19,20-tetranor-16-phenoxy PGI$_2$ in 10 ml of acetic anhydride was added 5 m of anhydrous pyridine, and the resulting solution was stirred at room temperature for 2 hours. This reaction mixture was concentrated under reduced pressure by a vacuum pump, the obtained residue was azeotropically treated 3 times with toluene and once with benzene to give 495 mg of a nearly pure diacetate.

IR (neat) ν cm$^{-1}$: 1740, 1595, 1585, 1230, 968, 758, 695. NMR (CDCl$_3$) δ: 1.75 (3H, s), 2.10 (3H, s) Mass: 578 (M$^+$), 494. Anal. Calcd. for C$_{34}$H$_{42}$O$_8$ C=70.59% H=7.27% Found C; 70.27% H; 7.21%.

EXAMPLE 56

2-decarboxy-2-hydromethyl-5,6,7-trinor-4,8-inter-m-phenylene-11,15-didehydroxy-11,15-diacetoxy-17,18,19,20-tetranor-16-phenoxy-PGI$_2$ (58)

To a solution of 480 mg of 2-decarboxy-2-tetrahydropyranyloxymethyl-5,6,7-trinor-4,8-inter-m-phenylene-11,15-didehydroxy-11,15-diacetoxy-17,18,19,20-tetranor-16-phenoxy PGI$_2$ in 10 ml of acetonitrile were added 5 ml of THF and 5 ml of ¼N hydrochloric acid, and the resulting solution was stirred at room temperature for 3 hours. Ether and water were added, and the mixture was extracted 3 times with ether. The combined ether layers were washed with water, a saturated aqueous solution of sodium hydrogen carbonate and saturated brine, dried and thereafter concentrated to afford 480 mg of an oily substance. The oily substance was purified by column chromatography (silica gel; ethyl acetate:cyclohexane (2:1)) to give 340 mg of the alcohol (58).

IR (neat) ν cm$^{-1}$: 3450, 1730, 1595, 1585, 1230, 960, 758, 690. NMR (CDCl$_3$) δ: 1.76 (3H, s), 2.10 (3H, s), 3.65 (3H, m), 4.10 (2H, d, J=5.0 Hz), 4.97 (1H, m), 5.20 (1H, m), 5.60 (1H, m), 5.78 (2H, m), 6.70 (1H, t, J=6.0 Hz), 6.95 (4H, m), 7.25 (3H, m). Mass (m/e): 494 (M$^+$). Anal Calcd. for C$_{29}$H$_{24}$O$_7$ C=70.45% H=6.88% Found C; 70.44% H; 6.85%.

EXAMPLE 57

5,6,7-trinor-4,8-inter-m-phenylene-11,15-didehydroxy-11,15-diacetoxy-17,18,19,20-tetranor-16-phenoxy PGI$_2$ (59)

To a solution of 330 mg of 2-decarboxy-2-hydroxymethyl-5,6,7-trinor-4,8-inter-m-phenylene-11,15-didehydroxy-11,15-diacetoxy-17,18,19,20-tetranol-16-phenoxy PGI$_2$ in 7.5 ml of anhydrous DMF was added 1.9 g of pyridinium dichromate, and the resulting mixture was stirred at room temperature for 14 hours. Water was added, and the mixture was extracted 5 times with ether, the combined organic layers were washed with saturated brine, thereafter dried and concentrated to afford 350 mg of an oily substance. The oily substance was purified by column chromatography (silica gel (Lobar Column which had been treated with acetic acid); ethyl acetate:cyclohexane (2:1)) to give 250 mg of a carboxylic acid.

IR (neat) ν cm$^{-1}$: 3600;14 2400, 1740, 1710, 1598, 1589, 1230, 965, 760, 690. NMR (CDCl$_3$) δ: 1.74 (3H, s), 2.10 (3H, s), 3.60 (1H, dd, J=9.0 Hz, 5.0 Hz), 4.10 (2H, d, J=4.5 Hz), 4.95 (1H, m), 5.20 (1H, m), 5.60 (1H, m), 5.80 (2H, m), 6.75 (1H, t, J=6.0 Hz), 6.95 (4H, m), 7.30 (3H, m). Mass (m/e): 508 (M$^+$). Anal. Calcd. for C$_{29}$H$_{32}$O$_8$ C=68.50% H=6.30% Found C; 68.42% H; 6.25%.

EXAMPLE 58

5,6,7-trinor-4,8-inter-m-phenylene-17,18,19,20-tetranor-16-phenoxy PGI$_2$ (60)

To a solution of 250 mg of 5,6,7-trinor-4,8-inter-m-phenylene-11,15-didehydroxy-11,15-diacetoxy-17,18,19,20-tetranor-16-phenoxy PGI$_2$ in 15 ml of methanol was added 3 ml of 1N NaOH, and the resulting solution was stirred at room temperature for 2 hours. The reaction mixture was concentrated under a reduced pressure, water was added, the pH of the mixture cooled in an ice bath was adjusted to 3 by 1N hydrochloric acid and the mixture was extracted 3 times with ethyl acetate. The combined organic layers were washed with water and saturated brine, thereafter dried and concentrated to give 204 mg of the nearly pure diol.

IR (neat) $\nu$ cm$^{-1}$: 3600–2400, 1710, 1595, 1585, 970, 858, 690. NMR (CDCl$_3$) $\delta$: 3.40 (1H, t, J=9 Hz), 4.00 (3H, m), 4.20 (4H, m) 5.10 (1H, m), 5.80 (2H, m), 6.75 (1H, t, J=6.0 Hz), 6.95 (4H, m), 7.30 (3H, m). Mass (m/e): 424 (M$^+$). Anal. Calcd. for C$_{25}$H$_{28}$O$_6$ C=70.75% H=6.60% Found C; 70.67% H; 6.54%.

EXAMPLE 59

2-decarboxy-2-tetrahydropyranyloxymethyl-5,6,7-trinor-4,8-inter-m-phenylene-17,18,19,20-tetranor-16-m-chlorophenoxy PGI$_2$ (61)

To a solution of 2.2 g of (m-chlorophenoxymethyl)-tributylstannane in 20 ml of annhydrous THF at −78° C. was added 3.4 ml of n-butyl lithium (1.5N), and the resulting solution was stirred at −78° C. for 8 minutes. A solution of 650 mg of 3a,8b-cis-2,3,3a,8b-tetrahydro-1H-5-(4-tetrahydropyranyloxybutyl)-1-$\beta$-(2-formyle-thenyl)-2-$\alpha$-hydroxycyclopenta[b]benzofuran in 4 ml of anhydrous THF was added. After stirring at −78° C. for 30 minutes, solid ammonium chloride and methanol were added, the resulting mixture was stirred at −78° C. for 10 minutes and at room temperature for 10 minutes, thereafter, water was added and the mixture was extracted 3 times with ether. The combined ether layers were washed with saturated brine, dried and thereafter concentrated to yield 3 g of an oily substance. The oily substance was purified by column chromatography (silica gel; ethyl acetate:cyclohexane (4:1)) to give 425 mg of the pure product (61).

IR (neat) $\nu$ cm$^{-1}$: 3350, 1590, 1580, 965, 770, 745, 680. NMR (CDCl$_3$) $\delta$: 3.42 (3H, m), 3.90 (4H, m), 4.56 (2H, m), 5.10 (1H, m), 5.80 (2H, m), 6.74 (1H, t, J=8.0 Hz), 6.96 (5H, m), 7.20 (1H, t, J=8.0 Hz). Mass (m/e): 528, 530 (M$^+$). Anal. Calcd. for C$_{30}$H$_{27}$O$_6$Cl C=68.18% H=7.01% Found C; 68.02% H; 6.88%.

EXAMPLE 60

2-decarboxy-2-tetrahydropyranyloxymethyl-5,6,7-trinor-4,8-inter-m-phenylene-11,15-didehydroxy-11,15-diacetoxy-17,18,19,20-tetranor-16-m-chlorophenoxy PGI$_2$ (62)

A solution of 400 mg of 2-decarboxy-2-tetrahydropyranyloxymethyl-5,6,7-trinol-4,8-inter-m-phenylene-17,18,19,20-tetranol-16-m-chlorophenoxy PGI$_2$ in 10 ml of acetic anhydride and 5 ml of pyridine was stirred at room temperature for 14 hours. The reaction mixture was concentrated under a reduced pressure by a vacuum pump and the resulting residue was azeotropically treated with toluene 2 times to give 464 mg of the roughly pure diacetate (62).

IR (neat) $\nu$ cm$^{-1}$: 1740, 1592, 1500, 965, 775, 750, 680. NMR (CDCl$_3$) $\delta$: 1.75 (3H, s), 2.10 (3H, s), 3.40–4.00 (4H, m), 4.08 (2H, d, J=4.0 Hz), 4.60 (1H, m), 4.98 (1H, m), 5.20 (1H, m), 5.60 (1H, m) 5.78 (2H, m), 6.62–7.10 (6H, m), 7.20 (1H, t, J=8.0 Hz). Mass (m/e): 612, 614 (M$^+$). Anal. Calcd. for C$_{34}$H$_{41}$O$_8$Cl C=66.67% H=6.70% Found C; 66.58% H; 6.62%.

EXAMPLE 61

2-decarboxy-2-hydroxymethyl-5,6,7-trinor-4,8-inter-m-phenylene-11,15-didehydroxy-11,15-diacetoxy-17,18,19,20-tetranor-16-m-chlorophenoxy PGI$_2$ (63)

To a solution of 400 mg of 2-decarboxy-2-tetrahydropyranyloxymethyl-5,6,7-trinor-4,8-inter-m-phenylene-11,15-didehydroxy-11,15-diacetoxy-17,18,19,20-tetranor-16-m-chlorophenoxy PGI$_2$ in 10 ml of acetonitrile and 5 ml of THF was added 5 ml of $\frac{1}{4}$N hydrochloric acid and the resulting solution was stirred at room temperature for 4 hours. Ether and water were added, and the mixture was extracted 3 times with ether. The combined ether layers were washed with water, a saturated aqueous solution of sodium hydrogen carbonate and saturated brine, dried and thereafter concentrated to yield 400 mg of an oily substance. The oily substance was purified by column chromatography [silica gel; ethyl acetate:cyclohexane (2:1)] to give 314 mg of the alcohol (63).

IR (neat) $\nu$ cm$^{-1}$: 3400, 1730, 1595, 1580, 965, 775, 680. NMR (CDCl$_3$) $\delta$: 1.72 (3H, s), 2.10 (3H, s), 3.62 (3H, s), 4.08 (2H, d, J=6.0 Hz), 4.95 (1H, dd, J=12.0 Hz, 5.0 Hz), 5.20 (1H, m), 5.60 (1H, dd, J=5.0 Hz, 2.0 Hz), 5.78 (2H, m), 6.60–7.00 (6H, m), 7.20 (1H, t, J=8.0 Hz). Mass (m/e): 528, 530 (M$^+$). Anal. Calcd. for C$_{29}$H$_{33}$O$_7$Cl C=65.90% H=6.25% Found C; 65.78% H; 6.09%.

EXAMPLE 62

5,6,7-trinor-4,8-inter-m-phenylene-11,15-didehydroxy-11,15-diacetoxy-17,18,19,20-tetranor-16-m-chlorophenoxy PGI$_2$ (64)

To a solution of 300 mg of 2-decarboxy-2-hydroxymethyl-5,6,7-trinor-4,8-inter-m-phenylene-11,15-didehydroxy-11,15-diacetoxy-17,18,19,20-tetranol-16-m-chlorophenoxy PGI$_2$ in 7.5 ml of DMF was added 1.9 g of pyridinium dichromate, and the resulting mixture was stirred at room temperature for 14 hours. Ether and water were added and the mixture was extracted 5 times with ether. The combined ether layers were washed with saturated brine, dried and thereafter concentrated to afford 300 mg of an oily substance. The oily substance was purified by column chromatography (silica gel (Lobar Column which had been treated with acetic acid); ethyl acetate:cyclohexane (2:1)) to give 210 mg of a carboxylic acid (64).

IR (neat) $\nu$ cm$^{-1}$: 3600–2400, 1730, 1710, 1595, 1580, 965, 775, 745, 680. NMR (CDCl$_3$) $\delta$: 1.74 (3H, s), 2.10 (3H, s), 3.60 (1H, m), 4.05 (2H, d, J=6.0 Hz), 4.90 (1H, m), 5.20 (1H, m), 5.60 (1H, m), 5.75 (2H, m), 6.60–7.00 (6H, m), 7.20 (1H, t, J=8.0 Hz). Mass (m/e): 542, 544 (M$^+$). Anal. Calcd. for C$_{29}$H$_{31}$O$_8$Cl C=64.21% H=5.72% Found C; 64.18% H; 5.68%.

EXAMPLE 63

5,6,7-trinor-4,9-inter-m-phenylene-17,18,19,20-tetranor-16-m-chlorophenoxy PGI$_2$ (65)

To a solution of 160 mg of 5,6,7-trinor-4,8-inter-m-phenylene-11,15-didehydroxy-11,15-diacetoxy-17,18,19,20-tetranor-16-m-chlorophenoxy PGI$_2$ in 10 ml of methanol was added 2 ml of 1N sodium hydroxide, and the resulting solution was stirred at room temperature for 1 hour. The reaction solution was concentrated, water was added, the pH of the mixture cooled in an ice bath was adjusted to 3 with 1N hydrochloric acid, the mixture was extracted 3 times with ethyl acetate. The combined organic layers were washed with water and saturated brine and thereafter concentrated to yield 125 mg of nearly pure crystals. The crystals were recrystallized from an ethyl acetate-hexane mixture to afford 80 mg of pure crystals (65), mp 103°–105° C.

IR (KBr) ν cm$^{-1}$: 3600–2400, 1700, 1690, 1680, 965, 770, 740, 680. NMR (CDCl$_3$) δ: 3.40 (1H, t, J=9.0 Hz), 3.94 (3H, m), 4.52 (1H, m), 5.05 (1H, m), 5.75 (2H, m), 6.60–7.10 (6H, m), 7.20 (1H, t, J=8.0 Hz) Anal. Calcd. for C$_{29}$H$_{27}$O$_6$Cl C=65.50% H=5.90% Found C; 65.44% H; 5.81%.

EXAMPLES 64–68

The procedure of Example 54 were followed except the use of (n-propoxymethyl)tri-n-butyl stannane, (n-butoxymethyl)tri-n-butylstannane, (cyclopentyloxymethyl)tri-n-butylstannane, (cyclohexyloxymethyl)tri-n-butylstannane, or (cycloheptyloxymethyl)tri-n-bulylstannane in place of (phenoxymethyl)tri-n-butyl stannane, and the procedures of Example 55-58 are followed successively except the uses of the each resulting compounds to give 5,6,7-trinor-4,8-inter-m-phenylene-17,18,19,20-tertranor-16-propoxy PGI$_2$ (66), 5,6,7-trinor-4,8-inter-m-phenylene-17,18,19,20-tetranor-16-butoxy PGI$_2$ (67), 5,6,7-trinor-4,8-inter-m-phenylene-17,18,19,20-tetranor-16-cyclopentyloxy PGI$_2$ (68), 5,6,7-trinor-4,8-inter-m-phenylene-17,18,19,20-tetranor-16-cyclohexyloxy PGI$_2$ (69), or 5,6,7-trinor-4,8-inter-m-phenylene-17,18,19,20-tetranor-16-cycloheptyloxy PGI$_2$ (70). In Table 4, the spectral data of these compounds are shown.

TABLE 4

| Example | Compound | Mass spectrum (m/e, M$^+$) | Infrared spectrum cm$^{-1}$ |
|---|---|---|---|
| 64 | 66 | 390 | 3600–2300, 1710, 1595, 1200, 970, 765, 745 |
| 65 | 67 | 404 | 1710, 1595, 970, 745 |
| 66 | 68 | 416 | 1710, 1595, 970, 745 |
| 67 | 69 | 430 | 1705, 1598, 970, 745 |
| 68 | 70 | 444 | 1710, 1594, 970, 945 |

REFERENTIAL EXAMPLE 82

2-decarboxy-2-tetrahydropyranyloxymethyl-5,6,7-trinor-4,8-inter-m-phenylene-17,18,19,20-tetranor-16,16-dimethyl-16-methoxycarbonyl PGI$_2$ To a solution of 0.9 ml of diisopropylamine in 20 ml of anhydrous THF was at −78° C. under argon atmosphere added dropwise 3.9 ml of n-butyl lithium (1.5N) and the resulting solution was stirred at that temperature for 15 minutes. A solution of 0.7 ml of isobutyric acid in 2 ml of anhydrous THF at −78° C. was added dropwise, the resulting solution was stirred for 30 minutes, thereafter, a solution of 500 mg of 3a,8b-cis-2,3,3a,8b-tetrahydro-1H-5-(4-tetrahydropyranyloxybutyl)-1-β-(2-formylethenyl)-2-α-hydroxycyclopenta[b]benzofuran in 2 ml of anhydrous THF was added dropwise thereto. The reaction mixture was stirred at −78° C. for 20 minutes, thereafter, methanol was added, the resulting mixture was stirred at room temperature for 10 minutes, water was added and the mixture was extracted 3 times with ether. The combined ether layers were washed with water and saturated brine, dried and thereafter concentrated to give 600 mg of an oily substance. The oily substance was purified by column chromatography' (silica gel; ethyl acetate:cyclohexane (4:1)) to afford 205 mg of an oily substance.

IR (neat) ν cm$^{-1}$: 3375, 1725, 1592, 1250, 970, 775, 745. NMR (CDCl$_3$) δ: 1.10 (3H, s), 1.12 (3H, s), 2.60 (4H, m), 3.82 (3H, m), 4.57 (1H, m), 5.10 (1H, m), 5.66 (2H, m), 6.76 (1H, t, J=7.0 Hz), 6.94 (2H, m). Mass (m/e): 488 (M$^+$), 404 (−THP). Anal. Calcd. for C$_{28}$H$_{40}$O$_7$ C=68.83% H=8.25% Found C; 68.80% H; 8.21%.

REFERENTIAL EXAMPLE 83

2-decarboxy-2-tetrahydropyranyloxymethyl-5,6,7-trinor-4,8-inter-m-phenylene-11,15,dideoxy-11,15-bis(t-butyldimethylsilyloxy)-17,18,19,20-tetranor-16,16-dimethyl-16-methoxycarbonyl PGI$_2$ To a solution of 300 mg of 2-decarboxy-2-tetrahydropyranyloxymethyl-5,6,7-trinor-4,8-inter-m-phenylene-17,18,19,20-tetranor-16,16-dimethyl-16-carbomethoxy PGI$_2$ in 1.3 ml of anhydrous DMF were added 390 mg of imidazole and 458 mg of t-butyldimethylsilyl chloride, and the resulting mixture was stirred for 30 hours. A pentane-ether (1:1) mixture and water were added, and the mixture was extracted 3 times with a pentane-ether (1:1) mixture. The combined organic layers were washed with a saturated aqueous solution of sodium hydrogen carbonate, water and saturated brine, dried and thereafter concentrated to give 400 mg of an oily substance. The oily substance was purified by column chromatography (silica gel; ethyl acetate:cyclohexane (1:16)) to afford 360 mg of an oily substance.

IR (neat) ν cm$^{-1}$: 1730, 1692, 1250, 970, 835, 780, 745. NMR (CDCl$_3$) δ: 0.75 (9H, s), 0.87 (9H, s), 1.09 (3H, s), 1.17 (3H, s) 2.56 (4H, m), 3.50 (4H, m), 3.66 (3H, s), 3.90 (1H, m), 4.36 (1H, d, J=6.0 Hz), 4.60 (1H, m), 5.10 (1H, m), 5.60 (2H, m), 6.77 (1H, t, J=7.0 Hz), 6.94 (1H, d, J=7.0 Hz), 7.00 (1H, d, J=7.0 Hz) Mass (m/e): 716 (M$^+$), 632 (−THP). Anal. Calcd. for C$_{40}$H$_{68}$O$_7$Si$_2$ C=67.04% H=9.50% Found C; 66.91% H; 9.28.

REFERENTIAL EXAMPLE 84

2-decarboxy-2-tetrahydropyranyloxymethyl-5,6,7-trinor-4,8-inter-m-phenylene-11-deoxy-11-t-butyldimethylsilyloxy-16,16-dimethyl-18,19,20-trinor-17-hydroxy PGI$_2$ To a stirred suspension of 200 mg of lithium aluminium hydride in 2 ml of anhydrous THF cooled in an ice bath was added dropwise a solution of 340 mg of 2-decarboxy-2-tetrahydropyranyloxymethyl-5,6,7-trinor-4,8-inter-m-phenylene-11,15-deoxy-11,15-bis(dimethyl-t-butylsilyloxy)-17,18,19,20-tetranor-16,16-dimethyl-16-methoxycarbonyl PGI$_2$ in 4 ml of anhydrous THF. The reaction mixture was stirred at room temperature for 2 hours, thereafter, a saturated aqueous solution of sodium potassium tartarate was added, and the separated precipitate was filtered, the filtrate was dried and thereafter concentrated to give 276 mg of a nearly pure product. This compound was used in the following reaction without purification.

IR (neat) ν cm$^{-1}$: 3375, 1592, 1250, 970, 835, 775, 740. NMR (CDCl$_3$) δ: 0.80 (9H, s), 0.92 (3H, s), 0.94 (3H, s), 2.04 (3H, s), 2.54 (5H, m), 3.50 (4H, m), 3.90 (4H, m), 4.60 (1H, m), 5.10 (1H, m), 5.70 (2H, m), 6.76 (1H, dd, J=9.0 Hz, 6.0 Hz), 6.96 (1H, d, J=6.0 Hz), 6.98 (1H, d, J=9.0 Hz). Mass (m/e): 574 (M$^+$), 526. Anal. Calcd. for C$_{33}$H$_{54}$O$_6$Si C=68.99% H=9.41% Found C; 68.91% H; 9.37%.

EXAMPLE 69

2-decarboxy-2-tetrahydropyranyloxymethyl-5,6,7-trinor-4,8-inter-m-phenylene-11-deoxy-11-t-butyldimethylsilyloxy-16,16-dimethyl-18,19,20-trinor-17-ethoxy PGI$_2$ (71)

Sodium hydride (500 mg of 50% mineral oil dispersion) was washed 3 times with n-hexane, hexane was removed under reduced pressure, and 2 ml of anhydrous DME was added under argon atmosphere. To the stirred suspension cooled in an ice bath was added dropwise a solution of 260 mg of 2-decarboxy-2-tetrahydropyranyloxymethyl-5,6,7-trinor-4,8-inter-m-phenylene-11-deoxy-11-t-butyldimethylsilyloxy-18,19,20-trinor-16,16-dimethyl-17-hydroxy PGI$_2$ in 5 ml of anhydrous DME. The reaction mixture was stirred at room temperature for 1 hour, thereafter, 0.5 ml of ethyl iodide was added, and the resulting mixture was stirred at room temperature for 1 hour. Ammonium chloride, methanol and water were added, and the mixture was stirred ar room temperature for 20 minutes. The reaction mixture was extracted 3 times with ether, the combined ether layers were washed with water and saturated brine, dried and thereafter concentrated to give 300 mg of an oily substance. The oily substance purified by column chromatography (silica gel; ethyl acetate:cyclohexane (1:5)) to afford 172 mg of an oily substance.

IR (neat) $\nu$ cm$^{-1}$: 3490, 1595, 1250, 970, 780, 745. NMR (CDCl$_3$) $\delta$: 0.80 (9H, s), 0.92 (3H, s), 0.96 (3H, s), 1.20 (3H, t, J=7.0 Hz), 2.60 (3H, m), 3.34 (2H, AB, J=8.0 Hz), 3.50 (4H, m), 3.58 (2H, q, J=7.0 Hz), 3.80 (3H, m), 4.60 (1h, m), 5.10 (1H, m), 5.66 (2H, m), 6.72 (1H, 5, J=7.0 Hz), 6.96 (1H, d, J=7.0 Hz), 6.98 (1H, d, J=7.0 Hz). Mass (m/e): 602 (M+), 518 (−THP). Anal. Calcd. for C$_{35}$H$_{58}$O$_6$Si C=69.77% H=9.63% Found C; 69.66% H; 9.60%.

EXAMPLE 70

2-decarboxy-2-tetrahydropyranyloxymethyl-5,6,7-trinor-4,8-inter-m-phenylene-16,16-dimethyl-18,19,20-trinor-17-ethoxy PGI$_2$ (72)

To a solution of 130 mg of 2-decarboxy-2-tetrahydropyranyloxymethyl-5,6,7-trinor-4,8-inter-m-phenylene-11-deoxy-11-t-butyldimethylsilyloxy-16,16-dimethyl-18,19,20-trinor-17-ethoxy PGI$_2$ in 5 ml of anhydrous THF was added 183 mg of tetrabutylammonium fluoride, and the resulting mixture was stirred at room temperature for 1 hour. Ether and a saturated aqueous solution of ammonium chloride were added, and the mixture was extracted 3 times with ether. The combined ether layers were washed with water and saturated brine, dried and thereafter concentrated to yield 106 mg of a nearly pure diol. This compound was used in the following reaction without purification.

IR (neat) $\nu$ cm$^{-1}$: 3450, 1595, 970, 770, 750. NMR (CDCl$_3$) $\delta$: 0.90 (3H, t, J=6.0 Hz), 0.92 (3H, s), 0.94 (3H, s), 1.10 (3H, t, J=7.0 Hz), 2.60 (5H, m), 3.40 (6H, m), 3.90 (4H, m), 4.58 (1H, m), 5.10 (1H, m), 5.65 (2H, m), 6.64 (1H, t, J=7.8 Hz), 6.96 (2H, d, J=7.8 Hz). Mass (m/e): 488 (M+), 470 (−H$_2$O). Anal. Calcd. for C$_{29}$H$_{44}$O$_6$ C=71.31% H=9.02% Found C; 71.22% H; 8.99%.

EXAMPLE 71

2-decarboxy-2-tetrahydropyranyloxymethyl-5,6,7-trinor-4,8-inter-m-phenylene-11,15-dideoxy-11,15-diacetoxy-16,16-dimethyl-18,19,20-trinor-17-ethoxy PGI$_2$ (73)

A solution of 130 mg of 2-decarboxy-2-tetrahydropyranyloxymethyl-5,6,7-trinor-4,8-inter-m-phenylene-16,16-dimethyl-18,19,20-trinor-17-ethoxy PGI in 3 ml of pyridine and 6 ml of acetic anhydride was stirred at room temperature for 14 hours. The reaction solution was concentrated and the resulting residue was azeotropically treated twice with toluene and once with benzene to give 155 mg of the nearly pure diacetate.

IR (liquid film method) $\nu$ cm$^{-1}$: 1740, 1595, 1240, 970, 745. NMR (CDCl$_3$) $\delta$: 0.90 (3H, s), 0.94 (3H, s), 1.16 (3H, t, J=7.0 Hz), 1.74 (3H, s), 2.07 (3H, s), 2.60 (3H, s), 2.82 (1H, m), 3.44 (2H, q, J=7.0 Hz), 3.10–3.90 (6H, complicated forms), 4.60 (1H, m), 4.92 (1H, q, J=6.0 Hz), 5.27 (2H, m), 5.65 (2H, m), 6.76 (1H, dd, J=8.0 Hz, 6.0 Hz), 6.94 (1H, d, J=6.0 Hz), 6.96 (1H, d, J=8.0 Hz). Mass (m/e): 572 (M+), 488 (−THP). Anal. Calcd. for C$_{33}$H$_{48}$O$_8$ C=69.23% H=8.39% Found C; 69.11% H; 8.28%.

EXAMPLE 72

2-decarboxy-2-hydroxymethyl-5,6,7-trinor-4,8-inter-m-phenylene-11,15-dideoxy-11,15-diacetoxy-16,16-dimethyl-18,19,20-trinor-17-ethoxy PGI$_2$ (74)

To a solution of 140 mg of 2-decarboxy-2-tetrahydropyranyloxymethyl-5,6,7-trinor-4,8-inter-m-phenylene-11,15-dideoxy-11,15-diacetoxy-16,16-dimethyl-18,19,20-trinor-17-ethoxy PGI$_2$ in 3.5 ml of acetonitrile were added 1.7 ml of THF and 1.7 ml of 1.4 H hydrochloric acid, and the resulting solution was stirred at room temperature for 8 hours. Water was added and the mixture was extracted 3 times with ether, the combined ether layers were washed with water and saturated brine, dried and thereafter concentrated to give 150 mg of an oily substance. The oily substance was purified by column chromatography (silica gel; ethyl acetate:cyclohexane (2:1)) to afford 103 mg of the pure alcohol (74).

IR (neat) $\nu$ cm$^{-1}$: 3450, 1740, 1595, 1240, 965, 760, 745. NMR (CDCl$_3$) $\delta$: 0.90 (3H, s), 0.93 (3H, s), 1.16 (3H, d, J=7.0 Hz), 1,74 (3H, s), 2.07 (3H, s), 2.20–3.00 (3H, m) 3.15 (2H, s), 3.45 (2H, q, J=7.0 Hz), 3.65 (3H, m), 4.94 (1H, q, J=6.0 Hz), 5.20 (2H, m), 5.62 (2H, m), 6.77 (1H, dd, J=8.0 Hz), 6.0 Hz), 6.96 (1H, d, J=6.0 Hz), 6.98 (1H, d, J=8.0 Hz). Mass (m/e): 488 (M+), 428, 368. Anal. Calcd. for C$_{28}$H$_{40}$O$_7$ C=68.85% H=8.12% Found C; 68.72% H; 8.06%.

EXAMPLE 73

5,6,7-trinor-4,8-inter-m-phenylene-11,15-dideoxy-11,15-diacetoxy-16,16-dimethyl-18,19,20-trinor-17-ethoxy PGI$_2$ (75)

To a solution of 93 mg of 2-decarboxy-2-hydroxymethyl-5,6,7-trinor-4,8-inter-m-phenylene-11,15-dideoxy-11,15-diacetoxy-16,16-dimethyl-18,19,20-trinor-17-ethoxy PGI$_2$ in 2.5 ml of anhydrous DMF was added 630 mg of pyridinium dichromate, and the resulting solution was stirred at room temperature for 14 hours. Water was added and the mixture was extracted 5 times with ether. The combined ether layers were washed with water and saturated brine, dried and thereafter concentrated to give 100 mg of an oil substance. The oily substance was purified by column chromatography (silica gel (which has been treated with acetic acid); ethyl acetate:cyclohexane (1:1)) to afford 8 mg of the pure carboxylic acid.

IR (neat) $\nu$ cm$^{-1}$: 3600–2300, 1740, 1710, 1595, 1240, 965, 765, 745. NMR (CDCl$_3$) δ: 0.90 (3H, s), 0.94 (3H, s), 1.17 (3H, t, J=7.0 Hz), 2.08 (3H, s), 2.10 (3H, s), 2.40 (2H, t, J=7.0 Hz), 2.64 (2H, t, J=8.0 Hz), 2.87 (1H, q, J=6.0 Hz), 3.16 (2H, s), 3.42 (2H, q, J=7.0 Hz), 3.42 (1H, dd, J=8.0 Hz, 6.0 Hz), 4.94 (1H, q, J=6.0 Hz), 5.26 (2H, m), 5.62 (2H, m), 6.77 (1H, dd, J=8.0 Hz, 7.0 Hz), 6.96 (1H, d, J=7.0 Hz), 6.98 (1 H, d, J=8.0 Hz). Mass (m/e): 502 (M+), 442, 382. Anal. Calcd. for C$_{28}$H$_{38}$O$_8$ C=66.93% H=7.57% Found C; 66.82% H; 7.49%.

EXAMPLE 74

5,6,7-trinor-4,8-inter-m-phenylene-16,16-dimethyl-18,19,20-trinor-17-ethoxy PGI$_2$ (76)

To a solution of 67 mg of 5,6,7-trinor-4,8-inter-m-phenylene-11,15-dideoxy-11,15-diacetoxy-16,16-dimethyl-18,19,20-trinor-17-ethoxy PGI$_2$ in 4.2 mml of methanol was added 0,85 ml of an aqueous solution of 1N sodium hydroxide, and the resulting solution was stirred ar room temperature for 14 hours. The reaction solution was concentrated, water was added to residue, the pH of the mixture was cooled in an ice bath was adjusted to 4 with in hydrocyloric and the mixture extracted 3 times with ethyl acetate. The combined organic layers were washed with water and saturated brine, dried and thereafter concentrated to give 52 mg of the pure diol.

IR (neat) $\nu$ cm$^{-1}$: 3600–2300, 1710, 1595, 1200, 970, 765, 745. NMR (CDCl$_3$) δ: 0.93 (3H, s), 0.95 (3H, s), 1.20 (3H, d, J=7.0 Hz), 2.00 (3H, m), 2.36 (2H, t, J=8.0 Hz), 2.64 (3H, t, J=7.0 Hz), 2.62 (1H, m), 3.36 (2H, AB, J=8.5 Hz), 3.48 (2H, q, J=7.0 Hz), 3.40 (1H, m), 4.00 (2H, m), 5.00 (4H, m), 5.68 (2H, m), 6.60 (1H, dd, J=8.0 Hz, 6.0 Hz), 6.94 (1H, d, J=6.0 Hz), 6.98 (1H, d, J=8.0 Hz). Mass (m/e): 418 (M+), 400, 382. Anal. Calcd. for C$_{24}$H$_{34}$O$_6$ C=68.90% H=8.13% Found C; 68.83% H; 8.08%.

EXAMPLE 75

2-decarboxy-2-tetrahydropyranyloxymethyl-5,6,7-trinor-4,8-inter-m-phenylene-20-isopropylidene PGI$_2$ (77)

To a solution of 500 mg of 3a,8b-cis-2,3,3a,8b-tetrahydro-1H-5(4-tetrahydropyranyloxybutyl-1-β-(2-formylethenyl)2-α-hydroxycyclopenta[b]benzofuran in 10 ml of anhydrous THF cooled in an ice bath was added 2 ml of an ether solution (1.3N) of 6-methyl-5-heptenylmagnesium bromide, and the resulting solution was stirred at 0° C. for 40 minutes. Ammonium chloride, methanol and water were added, and the mixture was extracted 3 times with ether. The combined ether layers were washed with water and saturated brine, dried and thereafter concentrated to give 600 mg of an oil substance. The oily substance was purified by column chromatography (silica gel; ethyl acetate:cyclohexane (5:1)) to give 300 mg of the diol (77).

IR (neat) $\nu$ cm$^{-1}$: 3350, 1952, 970, 810, 760, 740. NMR (CDCl$_3$)δ: 1.62 (3H, s), 1.70 (3H, s), 3.42 (4H, m), 3.82 (4H, m), 5.12 (1H, m), 5.58 (1H, m), 5.14 (2H, m), 5.62 (2H, m), 6.66 (1H, t, J=8.0 Hz), 6.96 (2H, d, J=8.0 Hz). Anal. Calcd. for C$_{31}$H$_{46}$O$_5$ C=74.66% H=9.30% Found C; 74.55% H; 9.22%.

EXAMPLE 76

2-decarboxy-2-tetrahydropyranyloxymethyl-5,6,7-trinor-4,8-inter-m-phenylene-11,15-dideoxy-11,15-diacetoxy-20-isopropylidene PGI$_2$ (78)

To a solution of 200 mg of 2-decarboxy-2-tetrahydropyranyloxymethyl-5,6,7-trinol-4,8-inter-m-phneylene-20-isopropylidene PGI$_2$ in 5 ml of acetic anhydride was added 2.6 ml of anhydrous pyridine and the resulting solution was stirred at room temperature for 3 hours. The reaction mixture was concentrated and the residue was azeotropically treated 2 times with toluene and with once benzene to give 2.33 mg of the nearly pure diacetate (78).

IR (neat) $\nu$ cm$^{-1}$: 1740, 1595, 1230, 970, 760, 745. NMR (CDCl$_3$) δ: 1.60 (3H, s), 1.69 (3H, s), 1.74 (3H, s), 2.06 (3H, s), 2.60 (2H, m), 2.80 (1H, q, J=7.0 Hz), 3.20–4.00 (5H, m), 4.60 (1H, m), 4.92 (1H, m), 5.20 (3H, m), 5.60 (2H, m), 6.74 (1H, dd, J=0.9 Hz, 7.0 Hz), 6.94 (1H, d, J=7.0 Hz), 6.96 (1H, d, J=9.0 Hz). Mass (m/e): 582 (M+). Anal. Calcd. for C$_{35}$H$_{50}$O$_7$ C=72.13% H=8.65% Found C; 72.00% H; 8.42%.

EXAMPLE 77

2-decarboxy-2-hydroxymethyl-5,6,7-trinor-4,8-inter-m-phenylene-11,15-dideoxy-11,15-diacetoxy-20-isopropylidene PGI$_2$ (79)

To a solution of 220 mg of 2-decarboxy-2-tetrahydropyranyloxymethyl-5,6,7-trinor-4,8-inter-m-phenylene-11,15-dideoxy-11,15-diacetoxy-20-isopropylidene PGI$_2$ in 5.5 ml of acetonitrie were added 2.6 ml of THF and 2.6 ml of ¼/N hydrochloric acid and the resulting mixture was stirred at room temperature for 5 hours. Water was added, and the mixture was extracted 3 times with ether, the combined ether layers were washed with water and saturated brine, dried and thereafter concentrated to give 230 mg of an oily substance. The oily substance was purified by column chromatography [silica gel; ethyl acetate:cyclohexane (2:1)] to give 138 mg of the alcohol (79).

IR (neat) $\nu$ cm$^{-1}$: 3450, 1735, 1595, 1240, 965, 840, 760, 745. NMR (CDCl$_3$) δ: 1.60 (3H, s), 1.68 (3H, s), 1.72 (3H, s), 2.04 (3H, s), 2.60 (2H, m), 2.80 (1H, q, J=6.0 Hz), 3.62 (3H, m), 4.92 (1H, m), 5.20 (3H, m), 5.60 (2H, m), 6.76 (1H, dd, J=9.0 Hz, 6.0 Hz), 6.94 (1H, d, J=6.0 Hz), 6.98 (1H, d, J=9.0 Hz). Mass (m/e): 498 (M+), 438, 378. Anal. Calcd. for C$_{30}$H$_{42}$O$_6$ C=72.26% H=8.49% Found C; 72.17% H; 8.41%.

EXAMPLE 78

5,6,7-trinor-4,8-inter-m-phenylene-11,15-dideoxy-11,15-diacetoxy-20-isopropylidene PGI$_2$ (80)

To a solution of 122 mg of 2-decarboxy-2-hydroxymethyl-4,8-inter-m-phenylene-11,15-dideoxy-11,15-diacetoxy-20-isopropylidene PGI$_2$ in 3.3 ml of anhydrous DMF, was added 820 mg of pyridinium dichromate, and the resulting mixture was stirred at room temperature for 14 hours. Water was added, and the mixture was extracted 5 times with ether, the combined ether layers were washed with water and saturated brine, dried and thereafter concentrated to give 130 mg of an oily substance. The oily substance was separated and refined by column chromatography (silica gel (which had been treated with acetic acid) ethyl acetate:cyclohexane (1:2)) to afford 90 mg of a carboxylic acid (80).

IR (neat) ν cm⁻¹: 3600-2300, 1720 (br), 1595, 1230, 960, 830, 760, 745. NMR (CDCl₃) δ: 1.60 (3H, s), 1.68 (3H, s), 1.72 (3H, s), 2.06 (3H, s), 2.40 (2H, t, J=7.0 Hz), 2.60 (2H, t, J=8.0 Hz), 2.80 (1H, m), 3.60 (1H, dd, J=9.0 Hz, 6.0 Hz), 4.94 (1H, m), 5.20 (3H, m), 5.60 (2H, m), 6.79 (1H, t, J=7.8 Hz), 6.96 (2H, d, J=7.8 Hz). Mass (m/e): 512 (M+), 452, 392. Anal. Calcd. for C₃₀H₄₀O₇ C=70.29% H=7.87% Found C; 70.02% H; 7.68%.

EXAMPLE 79

5,6,7-trinor-4,8-inter-m-phenylene-20-isopropylidine-PGI₂ (81)

To a solution of 78 mg of 5,6,7-trinor-4,8-inter-m-phenylene-11,15-dideoxy-11,15-diacetoxy-20-isopropylidene PGI₂ in 4.8 ml of methanol was added 1 ml of 1N sodium hydroxide, and the resulting solution was stirred at room temperature for 3 hours. The reaction solution was concentrated, water was added, the pH of the mixture cooled in an ice bath was adjusted to 3 with 1N hydrochloric acid and the mixture was extracted 3 times with ethyl acetate. The combined organic layers were washed with water and saturated brine, dried and thereafter concentrated to give 65 mg of the diol carboxylic acid (81).

IR (neat) ν cm⁻¹: 3600-2300, 1705, 1595, 970, 830, 765, 745. NMR (CDCl₃) δ: 1.60 (3H, s), 1.68 (3H, s), 2.00 (4H, m), 2,32 (2H, t, J=7.0 Hz), 2.60 (2H, t, J=7.0 Hz), 3.40 (1H, t, J=9.0 Hz), 3.90 (1H, m), 4.10 (1H, m), 4.65 (3H, m), 5.10 (2H, m), 5.60 (2H, m), 6.72 (1H, dd, J=6.4 Hz, 8.4 Hz), 6.92 (1H, d, J=6.4 Hz), 6.93 (1H, d, J=6.6 Hz). Mass (m/e): 428 (M+), 410, 382. Anal. Calcd. for C₂₆H₃₆O₅ C=72.86% H=8.47% Found C; 72.80% H; 8.43%.

EXAMPLE 80

2-decarboxy-2-tetrahydropyranyloxymethyl-5,6,7-trinor-3,8-inter-(5-methyl-1,3-phenylene)-PGI₂ (82)

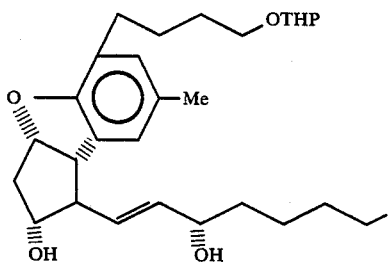

To a solution of 469 mg (1.17 mmol) of 1,2,3a,8b-cis-tetrahydro-1-exo-(2-formylethenyl)-2-endo-hydroxy-7-methyl-5-(4-tetrahydropyranyloxy-n-butyl)cyclopenta[b]benzofuran in 6 ml of THF at −78° C. under argon atmosphere was added 5.6 ml (0.63M, 3.53 mmol, 3.0 equiv.) of n-pentyl lithium, and resulting solution was stirred for 30 minutes. After confirming 2 products by thin layer chromatography, 2 ml of a saturated aqueous solution of ammonium chloride was added, the resulting solution was extracted with ethyl acetate (10 ml×5) and the organic layer was dried, and concentrated to afford 524 mg of a crude product. The product was purified by column chromatography (Merck Lobar Column; cyclohexane: ethyl acetate 1:5) to give 2 kinds of oily substances, 273 mg (49%) of the polar titled compound (82) and 139 mg (25%) of a less polar stereoisomer.

IR (neat) ν cm⁻¹: 3350 (3650-3100), 2390, 2860, 1610, 1470, 1200, 1135, 1120, 1070, 1030, 965, 860, 815, 730. NMR (CDCl₃) δ: 0.91 (t, J=6 Hz, 3H), 1.35 (m, 8H), 1.35 (m, 8H), 1.65 (m, 10H), 1.85 (m, 1H), 2.22 (s, 3H), 2.24 (m, 1H), 2.55 (m, 3H), 3.40 (m, 5H), 3.80 (m, 3H), 4.08 (m, 1H), 4.57 (m, 1H), 5.03 (q, J=7 Hz, 1H), 6.72 (s, 1H), 6.76 (s, 1H). Mass spectrum: M+ 472. Anal. Calcd. for C₂₉H₄₄O₅ C=73.69% H=9.38% Found C; 73.60% H; 9.32%.

EXAMPLE 81

2-decarboxy-2-tetrahydropyranyloxymethyl-5,6,7-trinor-4,8-inter-(5-methyl-1,3-phenylene) PGI₂ diacetate (83)

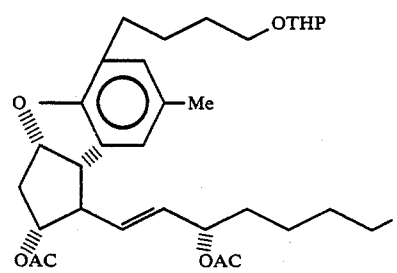

To a solution of 240 mg (0.508 mmol) of 2-decarboxy-2-tetrahydropyranyloxymethyl-5,6,7-trinor-3,7-inter-(5-methyl-1,3-phenylene) PGI₂ in 8 ml of pyridine was added 10 ml of acetic anhydride, and the resulting mixture was stirred at room temperature for 2 hours. After confirming the loss of the material by thin-layer chromatography, the mixture was concentrated to give 258 mg (0.464 mmol, 91%) of (83).

IR (neat) ν cm⁻¹: 2930, 2860, 1740, 1470, 1370, 1235, 1200, 1130, 1115, 1065, 1020, 960, 860, 810, 740. NMR (CDCl₃) δ: 0.89 (t, J=6 Hz, 3H), 1.30 (m, 8H), 166 (m, 10H), 1.77 (s, 3H), 1.90 (m, 1H), 2.06 (s, 3H), 2.24 (s, 3H), 2.54 (m, 3H), 2.80 (m, 1H), 3.50 (m, 3H), 3.80 (m, 2H), 4.58 (m, 1H), 4.92 (q, J=6 Hz, 1H), 5.22 (m, 2H), 5.62 (t, J=5 Hz, 2H), 6.76 (s, 2H). Mass spectrum: M+ 556. Anal. Calcd. for C₃₃H₄₈O₇ C=71.19% H=8.69% Found C; 71.11% H; 8.62%.

EXAMPLE 82

2-decarboxy-2-hydroxymethyl-5,6,7-trinor-4,8-inter-(5-methyl-1,3-phenylene) PGI₂ diacetate (84)

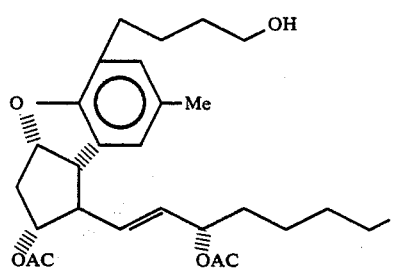

To a solution of 258 mg (0.464 mmol) of 2-decarboxy-2-tetrahydro-pyranyloxymethyl-5,6,7-trinor-4,8-inter-(5-methyl-1,3-phenylene) PGI₂ in 5 ml of THF were added 10 ml of acetonitrile and 4 ml of 0.25N hydrochloric acid, and the resulting mixture was stirred at room temperature. After confirming the loss of the material by thin-layer chromatography, 0.1 ml of trietyl amine, 3 ml of a saturated aqueous solution of sodium bicarbonate, and 3 ml of a saturated aqueous solution of sodium chloride were added and the resulting mixture was extracted with ethyl acetate (10 ml×5). The organic layer was dried and thereafter concentrated to give 365 mg of an oily substance. The oily substance was purified by column chromatography (Merck Lobar Column, cyclohexane:ethyl acetate 2:3) to afford 162 mg (0.343 mmol, 74%) of (84) as an oil.

IR (neat) $\nu$ cm$^{-1}$: 3400, (3600–3100), 2930, 2860, 1740, 1475, 1370, 1235, 1200, 1130, 1050, 1020, 960, 860, 730. NMR (CDCl$_3$) $\delta$: 0.91 (t, J=6 Hz, 3H), 1.31 (m, 6H), 1.66 (m, 8H), 1.78 (s, 3H), 1.78 (s, 3H), 2.03 (s, 3H), 2.08 (m, 1H), 2.25 (s, 3H), 2.56 (m, 3H), 2.79 (q, J=6 Hz, 1H), 3.55 (dd, J=8, 6 Hz, 1H), 3.68 (m, 2H), 4.91 (q, J=6 Hz, 1H), 5.20 (m, 2H), 5.60 (dd, J=6, 5 Hz, 1H), 6.75 (s, 2H). Mass spectrum: M$^+$ 472. Anal. Calcd. for C$_{28}$H$_{40}$O$_6$ C=71.16% H=8.53% Found C; 69.97% H; 8.46%.

EXAMPLE 83

5,6,7-trinor-4,8-inter-(5-methyl-1,3-phenylene) PGI$_2$ diacetate (85)

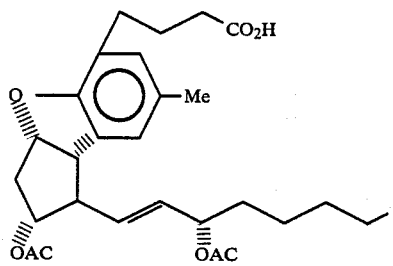

and 5,6,7-trinor-4,8-inter-(t-formyl-1,3-phenylene) PGI$_2$ diacetate (86)

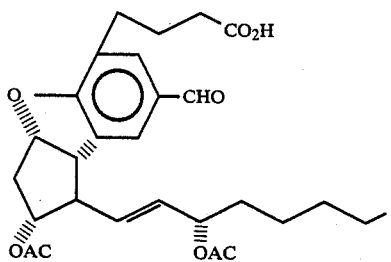

To a solution of 160 mg (0.339 mmol) of 2-decarboxy-2-hydroxymethyl-5,6,7-trinor-4,8-inter-(5-methyl-1,3-phenylene) PGI$_2$ diacetate in 5 ml of N,N-dimethyl formamide at room temperature under argon atmosphere was added 1.027 g (2.73 mmol, 8 equiv.) of pyridinium dichromate, and the resulting mixture was stirred for 7 hours. Five ml of water was added, the mixture was extracted with ether (1 ml×2), the ether layer was washed with a saturated aqueous solution of sodium chloride, dried and thereafter concentrated to give 210 mg of an oily crude product. The product was purified by column chromatography (Merck Lobar Column, cyclohexane:ethyl acetate 2:1) to afford 111 mg (67%) of (85) and 27 mg (16%) of (86) as oils.

5,6,7-trinor-4,8-inter-(5-methyl-1,3-phenylene) PGI$_2$ diacetate (85)

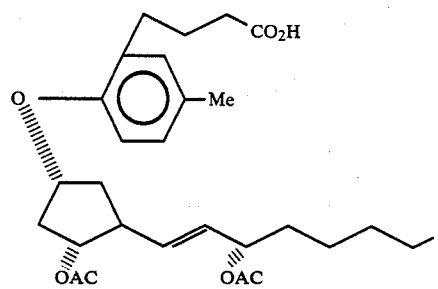

Anal. Calcd. for C$_{28}$H$_{38}$O$_7$ C=69.11% H=7.87% Found C; 68.82% H; 7.59%. NMR (CDCl$_3$) $\delta$: 0.91 (t, J=6 Hz, 3H), 1.30 (m, 6H), 1.64 (m, 2H), 1.76 (s, 3H), 1.96 (m, 3H), 2.07 (s, 3H), 2.24 (s, 3H), 2.26 (m, 1H), 2.40 (t, J=8 Hz, 2H), 2.58 (t, J=8 Hz, 2H), 2.80 (t, J=6 Hz, 1H), 3.54 (dd, J=10, 6 Hz, 1H), 4.89 (q, J=6 Hz, 1H), 5.22 (m, 2H), 5.59 (dd, J=6,5 Hz, 2H), 6.73 (s, 3H). IR (neat) $\nu$ cm$^{-1}$: 3300–2100, 2930, 2860, 1740, 1710, 1475, 1370, 1235, 1150, 1130, 1050, 1020, 960, 860. Mass spectrum: M$^+$ 486.

5,6,7-trinor-4,8-inter-(5-formyl-1,3-phenylene) PGI$_2$ diacetate (86)

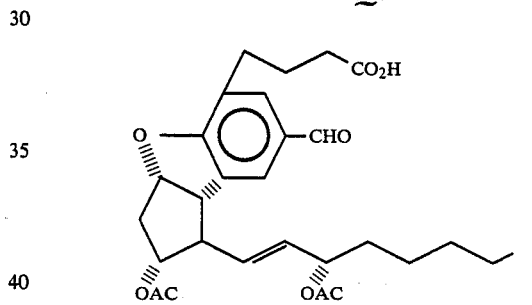

Anal. Calcd. for C$_{28}$H$_{36}$O$_8$ C=67.18% H=7.25% Found C; 67.00% H; 7.01%. NMR (CDCl$_3$) $\delta$: 0.90 (t, J=6 Hz, 3H), 1.30 (m, 6H), 1.64 (m, 2H), 1.68 (s, 3H), 1.96 (m, 3H), 2.07 (s, 3H), 2.26 (m, 1H), 2.42 (t, J=8 Hz, 2H), 2.68 (t, J=8 Hz, 2H), 2.89 (m, 1H), 3.72 (dd, J=8, 4 Hz, 1H), 4.95 (q, J=4 Hz, 1H), 5.21 (m, 1H), 5.40 (m, 1H), 5.60 (m, 2H), 7.52 (s, 2H), 9.76 (s, 1H). IR (neat) $\nu$ cm$^{-1}$: 3600–2200, 2930, 2860, 1740, 1690, 1600, 1430, 1370, 1235, 1110, 1050, 1020, 960. Mass spectrum: M$^+$ 500.

EXAMPLE 84

5,6,7-trinor-4,8-inter-(5-methyl-1,3-phenylene) PGI$_2$ (87)

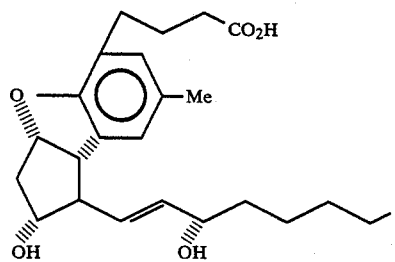

To a solution of 103 mg (0.212 mmol) of 5,6,7-trinor-4,8-inter-(5-methyl-1,3-phenylene) PGI$_2$ diacetate was added 1 ml (ca 5 equiv.) of an aqueous solution of 1N sodium hydroxide and the mixture was stirred at room temperature for 2 hours. After evaporation of methanol, 1N hydrochloric acid was added to adjust the pH of the solution to 4 and the mixture was extracted with ethyl acetate (10 ml×7). The organic layer was washed with saturated brine (1 ml×2), dried and thereafter concentrated to give 84 mg (98.6%) of (87) as white crystals (mp; 129.5°–131° C.).

IR (KBr) $\nu$ cm$^{-1}$: 3400 (3600–2200), 2930, 2860, 1705, 1470, 1375, 1275, 1225, 1200, 1150, 1080, 980, 960, 870, 860, 740. NMR (CDCl$_3$) δ: 0.90 (t, J=6 Hz, 3H), 1.34 (m, 8H), 1.96 (m, 3H), 2.22 (s, 3H), 2.33 (m, 3H), 2.59 (m 3H), 3.35 (t, J=8 Hz, 1H), 4.08 (m, 4H), 5.06 (m, 1H), 5.58 (m, 2H), 6.74 (s, 2H). Mass spectrum: M+ 402.

EXAMPLE 85

5,6,7-trinor-4,8-inter-(5-formyl-1,3-phenylene) PGI$_2$ (88)

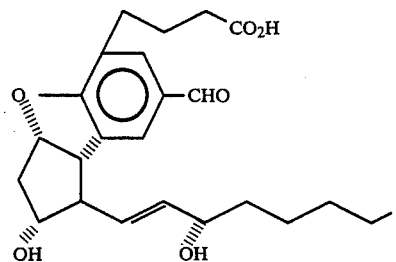

The procedure of Example 84 was followed except the use of 16 mg of 5,6,7-trinor-4,8-inter-(5-formly-1,3-phenylene) PGI$_2$ diacetate in place of (85), to give 12 mg (90%) of (88) as an oil.

Anal. Calcd. for C$_{24}$H$_{32}$O$_6$ C; 69.21% H; 7.74% Found C; 69.11% H; 7.62%.

NMR (CDCl$_3$) δ: 0.90 (t, J=6 Hz, 3H), 1.34 (m, 8H), 2.02 (m, 3H), 2.34 (m, 3H), 2.68 (m, 3H), 3.48 (t, J=8 Hz, 1H), 3.94 (m, 1H), 4.12 (m, 1H), 4.86 (a wide one-double line; 3H), 5.22 (m, 1H), 5.64 (m, 2H), 7.53 (s, 2H).

IR (neat) $\nu$ cm$^{-1}$: 3400 (3700–2200), 2930, 2860, 1710, 1690, 1600, 1470, 1435, 1280, 1220, 1125, 1080, 1025, 970, 890, 860, 740.

Mass (m/e): M+ 416.

EXAMPLE 86

2-decarboxy-2-tetrahydropyranyloxymethyl-5,6,7-trinor-4,8-inter-(5-methyl-1,3-phneylene)-15-phenyl-16,17,18,19,20-petanor PGI$_2$ (89)

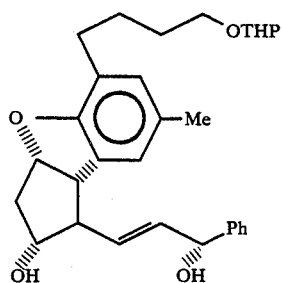

To a solution of 1.091 g (2.73 mmol) of 1,1,3a,8b-cis-tetrahydro-1-exo-(2-formylethenyl)-2-endo-hydroxy-7-methyl-5-(4-tetrahydropyranyloxy-n-butyl)cyclopenta[b]benzofuran in 16 ml of tetrahydrofuran at −78° C. under argon atmosphere was added 2.1 m (0.65M ether solution 13.7 mmol, 5 equiv.) of phenyl lithium, and the resulting solution was stirred for 2 hours. Five ml of a saturated aqueous solution of ammonium chloride was added, the temperature was allowed to warm to room temperature, and the mixture was extracted with ethyl acetate (10 ml×5), the combined organic layers were washed with 5 ml of saturated brine and dried over anhydrous Na$_2$SO$_4$. After concentration, the resulting 2.67 g of an oily substance was purified by column chromatography (Merck Co.'s Lobar Column, cyclohexane; ethyl acetate 1:4) to give 534 mg (1.12 mmol, 40.9%) of polar (89) and 325 mg (0.680 mmol, 24.9%) of less polar 15-epimer.

IR (neat) $\nu$]cm$^{-1}$: 3400 (3600–3100), 2930, 2850, 1600, 1470, 1450, 1200, 1135, 1115, 1070, 1020, 965, 860, 810, 760, 730, 700.

NMR (CDCl$_3$) δ: 1.62 (m, 10H), 1.94 (m, 1H), 2.14 (s, 3H), 2.45 (m, 1H), 2.53 (t, J=7 Hz, 2H), 2.65(m, 1H), 2.60 (a wide one-double line, 2H), 3.23 (m, 1H), 3.36 (t, J=8 Hz, 2H), 3.84 (m, 3H), 4.53 (m, 1H), 5.21 (m, 1H), 5.43 (m, 1H), 5.77 (m, 2H), 6.62 (s, 1H), 6.73 (s, 1H), 7.36 (m, 5H).

Mass (m/e): 478 (M+).

Anal. Calcd. for C$_{30}$H$_{38}$O$_5$ C; 75.29% H; 8.00% Found C; 75.21% H; 7.93%

EXAMPLE 87

2-decarboxy-2-tetrahydropyranyloxymethyl-5,6,7-trinor-4,8-inter-(5-methyl-1,3-phenylene)-15-phenyl-16,17,18,19,20-pentanor PGI$_2$ (90)

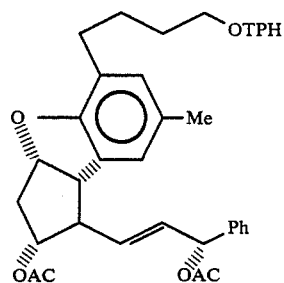

To a solution of 510 mg of 2-decarboxy-2-tetrahydropyranyloxy-methyl-5,6,7-trinor-4,8-inter-(5-methyl-1,3-phenylene-15-phenyl-16,17,18,19,20-pentanor PGI$_2$ in 10 ml of pyridine under nitrogen atmosphere was added 5 ml of acetic anhydride and the resulting solution was stirred at room temperature for 24 hours. Pyridine and acetic anhydride were evaporated to give 574 mg (1.02 mmol, 95.5%) of pure 2 as an oil.

IR (neat) $\nu$ cm$^{-1}$: 2930, 2850, 1740, 1600, 1475, 1370, 1230, 1135, 1110, 1060, 1020, 960, 860, 815, 760, 740, 700.

NMR (CDCl$_3$) δ: 1.63 (m, 10H), 1.77 (s, 3H), 2.00 (m, 1H), 2.11 (s, 3H), 2.20 (s, 3H), 2.54 (m, 3H), 2.75 (m, 1H), 3.48 (m, 3H), 3.89 (m, 2H) 4.57 (m, 1H), 4.92 (t, J=7 Hz, 1H), 5.14 (m, 1H), 5.76 (m, 2H), 6.65 (s, 1H), 6.76 (s, 1H), 7.16 (m, 5H).

Mass (m/e): 562 (M+).

Anal. Calcd. for C$_{34}$H$_{42}$O$_7$ C; 72.58% H; 7.52% Found C; 72.59% H; 7.57%.

Example 88

2-decarboxy-2-hydroxymethyl-5,6,7-trinor-4,8-inter-(5-methyl-1,3-phenylene)-15-phenyl-16,17,18,19,20-pentanor PGI₂ diacetate (91)

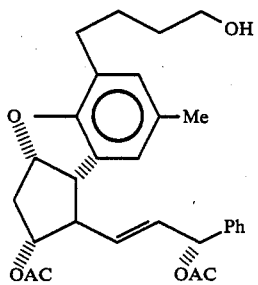

To a solution of 507 mg (0.902 mmol) of 2-decarboxy-2-tetrahydropyranyloxymethyl-5,6,7-trinor-4,8-inter-(5-methyl-1,3-phenylene)-15-phenyl-16,17,18,19,20-pentanor PGI₂ diacetate in 5 ml of tetrahydrofuran and 10 ml of acetonitrile was added 6 ml (1.5 mmol) of 0.25N hydrochloric acid, and the resulting solution was stirred at room temperature for 1.5 hours. After the solution was cooled to 0° C., 3 ml of saturated brine and 3 ml of a saturated aqueous solution of sodium bicarbonate were added, and the mixture was extracted with ethyl acetate (10 ml×4) and the organic layer was dried over anhydrous sodium sulfate. After concentration, the resulting 516 mg of an oily crude product was purified by column chromatography (Merck Co.'s Lobar Column, cyclohexane:ethyl acetate 1:2) to give 267 mg (0.559 mmol, 62%) of white solid (91), which was recrystallized from a cyclohexane:ethyl acetate (4:1) to give colorless needles (mp 76°-78° C.).

IR (KBr) ν cm⁻¹: 3450 (3650–3150), 2930, 2850, 1740, 1600, 1475, 1370, 1230, 1130, 1055, 1020, 960, 860, 760, 730, 700.

NMR (CDCl₃) δ: 1.64 (m, 5H), 1.78 (s, 3H), 1.97 (m, 1H), 2.11 (s, 3H), 2.20 (s, 3H), 2.54 (m, 3H), 2.78 (m, 1H), 3.52 (dd, J=8, 6 Hz, 1H), 3.66 (t, J=6 Hz, 2H), 4.86 (q, J=6 Hz, 1H), 4.96 (q, J=6 Hz, 1H), 5.17 (m, 1H), 5.76 (m, 2H), 6.30 (m, 1H), 6.88 (s, 1H), 6.76 (s, 1H), 7.37 (s, 5H).

Mass (m/e): 478 (M+).

Anal. Calcd. for C₂₉H₃₄O₆ C; 72.78% H; 7.16% Found C; 72.92% H; 7.10%.

EXAMPLE 89

5,6,7-trinor-4,8-inter-(5-methyl-1,3-phenylene)-15-phenyl-16,17,18,19,20-pentanor PGI₂ diacetate (92)

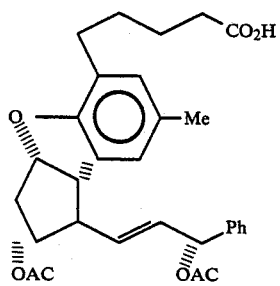

To a solution of 219 mg (0.458 mmol) of 2-decarboxy-2-hydroxymethyl-5,6,7-trinor-4,8-inter-(5-methyl-1,3-phenylene)-15-phenyl-16,17,18,19,20-pentanor PGI₂ diacetate in 4 ml of anhydrous N,N-dimethyl formamide was added 688 mg (1,83 mmol, 4.0 equiv.) of pyridinium dichromate, and the resulting mixture was stirred at room temperature for 12 hours. Water was added, and the mixture was extracted with ether (20 ml×5), the ether layers were washed with saturated brine (1 ml×2) and dried over anhydrous sodium sulfate. After concentration, the resulting 238 mg of an oily substance was purified by column chromatography (Merck Co.'s Lobar Column, cyclohexane-ethyl acetate 1:2) to give 128 mg (0.260 mmol, 56.8%) of white crystals (92), which was recrystallized from 4 ml of cyclohexane-ethyl acetate (4:1) to afford colorless needles (mp 111°-113° C.).

IR (KBr) ν cm⁻¹: 3450 (3650–2300), 2930, 2860, 1740, 1705, 1600, 1475, 1370, 1225, 1050, 1015, 955, 860, 765, 700.

NMR (CDCl₃) δ: 1.76 (s, 3H), 1.99 (m, 3H), 2.11 (s, 3H), 2.20 (s, 3H), 2.38 (m, 3H), 2.58 (t, J=8 Hz, 2H), 2.80 (m, 1H), 3.62 (dd, J=8, 6 Hz, 1H), 4.98 (q, J=7 Hz, 1H), 5.17 (m, 1H), 5.76 (m, 2H), 6.30 (m, 1H), 6.69 (0, 1H), 6.75 (s, 1H), 7.37 (s, 5H).

Mass (m/e): 492 (M+).

Anal. Calcd. for C₂₉H₃₂O₇ C; 70.72% H; 6.54% Found C; 70.46% H; 6.50%.

EXAMPLE 90

5,6,7-trinor-4,8-inter-(5-methyl-1,3-phenylene)-15-phenyl-16,17,18,19,20-pentanor PGI₂ (93)

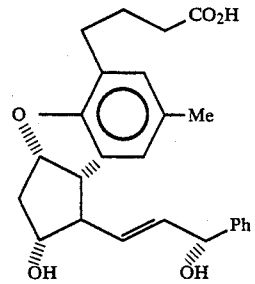

To a solution of 110 mg (0.223 mmol) of 5,6,7-trinor-4,8-inter-(5-methyl-1,3-phenylene)-15-phenyl-16,17,18,19,20-pentanor PGI₂ diacetate in 3 ml of methanol was added 1.0 ml (4.5 equiv.) of 1N sodium hydroxide, and the resulting solution was stirred at room temerature for 2 hours. Methanol was evaporated (bath temperature less than 40° C.), and the mixture was cooled to 0° C., 0.25N hydrochloric acid was added to adjust the pH to 4. The two ml of saturated brine was added, the mixture was extracted with ethyl acetate (10 ml×5), and the organic layer was washed with saturated brine and dried over anhydrous sodium sulfate. Evaporation of the solvent afforded 91 mg (0.223 mmol, 100%) of white crystals (93), which was recrystallized from 4 ml of a cyclohexane-ethyl acetate (1:1) to give colorless prisms (mp 141°-144° C.)

IR (KBr) ν cm⁻¹: 3400 (3650–2200), 2960, 2930, 2850, 1705, 1675, 1600, 1475, 1410, 1300, 1280, 1220, 1195, 965, 860, 855, 760, 700.

NMR (CDCl₃) δ: 1.99 (m, 3H), 2.15 (s, 3H), 2.31 (m, 3H), 2.58 (t, J=8 Hz, 2H), 2.72 (m, 1H), 3.40 (m, 4H), 3.95 (m, 1H), 5.06 (m, 1H), 5.24 A(m, 1H), 5.80 (m, 2H), 6.63 (s, 1H), 6.74 (s, 1H), 7.40 (m, 5H).

Mass (m/e): 408 (M+).

Anal. Calcd. for C$_{25}$H$_{28}$O$_5$ C; 73.51% H; 6.91%
Found C; 73.71% H; 6.93%.

EXAMPLES 91–92

The procedure of Example 86 if followed except the uses of 1,2,3a,8b-cis-tetrahydro-1-exo-(2-formylethenyl)-2-endohydroxy-7-bromo-5-(4-tetrahydropyranyloxybutyl)cyclopenta[b]benzofuran, or 1,2,3a,8b-cis-tetrahydro-1-exo-(2-formylethenyl)-2-endo-hydroxy-7-chloro-5-(4-tetrahydropyranyloxybutyl)cyclopenta[b]benzofuran and cyclohexylmagnesium chloride, in place of 1,2,3a-8b-cis-tetrahydro-1-exo-(2-formylethenyl)-2-endo-hydroxy-7-methyl-5-(4-tetrahydropyranyloxybutyl)cyclopena[b]benzofuran and phenyl lithium, and the procedures of Examples 87–90 are followed successively except the uses of the each resulting compounds to give 5,6,7-trinor-4,8-inter-(5-bromo-1,3-phenylene)-16,17,18,19,20-pentanor-15-cyclohexyl PGI$_2$ (94), or 5,6,7-trinor-4,8-inter-(5-chloro-1,3-phenylene)-16,17,18,19,20-pentanor-15-cyclohexyl PGI$_2$ (95).

REFERENTIAL EXAMPLE 85

2-phenylseleno-5,6,7-trinor-4,8-inter-m-phenylene-16,17,18,19,20-pentanor-15-phenyl-PGI methyl ester To a solution of 0.15 ml of diisopropyl amine in 10 ml of anhydrous THF at −78° C. was added 0.7 ml of 1.5N n-butyl lithium, and the resulting solution was stirred for 15 minutes. A solution of 90 mg of 5,6,7-trinor-4,8-inter-m-phenylene-16,17,18,19,20-pentanor-15-phenyl-PGI$_2$ methyl ester in 2 ml of anhydrous THF was added at −78° C., the resulting solution was stirred at that temperature for 30 minutes, a solution of 200 mg of diphenylselenide in 1 ml of anhydrous HMPA was added, and the resulting solution was stirred at −78° C. for 20 minutes. Solid ammonium chloride was added, and the mixture was stirred at −78° C. for 20 minutes and at room temperature for 10 minutes, water was added and the mixture was extracted 3 times with ether. The combined organic layer was washed with water and saturated brine, dried and thereafter concentrated to give 100 mg of an oily substance. The oily substance was purified by column chromatography (silica gel; ethyl acetate:cyclohexane (3:1) to afford 88 mg of the selenide.

IR (neat) ν cm$^{-1}$: 3350, 1730, 1590, 1500, 970, 748, 700.

NMR (CDCl$_3$) δ: 3.50 (m, 1H), 3.58 (s, 3H), 3.95 (m, 1H), 5.10 (m, 1H), 5.25 (dd, 1H, J=5.0 Hz, 3.0 Hz), 5.80 (m, 2H), 6.70 (1H, t, J=6.0 Hz), 6.88 (m, 2H), 7.32 (m, 3H), 7.55 (m, 2H).

Mass (m/e): 562 (M+).

Anal. Calcd. for C$_{31}$H$_{32}$O$_5$Se C; 66.61% H; 5.68%
Found C; 66.55% H; 5.69%.

EXAMPLE 93

Trans-2,3-didehydro-5,6,7-trinor-4,8-inter-m-phenylene-16,17,18,19,20-pentanor-15-phenyl-PGI$_2$ methyl ester (96)

To a solution of 40 mg of 2-phenylseleno-5,6,7-trinor-4,8-inter-m-phenylene-16,17,18,19,20-pentanor-15-phenyl-PGI$_2$ methyl ester in 5 ml of ethyl acetate was added 0.16 ml of 35% hydrogen peroxide, and the resulting mixture was stirred at room temperature for 1 hour. One ml of dimethyl sulfide and 200 mg of potassium acetate were added, and the mixture was stirred at room temperature for 10 minutes, thereafter, concentrated under reduced pressure. Water was added to the resulting residue, and the mixture was extracted 3 times with ethyl acetate, the extracts were washed with a saturated aqueous solution of sodium carbonate, water and saturated brine, dried and thereafter concentrated to give 40 mg of an oily substance. The oily substance was purified by column chromatography (silica gel; ethyl acetate:cyclohexane (2:1)) to afford 25 mg of the unsaturated ester (96).

IR (neat) ν cm$^{-1}$: 3350, 1710, 1650, 1595, 970, 750, 700.

NMR (CDCl$_3$) δ: 3.40 (2H, m), 3.68 (3H, s), 3.80 (1H, m), 5.02 (1H, m), 5.20 (1H, m), 5.78 (2H, m), 5.80 (1H, dt, J=15.0 Hz, 2.0 Hz), 6.70 (1H, dt, J=6.0 Hz, 8.5 Hz), 6.90 (2H, m), 7.10 (1H, m), 7.35 (5H, s).

Mass (m/e): 406 (M+).

Anal. Calcd. for C$_{25}$H$_{26}$O$_5$ C; 73.89% H; 6.40%
Found C; 73.92% H; 6.36%.

REFERENTIAL EXAMPLE 86

2-phenylseleno-5,6,7-trinor-4,8-inter-m-phenylene-16,17,18,19,20-pentanor-15-phenyl-PGI$_2$ To a solution of 42 mg of 2-phenylseleno-5,6,7-trinor-4,8-inter-m-phenylene-16,17,18,19,20-pentanor-15-phenyl-PGI$_2$ methyl ester in 4 ml of methanol was added 0.8 ml of 1N sodium hydroxide, and the resulting solution was stirred at room temperature for 14 hours. The reaction mixture was concentrated under reduced pressure, water was added to the residue, the pH of the mixture cooled in an ice bath was adjusted to 4 with ¼N hydrochloric acid and the product was extracted with ethyl acetate 3 times. The combined organic layers were washed with water and saturated brine, dried and thereafter concentrated to give 41 mg of the nearly pure carboxylic acid.

IR (neat) ν cm$^{-1}$: 3600–2400, 1700, 1595, 1580, 965, 740, 700.

NMR (CDCl$_3$) δ: 3.30 (1H, m), 3.90 (1H, m, 5.00 (1H, m), 5.20 (1H, m), 5.75 (2H, m), 6.65 (1H, t, J=7.0 Hz), 6.85 (2H, m), 7.30 (3H, m), 7.55 (2H, m).

Mass (m/e): 548 (M+).

Anal. Calcd. for C$_{30}$H$_{30}$O$_5$Se C; 65.69% H; 5.47%
Found C; 65.81% H; 5.38%.

EXAMPLE 94

5,6,7-trinor-4,8-inter-m-phenylene-2,3-dehydro-16,17,18,19,20-pentanor-15-phenyl-PGI$_2$ (97)

To a solution of 41 mg of 2-phenylseleno-5,6,7-trinor-4,8-inter-m-phenylene-16,17,18,19,20-pentanor-15-phenyl-PGI$_2$ in 5 ml of ethyl acetate was added, 0.16 ml of a 35% aqueous solution of hydrogen peroxide, and the resulting solution was stirred at room temperature for 1 hour. One ml of dimethyl sulfide and 100 mg of potassium acetate were added, and the mixture was stirred at room temperature for 10 minutes and thereafter concentrated under reduced pressure. Water was added to the residue, the pH of the mixture cooled in an ice bath was adjusted to 6 with ¼N hydrochloric acid. The product was extracted 3 times with ethyl acetate, the organic layer was washed with water and saturated brine, dried and thereafter concentrated to give 34 mg of an oily substance. The oily substance was purified by column chromatography (acidic silica gel; ethyl acetate:cyclohexane (3:1)) to afford 25 mg of the pure unsaturated carboxylic acid.

IR (neat) ν cm$^{-1}$: 3600–2400, 1700, 1640, 1600, 960, 765, 700.

NMR (CDCl₃) δ: 3.40 (3H, m), 3.90 (1H, m), 5.05 (1H, m), 5.20 (1H, m), 5.75 (2H, m), 5.77 (1H, d, J=15.0 Hz) 6.65 (1H, dd, J=8.5 Hz, 6.0 Hz) 6.90 (2H, m), 7.10 (1H, m), 7.35 (5H, m).

Mass (m/e): 392 (M⁺).

Anal. Calcd. for $C_{24}H_{24}O_5$ C; 76.53% H; 6.12% Found C; 76.55% H; 6.09%.

EXAMPLES 95–106

The procedure of Referential Example 85 was followed except the use of 5,6,7-trinor-4,8-inter-m-phenylene-16,17,18,19,20-pentanor-15-cyclohexyl PGI₂ methyl ester, 5,6,7-trinor-4,8-inter-m-phenylene-16,17,18,19,20-pentanor-15-cyclopentyl PGI₂ methyl ester, 5,6,7-trinor-4,8-inter-m-phenylene-13,14-dehydro-16,17,18,19,20-pentanor-15-phenyl PGI₂ methyl ester, 5,6,7-trinor-4,8-inter-m-phenylene-13,14-dehydro-16,17,18,19,20-pentanor-15-cyclopentyl PGI₂ methyl ester, 5,6,7-trinor-4,8-inter-m-phenylene-13,14-dehydro-16,17,18,19,20-pentanor-15-cyclohexyl PGI₂ methyl ester, 5,6,7-trinor-4,8-inter-m-phenylene-17,18,19,20-tetranor-16-phenyl PGI₂, 5,6,7-trinor-4,8-inter-m-phenylene-17-α-methyl ester, 5,6,7-trinor-4,8-inter-m-phenylene-17-β-methyl PGI₂ methyl ester, 5,6,7-trinor-4,8-inter-m-phenylene-17-α-methyl-ω-homo PGI₂ methyl ester, 5,6,7-trinor-4,8-inter-m-phenylene-17-β-methyl-ω-homo PGI₂ methyl ester, 5,6,7-trinor-4,8-inter-m-phenylene PGI₂ methyl ester, or 5,6,7-trinor-4,8-inter-m-phenylene-ω-homo PGI₂ methyl ester, in place of 5,6,7-trinor-4,8-inter-m-phenylene-16,17,18,19,20-pentanor-15-phenyl PGI₂ methyl ester and the obtained products were followed by the method of Example 93 to give 5,6,7-trinor-4,8-inter-m-phenylene-2,3-dehydro-16,17,18,19,20-pentanor-15-cyclohexyl PGI₂ methyl ester (98), 5,6,7-trinor-4,8-inter-m-phenylene-2,3-dehydro-16,17,18,19,20-pentanor-15-cyclopentyl PGI₂ methyl ester (99), 5,6,7-trinor-4,8-inter-m-phenylene-2,3,13,14tetrahydro-16,17,18,19,20-pentanor-15-phenyl PGI₂ methyl ester (100), 5,6,7-trinor-4,8-inter-m-phenylene-2,3,13,14-tetrahydro-16,17,18,19,20-pentanor-15-cyclopentyl PGI₂ methyl ester (101), 5,6,7-trinor-4,8-inter-m-phenylene-2,3,13,14-tetrahydro-16,17,18,19,20-pnetanor-15-cyclohexyl PGI₂ methyl ester (102), 5,6,7-trinor-4,8-inter-m-phenylene-2,3-dehydro-17,18,19,20-tetranor-16-phenyl PGI₂ methyl ester (103), 5,6,7-trinor-4,8-inter-m-phenylene-2,3-dehydro-17-α-methyl PGI₂ methyl ester (104), 5,6,7-trinor-4,8-inter-m-phenylene-2,3-dehydro-17-β-methyl PGI₂ methyl ester (105), 5,6,7-trinor-4,8-inter-m-phenylene-2,3-dehydro-17-α-methyl-ω-homo PGI₂ methyl ester (106), 5,6,7-trinor-4,8-inter-m-phenylene-2,3-dehydro-17-β-methyl-ω-homo PGI₂ methyl ester (107), 5,6,7-trinor-4,8inter-m-phenyene-2,3-dehydro PGI₂ methyl ester (108), or 5,6,7-trinor-4,8-inter-m-phenylene-2,3-dehydro-ω-homo PGI₂ methyl ester (109). In Table 5, the spectral data of these compounds are shown.

TABLE 5

| Example | Compound | Mass spectrum (m/e, M⁺) | Infrared spectrum cm⁻¹ |
|---|---|---|---|
| 95 | 98 | 412 | 3350, 1710, 1650, 1595, 970 |
| 96 | 99 | 398 | 3350, 1710, 1650, 1595, 970 |
| 97 | 100 | 406 | 3350, 1710, 1650, 1595, 970, 750, 700 |
| 98 | 101 | 396 | 1710, 1650, 970 |
| 99 | 102 | 410 | 1710, 1650, 970 |
| 100 | 103 | 422 | 1710, 1650, 1595, 970, 750, 700 |
| 101 | 104 | 414 | 1710, 1650, 1250, 970 |
| 102 | 105 | 414 | 1710, 1650, 1250, 970 |
| 103 | 106 | 428 | 1710, 1650, 1450, 1250, 970 |
| 104 | 107 | 428 | 1710, 1650, 1450, 1250, 970 |
| 105 | 108 | 400 | 1710, 1650, 1450, 1250, 970 |
| 106 | 109 | 414 | 1710, 1650, 1450, 1250, 970, 860 |

EXAMPLE 107–118

The procedure of Referential Example 86 was followed except the uses of 2-phenylseleno-5,6,7-trinor-4,8-inter-m-phenylene-16,17,18,19,20-pentanor-15-cyclohexyl PGI₂ methyl ester, 2-phenylseleno-5,6,7-trinor-4,8-inter-m-phenylene-16,17,18,19,20-pentanor-15-cyclopentyl PGI₂ methyl ester, 2-phenylseleno-5,6,7-trinor-4,8-inter-m-phenylene-13,14-dehydro-16,17,18,19,20-pentanor-15-phenyl PGI₂ methyl ester, 2-phenylseleno-5,6,7-trinor-4,8-inter-m-phenylene-13,14-dehydro-16,17,18,19,20-pentanor-15-cyclopentyl PGI₂ methyl ester, 2-phenylseleno-5,6,7-trinor-4,8-inter-m-phenylene-13,14-dehydro-16,17,18,19,20-pentanor-15-cyclohexyl PGI₂ methyl ester, 2-phenylseleno-5,6,7-trinor-4,8-inter-m-phenylene-17,18,19,20-tetranor-16-phenyl PGI₂ methyl ester, 2-phenylseleno-5,6,7-trinor-4,8-inter-m-phenylene-17-α-methyl PGI₂ methyl ester, 2-phenylseleno-5,6,7-trinor-4,8-inter-m-phenylene-17-β-methyl PGI₂ methyl ester, 2-phenylseleno-5,6,7-trinor-4,8-inter-m-phenylene-17-α-methyl-ω-homo PGI₂ methyl ester, 2-phenylseleno-5,6,7-trinor-4,8-inter-m-phenylene-17-β-methyl-ω-homo PGI₂ methyl ester, 2-phenylseleno-5,6,7-trinor-4,8-inter-m-phenylene PGI₂, or 2-phenylseleno-5,6,7-trinor-4,8-inter-m-phenylene-ω-homo PGI₂ methyl ester, in place of 2-phenylseleno-5,6,7-trinor-4,8-inter-m-phenylene-16,17,18,19,20-pentanor-15-phenyl PGI₂ and the products thus obtained were followed the method of Example 94 to give 5,6,7-trinor-4,8-inter-m-phenylene-2,3-dehydro-16,17,18,19,20-pentanor-15-cyclohexyl PGI₂ (110), 5,6,7-trinor-4,8-inter-m-phenylene-2,3-dehydro-16,17,18,19,20-pentanor-15-cyclopentyl PGI₂ (111), 5,6,7-trinor-4,8-inter-m-phenylene-2,3,13,14-tetrahydro-16,17,18,19,20-pentanor-15-phenyl PGI₂ (112), 5,6,7-trinor-4,8-inter-m-phenylene-2,3,13,14-tetrahydro-16,17,18,19,20-pentanor-15-cyclopentyl PGI₂ (113), 5,6,7-trinor-4,8-inter-m-phenylene-2,3,13,14-tetrahydro-16,17,18,19,20-pentanor-15-cyclohexyl PGI₂ (114), 5,6,7-trinor-4,8-inter-m-phenylene-2,3-dehydro-17,18,19,20-tetranor-16-phenyl PGI₂ (115), 5,6,7-trinor-4,8-inter-m-phenylene-2,3-dehydro-17-α-methyl PGI₂ (116), 5,6,7-trinor-4,8-inter-m-phenylene-2,3-dehydro-17-β-methyl PGI₂ (117), 5,6,7-trinor-4,8-inter-m-phenylene-2,3-dehydro-17-α-methyl-ω-homo PGI₂ (118), 5,6,7-trinor-4,8inter-m-phenylene-2,3-dehydro-17-β-methyl-ω-homo PGI₂ (119), 5,6,7-trinor-4,8-inter-m-phenylene-2,3-dehydro PGI(120), or 5,6,7-trinor-4,8-inter-m-phenylene-2,3-dehydro-ω-homo PGI₂ (121). In Table 6, the spectral data of these compounds are shown.

TABLE 6

| Example | Compound | Mass spectrum (m/e, M⁺) | Infrared spectrum cm⁻¹ |
|---|---|---|---|
| 107 | 110 | 398 | 3600–2400, 1700, 1640, 1600, 960 |

TABLE 6-continued

| Example | Compound | Mass spectrum (m/e, M+) | Infrared spectrum cm$^{-1}$ |
|---|---|---|---|
| 108 | 111 | 384 | 3600–2400, 1700, 1640, 1600, 960 |
| 109 | 112 | 392 | 3600–2400, 1700, 1640, 1595, 965, 765, 695 |
| 110 | 113 | 382 | 3600–2400, 1700, 1640, 1595, 970 |
| 111 | 114 | 396 | 3600–2400, 1700, 1640, 1595, 970 |
| 112 | 115 | 408 | 3600–2400, 1700, 1640, 1600, 965, 765, 700 |
| 113 | 116 | 400 | 3600–2400, 1700, 1640, 965 |
| 114 | 117 | 400 | 3600–2400, 1700, 1640, 965 |
| 115 | 118 | 414 | 3600–2400, 1700, 1642, 970 |
| 116 | 119 | 414 | 3600–2400, 1700, 1640, 970 |
| 117 | 120 | 386 | 3600–2400, 1700, 1640, 1595, 970 |
| 118 | 121 | 400 | 3600–2400, 1700, 1640, 1595, 970 |

EXAMPLE 119

5,6,7-trinor-4,8-inter-m-phenylene-3,4-didehydro-16,17,18,19,20-pentanor-15-cyclohexyl PGI$_2$ (122)

To a solution of 20 mg of 5,6,7-trinor-4,8-inter-m-phenylene-2,3-didehydro-16,17,18,19,20-pentanor-15-cyclohexyl PGI$_2$ methyl ester (98) in 1.5 ml of methanol was added, 0.5 ml of an aqueous solution of 1N sodium hydroxide, and the resulting solution was stirred at room temperature for 3 hours. The reaction solution was concentrated, water was added to the residue, the pH of the mixture cooled in an ice bath was adjusted to 3 with 1N hydrochloric acid and the product was extracted 3 times with ethyl acetate. The combined organic layer was washed with water and saturated brine, dried and thereafter concentrated to give 20 mg of an oily substance. The oily substance was purified by column chromatography (silica gel; 5% methanol-ethyl acetate) to afford 10 mg of a pure product (122).

IR (neat) ν cm$^{-1}$: 3600–2300, 1715, 975.

NMR (CDCl$_3$) δ: 3.00–4.00 (5H, m), 5.10 (1H, m), 5.60 (3H, m), 6.50 (2H, s), 6.75 (1H, t, J=7.0 Hz), 6.90 (1H, d, J=7.0 Hz), 7.15 (1H, d, J=7.0 Hz).

Mass (m/e): 369 (M+).

EXAMPLES 120–131

The procedure of Example 119 was followed except the uses of (96), (99), (100), (101), (102), (103), (104), (105), (106), (107), (108) or (109) in place of (98) to give 5,6,7-trinor-4,8-inter-m-phenylene-3,4-dehydro-16,17,18,19, 20-pentanor-15-phenyl PGI$_2$ (123), 5,6,7-trinor-4,8-inter-m-phenylene-3,4-dehydro-16,17,18,19,20-pentanor-15-cyclopentyl PGI$_2$ (124), 5,6,7-trinor-4,8-inter-m-phenylene-3,4,13,14-tetrahydro-16,17,18,19,20-pentanor-15-phenyl PGI$_2$ (125), 5,6,7-trinor-4,8-inter-m-phenylene-3,4,13,14-tetrahydro-16,17,18,19,20-pentanor-15-cyclopentyl PGI$_2$ (126), 5,6,7-trinor-4,8-inter-m-phenylene-3,4,13,14-tetrahydro-16,17,18,19,20-pentanor-15-cyclohexyl PGI$_2$ (127), 5,6,7-trinor-4,8-inter-m-phenylene-3,4-dehydro-17,18,19,20-tetranor-16-phenyl PGI$_2$ (128), 5,6,7-trinor-4,8-inter-m-phenylene-3,4-dehydro-17-α-methyl PGI$_2$ (129), 5,6,7-trinor-4,8-inter-m-phenylene-3,4-dehydro-17-β-methyl PGI$_2$ (130), 5,6,7-trinor-4,8-inter-m-phenylene-3,4-dehydro-17-α-methyl-ω-homo PGI$_2$ (131), 5,6,7-trinor-4,8-inter-m-phenylene-3,4-dehydro-17-β-methyl-ω-homo PGI$_2$ (132), 5,6,7;1-trinor-4,8-inter-m-phenylene-3,4-dehydro PGI$_2$ (133), or 5,6,7-trinor-4,8-inter-m-pheylene-3,4-dehydro-ω-homo PGI$_2$ (134). The spectral data of these compounds are shown in Table 7.

TABLE 7

| Example | Compound | Mass spectrum (m/e, M+) | Infrared spectrum cm$^{-1}$ |
|---|---|---|---|
| 120 | 123 | 392 | 3600–2300, 1715, 975, 750, 695 |
| 121 | 124 | 384 | 3600–2300, 1715, 970 |
| 122 | 125 | 392 | 3600–2300, 1715, 970, 760, 695 |
| 123 | 126 | 382 | 3600–2300, 1715, 970 |
| 124 | 127 | 396 | 3600–2300, 1715, 970 |
| 125 | 128 | 408 | 3600–2300, 1715, 970, 765, 700 |
| 126 | 129 | 400 | 3600–2300, 1715, 970 |
| 127 | 130 | 400 | 3600–2300, 1715, 970 |
| 128 | 131 | 414 | 3600–2300, 1715, 970 |
| 129 | 132 | 414 | 3600–2300, 1712, 970 |
| 130 | 133 | 386 | 3600–2300, 1710, 970 |
| 131 | 134 | 400 | 3600–2300, 1710, 970 |

EXAMPLE 132

5,6,7-trinor-4,8-inter-m-phenylene-13,14-didehydro-3-oxa-16,17,18,19,20-pentanor-15-cyclohexyl PGI$_2$ methyl ester 15-t-butyl ether (135)

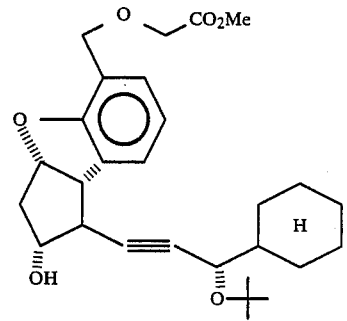

To a solution of 1.44 g of 3-t-butoxy-3-cyclohexyl-1-propyne in 6 ml of toluene at °C. under argon atmosphere was added 4.24 ml of n-butyl lithium (1.58M hexane solution), and the resulting solution was stirred for 15 minutes. A toluene solution (1.98M) of diethyl aluminium chloride (3.2 ml) at 0° C. was added, the temperature was allowed to warm to room temperature, and the resulting solution was stirred for 1 hour. The reaction mixture was again cooled to 0° C., 4 ml of a toluene solution of 168 mg of methyl (1,2,3a,8b-tetrahydro-1,2-synepoxycylopenta[b]benzofuran-5-yl methoxy) acetate was added, and the resulting solution was stirred for 1 hour. A saturated aqueous solution of sodium sulfate (0.5 ml) was added, white precipitate was filtered and the filtrate was concentrated to give 2.10 g of an oily substance, which was purified by column chromatography (silica gel; cyclohexane:ethyl acetate 2:1) to afford 25.0 mg of the subject compound (135).

IR (neat) ν cm$^{-1}$: 3650–3000, 1760, 1600.

NMR (CDCl$_3$) &: 1.14 (1H, a wide one-double line), 1.24 (9H, s), 1.5–2.1 (11H, m), 2.21 (1H, m), 2.48 (1H, m), 2.88 (1H, dt, J=2.0, 5.0 Hz), 3.75 (3H, s), 3.86 (2H, m), 4.08 (2H, s), 4.29 (1H, m), 4.63 (2H, s), 5.32 (1H, m), 6.88 (1H, dd, J=7.0, 8.0 Hz), 7.22 (2H, m).

Mass: 470 (M+).

EXAMPLE 133

5,6,7-trinor-4,8-inter-m-phenylene-13,14-didehydro-3-oxa-16,17,18,19,20-pentanor-15-cyclohexyl PGI$_2$ methyl ester (136)

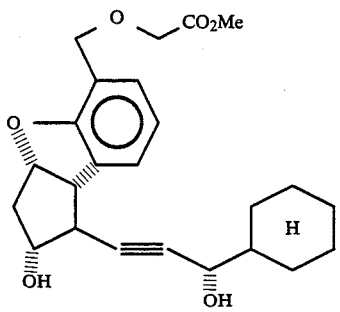

To a solution of 21.2 mg of 3-oxa-5,6,7-trinor-4,8-inter-m-phenylene-13,14-didehydro-15-cyclohexyl-16,17,18,19,20-pentanor PGI$_2$ methyl ester in 1 ml of methylene chloride at 0° C. under argon atmosphere, 0.2 ml of trifluoroacetic acid was added and the resulting solution was stirred for 1 hour. Removal of the solvent afford 22.5 mg of an oily substance, which was purified by thin-layer chromatography (silica gel; cyclohexane:ethyl acetate; 2:1) to give 1.9 mg of the subject compund (136).

IR (neat) $\nu$ cm$^{-1}$: 3650–3000, 1760, 1600.
Mass: 414 (M+).

EXAMPLE 134

5,6,7-trinor-4,8-inter-m-phenylene-13,14-didehydro-3-oxa-16,17,18,19,20-pentanor-15-cyclohexyl PGI$_2$ (137)

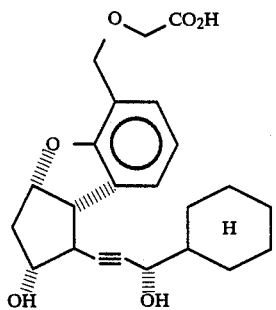

To a solution of 12.3 mg of 5,6,7-trinor-4,8-inter-m-phenylene-13,14-didehydro-3-oxa-16,17,18,19,20-pentanor-15-cyclohexyl PGI$_2$ methyl ester in 1 ml of methanol was added 1.0 ml of 0.1N sodium hydroxide, and the resulting solution was stirred at room temperature for 24 hours. After removal of methanol, the reaction mixture was cooled to 0° C., the pH of the mixture was adjusted to 4 with 0.1N hydrochloric acid. The product was extracted wih ethyl acetate (10 ml×5) and the organic layer was washed with saturated brine (2 ml) and dried. Removal of the solvent afford 9.5 mg of the subject compound (137) in nearly pure state.

IR (neat) $\nu$ cm$^{-1}$: 3650–2200, 1710, 1600.
Mass: 400 (M+).

EXAMPLES 135–142

The procedure of Example 132 is followed except the uses of 3-t-butoxy-3-cyclopentyl-1-propyne, 3-t-butoxy-4-cyclohexyl-1-butyne, 3-t-butoxy-4-cyclopentyl-1-butyne, 3-t-butoxy-4-phenyl-1-butyne, 3-t-butoxy-5-phenyl-1-pentyne, 3-t-butoxy-3-(4-methylcyclohexyl)-1-propyne, 3-t-butoxy-3-(3-methylcyclohexyl)-1-propyne, or 3-t-butoxy-5-methyl-1-nonyne, in place of 3-t-butoxy-3-cyclohexyl-1-propyne and the each resulting product was followed by the methods of Examples133–134 successively to give 5,6,7-trinor-4,8-inter-m-phenylene-13,14-didehydro-3-oxa-16,17,18,19,20-pentanor-15-cyclopentyl PGI$_2$ (138), 5,6,7-trinor-4,8-inter-m-phenylene-13,14-didehydro-3-oxa-17,18,19,20-tetranor-16-cyclohexyl PGI$_2$ (139), 5,6,7-trinor-4,8-inter-m-phenylene-13,14-didehydro-3-oxa-17,18,19,20-tetranor-16-cyclopentyl PGI$_2$ (140), 5,6,7-trinor-4,8-inter-m-phenylene-13,14-didehydro-3-oxa-17,18,19,20-tetranor-16-phenyl PGI$_2$ (141), 5,6,7-trinor-4,8-inter-m-phenylene-13,14-didehydro-3-oxa-18,19,20-trinor-17-phenyl PGI$_2$ (142), 5,6,7-trinor-4,8-inter-m-phenylene-13,14-didehydro-3-oxa-16,17,18,19,20-pentanor-15-(4-methylcyclohexyl) PGI$_2$ (143), 5,6,7-trinor-4,8-inter-m-phenylene-13,14-didehydro-3oxa-16,17,18,19,20-pentanor-15-(3-methylcyclohexyl) PGI$_2$ (144) or 5,6,7-trinor-4,8-inter-m-phenylene-13,14-didehydro-3-oxa-17-methyl-$\omega$-homo PGI$_2$ (145). The spectral date of these compounds are shown in Table 8.

TABLE 8

| Example | Compound | Mass spectrum (m/e, M+) | Infrared spectrum cm$^{-1}$ |
|---|---|---|---|
| 135 | 138 | 386 | 3650–2200, 1710, 1600 |
| 136 | 139 | 414 | 3650–2200, 1710, 1600, 1190 |
| 137 | 140 | 400 | 3650–2200, 1710, 1600, 1190 |
| 138 | 141 | 408 | 3650–2200, 1710, 1600, 765, 700 |
| 139 | 142 | 422 | 3650–2200, 1715, 1600, 765, 695 |
| 140 | 143 | 414 | 3650–2200, 1715, 1600 |
| 141 | 144 | 414 | 3650–2200, 1710, 1600 |
| 142 | 145 | 416 | 3650–2200, 1715, 1600 |

EXAMPLE 143

5,6,7-trinor-4,8-inter-m-phenylene-13,14-didehydro-16,17,18,19,20-pentanor-15-cyclohexyl-PGI$_2$ methyl ester (146)

To a solution of 500 mg (1.25 mmol) of 5,6,7-trinor-4,8-inter-m-phenylene-13,14-dehydro-16,17,18,19,20-pentanor-15-cyclohexyl-PGI$_2$ (9) in 5 ml of methanol was added slowly a large excess of diazomethane ether solution. The resulting mixture was concentrated, the residue was purified by column chromatography (Merck Co.'s Lobar Column B; ethyl acetate) to give 467 mg (90%) of the titled compound.

EXAMPLE 144–152

The procedure of Example 143 was followed except the uses of the compound (10), (11), (12), (13), (14), (15), (16), (17) or (18) in place of (9) to give 5,6,7-trinor-4,8-inter-m-phenylene-13,14-didehydro-16,17,18,19,20-pentanor-15-(4-methylcyclohexyl) PGI$_2$ methyl ester (147), 5,6,7-trinor-4,8-inter-m-phenylene-13,14-didehydro-16,17,18,19,20-pentanor-15-(3-methylcyclohexyl) PGI$_2$ methyl ester (148), 5,6,7-trinor-4,8-inter-m-pheylene-13,14-didehydro-16,17,18,19,20-pentanor-15-(2,2-dimethyl-4-methylcyclohexyl) PGI$_2$ methyl ester (149), 5,6,7-trinor-4,8-inter-m-phenylene-13,14-didehydro-16,17,18,19,20-pentanor-15-(2-methylcyclohexyl) PGI$_2$ methyl ester (150), 5,6,7-trinor-4,8-inter-m-phenylene-13,14-didehydro-16,17,18,19,20-pentanor-15-cyclopentyl PGI$_2$ methyl ester (151), 5,6,7-trinor-4,8-inter-m- phenylene-13,14-didehydro-16,17,18,19,20-pentanor-15-(2-methylcyclopentyl) PGI₂ methyl ester (152), 5,6,7-trinor-4,8-inter-m-phenylene-13,14-didehydro-17,18,19,20-tetranor-16-cyclohexyl PGI₂ methyl ester (153), 5,6,7-trinor-4,8-inter-m-phenylene-13,14-didehydro-17,18,19,20-tetranor-16-cyclopentyl PGI₂ methyl ester (154), or 5,6,7-trinor-4,8-inter-m-phenylene-13,14-didehydro-18,19,20-trinor-17-cyclohexyl PGI₂ methyl ester (155). The spectra of the compounds (147)-(155) are shown in Table 9.

TABLE 9

| Example | Compound | Mass spectrum (m/e, M⁺) | Infrared spectrum cm⁻¹ |
|---|---|---|---|
| 144 | 147 | 426 | 3450, 1740, 1595, 1450, 1195, 865, 745 |
| 145 | 148 | 426 | 3450, 1740, 1595, 1450, 1195 |
| 146 | 149 | 454 | 3450, 1740, 1595, 1450 |
| 147 | 150 | 426 | 1740 |
| 148 | 151 | 398 | 1740 |
| 149 | 152 | 412 | 1740 |
| 150 | 153 | 426 | 1740 |
| 151 | 154 | 412 | 1740 |
| 152 | 155 | 440 | 1740 |

EXAMPLES 153-163

The procedure of Example 143 was followed except the uses of the compound (29), (30), (31), (39), (48), (49), (55), (60), (65), (76), or (81) in place of (9) to give 5,6,7-trinor-4,8-inter-m-phenylene-13,14-didehydro-17-methyl PGI₂ methyl ester (156), 5,6,7-trinor-4,8-inter-m-phenylene-13,14-didehydro-17-methyl-ω-homo PGI₂ methyl ester (157), 5,6,7-trinor-4,8-inter-m-phenylene-13,14-didehydro-16,16-dimethyl PGI₂ methyl ester (158), 5,6,7-trinor-4,8-inter-m-phenylene-16,16-dimethyl PGI₂ methyl ester (159), 5,6,7-trinor-4,8-inter-m-phenylene-17-α-methyl PGI₂ methyl ester (160), 5,6,7-trinor-4,8-inter-m-phenylene-17-β-methyl PGI₂ methyl ester (161), 5,6,7-trinor-4,8-inter-m-phenylene-17-α-methyl-20-homo PGI₂ methyl ester (162), 5,6,7-trinor-4,8-inter-m-phenylene-17,18,19,20-tetranor-16-phenoxy PGI₂ methyl ester (163) 5,6,7-trinor-4,8-inter-m-phenylene-17,18,19,20-tetranor-16-(m-chlorophenoxy) PGI₂ (164), 5,6,7-trinor-4,8-inter-m-phenylene-16,16-dimethyl-18,19,20-trinor-17-ethoxy PGI₂ methyl ester (165), or 5,6,7-trinor-4,8-inter-m-phenylene-20-isopropylidene PGI₂ methyl ester (166). The spectra of the compounds (156)-(166) are shown in Table 10.

TABLE 10

| Example | Compound | Mass spectrum (m/e, M⁺) | Infrared spectrum cm⁻¹ |
|---|---|---|---|
| 153 | 156 | 414 | 1730 |
| 154 | 157 | 428 | 1730 |
| 155 | 158 | 442 | 1730 |
| 156 | 159 | 430 | 1735, 970 |
| 157 | 160 | 416 | 1735, 970, 760, 740 |
| 158 | 161 | 416 | 1735, 970, 760, 740 |
| 159 | 162 | 430 | 1730, 970, 760, 740 |
| 160 | 163 | 438 | 1735, 1595, 970, 760, 695 |
| 161 | 164 | 472, 474 | 1735, 965 |
| 162 | 165 | 432 | 1735, 970, 765, 745 |
| 163 | 166 | 442 | 1735, 1595, 970, 765, 745 |

EXAMPLE 164

5,6,7-trinor-4,8-inter-m-phenylene-13,14-didehydro-16,17,18,19,20-pentanor-15-cyclohexyl-PGI₂ benzyl ester (167)

To a solution of 35 mg of 5,6,7-trinor-4,8-inter-m-phenylene-13,14-didehydro-16,17,18,19,20-pentanor-15-cyclohexyl-PGI₂ in 1 ml of dimethyl formamide 100 μl of triethylamine and 100 μl of benzyl bromide, and the resulting solution was stirred ar room temperature for 5 hours. After completion of the reaction, 3 ml of water was added, thereafter, the product was extracted with ether, and the ether layer was dried over Na₂SO₄ and thereafter concentrated to give a crude product of (167), which was purified by column chromatography (silica gel; developing solvent:ethyl acetate) to afford 30 mg of the pure subject compound (167).

IR (neat) ν cm⁻¹: 3350, 1710, 1650, 965, 760, 695.
Mass (m/e): 488.

EXAMPLE 165

5,6,7-trinor-4,8-inter-m-pheylene-13,14-didehydro-16,17,18,19,20-pentanor-15-cyclohexyl-PGI₂ (2-pyridylmethyl) ester (168)

To a solution of 350 mg of 5,6,7-trinor-4,8-inter-m-pheylene-13,14-didehydro-16,17,18,19,20-pentanor-15-cyclohexyl PGI₂ (9) in 4 ml of anhydrous tetrahydrofuran, cooled in an ice bath were added 0.16 ml of triethlamine and 0.09 ml of ethyl choroformate, and the resulting solution was stirred at room temperature for 20 minutes. After addition of 0.4 ml of 2-pyridyl methanol, the mixture was stirred for 14 hours at 60° C. under argon atmosphere. Ethyl acetate was added to the cooled mixture and the organic layer was washed with a saturated aqueous solution of sodium hydrogen carbonate and water, thereafter, dried over Na₂SO₄ and concentrated to give 700 mg of an oily substance. The oily substance was purified by column chromatography (silica gel; ethyl acetate: isopropanol:methanol (97:3:0.5)) to afford 300 mg of the subject compound (169) as a light yellow oil.

IR (neat) ν cm⁻¹: 3350, 1710, 1650, 1590, 965.
Mass (m/e): 489.

EXAMPLES 166-176

The produre of Example 165 is followed except the uses of butanol, ethanol, cyclohexyl methanol, cyclopentyl methanol, 2-methoxy ethanol, methyl glycolate, methyl lactate ester, 2-butyne-1-ol, 1,3-di-(0)-acetylglycerin, phenol or p-acetaminophenol in place of 2-pyridyl methanol to give 5,6,7-trinor-4,8-inter-m-pheylene-13,14-didehydro-16,17,18,19,20-pentanor-15-cyclohexyl PGI₂ butyl ester (169), 5,6,7-trinor-4,8-inter-m-pheylene-13,14-didehydro-16,17,18,19,20-pentanor-15-cyclohexyl-PGI₂ ethyl ester (170), 5,6,7-trinor-4,8-inter-m-pheylene-13,14-didehydro-16,17,18,19,20-pentanor-15-cyclohexyl PGI₂ cyclohexylmethyl ester (171), 5,6,7-trinor-4,8-inter-m-pheylene-13,14-didehydro-16,17,18,19,20-pentanor-15-cyclohexyl PGI₂ cyclopentylmethyl ester (172), 5,6,7-trinor-4,8-inter-m-pheylene-13,14-didehydro-16,17,18,19,20-pentanor-15-cyclohexyl PGI₂ (2-methoxyethyl) ester (173), 5,6,7-trinor-4,8-inter-m-pheylene-13,14-didehydro-16,17,18,19,20-pentanor-15-cyclohexyl PGI₂ carbomethoxymethyl ester (174), 5,6,7-trinor-4,8-inter-m-pheylene-13,14-didehydro-16,17,18,19,20-pentanor-15-cyclohexyl PGI₂ (1-carbomethyoxyethyl) ester (175), 5,6,7-trinor-4,8-inter-m-phenylene-13,14-didehydro-16,17,18,19,20-pentanor-15-cyclohexyl PGI$_2$ (2-butynyl) ester (176), 5,6,7-trinor-4,8-inter-m-pheylene-13,14-didehydro-16,17,18,19,20-pentanor-15-cyclohexyl PGI$_2$ (1,3-diacetoxy-2-propyl) ester (177), 5,6,7-trinor-4,8-inter-m-pheylene-13,14-didehydro-16,17,18,19,20-pentanor-15-cyclohexyl PGI$_2$ phenyl ester (178), or 5,6,7-trinor-4,8-inter-m-phenylene-13,14-didehydro-16,17,18,19,20-pentanor-15-cyclohexyl PGI$_2$ (p-acetaminophenyl) ester (179). The spectra of the compounds (169)–(179) are shown in Table 11.

TABLE 11

| Example | Compound | Mass spectrum (m/e, M$^+$) | Infrared spectrum cm$^{-1}$ |
|---|---|---|---|
| 166 | 169 | 454 | 1740, 1595 |
| 167 | 170 | 430 | 1740, 1595 |
| 168 | 171 | 494 | 1735 |
| 169 | 172 | 480 | 1740 |
| 170 | 173 | 456 | 1735 |
| 171 | 174 | 470 | 1740 |
| 172 | 175 | 484 | 1740 |
| 173 | 176 | 450 | 1735 |
| 174 | 177 | 556 | 1740 |
| 175 | 178 | 474 | 1745, 1600, 760, 695 |
| 176 | 179 | 531 | 1745 |

EXAMPLE 177

5,6,7-trinor-4,8-inter-m-pheylene-13,14-didehydro-16,17,18,19,20-pentanor-15-cyclohexyl PGI$_2$ carboxamide (180)

To a solution of 11 mg of 5,6,7-trinor-4,8-inter-m-pheylene-13,14-didehydro-16,17,18,19,20-pentanor-15-cyclohexyl PGI$_2$ (9) in 1 ml of anhydrous THF cooled in an ice bath were added 0.3 ml of triethylamine and 0.02 ml of ethyl chloroformate and the resulting solution was stirred at room temperature for 1 hour. This reaction mixture was added slowly dropwise to 5 ml of liquid ammonia in a flask whose temperature had been adjusted to −33° C. and the mixture was stirred at −33° C. for 2 hours. After removal of ammonia, saturated brine was added to the residue, and the the product was extracted twice with ether. The combined ether layers were washed with saturated brine, dried and thereafter concentrated to give 15 mg of an oily substance. The oily substance was purified by column chromatography (silica gel: 20% methanol-ethyl acetate) to affored 7.1 mg of the amide (180).

IR (neat) $\nu$ cm$^{-1}$: 3600–3000, 1660, 1600.
Mass (m/e): 397 (M$^+$).

EXAMPLES 178–197

The procedure of Example 177 was followed except the uses of the compound (10), (11), (12), (13), (14), (15), (16), (17), (18), (29), (30), (31), (39), (48), (49), (55), (60), (65), (76), or (81) in place of (9) to give 5,6,7-trinor-4,8-inter-m-phenylene-13,14-didehydro-16,17,18,19,20-pentanor-15-(4-methylcyclohexyl) PGI$_2$ carboxamide (181), 5,6,7-trinor-4,8-inter-m-phenylene-13,14-didehydro-16,17,18,19,20-pentanor-15-(3-methyl cyclohexyl) PGI$_2$ carboxamide (182), 5,6,7-trinor-4,8-inter-m-pheynlene-13,14-didehydro-16,17,18,19,20-pentanor-15-(2,2-dimethyl-4-methylcyclohexyl) PGI$_2$ carboxamide (183), 5,6,7-trinor-4,8-inter-m-phenylene-13,14-didehydro-16,17,18,19,20-pentanor-15-(2-methylcyclohexyl) PGI$_2$ carboxamide (184), 5,6,7-trinor-4,8-inter-m-phenylene-13,14-didehydro-16,17,18,19,20-pentanor-15-cyclopentyl PGI$_2$ carboxamide (185), 5,6,7-trinor-4,8-inter-m-phenylene-13,14-didehydro-16,17,18,19,20-pentanor-15-(2-methlcyclopentyl) PGI$_2$ carboxamide (186), 5,6,7-trinor-4,8-inter-m-phenylene-13,14-didehydro-17,18,19,20-tetranor-16-cyclohexyl-PGI$_2$ carboxamide (187) 5,6,7-trinor-4,8-inter-m-phenylene-13,14-didehydro-17,18,19,20-tetranor-16-cyclopentyl-PGI$_2$ carboxamide (188), 5,6,7-trinor-4,8-inter-m-phenylene-13,14-didehydro-18,19,20-trinor-17-cyclohexyl-PGI$_2$ carboxamide (189), 5,6,7-trinor-4,8-inter-m-phenylene-13,14-didehydro-17-methyl PGI$_2$ carboxamide (190), 5,6,7-trinor-4,8-inter-m-phenylene-13,14-didehydro-17-methyl-$\omega$-homo PGi$_2$ carboxamide (191), 5,6,7-trinor-4,8-inter-m-phenylene-13,14-didehydro-16,16-dimethyl PGI$_2$ carboxamide (192), 5,6,7-trinor-4,8-inter-m-phenylene-16,16-dimethyl PGI$_2$ carboxamide (193), 5,6,7-trinor-4,8-inter-m-phenylene-17-$\alpha$-methyl PGI$_2$ carboxamide (194), 5,6,7-trinor-4,8-inter-m-phenylene-17-$\beta$-methyl PGI$_2$ carboxamide (195), 5,6,7-trinor-4,8-inter-m-phenylene-17-$\alpha$-methly-$\omega$-homo PGI$_2$ carboxamide (196), 5,6,7-trinor-4,8-inter-m-phenylene-17,18,19,20-tetranor-16-phenoxy PGI$_2$ carboxamide (197), 5,6,7-trinor-4,8-inter-m-phenylene-17,18,19,20-tetranor-16-(m-chlorophenoxy) PGI$_2$ carboxamide (198), 5,6,7-trinor-4,8-inter-m-phenylene-16,16-dimethyl-18,19,20-trinor-17-ethoxy PGI$_2$ carboxamide (199), or 5,6,7-trinor-4,8-inter-m-phenylene-20-isopropylidene PGI$_2$ carboxamide (200). The spectra of the compounds (181)–(200) are shown in Table 12.

TABLE 12

| Example | Compound | Mass spectrum (m/e, M$^+$) | Infrared spectrum cm$^{-1}$ |
|---|---|---|---|
| 178 | 181 | 411 | 1660 |
| 179 | 182 | 411 | 1660 |
| 180 | 183 | 439 | 1660 |
| 181 | 184 | 411 | 1660 |
| 182 | 185 | 383 | 1660 |
| 183 | 186 | 397 | 1660 |
| 184 | 187 | 411 | 1660 |
| 185 | 188 | 397 | 1660 |
| 186 | 189 | 425 | 1660 |
| 187 | 190 | 399 | 1660 |
| 188 | 191 | 413 | 1660 |
| 189 | 192 | 427 | 1660 |
| 190 | 193 | 415 | 1660, 970 |
| 191 | 194 | 401 | 1660, 970 |
| 192 | 195 | 401 | 1660, 970 |
| 193 | 196 | 415 | 1660, 970 |
| 194 | 197 | 423 | 1660, 1600, 970, 760, 695 |
| 195 | 198 | 457, 459 | 1660, 1600, 970 |
| 196 | 199 | 417 | 1660 |
| 197 | 200 | 427 | 1660 |

EXAMPLE 198

5,6,7-trinor-4,8-inter-m-phenylene-13,14-didehydro-17,18,19,20-tetranor-16-cyclohexyl PGI$_2$ [N-(p-toluenesulfonyl)] carboxamide (201)

50 mg of sodium hydride (50% mineral oil dispersion) was washed 3 times with hexane and dried, 1 ml of anhydrous 1,2-dimethoxyethane was added. To the stirred mixture cooled in an ice bath was added, a solution of 260 mg of p-toluene sulfoneamide in 2 ml of 1,2-dimethyl ethane, and the resulting mixture was stirred at room temperature for 1 hour. To a solution of 80 mg of 5,6,7-trinor-4,8-inter-m-pheylene-13,14-didehydro-17,18,19,20-pentanor-16-cyclohexyl-PGI$_2$ (16) in 2 ml of anhydrous tetrahydrofuran cooled in an ice bath were added 0.1 ml of triethylamine and 0.06 ml of ethyl chloroformate the resulting solution was stierred at room temperature for 1 hour to give an acid anhydride. The mixture was added dropwise to the stirred ice-cooled above-prepared 1,2-dimethoxyethane suspension of a sodium salt of sulfoneamide. This reaction mixture was stirred at room temperature for 2 hours, water was added under ice cold conditions, the mixture was washed with ether. The pH of the water layer was adjusted to 3–2 under ice cold conditions and the mixture was extracted 3 times with ethyl acetate. The combined ethyl acetae layers were washed with water and saturated brine, dried and thereafter concentrated to give 300 mg of an oily substance. The oily substance was purified by column chromatography (silica gel; after elution with ethyl acetate, eluted with methanol) to afford 79 mg of powder.

IR (CDCl$_3$) $\nu$ cm$^{-1}$: 3600–3000, 1720, 1600, 1450, 1340, 1165, 1085.

EXAMPLE 199

5,6,7-trinor-4,8-inter-m-pheylene-13,14-dihydro-16,16-dimethyl PGI$_2$ methyl ester (202)

To a solution of 44.2 mg of 5,6,7-trinor-4,8-inter-m-phenylene-16,16-dimethyl PGI$_2$ methyl ester (159), in 10 ml of ethyl acetate was added 50 mg of a 5% palladium-activated charcoal mixture, and the resulting mixture was hydrogenated at atmospheric pressure. After completion of the reaction, the reaction mixture was filtered and the filtrate was concentrated to give an oily crude product. The product was purified by column chromatography (silica gel; ethyl acetae-cyclohexane 9:1) to afford 14 mg of (202).

IR (cm$^{-1}$): 1735.
Mass (m/e): 444.

EXAMPLE 200–206

The procedure of Example 199 is followed except the uses of the compound (48), (49), (55), (60), (160), (161), or (162) in place of (159) to give 5,6,7-trinor-4,8-inter-m-phenylene-13,14-didehydro-17-α-methyl PGI$_2$ (203), 5,6,7-trinor-4,8-inter-m-phenylene-13,14-dihydro-17-β-methyl PGI$_2$ (204), 5,6,7-trinor-4,8-inter-m-phenylene-13,14-dihydro-17-α-methyl-ω-homo-PGI$_2$ (205), 5,6,7-trinor-4,8-inter-m-phenylene-13,14-dihydro-17,18,19,20-tetranor-16-phenoxy PGI$_2$ (206), 5,6,7-trinor-4,8-iner-m-phenylene-13,14-dihydro-17-α-methyl PGI$_2$ methyl ester (207), 5,6,7-trinor-4,8-inter-m-phenylene-13,14-dihydro-17-β-methyl PGI$_2$ methyl ester (208), or 5,6,7-trinor-4,8-inter-m-phenylene-13,14-dihydro-17-α-methyl-ω-homo-PGI$_2$ methyl ester (209). The spectra of the compounds (203)–(209) are shown in Table 13.

TABLE 13

| Example | Compound | Mass spectrum (m/e, M$^+$) | Infrared spectrum cm$^{-1}$ |
|---|---|---|---|
| 200 | 203 | 404 | 3600–2300, 1710, 1595, 760, 740 |
| 201 | 204 | 404 | 3600–2300, 1710, 1595, 760, 740 |
| 202 | 205 | 418 | 1710 |
| 203 | 206 | 426 | 1710, 760, 695 |
| 204 | 208 | 418 | 1735 |
| 205 | 209 | 432 | 1735 |

EXAMPLE 207

2-decarboxy-2-hydroxymethyl-5,6,7-trinor-4,8-inter-m-phenylene-17-methyl PGI$_2$ (210)

To a solution of 40 mg of 2-decarboxy-2-hydroxymethyl-5,6,7-trinor-4,8-inter-m-phenylene-11,15-didehydroxy-11,15-diacetoxy-17-α-methyl PGI$_2$ (44) in 1 ml of methanol was added 0.5 ml of an aqueous solution of 1N sodium hydroxide, and the resulting solution was stirred at room temperature overnight. After removing methanol under reduced pressure from the reaction solution, the residue was neutralized with 1N hydrochloric acid and extracted with ethyl acetate (3 ml×4). The ethyl acetate layer was dried and thereafter concentrated to give 21 mg of the subject compound.

IR $\nu$(cm$^{-1}$): 3500–3300, 1595, 970.
Mass (m/e): 472.

EXAMPLES 208–213

The procedure of Example 207 was followed except the uses of the compound (36), (37), (45), (53), (58) or (79) in place of (44) to give 2-decarboxy-2-hydroxymethyl-5,6,7-trinor-4,8-inter-(5-bromoyl-1,3-phenylene)-16,16-dimethyl PGI$_2$ (211), 2-decarboxy-2-hydroxymethyl-5,6,7-trinor-4,8-inter-m-phenylene-16,16-dimethyl PGI$_2$ (212), 2-decarboxy-2-hydroxymethyl-5,6,7-trinor-4,8-inter-m-phenylene-17-β-methyl PGI$_2$ (213), 2-decarboxy-2-hydroxymethyl-5,6,7-trinor-4,8-inter-m-phenylene-17-α-methyl 20-homo PGI$_2$ (214), 2-decarboxy-2-hydroxymethyl-5,6,7-trinor-4,8-inter-m-phenylene-17,18,19,20-tetranor-16-phenoxy PGI$_2$ (215), or 2-decarboxy-20-hydroxymethyl-5,6,7-trinor-4,8-inter-m-phenylene-20-isopropylidene PGI$_2$ (216).

The spectra of these compounds are shown in Table 14.

TABLE 14

| Example | Compound | Mass spectrum (m/e, M$^+$) | Infrared spectrum cm$^{-1}$ |
|---|---|---|---|
| 208 | 211 | 483, 481 | 3600–3300, 970 |
| 209 | 212 | 402 | 3600–3300, 970 |
| 210 | 213 | 472 | 3600–3300, 970 |
| 211 | 214 | 402 | 3600–3300, 970 |
| 212 | 215 | 408 | 3600–3300, 970, 760, 695 |
| 213 | 216 | 414 | 3600–3300, 970 |

EXAMPLE 214

5,6,7-trinor-4,8-inter-m-phenylene-15,17-α-dimethyl PGI$_2$ (217)

To solution of 860 mg (2 mmol) of 5,6,7-trinor-4,8-inter-m-phenylene-17-α-methyl PGI$_2$ methyl ester (160) in 80 ml of methylene chloride was added 28 mg of active manganese dioxide, and the resulting mixture was stirred for 2 hours. Active manganese dioxide was filtered off and the obtained methylene chloride solution was concentrated to give 702 mg of the corresponding 15-oxo compound. To a solution of this 15-oxo compound in 30 ml of tetrahydrofuran were added 5 ml of hexamethyldisilazane and 1 ml of trimethylchlorosilane, and the resulting mixture was allowed to stand at room temperature overnight. The mixture was filtered, the filtrate was concentrated under a reduced pressure, thereafter, 10 ml of xylene was added to the residue and the mixture was concentrated under a reduced pressure. The residue was dissolved in ether, methyl magnesium bromide (1.5M) (1.05 equivalent of the theoretical amount was added to the solution. After standing the mixture at room temperature for 30 minutes, it was poured into 100 ml of a saturated aqueous solution of ammonium chloride. The ether layer was separated and the water layer was further extracted twice with 20 ml of ether. After the combined ether layer was washed with brine, dried and concentrated, the residue was dissolved in 300 ml of ethanol and 30 ml of water containing a few drops of acetic acid, and the mixture was stirred at room temperature for 2 hours. This mixture was concentrated under reduced pressure to the aqueous residue and the residue was extracted with dichloromethane. The dichloromethane solution was concentrated and the residue was purified by silica gel chromatography (developing solvent; water:saturated ethyl acetate) to give 117 mg of the methyl ester of the subject compound. To this methyl ester solution in 2 ml of ethanol was added 1 ml of an aqueous solution of 1N potassium hydroxide and the resultant mixture was stirred at room temperature for 20 hours. Ethanol was removed under reduced pressure, the residue was cooled to 0° C., and the pH of the residue was adjusted to 3.5–4.0 and the mixture was extracted with ethyl acetate. The ethyl acetate layer was dried and concentrated to give 81 mg of the subject compound (217) (174):

IR $\nu$(cm$^{-1}$): 3500–2800, 1705, 970.
Mass (m/e): 430.

REFERENTIAL EXAMPLE 82

2-endohydroxy-1-exohydroxymethyl-3a,8b-cis-2,3,3a,8b-tetrahydro-5,7-dibromo-1H-cyclopenta(b)benzofuran

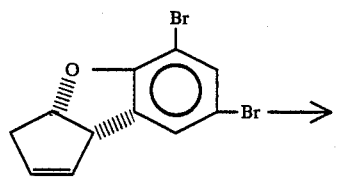

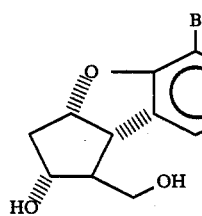

To a stirred solution of 33 gr. of 3a,8b-cis-dihydro-3H-5,7-dibromo-cyclopenta(b)benzofuran and 66 gr. of S-trioxane in 400 ml of acetic acid was added 30 ml of concentrated sulfuric acid at 80° C., and the resultant solution was stirred for 15 hours. After the resultant mixture was cooled, the acetic acid was removed. To the residue was 100 ml of ethyl acetate and the resultant mixture was washed with 500 ml of water and 500 ml×5 of saturated aqueous sodium bicarbonate solution. The combined aqueous layers were extracted with 500 ml of ethyl acetate. The combined ethyl acetate layers were dried, and concentrated to give 46 gr. of an oily material. The oily material was dissolved with 400 ml of methanol and 150 ml of the aqueous sodium hydroxide solution was added, and the resultant solution was stirred at room temperature for 30 minutes. The resultant reaction mixture was concentrated and, 50 ml of the hydrochloric acid (6N) was added, and the resultant product was extracted with 300 ml×5 of ethyl acetate. The combined organic layers were washed with 200 and 100 ml of water and 100 ml of saturated sodium chloride solution, dried, and concentrated to give 30 gr. of an oily material. The material was recrystallized from n-hexane-ethyl acetate to give 16 gr. of a colorless crystal.

Melting point: 126°–128° C.
IR (KBr) cm$^{-1}$: 3300, 2970, 2925, 2870, 1600, 1575, 750. 730 cm$^{-1}$.
NMR (90 MHz, CDCl$_3$)δ: 2.05 (2H, m), 2.54 (1H, m), 3.68 (3H, m), 4.04 (3H, m), 5.24 (1H, ddd J=9.5, 7.2, 5.0 Hz), 7.22 (1H, d, J=2.0 Hz), 7.39 (1H, d, J=2.0 Hz).
Mass (m/e): 366, 364, 362.

REFERENTIAL EXAMPLE 83

2-endohydroxyl-1-exohydroxymethyl-3a,8b-cis-2,3,3a,8b-tetrahydro-7-bromo-5-formyl-1H-cyclopenta(b)benzofuran

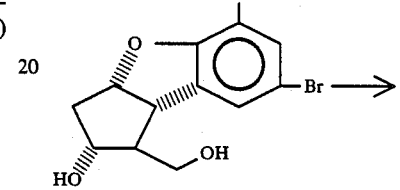

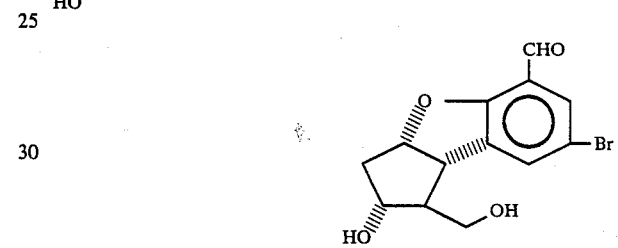

To a solution of 100 gr. (275 mmol) of 2-endohydroxyl-1-exohydroxymethyl-3a,8b-cis-2,3,3a,8b-tetrahydro-5,7-dibromo-1H-cyclopenta(b)benzofuran in 1,900 ml of anhydrous THF was added a solution of 327 ml (1.85N, 605 mmol) of cyclohexylmagnesium chloride in THF at 0° C. under argon. The resultant mixture was stirred at room temperature for 10 minutes. To the resultant reaction mixture was added 273 ml (505 mmol) of the aforesaid Grignard reagent and the resultant solution was stirred at 40° C. for 2 hours. After the solution was cooled to room temperature, 150 ml of anhydrous DMF added dropwise to the resultant reaction mixture, and the resultant solution was stirred for 30 minutes. The resultant reaction mixture was cooled to 0° C. and, 800 ml of ether and 600 ml of hydrochloric acid were added, and the resultant product was extracted with ethyl acetate 5 times. The combined organic layers were washed with saturated sodium bicarbonate solution and saturated sodium chloride solution. The resultant solution was dried over magnesium sulfate, concentrated, and recrystallized from ethyl acetate to give 52.3 gr. (167 mmol) of 2-endohydroxy-1-exohydroxymethyl-3a,8b-cis-2,3,3a,8b-tetrahydro-7-bromo-5'-formyl-1H-cyclopenta(b)benzofuran. The mother liquor was concentrated again and recrystallized from ethyl acetate to give 16.5 gr. (52.7 mmol) (total yield 80%) of the aforesaid aldehyde.

Melting point: 143°–144° C.
IR(KBr): cm$^{-1}$ 3440, 3050, 2960, 2890, 2740, 1680, 1595, 1580, 1440, 1385, 1325, 1220, 1200, 1100, 1070, 1045, 1010, 950, 900, 870, 830, 780, 740, 695, 600, 560, 515.

NMR (90 MHz, DMSO-db) δ: 1.7–2.5 (3H, m), 3.2–4.0 (4H, m), 4.5–4.9 (2H, m), 5.37 (1H, ddd, J=4.6, 7.2, 9.0 Hz), 7.5–7.7 (2H, m), 10.02 (1H, S).

Mass (m/e): 312, 314 (M+).

Anal. calcd. for $C_{13}H_{13}O_4Br$: C; 49.86 H; 4.19 Br; 25.52; Found: C; 49.75 H; 4.30 Br; 25.48.

REFERENTIAL EXAMPLE 84

Methyl 3-(2-endohydroxy-1-exohydroxymethyl-3a,8b-cis-2,3,3a,8b-tetrahydro-1H-5-cyclopenta(b)benzofuranyl)-propionate

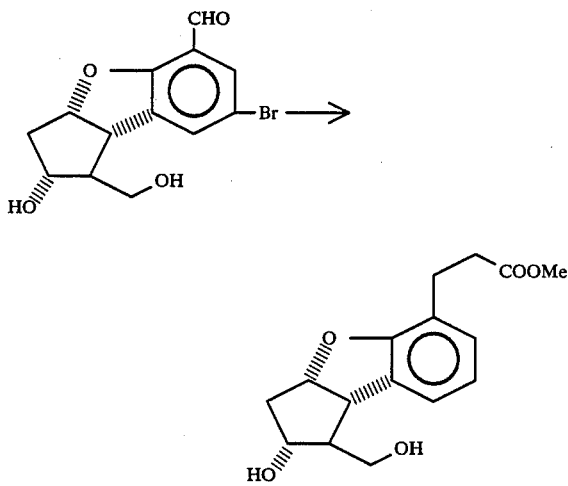

To a solution of 31.2 ml (223 mmol) diisopropylamine in 400 ml of anhydrous THF was added 134 ml (1.66N, 223 mmol) of n-butyllithium in hexane at −10° C., and the resultant mixture was stirred for 30 minutes. The resultant reaction mixture was cooled to −78° C. and, 21.9 ml (223 mmol) of anhydrous ethyl acetate was added, and the resultant mixture was stirred for 30 minutes. To the resultant reaction mixture was added dropwise a solution of 10 gr. (31.9 mmol) of 2-endohydroxy-1-exohydroxymethyl-3a,8b-cis-2,3,3a,8b-tetrahydro-7-bromo-5-formyl-1H-cyclopenta(b)benzofuran in anhydrous HMPA (100 ml) at below −60° C. for 5 minutes. After 10 minutes, 300 ml of ether and 180 ml of hydrochloric acid (3N) were added, the resultant mixture was stirred and the resultant product was extracted with ethyl acetate 3 times. The combined organic layers were washed with saturated sodium bisulfite solution and water to remove unreacted aldehyde and washed with saturated sodium bicarbonate, water and saturated sodium chloride solution, dried, and concentrated to give about 20 gr. of an oily material. The material was dissolved in 100 ml of methanol. To the resultant solution was added 4 gr. of 10% palladium-carbon, and the resultant mixture was stirred under hydrogen for 20 hours. The resultant mixture was filtered and, after addition of sodium bicarbonate, the filtrate was concentrated. Water and ethyl acetate were added to the residue, and the resultant reaction product extracted. The organic layers were washed with water and saturated sodium chloride solution and dried over magnesium sulfate. The solution was concentrated and the residue was dissolved in 100 ml of anhydrous methanol. To the solution was 1.6 ml of the sodium methoxide (4.89N) and the resultant solution was stirred at room temperature for 3 hours. To the resultant mixture was 0.58 ml of acetic acid, the resultant mixture was concentrated and the residue was dissolved in ethyl acetate. The resultant solution was washed with sodium bicarbonate, water and saturated sodium chloride solution, dried, and concentrated to give an oily material. The material was purified by column chromatography (ethyl acetate:cyclohexane 1:1) to give 5.91 gr. (yield 74%) of methyl 3-(2-endohydroxy-1-exohydroxymethyl-3a,8b-cis-2,3,3a,8b-tetrahydro-1H-5-cyclopenta(b)benzofuranyl)-propionate.

Melting point: 88.5°–90.0° C. (ethyl acetate-cyclohexane).

IR(KBr): cm⁻¹ 3400, 2960, 2910, 2860, 1700, 1590, 1470, 1440, 1360, 1330, 1290, 1280, 1250, 1220, 1185, 1105, 1055, 1010, 980, 950, 915, 895, 850, 835, 805, 770, 745, 590, 450, 340.

NMR (400 MHz, CDCl₃)δ: 1.97 (1H, ddd, J=5.4, 8.3, 13.7 Hz), 2.05 (1H, dq, J=5.4, 7.8 Hz) 2.51 (1H, dt, J=6.8, 13.7 Hz) 2.5–2.7 (2H, m), 2.8–3.0 (2H, m) 3.15 (1H, br.s), 3.2 (1H, m) 3.38 (1H, dd, J=7.8, 8.6 Hz), 3.64 (3H, S) 3.65–3.7 (1H m,), 3.8–3.9 (1H, m) 4.0–4.1 (1H, m), 5.08 (1H, ddd, J=5.4, 6.8, 8.6 Hz) 6.76 (1H, dd, J=6.8, 7.3 Hz) 6.94 (1H, d, J=6.8 Hz), 7.02 (1H, d, J=7.3 Hz).

Mass (m/e): 292 (M+), 274 (M+-H₂O), 232 (M+-C₂H₄O₂).

Anal. calcd. for $C_{16}H_{20}O_5$: C; 65.74 H; 6.90; Found: C; 65.71 H; 6.90.

REFERENTIAL EXAMPLE 85

Methyl 3-(2-endoacetoxy-1-exohydroxymethyl-3a,8b-cis-2,3,3a,8b-tetrahydro-1H-5-cyclopenta(b)benzofuranyl)-propionate

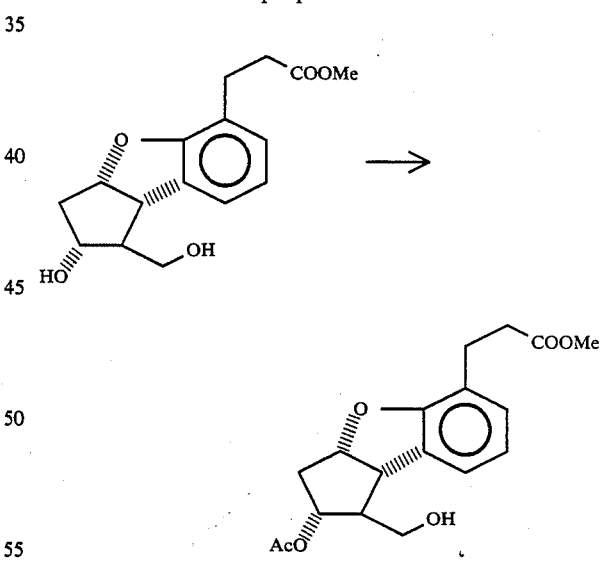

To a solution of 46 gr. (158 mmol) of methyl 3-(2-endohydroxy-1-exohydroxymethyl-3a,8b-cis-2,3,3a,8-b-tetrahydro-1H-5-cyclopenta(b)benzofuranyl)propionate in 600 ml of anhydrous THF were added 88 ml (632 mmol) of anhydrous triethylamine and 88 gr. (316 mmol) of trityl chloride, and the resultant mixture was refluxed for 6 hours. To the mixture were added 165 ml (2.05 mol) of anhydrous pyridine and 193 ml (2.05 mol) of acetic anhydride, and the resultant mixture was stirred at room temperature for 48 hours. The resultant mixture was cooled to 0° C., and, 500 ml of the methanol-hydrochloric acid (5.5N) was added. The mixture was stirred at room temperature for 8 hours. The resultant mixture was cooled to 0° C. and, 280 gr. of sodium bicarbonate was added to adjust to pH6 and the resultant mixture was concentrated. To the residue was added 800 ml of ethyl/acetate and the resultant mixture was filtered. The filtrate was washed with the hydrochloric acid (6N), water and saturated sodium chloride solution, dried, and concentrated. The residue was purified by column chromatography (silica gel 1 kg, ethyl acetate:cyclohexane—1:3) to give 43.2 gr. (yield 82%) of methyl 3-(2-endoacetoxy-1-exohydroxymethyl-3a,8b-cis-2,3,3a,8b-tetrahydro-1H-5-cyclophenta(b)benzofuranyl)propionate.

Melting point: 56°–57° C. (ether-hexane).

IR(KBr): $cm^{-1}$ 3530, 3480, 3050, 2950, 2875, 1720, 1600, 1455, 1375, 1330, 1245, 1200, 1170, 1080, 1060, 1010, 980, 940, 850, 790, 760, 740, 650, 610, 530, 390, 325.

NMR (400 MHz, CDCl$_3$) δ: 1.83 (3H, S), 2.1–2.3 (3H, m) 2.55 (1H, dt, J=6.3, 14.2 Hz), 2.6–2.8 (2H, m), 2.8–3.0 (2H, m), 3.6–3.8 (3H, m), 3.67 (3H, S), 5.07 (1H, q, J=6.3 Hz), 5.20 (1H, ddd, J=3.4, 6.3, 8.3 Hz), 6.77 (1H, t, J=7.3 Hz), 6.96 (1H, d, J=7.3 Hz), 7.05 (1H, d, J=7.3 Hz).

Mass (m/e): 334 (M+), 274 (M+-C$_2$H$_4$O$_2$)

Anal. calcd. for C$_{18}$H$_{22}$O$_6$: C; 64.65 H; 6.63; Found: C; 64.62 H; 6.62.

REFERENCE EXAMPLE 86

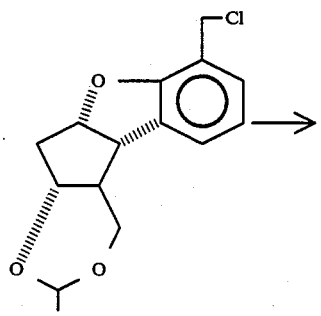

Ethyl 2-ethoxycarbonyl-3-(3-methyl-trans-4a-cisoid-4a,5a-cis-5a-1,4a,5,5a,10b,10c-hexahydrodioxyno(5,4-a)cyclopenta(b)benzofuranyl)propionate To a suspension of 1.098 gr. of sodium hydride (60% mineral oil dispersion, which was washed with 15 ml of n-pentane under argon) in 70 ml of anhydrous THF was added 5.21 ml of diethyl malonate in an ice bath. Next a solution of 3.8514 gr. of 7-chloromethyl-3-methyl-trans-4a-cisoid-4a,5a-cis-5a-1,4a,5,5a,10b,10c-hexahydrodioxyno(5,4-a)cyclopenta(b)benzofuran in 30 ml of anhydrous THF was added to the resultant mixture. The resultant solution was refluxed for 3 hours and 40 minutes. To the mixture was added 100 ml of saturated aqueous ammonium chloride solution, and the resultant mixture was extracted with 70, 60 and 50 ml of ethyl acetate. The combined organic layers were washed with 180 ml of water and 150 ml of saturated sodium chloride solution, dried over anhydrous magnesium sulfate and concentrated to give 9.5580 gr. of an oily material. The material was purified by silica gel (Art. 7734) column chromatography (ethyl acetate:cyclohexane=1:5) to give 5.541 gr. (yield 88%) of the titled compound.

Melting point: 49°–50° C. (ethyl acetate:cyclohexane=1:10)

IR(KBr) ν: 2975, 2930, 2898, 2851, 2810, 1738, 1725, 1598, 1455, 1415, 1380, 1362, 1339, 1308, 1208, 1241, 1199, 1178, 1152, 1110, 1080, 1057, 1034, 1002, 963, 941, 882, 863, 837, 782, 746, 708, 697, 668, 637, 602 $Cm^{-1}$.

Mass (m/e): 404 (M+, b.p.).

NMR (CDCl$_3$) δ: 1.20 (6H, t, J=7.04), 1.36 (3H, d, J=5.06), 1.55–2.18 (2H, m), 2.55–3.98 (5H, m), 4.15 (4H, q, J=7.04), 3.98–4.28 (2H, m), 5.39 (1H, dd, J=4.48, 10.38), 4.72 (1H, q, J=5.06), 4.97–5.27 (1H, m), 6.63–7.10 (3H, m).

REFERENCE EXAMPLE 87

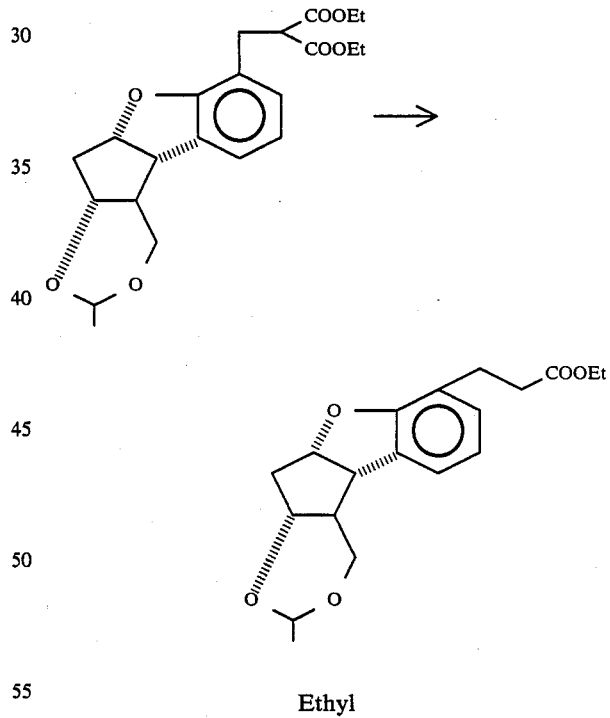

Ethyl 3-(3-methyl-trans-4a-cisoid-4a,5a-cis-5a-1,4a,5,,5a,10b,10c-hexahydrodioxyno(5,4-a)cyclopenta(b)benzofuranyl) propionate To a solution of ethyl 2-ethoxycarbonyl-3-(3-methyl-trans-4a-cisoid-4a,5a-cis-5a-1,4a,5,5a,10b,10c-hexahydrodioxyno(5,4-a)cyclo-penta(b)benzofuranyl) propionate in 50 ml of DMSO were added 0.81 ml of water and 878 mg of sodium chloride, and the resultant mixture was heated under argon at 180°–183° C. for 5 hours and 30 minutes. To the mixture was added 100 ml of water, and the resultant mixture was extracted with 70, 60 and 50 ml of ethyl acetate. The combined organic layers were washed with 100 ml of saturated sodium chloride solution, dried over anhydrous magnesium sulfate and concentrated to give 4.108 gr. of an oily material. The material was purified by silica gel (Art. 7734) column chromatography to give 3.2924 gr. (yield 82.7%) of the titled compound.

Melting Point: 70°–71° C.(ethyl acetate:cyclohexane=1.15).

IR(KBr) ν: 2980, 2930, 2850, 1725, 1593, 1444, 1410, 1380, 1350, 1331, 1302, 1259, 1231, 1210, 1180, 1159, 1116, 1084, 1068, 1035, 1010, 959, 881, 860, 809, 782, 741, 600 cm$^{-1}$.

Mass (m/e): 332 (M$^+$, b.p.).

NMR (CDCl$_3$) δ: 1.23 (3H, t, J=7.15), 1.36 (3H, d, J=5.06), 1.72–2.15 (2H, m), 2.50–3.50 (7H, m), 3.71 (1H, t, J=10.7), 4.12 (2H, q, J=7.15), 4.40 (1H, dd, J=4.40, 10.60), 4.72 (1H, q. J=5.06), 5.00–5.24 (1H, m), 6.67–7.08 (3H, m).

Referential Example 88

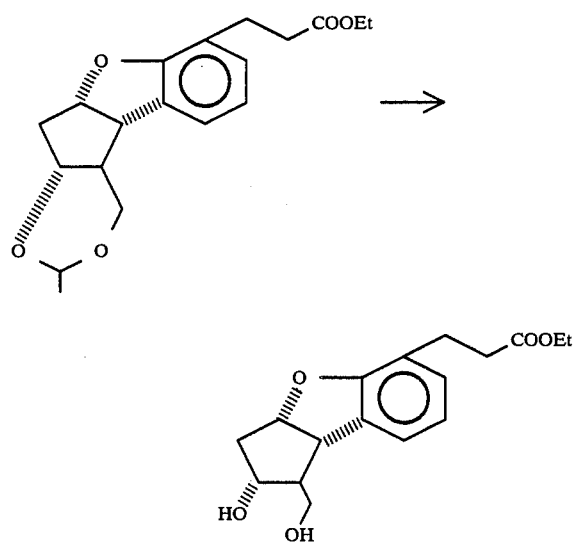

Ethyl
3-(2-endo-hydroxy-1-exo-hydroxymethyl-3a,8b-cis-2,3,3a,8b-tetrahydro-1H-5-cyclopenta(b)benzofuranyl) propionate To a solution of 1.1172 gr. of ethyl 3-(3-methyltrans-4a-cisoid-4a,5a-cis-5a-1,4a,5,5a,10b,10c-hexahydrodioxyno(5,4-a)cyclopenta(b)benzofuranyl) propionate in 15 ml of methanol was added 3.5 ml of hydrochloric acid (1N) in an ice bath, and the resultant mixture was stirred at room temperature for 4 hours. To the resultant mixture was added 4.0 gr. of sodium bicarbonate, and the resultant mixture was concentrated and, after addition of 70 ml of water, the resultant products was extracted with 50, 40 and 30 ml of ethyl acetate. The combined organic layers were washed with water and 100 ml of saturated sodium chloride solution, dried over anhydrous magnesium sulfate and concentrated to afford 1.2211 gr. of an oily material. The material was purified by Robar column (Merk Type B, ethyl acetate) to give 1.02810 gr. (yield 99%) of the titled compound.

Melting point: 69°–70° C.(ethyl acetate:cyclohexane=2:1).

IR(KBr) δ: 3348, 2980, 2925, 2865, 1725, 1590, 1443, 1418, 1370, 1345, 1299, 1244, 1182, 1110, 1080, 1061, 1045, 1012, 999, 981, 958, 910, 896, 863, 840, 810, 765, 743, 663 cm$^{-1}$.

Mass (m/e): 306 (M$^+$, b.p.)

NMR (CDCl$_3$) δ: 1.22 (3H, t, J=7.15), 2.05 (2H, S), 1.81–2.29 (3H, m), 2.42–3.00 (4H, m), 3.30–3.50 (1H, m), 3.65–4.26 (3H, m), 4.11 (2H, q, J=7.15), 5.02–5.26 (1H, m) 6.68–7.08 (3H, m).

REFERENTIAL EXAMPLE 89

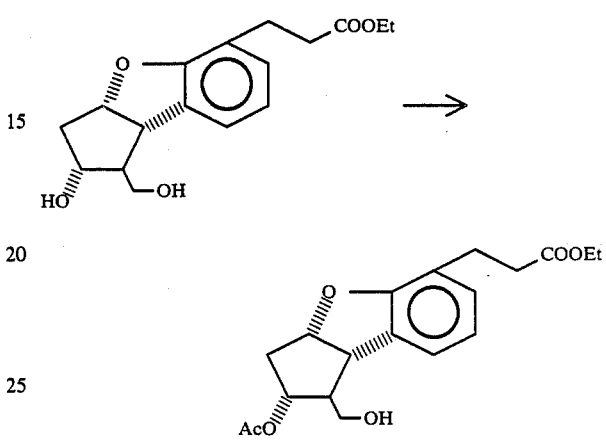

Ethyl
3-(2-endo-acetoxy-1-exo-hydroxymethyl-3a,8b-cis-2,3,3a,8b-tetrahydro-1H-5-cyclopenta(b)benzofuranyl) propionate To a solution of 1,0002 gr. of ethyl 3-(1-exohydromethyl-2-endo-hydroxy-3a,8b-cis-2,3,3a,8b-tetrahydro-1h-cyclopenta(b)benzofuranyl) propionate in 20 ml of anhydrous THF were added 1.14 ml of triethylamine and 1.24 gr. of trityl chloride, and the resultant mixture was heated under argon for 5 hours and 45 minutes. The resultant mixture was cooled to room temperature, and to the mixture were added 0.8 ml pyridine and 0.72 ml of acetic anhydride and after 2 hours and 30 minutes, 9 ml of pyridine and 7 ml of acetic anhydride. The resultant mixture was concentrated and, 50 ml of hydrochloric acid (1N) was added and the resultant mixture was extracted with 50 ml of ethyl acetate three times. The combined organic layers were washed with saturated sodium bicarbonate solution and 100 ml of saturated sodium chloride, dried over anhydrous magnesium sulfate and concentrated. To the residue were added 9 ml of methanol, 6 ml of THF and 6 ml of hydrochloric acid-methanol (5.2N), and the resultant mixture was stirred at room temperature for 24 minutes. To the reaction mixture was added 4.5 gr. of sodium bicarbonate, the resultant mixture was concentrated. To the residue was added 70 ml of water and the resultant mixture was extracted with 50 and 30 ml of ethyl acetate once and twice respectively. The combined organic layers were washed with 100 ml of water and saturated sodium chloride, dried over anhydrous magnesium sulfate, and concentrated to give 2.3615 gr. of an oily material. The material was purified by silica gel (Art. 7734) column chromatography to give 794.1 mg (yield 69.7%) of the titled compound. At this time a methylester was obtained (33%). The amount of the starting material is 298.4 mg (yield 29.8%).

IR (film) ν: 3450, 2930, 1725, 1592, 1447, 1366, 1242, 1386, 1061, 1015, 951, 935, 844, 742 cm$^{-1}$.

Mass (m/d): 348 (M+, b.p.)
NMR (CDCl$_3$) δ: 1.24 (3H, t, J=7.03), 1.83 (3H, S), 1.97 (1H, S), 2.02-3.02 (7H, m), 3.55-3.79 (3H, m), 4.13 (2H, q, J=7.03), 3.95-5.33 (2H, m), 6.63-7.13 (3H, m), (ethylester:methylester=2:1).

REFERENTIAL EXAMPLE 90

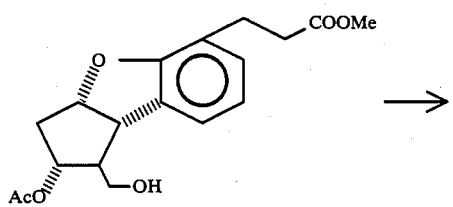

5,6,7-trinor-4,8-inter-m-phenylene-2-nor-11,15-didehydroxy-11-acetoxy-16,16-dimethyl-15-oxo-PGI$_2$-methylester To a solution of 1.0011 gr. of methyl 3-(2-endoacetoxy-1-exo-hydroxylmethyl-3a,8b-cis-2,3.3a,8b-tetrahydro-1H-5-cyclopenta(b)benzofuranyl) propionate in 20 ml of anhydrous THF were added 0.24 ml of anhydrous pyridine, 6 ml of anhydrous dimethyl sulfoxide (DMSO) and 0.18 ml of trifluoroacetic acid and 1.25 gr. of dicyolohexylcarbodiimide (DCC), and the resultant mixture was stirred at room temperature for 2 hours. The resultant reaction mixture was cooled in an ice bath and, 1.48 gr. of calcium carbonate was added, and the resultant mixture was stirred for 20 minutes and allowed to stand.

To the suspension of 216 mg of sodium hydride (60% mineral oil dispersion) in 30 ml of anhydrous THF was added a solution of 1.5 gr. of 3,3-dimethyl-2-oxo-heptyl-dimethylester phosphate in 5 ml of anhydrous THF, and the resultant solution was stirred under argon at room temperature for 30 minutes. To the resultant reaction mixture was added the supernatant of the above mentioned aldehyde ester suspension. The residue was washed with 10 and 5 ml of anhydrous THF, the supernatant was added, and the resultant mixture was stirred at room temperature for 30 minutes. To the resultant reaction mixture was added 60 ml of saturated aqueous ammonium chloride solution, and the resultant mixture was extracted with 40 ml of ethyl acetate 3 times. The combined organic layers were washed with 80 ml of water and saturated sodium chloride solution, dried over magnesium sulfate, and concentrated. The cyclohexylurea and the byproduct derived from Wadsworth reagent were removed by silica gel (Art. 7734) column chromatography (ethyl acetate:cyclohexane=1:2) to give 1.7469 gr. of an oily material. The material was purified by Robar column (Merk Type B, ethyl acetate:cyclohexane=1:3) to give 1.1883 gr. (yield 86.8%) of the titled compound.

IR (film) ν: 2930, 2860, 1735, 1682, 1620, 1598, 1444, 1362, 1239, 1192, 1062, 1044, 1080, 945, 050, 784, 746 cm$^{-1}$.
Mass (m/e): 456 (M+) 57 (b.p.).
NMR (CDDl$_3$) δ: 0.73-1.01 (3H, m), 1.13 (6H, S), 1.78 (3H, S), 1.01-2.29 (7H, m), 2.45-3.08 (6H, m), 3.67 (3H, S), 3.52-3.78 (1H, m), 4.98 (1H, J=6.21), 5.10-5.41 (1H, m), 6.47-7.11 (5H, m).

REFERENTIAL EXAMPLE 91

5,6,7-trinor-4,8-inter-m-phenylene-2,17,18,19,20-pentanor-11,15-didehydroxy-11-acetoxy-15-oxo-16-propoxy PGI$_2$-methylester

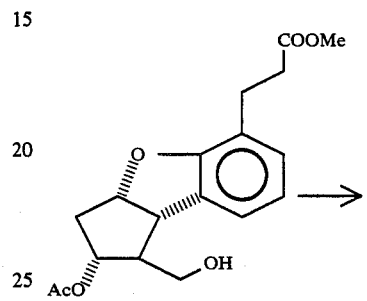

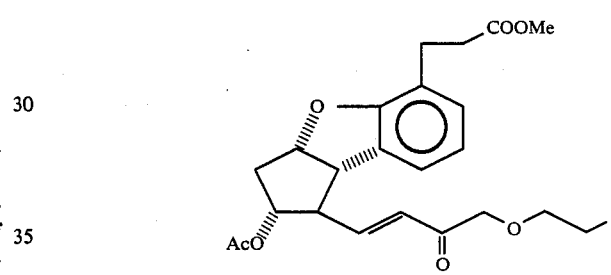

To a solution of 1.27 gr. of methyl 3-(2-endoacetoxy-1-exohydroxymethyl-3a,8b-cis-2,3,3a,8b-tetrahydro-1H-5-cyclopenta(b)benzofuranyl) propionate in 15 ml of anhydrous THF were added 5 ml of anhydrous DMSO and 1.57 gr. of D.C.C. (dicyclohexylcarbodiimide), 0.36 ml of anhydrous pyridine and 0.22 ml of trifluoroacetic acid and the resultant mixture was stirred under argon at room temperature for 2.5 hours. To the resultant reaction mixture was added 1.91 gr. of calcium carbonate, and resultant mixture was stirred. To a suspension of 0.18 gr. of sodium hydride (60% mineral oil dispersion) in anhydrous THF was added dropwise a solution of 1.28 gr. of dimethylester 1-oxo-2-propoxypropanylphosphate in 2 ml of anhydrous THF, and the resultant solution was stirred under argon at room temperature for 15 minutes. To the resultant reaction mixture was added the supernatant of the above mentioned aldehyde mixture. The residue was washed with 3 ml of THF 3 times and the supernatant was added. The resultant reaction mixture was stirred overnight and adjusted to pH7 by adding 100 ml of saturated aqueous ammonium chloride solution and the resultant product was extracted with 70 ml of ethyl acetate 3 times. The combined organic layers were washed with water and saturated sodium chloride solution, dried over sodium sulfate, and concentrated. The resultant mixture was purified by a silicon gel short column to remove solids and purified by column chromatography (Merk Robar Type, ethyl acetate:cyclohexane=1:3) to give 699 mg (yield 42%) of 5,6,7-trinor-4,8-inter-m-phenylene-2,17,18,19,20-pentanor-11,15-didehydroxy-11-acetoxy-15-oxo-16-propoxy PGI₂ methylester.

IR (liquid film): cm⁻¹, 3160, 2960, 2880, 1735, 1695, 1670, 1620, 1600, 1480, 1455, 1440, 1420, 1370, 1320, 1300, 1270, 1240, 1200, 1160, 1120, 1060, 1045, 1010, 980, 955, 915, 860, 740, 700.

NMR (90 MHz, CDCl₃): ppm 0.85–1.05 (3H, m) 1.10–1.72 (4H, m) 1.77 (3H, S) 1.98–2.32 (1H, m) 2.45–3.12 (5H, m) 3.47 (2H, t, J=6.6 Hz) 3.67 (3H, S) 4.18 (2H, S) 4.87–5.13 (1H, m) 5.13–5.40 (1H, m) 6.44 (1H, d, J=15.8 Hz) 6.65–7.10 (4H, m).

Mass (m/e): 430 (M+), 43 (b.p.).

REFERENTIAL EXAMPLE 92

5,6,7-trinor-4,8-inter-m-phenylene-2-nor-11-acetoxy-17-(S)-methyl-15-didehydro PGI₂ methylester

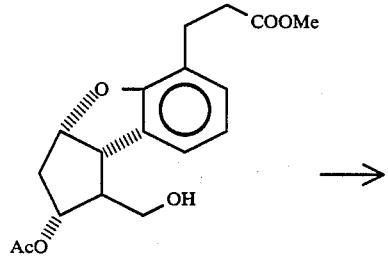

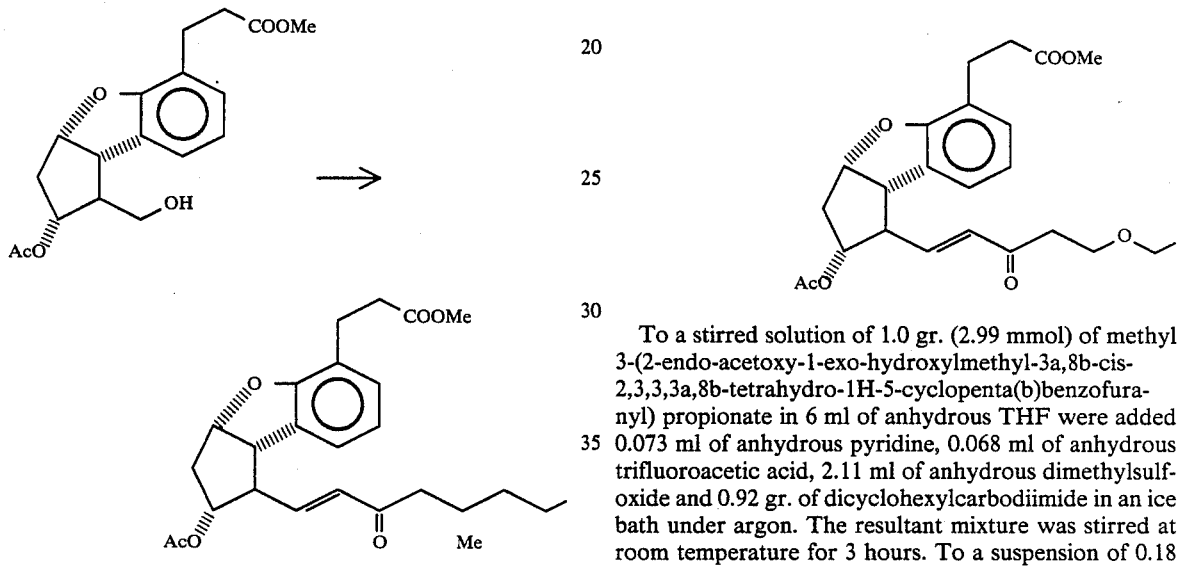

To a stirred solution of 1 gr. (2.99 mmol) of methyl 3-(2-endo-acetoxy-1-exo-hydroxylmethyl-3a,8b-cis-2,3,3a,8b-tetrahydro-1H-5-cyclopenta(b)benzofuranyl) propionate in 6 ml of anhydrous THF were added 0.073 ml of anhydrous pyridine, 0.068 ml of anhydrous trifluoroacetic acid, 11 ml of anhydrous DMSO and 0.92 gr. (4.46 mmol) of DCC in an ice bath. The resultant mixture was stirred at room temperature for 3 hours. To a stirred suspension of 0.18 gr. of sodium hydride (60% mineral oil dispersion) in 8 ml of anhydrous THF was added a solution of 0.9 gr. of 4(S)-methyl-2-oxo-heptphosphonic acid-dimethylester in 5 ml of anhydrous THF in an ice bath, and the resultant mixture was stirred at room temperature for 30 minutes. To the reaction mixture was added the above mentioned aldehyde mixture and the resultant mixture was stirred in an ice bath for 10 minutes. The resultant reaction mixture was adjusted to pH7 with acetic acid, the precipitate was filtered, and the filtrate was concentrated. The residue was purified by column chromatography (silica gel (40 gr.); ethyl acetate:cyclohexane=1:6) to give 1.2 gr. (yield 94%) of conjugate ketone.

IR (liquid film) cm⁻¹: 2950, 2920, 2850, 1735, 1690, 1670, 1620, 1440, 1365, 1230, 1180, 1050, 980, 740.

NMR (90 MHz, CDDl₃) δ: 0.80–1.00 (6H, m), 1.00–1.50 (6H, m), 1.85 (3H, S), 1.90–3.10 (8H, m), 3.65 (3H, S), 3.70 (1H, m), 5.00 (1H, q, J=5.9 Hz) 5.25 (1H, m), 6.20 (1H, dd, J=15.6 Hz, 0.7 Hz), 6.60–7.05 (4H, m).

Mass (m/e): 442 (M+), 382.

REFERENTIAL EXAMPLE 93

5,6,7-trinor-4,8-inter-m-phenylene-2,18,19,20-tetranor-11,15-didehydroxy-11-acetoxy-15-oxo-17-ethoxy PGI₂ methylester

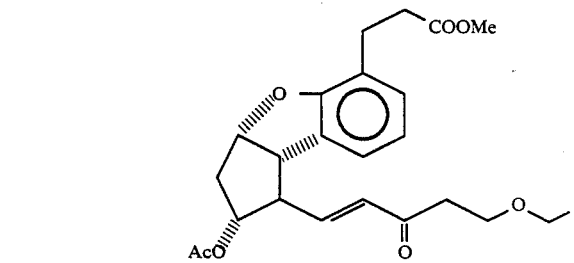

To a stirred solution of 1.0 gr. (2.99 mmol) of methyl 3-(2-endo-acetoxy-1-exo-hydroxylmethyl-3a,8b-cis-2,3,3,3a,8b-tetrahydro-1H-5-cyclopenta(b)benzofuranyl) propionate in 6 ml of anhydrous THF were added 0.073 ml of anhydrous pyridine, 0.068 ml of anhydrous trifluoroacetic acid, 2.11 ml of anhydrous dimethylsulfoxide and 0.92 gr. of dicyclohexylcarbodiimide in an ice bath under argon. The resultant mixture was stirred at room temperature for 3 hours. To a suspension of 0.18 gr. (4.5 mmol) of sodium hydride (60% mineral oil dispersion) in 8 ml of anhydrous tetrahydrofuran was added dropwise a solution of 1.01 gr. (4.49 mmol) of 2-oxo-4-ethoxy-butylphosphonate dimethylester in 5 ml of anhydrous tetrahydrofuran at room temperature and the resultant mixture was stirred under argon at room temperature for 30 minutes To the resultant mixture was added, the above mentioned aldehyde ester reaction mixture in an ice bath, and the resultant mixture was stirred in an ice bath at room temperature for 30 minutes. The resultant reaction mixture was neutralized with acetic acid and filtered. The filtrate was concentrated, 20 ml of water was added, the resultant product was extracted with 60 ml of ethyl acetate 2 times. The combined organic layers were washed with 20 ml of water and saturated sodium chloride solution, dried over magnesium sulfate, and concentrated. The residue was purified by silica gel column chromatograph (ethyl acetate:cyclohexane=1:5) to separate byproducts and excess Wadsworth reagent and the obtained oil was purified by a Robar column (ethyl acetate:cyclohexane=1:4) to give 1.14 gr. (yield 88.6%) of 5,6,7-trinor-4,8-inter-m-phenylene-2,18,19,20-tetranor-11,15-didehydroxy-11-acetoxy-15-oxo-17-ethoxy PGI₂ methylester.

IR (liquid film) ν: 2970, 2950, 2875, 1730, 1690, 1670, 1630, 1600, 1550, 1450, 1370, 1230, 1190, 1100, 1060, 980, 940, 850, 750, cm⁻¹.

NMR(CDCl₃) δ: 1.2 (3H, t, J=7.0 Hz), 1.78 (3H, S), 2.15 (1H, d, d, d, J=3.6, 6.1, 14.4 HZ), 2.6–2.7 (3H, m), 2.8–3.0 (5H, m), 3.51 (2H, q, J=7.0 HZ), 3.68 (3H, S), 3.65–3.8 (3H, m), 5.00 (1H, q, J–6.1 HZ), 5.26 (1H, d, d, d, J=3.6, 7.1, 8.5 HZ), 6.23 (1H, d, d, J=1.0, 16.1 HZ), 6.77 (1H, t, J=7.5 HZ), 6.8 (1H, d, d, J=7.8, 16.1 HZ), 6.9–7.0 (2H, m).

Mass (m/e): 430 (M+), 384 (M+—C₂H₅OH)

REFERENTIAL EXAMPLE 94

5,6,7-trinor-4,8-inter-m-phenylene-2,17,18,19,20-pentanor-11,15-dideoxy-11-acetoxy-15-oxo-16-phenoxy PGI₂-methylester

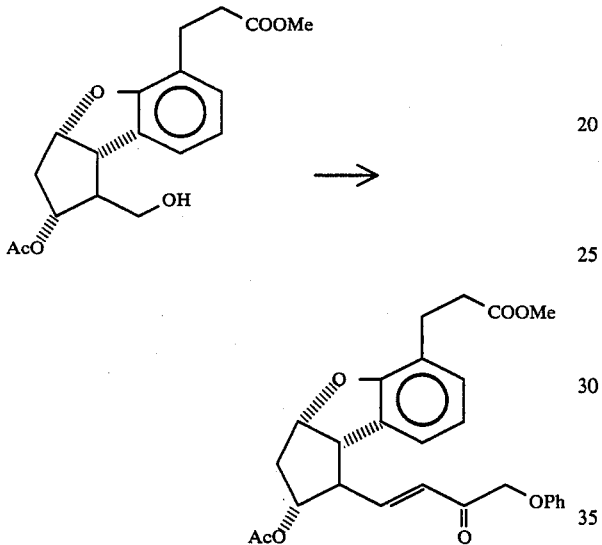

To a solution of 1.5 gr. (4.48 mmol) of methyl 3-(2-endo-acetoxy-1-exo-hydroxylmethyl-3a,8b-cis-2,3,3-a,8b-tetrahydro-1H-5-cyclopenta(b)benzofuranyl) propionate in 25 ml of anhydrous THF were added 3.2 ml of anhydrous DMSO, 0.11 ml (1.39 mmol) of anhydrous pyridine, 0.097 ml (1.25 mmol) of trifluoroacetic acid and 1.39 gr. (6.72 mmol) of D.C.C. (dicyclohexylcarbodiimide) under argon, and the resultant mixture was stirred at room temperature for 2 hours. To a suspension of 249 mg (6.50 mmol) of sodium hydride (60% mineral oil dispersion) in 10 ml of anhydrous THF was added to a solution of 1.74 gr. (6.72 mmol) of 3-phenoxy-2-oxo-propylphosphonate dimethylester in 10 ml of anhydrous THF and the resultant solution was stirred at room temperature for 30 minutes. The above mentioned aldehyde mixture was added to the resultant reaction mixture at 0° C. and, the resultant mixture was stirred at room temperature for 30 minutes. The resultant mixture was adjusted to pH7 with acetic acid and concentrated. Ethyl acetate was added to the residue and the resultant was filtered. The filtrate was washed with water and saturated sodium chloride solution, dried and concentrated. The resultant residue was purified by silica gel short column to remove solids and the obtained oil was purified by column chromatography (Merk Robar Column, ethyl acetate:cyclohexane=1:3) to give 1.35 gr. (yield 65%) of 5,6,7-trinor-4,8-inter-m-phenylene-2,17,18,19,20-pentanor-11,15-dideoxy-11-acetoxy-15-oxo-16-phenoxy PGI₂ methylester.

IR (liquid film): cm⁻¹, 2950, 1730, 1620, 1600, 1490, 1450, 1365, 1300, 1260, 1060, 850, 750, 690.

(NMR (90 MHz, CDCl₃) δ: 1.76 (3H, S), 2.09 (1H, ddd, J=3.8, 6.5, 14.3 Hz) 2.5–3.1 (6H, m), 3.5–3.8 (1H, m) 3.67 (3H, S), 4.71 (2H, S) 4.98 (1H, q, J=6.5 Hz), 5.1–5.4 (1H, m) 6.54 (1H, dd, J=0.7, 15.6 Hz), 6.7–7.5 (9H, m).

Mass (m/e): 464 (M+), 404 (M+—C₂H₄O₂).

REFERENTIAL EXAMPLE 95

5,6,7-trinor-4,8-inter-m-phenylene-2,17,18,19,20-tetranor-11,15-dideoxy-11-acetoxy-15-oxo-16-cyclopentyloxy PGI₂ methylester

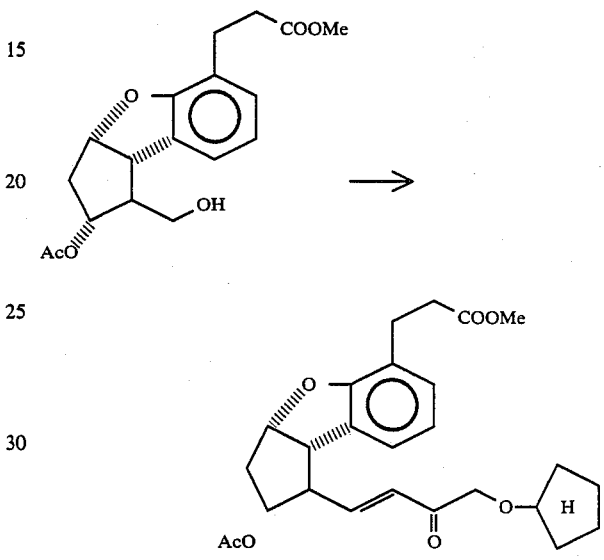

To a solution of 1.5 gr. (4.48 mmol) of methyl 3-(2-endo-acetoxy-1-exohydroxymethyl-3a,8b-cis-2,3,3a,8b-tetrahydro-1H-5-cyclopenta(b)benzofuranyl)propionate in 25 ml of anhydrous THF were added 3.2 ml of anhydrous DMSO, 0.11 ml (1.39 mmol) of anhydrous pyridine, 0.097 ml (1.25 mmol) of trifluoroacetic acid and 1.39 gr. (6.72 mmol) of D.C.C. (dicyclohexylcarbodiimide) under argon, and the resultant mixture was stirred at room temperature for 3 hours. To a suspension of 249 mg (6.50 mmol) of sodium hydride (60% mineral oil dispersion) in 10 ml of anhydrous THF was added a solution of 1.68 gr. (6.72 mmol) of 3-(cyclopentyloxy)-2-oxo-propylphosphonate dimethylester in 10 ml of anhydrous THF and the resultant solution was stirred at room temperature for 30 minutes. The above mentioned aldehyde mixture was added to the resultant reaction mixture and, the resultant mixture was stirred at room temperature for 30 minutes. The resultant mixture was adjusted to pH6 with acetic acid and concentrated. Ethyl acetate was added to the residue and the resultant mixture was filtered. The filtrate was washed with water and saturated sodium chloride solution, dried and concentrated. The resultant residue was purified by silica gel short column to remove solids and the obtained oil was purified by column chromatography (Merk Robar Column, ethyl acetate:cyclohexane=1:4) to give 1.67 gr. (yield 82%) of 5,6,7-trinor-4,8-inter-m-phenylene-2,17,18,19,20-pentanor-11,15-dideoxy-11-acetoxy-15-oxo-16-cyclopentyloxy PGI₂ methylester.

IR (liquid film): cm⁻¹, 2950, 1730, 1690, 1620, 1600, 1450, 1370 1240, 1110, 1065, 980, 850, 750.

NMR (90 MHz, CDClH3) δ: 1.4–1.9 (8H, m), 1.77 (B 3H, S), 2.0–2.3 (1H, m), 2.4–3.1 (6H, m), 3.6–3.8 (1H, m), 3.67 (3H, S) 3.8–4.1 (1H, m), 4.14 (2H, S), 5.00 (1H, q, J=5.9 Hz), 5.1–5.4 (1H, m), 6.47 (1H, dd, J=0.7, 15.8 Hz), 6.7–7.1 (4H, m).

Mass (m/e): 456 (M+), 396 (M+—$C_2H_4O_2$).

EXAMPLE 216

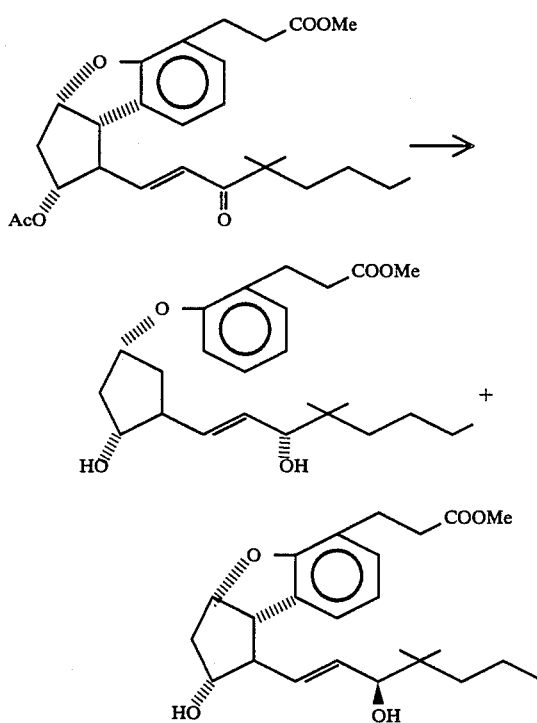

5,6,7-tetranor-4,8-inter-m-phenylene-2-nor-16,16-dimethyl $PGI_2$ methylester

To a solution of 1.1576 gr. of 5,6,7-tetranor-4,8-inter-m-phenylene-2-nor-11,15-didehydroxy-11-acetoxy-16,16-dimethyl-15-oxo $PGI_2$ methylester in 20 ml of methanol were added 1.47 gr. of cerium chloride.$7H_2O$, and to the stirred resultant mixture was added 1.33 mg of sodium borohydride in an ice bath, and the resultant mixture was stirred for 10 minutes. To the resultant reaction mixture was added 20 ml of saturated aqueous sodium bicarbonate solution, and the resultant mixture was stirred for 10 minutes. The resultant reaction mixture was concentrated and, 50 ml of water was added to the residue and the mixture was extracted with 50 ml of ethyl acetate 3 times. The combined organic layers were washed with 100 ml of water and saturated sodium chloride solution, dried over magnesium sulfate, and concentrated. To the residue were added 15 ml of anhydrous methanol and 0.021 ml of the sodium methoxide (4.89N), and the resultant solution was stirred at room temperature for 3 hours. To the resultant mixture was added 0.1 ml of acetic acid, and the resultant solution was concentrated. To the residue were added 25 ml of water and 20 ml of ethyl acetate and the resultant mixture was extracted 3 times. The combined organic layers were washed with 50 ml of each of water and saturated sodium chloride solution, dried over magnesium sulfate, and concentrated to give 1.2653 gr. of an oily material. The material was purified by a Robar column (Merk Type B, ethyl acetate:cyclohexane=6:1) to give 468.5 mg (yield 44.3%) of 5,6,7-tetranor-4,8-inter-m-phenylene-2-nor-16,16-dimethyl $PGI_2$ methylester and 452.6 mg (yield 42.8%) of 5,6,7-tetranor-4,8-inter-m-phenylene-2-nor-16,16-dimethyl-15β-hydroxy $PGI_2$ methylester. 5,6,7-tetranor-4,8-inter-m-phenylene-2-nor-16,16-dimethyl $PGI_2$ methylester Melting point: 67°–68° C. (ethyl acetate:n-hexane=1:12).

IR (KBr) ν: 3360, 2950, 2867, 1735, 1597, 1450, 1370, 1330, 1300, 1270, 1222, 1190, 1175, 1150, 1100, 1072, 1032, 1013, 990, 970, 881, 859, 830, 743, 618, $cm^{-1}$.

Mass (m/e): 416 (M+), 57 (b.p.).

High Resolution Mass: obs. 416, 2579 calcd. 416, 1563.

NMR ($CDCl_3$) δ: 0.87–0.94 (3H, m) 0.87 (3H, S), 0.90 (3H, S) 1.17–1.38 (6H, m), 1.76–1.82 (1H, m), 1.96–2.03 (1H, m), 2.25–2.32 (1H, m) 2.44–2.49 (1H, m), 2.61–2.67 (3H, m) 2.85–2.93 (2H, m), 3.46 (1H, t, J=8.61) 3.66 (3H, S), 3.84–3.89 (1H, m), 3.90–3.98 (1H, m), 5.09–5.18 (1H, m), 5.61–5.73 (2H, m) 6.76 (1H, t, J=7.33), 6.96–6.99 (2H, m).

5,6,7-tetranor-4,8-inter-m-phenylene-2-nor-16,16-dimethyl-15β-hydroxy $PGI_2$ methylester Melting point: 105° C. (ethyl acetate:n-hexane=1:3).

IR (KBr) ν: 3415, 2940, 2852, 1735, 1624, 1598, 1448, 1440, 1361, 1342, 1303, 1270, 1244, 1230, 1184, 1150, 1061, 1020, 983, 955, 882, 863, 806, 760, 740, 620, $cm^{-1}$.

Mass (m/e): 416 (M+), 57 (b.p.).

High Mass: obs 416, 2552 calcd. 416, 2563.

NMR ($CDCl_3$) δ: 0.88–0.96 (3H, m), 0.88 (3H, S), 0.91 (3H, S), 1.18–1.38 (6H, m), 1.48–1.53 (1H, m), 1.66–1.74 (1H, m), 1.99–2.05 (1H, m), 2.51–2.56 (1H, m), 2.59–2.67 (3H, m), 2.87–2.91 (2H, m) 3.52 (1H, t, J=8.24), 3.66 (3H, S) 3.88–3.90 (1H, m) 3.93–4.00 (1H, m), 5.14–5.19 (1H, m) 5.65–5.77 (2H, m), 6.77 (1H, t, J=7.33), 6.98 (1H, d, J=7.33), 7.01 (1H, d, J=7.33).

EXAMPLE 217

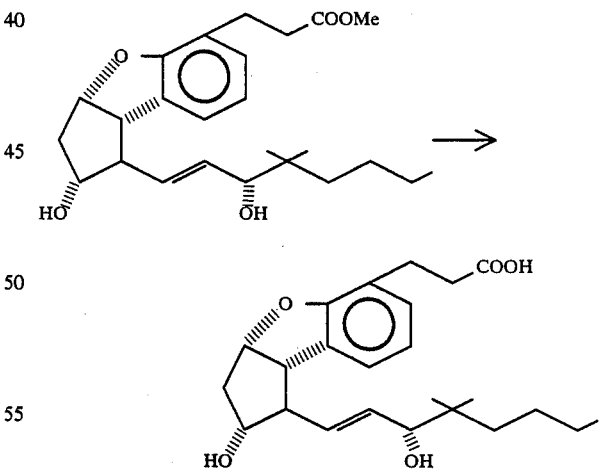

5,6,7-tetranor-4,8-inter-m-phenylene-2-nor-16,16-dimethyl $PGI_2$

To a solution of 301.2 mg of 5,6,7-tetranor-4,8-inter-m-phenylene-2-nor-16,16-dimethyl $PGI_2$-methylester in 10 ml of methanol was added a solution of 3.8 ml of the sodium hydroxide (1N), and the resultant solution was stirred at room temperature for 2 hours and 30 minutes. The resultant mixture was concentrated, 10 ml of water and 3.8 ml of hydrochloric acid (1N) added to the residue and the resultant mixture was extracted with 10 ml of ethyl acetate 3 times. The combined organic layers were washed with 20 ml of water and saturated sodium chloride solution, dried over magnesium sulfate and concentrated to give 270.2 mg (yield 93.3%) of the titled compound.

Melting point: 148°–148.5° C. (acetone:n-hexane=5:2).

IR (KBr) ν: 3410 (3675–2200), 2960, 2930, 2860, 1700, 1595, 1455, 1420, 1375, 1298, 1267, 1248, 1204, 1105, 1065, 1015, 990, 960, 918, 848, 823, 804, 785, 765, 743.

Mass (m/e): 402 (M+), 57 (b.p.).

High Mass: obs. 402, 2401 calcd. 402, 2406.

NMR (CDCl$_3$, 10% DMSO) δ: 0.90–0.94 (3H, m), 0.86 (3H, S), 0.90 (3H, S), 1.17–1.40 (6H, m), 1.88–1.97 (1H, m), 2.30–2.37 (1H, m), 2.56–2.72 (4H, m), 2.83–2.92 (2H, m), 3.39 (1H, t, J=9.16), 3.78–4.04 (3H, m), 5.06–5.12 (1H, m), 5.56–5.69 (2H, m), 6.74 (1H, t, J=7.33), 6.93 (1H, d, J=7.33), 6.99 (1H, d, J=7.33)

EXAMPLE 218

5,6,7-trinor-4,8-inter-m-phenylene-2-nor-16-methyl PGI$_2$-methylester

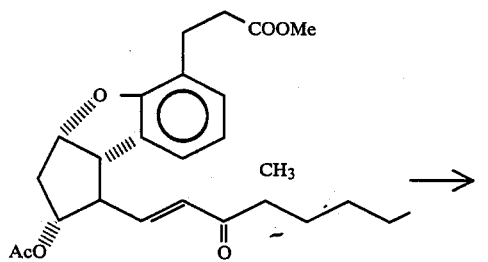

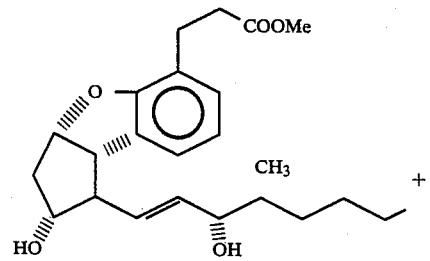

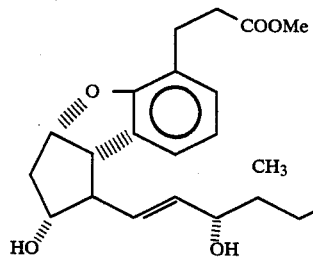

To a stirred solution of 965 mg (2.18 mmol) of 5,6,7-trinor-4,8-inter-m-phenylene-2-nor-11,15-didehydroxy-11-acetoxy-16-methyl-15-oxo-PGI$_1$-methylester in 50 ml of methanol was added 815 mg (2.18 mmol) cerium chloride (7H$_2$O), and to the solution was added 124 mg (3.28 mmol) of sodium boro-hydride in an ice bath, and the mixture was stirred for 10 minutes. To the resultant reaction mixture was added 20 ml of saturated sodium bicarbonate solution and the resultant mixture was concentrated. To the residue were 30 ml of water and 100 ml of ethyl acetate, the resultant mixture was filtered, and the precipitate was washed with 30 ml of ethyl acetate 3 times. The combined filtrates were washed with 30 ml of water and saturated sodium chloride solution, dried over magnesium sulfate and concentrated to give 960 mg of an oily material, which was dissolved in 25 ml of anhydrous methanol. To a stirred solution of 0.096 ml (2.16 mmol) of the sodium methoxide (0.522N) at room temperature and the solution was stirred under argon for 3 hours. To the resultant mixture was 0.05 ml of acetic acid, the resultant mixture was concentrated, 20 ml of water was added, and the mixture was extracted with 50 ml of ethyl acetate 2 times. The combined organic layers were washed with 20 ml of water and saturated sodium chloride solution, dried over magnesium sulfate and concentrated. The residue was purified by a Robar column (ethyl acetate:cyclohexane=2:1) to give 376 mg (yield 43.3%) of 5,6,7-trinor-4,8-inter-m-phenylene-2-nor-deoxy-15-hydroxy-16-methyl PGI$_2$-methylester and 330 mg (yield 38%) of 5,6,7-trinor-4,8-inter-m-phenylene-2-nor-16-methyl PGI$_2$-methylester.

Analytical value of 15-β isomer

Melting point: 84.8°–86.0° C. (ethyl acetate:n-hexane=2:1).

IR (KBr) ν: 3350, 2975, 2930, 1735, 1600, 1450, 1370, 1345, 1330, 1295, 1250, 1190, 1150, 1095, 1085, 1010, 960, 860, 750, cm$^{-1}$.

NMR (CDCl$_3$) δ: 0.85–1.0 (6H, m), 1.05–1.8 (9H, m), 2.02 (1H, ddd, J=5.0, 8.4, 3.6 HZ), 2.52 (1H, q, J=8.1 HZ), 2.6–2.7 (3H, m), 2.85–2.95 (2H, m), 3.51 (1H, t, J=8.1 HZ), 3.66 (3H, S), 3.9–4.1 (2H, m), 5.16 (1H, d, dd, J=5.0, 7.0, 8.1 HZ), 5.6–5.75 (2H, m), 6.77 (1H, t, J=7.3 Hz), 6.98 (1H, d, J=7.3 Hz), 7.01 (1H, d, J=7.3 Hz).

Mass (m/e): 402 (M+), 384 (M+—H$_2$O). Anal. calcd. for C$_{24}$H$_{34}$O$_5$: C(%); 71.61 H(%); 8.51; Found: C(%); 71.68 H(%); 8.65.

Analytical value of 15-α isomer

Melting point: 87.9° C.–89.5° C. (ethyl acetate:cyclohexane=2:1).

IR (KBr) ν: 3370, 2960, 2920, 1730, 1590, 1440, 1360, 1290, 1185, 1060, 1030, 995, 960, 880, 850, 740, cm$^{-1}$.

NMR (CDCl$_3$) δ: 0.85–1.0 (6H, m), 1.05–1.7 (7H, m), 1.75–1.9 (1H, m), 1.99 (1H, ddd, J=5.0, 8.6, 13.6 HZ), 2.2–2.25 (1H, m), 2.47 (1H, q, J=8.4 HZ), 2.6–2.7 (3H, m), 2.85–2.95 (2H, m), 3.46 (1H, t, J=8.4 HZ), 3.66 (3H, S), 3.9–4.05 (2H, m), 5.13 (1H, ddd, J=5.0, 7.3, 8.4 HZ).

Mass (m/e): 402 (M+), 384 (M+—H$_2$O). Anal. calcd. for C$_{24}$H$_{34}$O$_5$: C(%); 71.61 H(%); 8.51; Found: C(%); 71.53 H(%); 8.63.

EXAMPLE 219

5,6,7-trinor-4,8-inter-m-phenylene-2-nor-16-methyl PGI$_2$

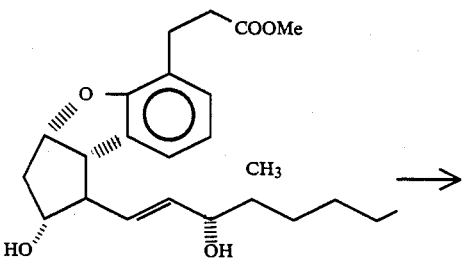

147

-continued

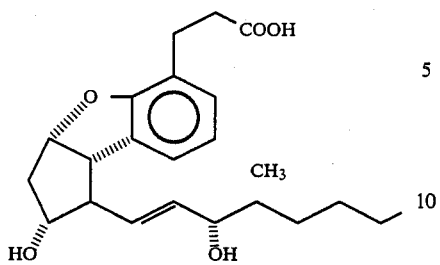

To a stirred solution of 242 mg (0.602 mmol) of 5,6,7-trinor-4,8-inter-m-phenylene-2-nor-16-methyl PGI$_2$-methylester in 25 ml of methanol was added a solution of 5.5 ml (5.42 mmol) of the sodium hydroxide (0.986N) in an ice bath and the solution was further stirred at room temperature for 5 hours. To the resultant reaction mixture was added 5.5 ml (5.42 mmol) of hydrochloric acid (1N), and the resultant mixture was concentrated. To the residue was added 20 ml of water, and the resultant mixture was extracted with 50 ml of ethyl acetate 2 times. The combined organic layers were washed with 10 ml of water and saturated sodium chloride solution, dried over sodium sulfate, and concentrated. The crude crystal was recrystallized from 1.5 ml of ethyl acetate and 0.5 ml of n-hexane to give 180 mg (yield 77%) of a white crystal.

Melting point: 122.1°–123° C. (ethyl acetate:n-hexane=2:1).

IR (KBr) $\nu$: 3460, 2960, 2930, 2860, 1700, 1595, 1455, 1420, 1370, 1300, 1265, 1200, 1070, 1020, 985, 970, 920, 855, 745, cm$^{-1}$.

NMR (CDCl$_3$) $\delta$: 0.85–1.0 (6H, m), 1.05–1.7 (7H, m), 1.97 (1H, ddd, J=5.1, 8.8, 13.9 HZ), 2,41 (1H, q, J=8.4 HZ), 2.55–2.75 (3H, m), 2.8–3.0 (2H, m), 3.42 (1H, t, J=8.4 HZ), 3.85–4.0 (2H, m), 3.0–5.0 (2H, m), 5.11 (1H, ddd, J=5.1, 7.3, 8.4 HZ), 5.55–5.7 (2H, m), 6.75 (1H, t, J=7.3 HZ), 6.95 (1H, d, 7.3 HZ), 6.98 (1H, d, J=7.3 HZ).

Mass (m/e): 388 (M+), 370 (M+—H$_2$O). Anal. calcd. for C$_{23}$H$_{32}$O$_5$: C(%); 71.10 H(%); 8.30; Found: C(%); 71.02 H(%); 8.43.

EXAMPLE 220

5,6,7-trinor-4,8-inter-m-phenylene-2-nor-15-deoxy-5$\beta$-hydroxy-16-methyl PGI$_2$

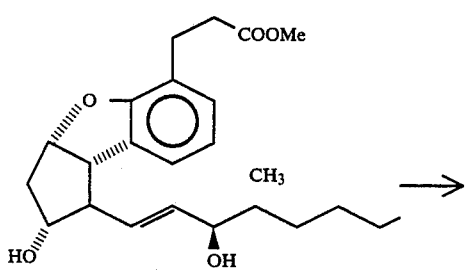

148

-continued

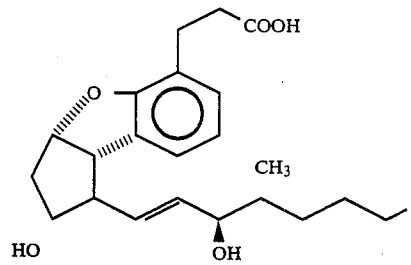

To a stirred solution of 290 mg (0.72 mmol) of 5,6,7-trinor-4.8-inter-m-phenylene-2-nor-15-deoxy-15$\beta$-hydroxy-16-methyl-2-nor PGI$_2$-methylester in 20 ml of methanol was added 5.9 ml (5.8 mmol) of the sodium hydroxide (0.986N) in an ice bath. The solution was stirred at room temperature for 5 hours. After addition of 5.8 ml (5.8 mmol) of hydrochloric acid (1N), the resultant reaction mixture was concentrated. After addition of 20 ml of water, the mixture was extracted with 50 ml of ethyl acetate 2 times. The combined organic layers were washed with 10 ml of water and saturated sodium chloride solution, dried over sodium sulfate, and concentrated. The crude crystal was recrystallized from 1.5 ml of ethyl acetate and 0.5 ml of n-hexane to give 228 mg (yield 81.6%) of a white crystal.

Melting point: 97.4° C.–98.1° C. (ethyl acetate:n-hexane=2:1).

IR (KBr) $\nu$: 3400, 2960, 2930, 1715, 1695, 1600, 1450, 1400, 1375, 1350, 1315, 1290, 1260, 1230, 1200, 1190, 1155, 1090, 1080, 1040, 1000, 970, 860, 835, 785, 770, 740, cm$^{-1}$.

NMR (CDCl$_3$) $\delta$: 0.85–1.0 (6H, m), 1.05–1.7 (7H, m), 2.00 (1H, ddd, J=5.0, 8.1, 13.7 HZ), 2.50 (1H, q, J=8.1 Hz), 2.60 (1H, dt, J=6.7, 13.7 HZ), 2.6–2.75 (2H, m), 2.85–2.95 (2H, m), 3.48 (1H, t, J=8.1 HZ), 3.95 (1H, m), 4.0–4.1 (1H, m), 3.5–5.0 (2H, m), 5.14 (1H, ddd, J=5.0, 6.7, 8.1 HZ), 5.6–5.75 (2H, m), 6.76 (1H, t, J=7.3 Hz), 6.95–7.05 (2H, m).

Mass (m/e): 388 (M+), 370 (M+—H$_2$O).

Anal. calcd. for C$_{23}$H$_{32}$O$_5$: C(%), 71.10 H(%), 8.30 Found: C(%), 71.02 H(%), 8.43.

EXAMPLE 221

5,6,7-trinor-4,8-inter-m-phenylene-2,17,18,19,20-pentanor-16-propoxy PGI$_2$-methylester and 5,6,7-trinor-4,8-inter-m-phenylene-2,17,18,19,20-pentanor-15-dioxy-15-hydroxy-16-propoxy PGI$_2$-methylester

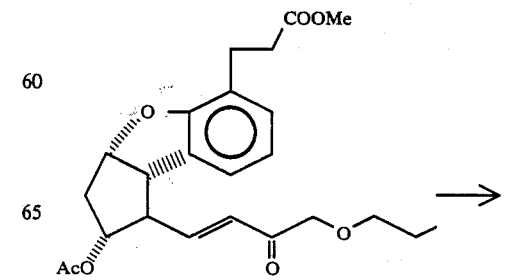

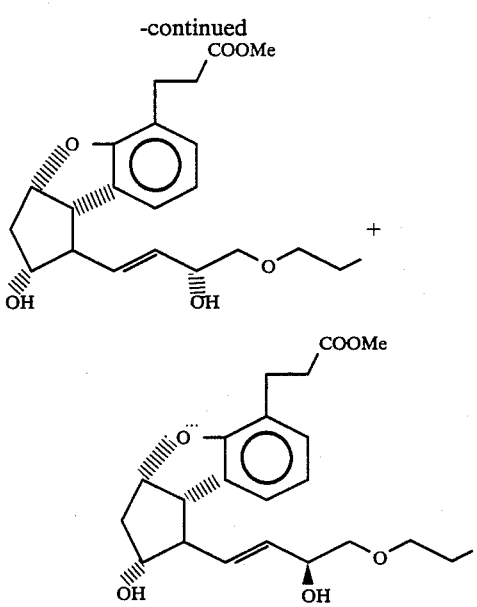

To a solution of 672 mg of 5,6,7-tetranor-4,8-inter-m-phenylene-2,17,18,19,20-pentanor-11,15-didehydroxy-11-acetoxy-15-oxo-16-propoxy $PGI_2$-methylester in 10 ml of methanol was added 870 mg of cerium chloride ($7H_2O$), and to the stirred resultant solution was added 59 mg of sodium borohydride in an ice bath and the mixture was stirred for 20 minutes. To the resultant reaction mixture was added 10 ml of saturated sodium bicarbonate and the resultant mixture was concentrated. After addition of 30 ml of water, the resultant mixture was extracted with 50 ml of ethyl acetate 3 times. The combined organic layers were washed with water and saturated sodium chloride solution, dried over sodium sulfate, and concentrated to give 621 mg of oily material. The material was dissolved in 10 ml of anhydrous methanol, and 54 ml of the sodium methoxide (5.22N) was added and the resultant solution was stirred under argon at room temperature for 2.5 hours. The resultant reaction solution was adjusted to pH4 with acetic acid and concentrated. To the residue was added 30 ml of water, the resultant mixture was extracted with 30 ml of ethyl acetate 3 times. The combined organic layers were washed with saturated aqueous sodium bicarbonate solution, water and saturated sodium chloride solution, dried over sodium sulfate, and concentrated to give 539 mg of an oily material. The material was purified by column chromatography (Merk Robar column, ethyl acetate:cyclohexane=1.8) to give 227 mg (yield 41%) of 5,6,7-tetranor-4,8-inter-m-phenylene-2,17,18,19,20-pentanor-15-dioxy-15-hydroxy-16-propoxy $PGI_2$-methylester and 177 mg (yield 32%) of more polar 5,6,7-tetranor-4,8-inter-m-phenylene-2,17,18,19,20-pentanor-16-propoxy $PGI_2$-methylester.

15-αisomer

Melting point: 81.5°–83.0° C. (ethyl acetate:n-hexane=5:7).

IR (KBr): cm$^{-1}$, 3350, 3050, 3030, 2975, 2950, 2900, 2870, 1735, 1715, 1600, 1480, 1455, 1445, 1425, 1380, 1365, 1300, 1285, 1270, 1255, 1240, 1195, 1180, 1160, 1140, 1120, 1100, 1080, 1065, 1055, 1025, 1000, 970, 960, 890, 870, 840, 820, 780, 750, 700, 560, 500.

NMR (400 MHz, $CDCl_3$): 0.94 (3H, t, J=7.3 Hz) 1.58–1.70 (2H, m) 1.95–2.07 (1H, m) 2.35–2.41 (1H, bs) 2.46 (1H, q, J=16.1 Hz, 7.3 Hz) 2.58–2.70 (3H, m) 2.80 (1H, bs) 2.85–2.93 (2H, m) 3.31–3.38 (1H, m) 3.42–3.55 (4H, m) 3.66 (3H, S) 3.91–3.98 (1H, bs) 4.32–4.40 (1H, bs) 5.10–5.18 (1H, m) 5.54–5.63 (1H, m) 5.75–5.84 (1H, m) 6.75 (1H, t, J=7.3 Hz) 6.97 (2H, d, J=7.3 Hz).

Mass (m/e): 390 (M+), 43 (b.p.).

High Mass: obsd. 390, 2031 calcd. 390, 2042.

15-βisomer

Melting point: 99.0°–100.0° C. (ethyl acetate:n-hexane=6:7).

IR (KBr): cm$^{-1}$, 3500, 3400, 2960, 2950, 2900, 2860, 2800, 1740, 1600, 1480, 1450, 1440, 1425, 1360, 1345, 1330, 1300, 1290, 1260, 1235, 1190, 1175, 1150, 1120, 1100, 1070, 1035, 1020, 1000, 980, 950, 890, 860, 850, 840, 820, 795, 770, 750, 700, 620, 600, 530, 510, 480, 440, 400.

NMR (400 MHz, $CDCl_3$): ppm 0.94 (3H, t, J=7.5 Hz) 1.59–1.62 (2H, m) 1.96–2.07 (2H, m) 2.50 (1H, q, J=15.6 Hz, 7.8 Hz) 2.56–2.72 (2H, m) 3.30–3.38 (1H, m) 3.41–3.55 (4H, m) 3.66 (3H, S) 3.91–4.00 (1H, bs) 4.32–4.40 (1H, bs) 5.10–5.19 (1H, m) 5.57–5.67 (1H, m) 5.76–5.86 (1H, m) 6.76 (1H, t, J=7.5 Hz) 6.94–7.04 (2H, m).

Mass (m/e): 390 (M+), 43 (b.p.).

High Mass: obsd. 390, 2056 calcd. 390, 2042.

EXAMPLE 222

5,6,7-trinor-4,8-inter-m-phenylene-2,17,18,19,20-pentanor-16-propoxy $PGI_2$

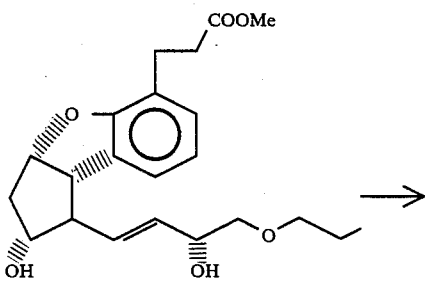

→

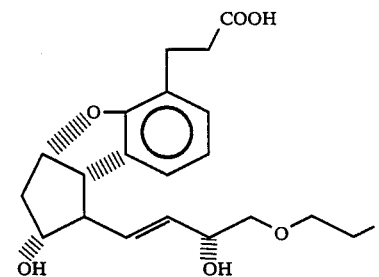

To a solution of 113 mg of 5,6,7-tetranor-4,8-inter-m-phenylene-16-propoxy-17,18,19,20-tetranor $PGI_2$-methylester in 5 ml of methanol was added 1.5 ml of the sodium hydroxide (1N), and the resultant mixture was stirred at room temperature overnight. The resultant reaction mixture was adjusted to pH4 with the hydrochloric acid (1N) and 30 ml of water was added, and the resultant mixture was extracted with 30 ml of ethyl acetate 3 times. The combined organic layers were washed with water and saturated sodium chloride solution, dried over sodium sulfate, and concentrated to give 107 mg (yield 98%) of 16-propoxy-17,18,19,20-tetranor-2,5,6,7-tetranor-4,8-inter-m-phenylene PGI$_2$ Melting point: 112.0°–114.5° C. (ethyl acetate:n-hexane=2:1).

IR (KBr): cm$^{-1}$, 3440, 3050, 2960, 2940, 2880, 2800, 1695, 1595, 1480, 1450, 1440, 1415, 1380, 1360, 1350, 1315, 1290, 1250, 1220, 1190, 1170, 1160, 1120, 1105, 1075, 1050, 1040, 1005, 980, 945, 920, 900, 860, 840, 820, 790, 765, 740, 700, 620, 600, 560, 520, 500, 460, 400.

NMR (400 MHz, CDCl$_3$): 0.94 (3H, t, J=7.5 Hz) 1.57–1.69 (2H, m) 1.95–2.06 (1H, m) 2.45 (1H, q, J=16.1 Hz, 8.6 Hz) 2.68–2.75 (3H, m) 2.81–2.98 (2H, m) 3.32–3.39 (1H, m) 3.42–3.54 (4H, m) 3.90–3.99 (1H, m) 4.31–4.40 (1H, bs) 5.08–5.18 (1H, m) 5.53–5.62 (1H, m) 5.75–5.84 (1H, m) 6.76 (1H, t, J=7.3 Hz).

Mass (m/e): 376 (M$^+$), 43 (b.p.).

High Mass: obsd. 376, 1879 calcd. 376, 1886.

EXAMPLE 223

5,6,7-trinor-4,8-inter-m-phenylene-2-nor-17(S)-methyl PGI$_2$-methylester

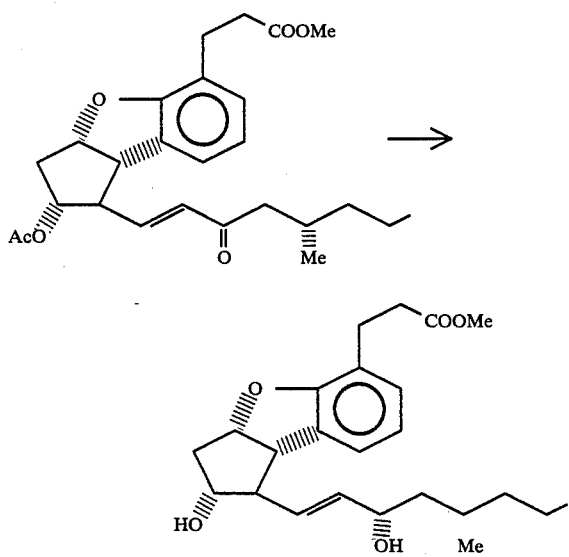

To a solution of 1.2 gr. of 5,6,7-trinor-4,8-inter-m-phenylene-2-nor-11,15-didehydroxy-11-acetoxy-15-oxo-17(S)-methyl PGI$_2$ methylester in 44 ml of anhydrous methanol was added 1.3 gr. of cerium chloride (7H$_2$O). To the resulting solution was added 125 mg of sodium borohydride in an ice bath, and the resultant mixture was stirred for 10 minutes. Saturated aqueous sodium bicarbonate was added to the resultant reaction mixture and the reaction mixture was concentrated. To the residue was added 20 ml of ethyl acetate, and the resultant mixture was filtered. The filtrate was separated and the water layer was extracted with 20, 10 and 5 ml of ethyl acetate. The combined organic layers were washed with 10 ml of water and 5 ml of saturated sodium chloride solution, dried, and concentrated to give 1.3 gr. of an oily material. The material was treated azeotropically with benzene 3 times and dissolved in 48 ml of anhydrous methanol, 0.144 ml of sodium methoxide (5.22N) was added, and the resultant solution was stirred under argon at room temperature for 3 hours and 30 minutes. The resultant reaction solution was adjusted to pH7 with acetic acid and concentrated. To the residue was added 50 ml of ethyl acetate, and the resultant mixture was washed with 5 ml of water and saturated sodium chloride solution, dried and concentrated to give 1.2 gr. of diol, which was purified by column chromatography (Merk Robar column Type B; ethyl acetate:cyclohexane (3:1) to give 240 mg of the titled compound.

$[\alpha]_D^{23°}$ +67.73 (C 3.36, CHCl$_3$).

IR (liquid film) cm$^{-1}$: 3350, 2950, 2920, 2850, 1740, 1595, 1440, 1360, 1295, 1250, 1190, 1160, 965, 925, 885, 860, 835, 745.

NMR (400 MHz, CDCl$_3$)δ: 0.90 (6H, m), 1.15 (1H, m), 1.20–1.60 (6H, m), 1.90 (1H, m), 2.35 (1H, q, J=8.3 Hz), 2.65 (2H, m), 2.88 (1H, t, J=7.0 Hz), 3.40 (1H, t, J=8.8 Hz), 3.65 (3H, S), 3.88 (1H, dd, J=14.1 Hz, 6.8 Hz), 4.2 (1H, dd, J=15.6 Hz, 9.0 Hz), 5.08 (1H, m), 5.52 (1H, dd, J=15.1 Hz, 7.3 Hz), 5.60 (1H, dd, J=15.1 Hz, 8.3 Hz) 6.73 (1H, t, J=7.3 Hz) 6.92 (1H, d, J=7.3 Hz) 6.97 (1H, d, J=7.3 Hz).

Mass (m/e) 402 (M$^+$), 384, 340.

EXAMPLE 224

5,6,7-trinor-4,8-inter-m-phenylene-2-nor-17(S)-methyl PGI$_2$

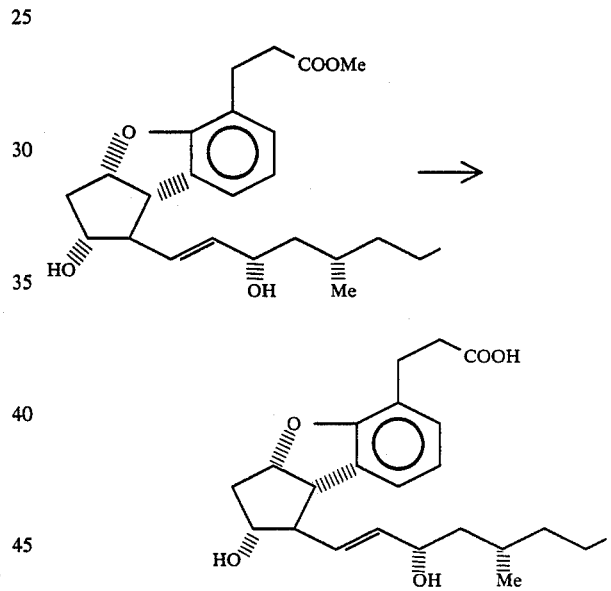

To a solution of 160 mg of 5,6,7-trinor-4,8-inter-m-phenylene-2-nor-17(S)-methyl PGI$_2$-methylester in 17 ml of methanol was added 4.45 ml of the sodium hydroxide (1N), and the resultant solution was stirred under argon at room temperature for 18 hours. The resultant reaction solution was concentrated. The residue was adjusted to pH4 with 4.45 ml of the hydrochloric acid (1N) in an ice bath, and the resultant mixture was extracted with ethyl acetate 3 times. The combined organic layers were washed with 5 ml of water and saturated sodium chloride solution, dried, and concentrated to give 120 mg of the titled compound, which was recrystallized from ethyl acetate-hexane to give 90 mg of a pure compound titled above.

Melting point: 61°–63° C.

IR (KBr) cm$^{-1}$: 3650–2200, 1705, 1595, 1450, 1420, 1345, 1305, 1270, 1205, 1150, 1080, 1025, 975, 950, 925, 862, 745.

NMR (CDCl$_3$) δ: 1.90 (6H, m), 1.15 (1H, m) 1.20–1.55 (6H, m), 1.90 (1H, m), 2.30 (1H, q, J=8.3 Hz), 2.62 (3H, m), 2.85 (2H, m), 3.35 (1H, t, 8.8 Hz), 3.83 (1H, dd, J=15.2 Hz, 6.7 Hz), 4.17 (1H, dd, J=14.2 Hz, 6.9 Hz), 5.04 (1H, m), 5.45 (1H, dd, J=15.1 Hz, 7.2 Hz), 5.55 (1H, dd, J=15.1 Hz, 8.8 Hz), 6.71 (1H, t, J=7.8 Hz), 6.86 (1H, d, J=7.3 Hz), 6.90 (1H, d, J=6.9 Hz).

Mass (m/e): 388(Mt) 370, 326.

High resolution Mass obs. 388, 2240; Error −1.0 mU U.S. 8.0 Composition $C_{23}{}^1H_{32}O_5$.

EXAMPLE 225

5,6,7-trinor-4,8-inter-m-phenylene-2,18,19,20-tetranorethoxy PGI2-methylester

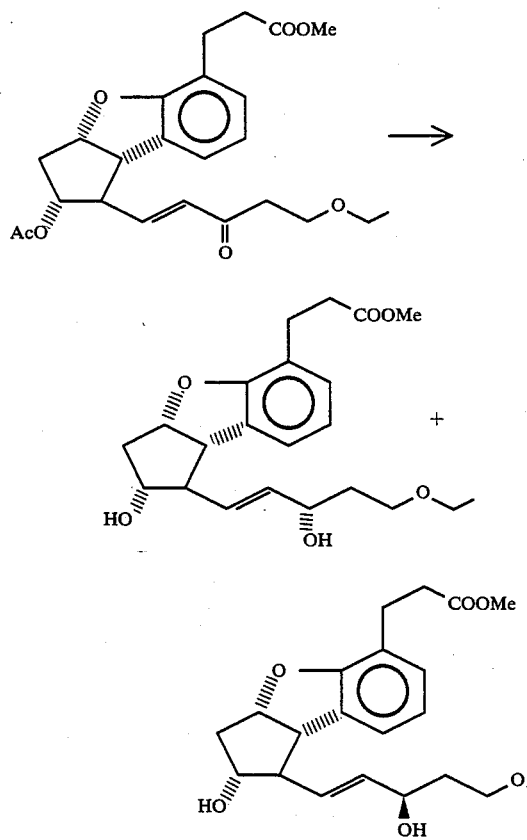

To a stirred solution of 1.14 gr. (2.65 mmol) of 5,6,7-trinor-4,8-inter-m-phenylene-2,18,19,20-terano-11,15-dihydroxy-11-acetoxy-15-oxo-17-ethoxy PGI2-methylester in 60 ml of methanol was added 990 mg (2.65 mol) of cerium chloride (7H2O). To the solution was added 151 mg (3.98 mmol) of sodium borohydride in an ice bath, and the resultant mixture was stirred for 10 minutes. To the resulant reaction mixture was added 20 ml of saturated sodium bicarbonate, and the resultant mixture was concentrated. To the residue were added 30 ml of water and 100 ml of ethyl acetate, and the resultant mixture was filtered. The precipitate was washed with 30 ml of ethyl acetate 3 times. The combined filtrate was washed with 30 ml of water and saturated sodium chloride solution, dried over sodium sulfate, and concentrated to give 1.04 gr. of an oily material. The material was dissolved in 25 ml of anhydrous methanol. To the stirred solution was added 0.117 ml (0.613 mmol) of the sodium methoxide (5.22N) under argon atmosphere at room temperature and the solution was stirred at room temperature for 3 hours. To the resultant mixture was added 0.05 ml of acetic acid, and the resultant mixture was concentrated. To the residue was added 20 ml of water and the resultant product was extracted with 50 ml of ethyl acetate 2 times. The combined organic layers were washed with 20 ml of water and saturated sodium chloride solution, dried over sodium sulfate, and concentrated. The residue was purified by a Robar colummn (ethyl acetate:cyclohexane=2:1) to give 451 mg (yield 47.2%) of 5,6,7-trinor-4,8-inter-m-phenylene-2,18,19,20-tetranor-17-ethoxy-15-dehydroxy-15β-hydroxy PGI2-methylester and 430 mg (yield 45%) of 5,6,7-trinor-4,8-inter-m-phenylene-2,18,19,20-tetranor-17-ethoxy PGI2-methylester.

Analytical value of 15-β isomer

IR (liquid film) ν: 3400, 2970, 2930, 2860, 1730, 1595, 1450, 1370, 1350, 1300, 1255, 1190, 1150, 1100, 1065, 1030, 970, 920, 885, 860, 840, 780, 760, 740.

NMR (CDCl3): δ: 1.22 (3H, t, J=7.1 Hz), 1.75–1.9, (2H, m), 2.00 (1H, ddd, J=4.9, 8.5, 13.7 Hz), 2.05–2.1 (1H, m), 2.49 (1H, q, J=8.0 Hz), 2.55–2.75 (3H, m), 2.85–2.95 (2H, m), 3.35–3.4 (1H, m), 3.45–3.55 (3H, m), 3.6–3.75 (2H, m), 3.66 (3H, S), 3.9–4.0 (1H, m), 4.3–4.4 (1H, m), 5.15 (1H, ddd, J=4.9, 7.3, 8.8 Hz), 5.67 (1H, dd, J=4.9, 15.4 Hz), 5.74 (1H, d, d, J=8.0, 15.4 Hz), 6.76 (1H, t, J=7.5 Hz), 6.97 (1H, d, J=7.5 Hz), 7.01 (1H, d, J=7.5 Hz).

Mass (m/e): 390 (M+), 372 (M+—H2O).

High resolution Mass: OBSD 390,2047 ERROR 0.5 mmU COMPOSITION $C_{22}H_{30}O_6$.

Analytical value of 15-α isomer.

Melting point: 62.3° C.-63.2° C. (ethyl acetate:cyclohexane=2:1).

IR (KBr) ν: 3370, 2970, 2930, 2870, 1730, 1595, 1445, 1375, 1325, 1295, 1250, 1185, 1175, 1155, 1130, 1120, 1100, 1085, 1060, 1030, 1005, 960, 940, 910, 890, 875, 860, 830, 790, 760, 730, 620, cm−1.

NMR (CDCl3) δ: 1.22 (3H, t, J=6.8 Hz), 1.8–1.9 (2H, m), 1.98 (1H, ddd, J=5.4, 8.8, 13.7 Hz), 2.4–2.5 (2H, m), 2.6–2.7 (3H, m), 2.85–2.95 (2H, m), 3.4–3.55 (4H, m), 3.6–3.75 (2H, m), 3.66 (3H, s) 3.9–4.0 (1H, m), 5.13 (1H, ddd, J=5.4, 7.3, 8.8 Hz), 5.64 (1H, d, d, J=5.5, 15.5 Hz), 5.71 (1H, d, d, J=7.8, 15.5 Hz), 6.75 (1H, t, J=7.3 Hz), 6.97 (2H, d, J=7.3 Hz).

Mass (m/e): 390 (M+), 372 (M+—H2O).

Anal. calcd. for for $C_{24}H_{30}O_7$: C(%); 67.67 H(%); 7.74 Found: C(%); 67.56 H(%); 7.69.

EXAMPLE 226

5,6,7-trinor-4,8-inter-m-phenylene-2,18,19,20-tetranor-17-ethoxy PGI2

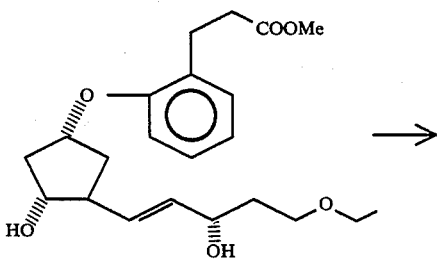

155
-continued

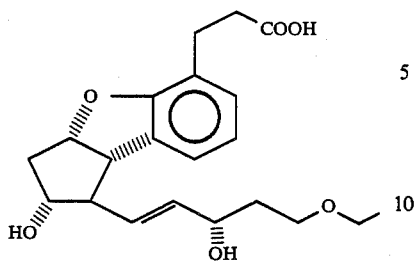

To a stirred solution of 334 mg (0.86 mmol) of 5,6,7-trinor-4,8-inter-m-phenylene-2,18,19,20-tetranor-17-ethoxy PGI₂-methylester in 30 ml of methanol was added 6.95 ml (6.85 mmol) of the sodium hydroxide (0.986N) in an ice bath, and the resultant solution was further stirred for 5 hours. To the resultant reaction mixture was 7 ml (7 mmol) of hydrochloric acid (1N), and the resultant mixture was concentrated. After addition of 20 ml of water, the resultant mixture was extracted with 50 ml of ethyl acetate 2 times. The combined organic layers were washed with 10 ml of water and saturated sodium chloride solution, dried over sodium sulfate, and concentrated to afford crude crystal which was recrystallized from 1.0 ml of ethyl acetate and 0.4 ml of n-hexane to give 164 mg (yield 51%) of the white crystal of 5,6,7-trinor-4,8-inter-m-phenylene-2,18,19,20-tetranor-17-ethoxy PGI₂.

Melting point: 96.3°–97.1° C. (ethyl acetate:n-hexane=2:1).

IR (KBr) ν: 3380, 2970, 2925, 2860, 1710, 1595, 1450, 1370, 1350, 1240, 1190, 1150, 1090, 1060, 1040, 1000, 965, 930, 780, 760, 740.

NMR(COCl₃) δ: 1.21 (3H, S), 1.75–1.9 (2H, m) 1.96 (1H, ddd, J=5.1, 9.0, 13.4 Hz) 2.40 (1H, q, J=8.3 Hz), 2.6–2.75 (3H, m), 2.8–3.0 (2H, m), 3.42 (1H, t, J=8.3 Hz), 3.51 (2H, q, J=7.1 Hz), 3.55–3.7 (2H, m) 3.85–4.0 (1H, m), 4.3–4.4 (1H, m) 4.4–5.4 (2H, m), 5.0–5.1 (1H, m) 5.59 (1H, dd, J=6.0, 15.4 Hz), 5.67 (1H, dd, J=8.3, 75.4 Hz), 6.74 (1H, t, J=7.5 Hz) 6.94 (1H, d, J=7.5 Hz), 6.96 (1H, d, J=7.5 Hz).

Mass (m/e): 376 (M⁺), 358 (M⁺—H₂O).

Anal. calcd. for C₂₃H₂₈O₇: C(%); 67.00 H(%); 7.50 Found: C(%); 66.85 H(%); 7.58.

EXAMPLE 227

5,6,7-trinor-4,8-inter-m-phenylene-2,18,19,20-tetranor-17-ethoxy-15-dehydroxy-15β-hydroxy PGI₂

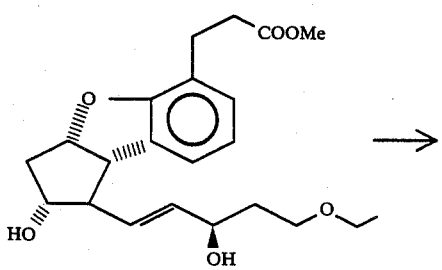

156
-continued

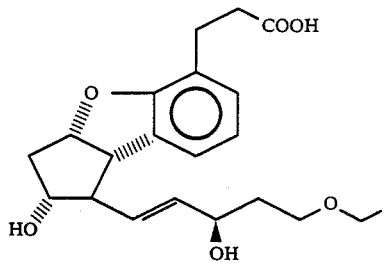

To a stirred solution of 369 mg (0.95 mmol) of 5,6,7-trinor-4,8-inter-m-phenylene-2,18,19,20-tetranor-17-ethoxy-15-dehydroxy-15β-hydroxy PGI₂ methylester in 30 ml of methanol was added 8.6 ml (8.5 mmol) of the sodium hydroxide (0.986N) in an ice bath, and the resultant solution was stirred at room temperature for 5 hours. To the resultant reaction mixture was 8.5 ml (8.5 mmol) of hydrochloric acid (1N), and the resultant mixture was concentrated. To the residue was added 20 ml of water, and the resultant product was extracted with 50 ml of ethyl acetate 2 times. The combined organic layers were washed with 10 ml of water and saturated sodium chloride solution, dried over sodium sulfate and concentrated. The obtained crystal was recrystallized from 1.0 ml of ethyl acetate and 0.4 ml of n-hexane to give 273 mg (yield 76.8%) of the white crystal of 5,6,7-trinor-4,8-inter-m-phenylene-2,18,19,20-tetranor-17-ethoxy-15-dehydroxy-15β-hydroxy PGI₂.

Melting point: 111.2°–111.5° C. (ethyl acetate:n-hexane=2:1).

IR (KBR) ν: 3330, 2970, 2925, 2870, 1730, 1445, 1375, 1320, 1260, 1160, 1120, 1080, 1020, 980, 855, 790, 745, cm⁻¹.

NMR (CDCl₃) δ: 1.22 (3H, S), 1.75–1.9 (2H, m), 2.0–2.1 (1H, m), 2.49 (1H q, J=7.8 Hz) 2.55–2.8 (3H, m), 2.8–3.0 (2H, m), 3.45–3.6 (3H, m), 3.6–3.8 (2H, m), 3.9–4.0 (1H, m) 3.1–4.2 (2H, m), 4.3–4.4 (1H, m), 5.1–5.2 (1H, m), 5.65 (1H, dd, J=4.9, 15.1 Hz) 5.74 (1H, dd, J=7.8, 15.1 Hz), 6.76 (1H, d, J=7.3 Hz), 6.98 (1H, d, J=7.3 Hz), 7.02 (1H, d, J=7.3 Hz)

Mass (m/e): 376 (M⁺), 358 (M⁺—H₂O).

Anal. calcd. for C₂₃H₂₈O₇: C(%); 67.00 H(%); 7.50 Found: C(%); 66.92 H(%); 7.57.

EXAMPLE 228

5,6,7-trinor-4,8-inter-m-phenylene-2,17,18,19,20-pentanor-16-phenoxy PGI₂-methylester and
5,6,7-trinor-4,8-inter-m-phenylene-2,17,18,19,20-pentanor-15-dehydroxy-15β-hydroxy-16-phenoxy PGI₂ methylester

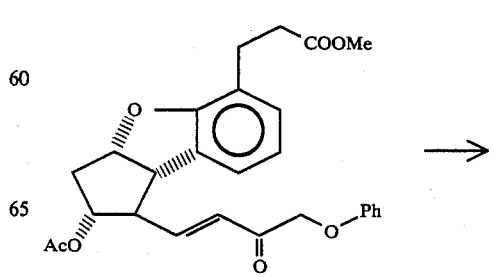

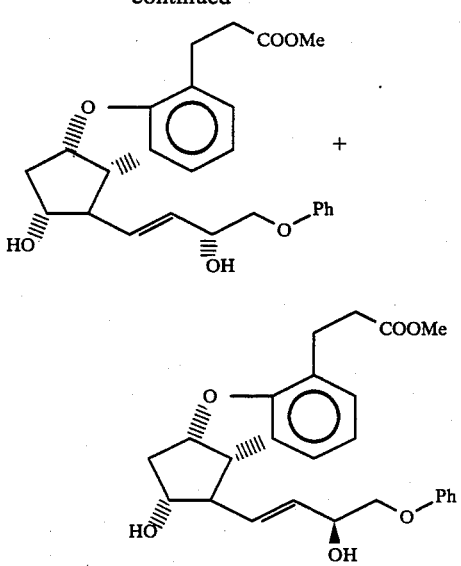

+

To a solution of 1.25 gr. (2.69 mmol) of 5,6,7-trinor-4,8-inter-m-phenylene-2,17,18,19,20-tetranor-11,15-dideoxy-11-acetoxy-15-oxo-16-phenoxy PGI$_2$ methylester in 50 ml of methanol was added 1.30 gr. (3.50 mmol) of cerium chloride (7H$_2$O). After the resultant mixture was cooled to 0° C., 122 mg (3.23 mmol) sodium hydroxide was added, and the resultant mixutre was stirred at 0° C. for 10 minutes. To the resultant reaction mixture was added 15 ml of saturated aqueous sodium bicarbonate, and the resultant mixture was concentrated. To the residue was added ethyl acetate, the resultant mixture was filtered and, the resultant precipitate was washed with ethyl acetate. The combined filtrate was washed with water and saturated sodium chloride solution, dried, and concentrated to give 1.20 gr. of an oily material, which was dissolved in 20 ml of anhydrous material. After addition of 0.13 ml (0.68 mmol) of the sodium methoxide (5.22N) the resultant solution was stirred for 2 hours. The resultant reaction mixture was concentrated and adjusted to pH7 with acetic acid, and the residue was dissolved in ethyl acetate. The resultant solution was washed with the saturated aqueous sodium bicarbonate and saturated sodium chloride solution, dried over magnesium sulfate, and concentrated. The resulting crude crystal was recrystallized from ethyl acetate to give 250 mg of 5,6,7-trinor-4,8-inter-m-phenylene-2,17,18,19,20-pentanor-15-dehydroxy-15-$\beta$-hydroxy-16-phenoxy PGI$_2$. The resulting mother liquor was purified by column chromatography (acetonitiril:methylene chloride=1:3) to 128 mg of 5,6,7-trinor-4,8-inter-m-phenylene-2,17,18,19,20-tetranor-15-dehydroxy-15-$\beta$-hydroxy-16-phenoxy PGI$_2$-methylester and 317 mg of 5,6,7-trinor-4,8-inter-m-phenylene-2,17,18,19,20-pentanor-16-phenoxy PGI$_2$ methylester.

Yield: 15-$\alpha$ isomer 28%, 15-$\beta$ isomer 33%.

15-$\alpha$ isomer IR (liquid film): cm$^{-1}$ 3400, 2920, 1730, 1600, 1490, 1450, 1240, 1070, 1035, 970, 890, 860, 750, 690.

NMR (400 MHz, CDCl$_3$) $\delta$: 2.00 (1H, ddd, J=5.1, 9.0, 13.9 Hz) 2.36 (1H, d, J=4.9 Hz), 2.48 (1H, q, J=8.6 Hz), 2.6-2.75 (3H, m), 2.80 (1H, d, J=3.4 Hz), 2.85-3.0 (2H, m), 3.47 (1H, t, J=8.6 Hz), 3.66 (3H, S), 3.93 (1H, dd, J=7.8, 9.3 Hz) 3.9-4.0 (1H, m), 4.03 (1H, dd, J=3.9, 9.3 Hz), 4.5-4.6 (1H, m) 5.13 (1H, ddd, J=5.1, 7.3, 8.6 Hz) 5.69 (1H, dd, J=6.8, 15.4 Hz) 5.88 (1H, dd, J=8.6, 15.4 Hz) 6.74 (1H, t, J=7.3 Hz) 6.85-7.0 (5H, m), 7.2-7.35 (2H, m).

Mass (m/e): 424 (M+), 317 (M+—CH$_2$OPh).

15-$\beta$ isomer

Melting point: 130°-130.5° C. (ethyl acetate).

IR (KBr): cm$^{-1}$ 3290, 2920, 1735, 1600, 1580, 1490, 1450, 1440, 1360, 1310, 1290, 1230, 1200, 1170, 1150,1080, 1035 970, 950, 890, 870, 860, 840, 760, 740, 700, 520.

NMR (400 MHz, COCl$_3$) $\delta$: 1.85 (1H, d, J=5.5 Hz) 2.03 (1H, ddd, J=5.1, 8.4, 13.6 Hz) 2.5-2.6 (2H, m), 2.6-2.75 (3H, m) 2.85-3.0 (2H, m), 3.53 (1H, t, J=8.3 Hz), 3.66 (3H, S), 3.92 (1H, dd, J=7.8, 9.3 Hz) 3.95-4.05 (1H, m), 4.06 (1H, dd, J=3.4, 9.3 Hz), 4.55-4.65 (1H, m) 5.16 (1H, ddd, J=5.1, 7.2, 8.4 Hz) 5.73 (1H, dd, J=5.6, 15.5 Hz) 5.91 (1H, dd, J=8.4, 15.5 Hz) 6.76 (1H, t, J=7.3 Hz) 6.9-7.1 (5H, m), 7.3-7.4 (2H, m).

Mass (m/e): 424 (M+) 406 (M+—H$_2$O) 317 (M+—CH$_2$OPh).

Anal. calcd. for C$_{25}$H$_{28}$O$_6$: C(%); 70.74 H(%) 6.65 Found: C(%); 70.66 H(%) 6.58.

EXAMPLE 229

5,6,7,-trinor-4,8-inter-m-phenylene-2,17,18,19,20-pentanor-16-phenoxy PGI$_2$

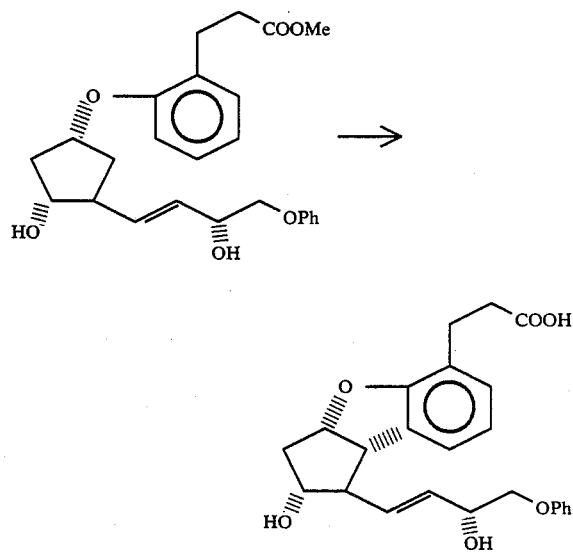

To a solution of 248 mg (0.58 mmol) of 5,6,7-trinor-4,8-inter-m-phenylene-2,17,18,19,20-pentanor-16-phenoxy PGI$_2$ methylester in 15 ml of methanol was added 3 ml of the sodium hydroxide (1N), the resultant mixture was stirred at room temperature for 18 hours. The resultant reaction mixture was concentrated. Water was added to its residue, the resultant mixture was adjusted to pH4 with hydrochloric acid (3N), and the resultant mixture was extracted with ethyl acetate. The combined organic layers were washed with water and saturated sodium chloride solution, dried and concentrated to give 231 mg of crude crystal, which was recrystallized from ethyl acetate—cyclohexane to give 5,6,7-trinor-4,8-inter-m-phenylene-2,17,18,19,20-pentanor-16 phenoxy PGI$_2$ (yield 78%).

Melting point: 150°-150.5° C.

IR (KBr): cm$^{-1}$, 3570, 3460, 2940, 1730, 1600 1590, 1495, 1450, 1400, 1380, 1335, 1285, 1250, 1200, 1170, 1080, 1050, 1030, 1010, 975, 940, 900, 869, 840, 800, 750, 700, 580, 550, 520, 440.

NMR (400 MHz, DMSO-db) δ: 1.69 (ddd, J=5.9, 9.8, 12.7 Hz) 2.15–2.25 (1H, m), 2.45–2.6 (3H, m) 3.3–3.4 (1H, m), 2.71 (2H, t, J=7.6 Hz) 3.7–3.85 (1H, m), 3.91 (2H, t, J=5.9 Hz) 4.3–4.4 (1H, m), 4.8–4.9 (1H, m) 5.06 (1H, br.q J=7–8 Hz) 5.2–5.3 (1H, m) 5.62 (1H, dd, J=5.9, 15.5 Hz) 5.83 (1H, dd, J=7.6, 15.5 Hz) 6.64 (1H, t, J=7.6 Hz) 6.9–7.0 (5H, m) 7.29 (1H, d, J=7.3 Hz), 7.31 (1H, d, J=8.3 Hz).

Mass (m/e): 410 (M+) 392 (M+—H$_2$O) 303 (M+—CH$_2$OPh).

Anal. calcd. for C$_{24}$H$_{26}$O$_6$: C(%); 70.23 H(%) 6.39 Found: C(%); 70.15 H(%) 6.32.

EXAMPLE 230

5,6,7-trinor-4,8-inter-m-phenylene-2,17,18,19,20-pentanor-15-deoxy-15-β-hydroxy-16-phenoxy PGI$_2$

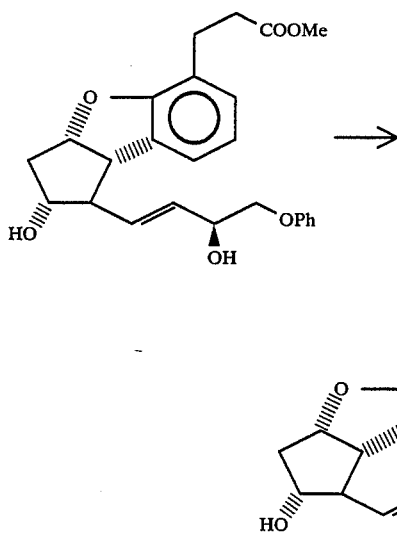

To a solution of 198 mg (0.47 mmol) of 5,6,7-trinor-4,8-inter-m-phenylene-2,17,18,19,20-pentanor-15-dehydroxy-15-β-hydroxy-16-phenoxy PGI$_2$ methylester in 15 ml of methanol was added 3 ml of the aqueous sodium hydroxide (1N), the resultant mixture was stirred at room temperature for 24 hours. The resultant reaction mixture was concentrated. Water was added to the residue, the resultant mixture was adjusted to pH4 with hydrochloric acid (3N) and the resultant mixture was extracted with ethyl acetate. The organic layer was washed with water and saturated sodium chloride solution, dried and concentrated to give 170 mg of a crude crystal, which was recrystallized from ethyl acetate to give 150 mg of 5,6,7-trinor-4,8-inter-m-phenylene-2,17,18,19,20-pentanor-15-dehydroxy-15-β-hydroxy-16-phenoxy PGI$_2$ (yield 78%).

Melting point: 170°–170.5° C.

IR (KBr): cm$^{-1}$ 3260, 2975, 2940, 2920, 2875, 1730, 1655, 1600, 1585, 1500, 1450, 1380, 1300, 1285, 1230, 1190, 1140, 1090, 1060, 1040, 970, 950, 900, 890, 860, 840, 755, 695, 650, 520, 470.

NMR (400 MHz, DMSO-db) δ: 1.69 (1H, ddd, J=6.1, 10.0, 12.9 Hz) 2.1–2.25 (1H, m), 2.4–2.6 (3H, m) 2.71 (2H, t, J=7.6 Hz), 3.2–3.4 (1H, m) 3.7–3.8 (1H, m), 3.89 (1H, dd, J=6.8, 9.8 Hz), 3.94 (1H, dd, J=4.4, 9.8 Hz), 4.3–4.4 (1H, m), 4.8–4.9 (1H, m) 5.06 (1H, br, q, J=7–8 Hz), 5.2–5.3 (1H, m), 5.66 (1H, dd, J=5.7, 15.5 Hz), 5.85 (1H, dd, J=8.0, 15.5 Hz) 6.67 (1H, t, J=7.3 Hz), 6.9–7.0 (5H, m), 7.29 (1H, d, J=7.3 Hz), 7.31 (1H, d, J=8.8 Hz).

Mass (m/e): 410 (M+), 392 (M+—H$_2$O), 303 (M+—CH$_2$OPh).

Anal. calcd. for C$_{24}$H$_{26}$O$_6$: C(%); 70.23 H(%); 6.39 Found: C(%); 70.27 H(%); 6.28.

EXAMPLE 231

5,6,7-trinor-4,8-inter-m-phenylene-2,17,18,19,20-pentanor-16-(cyclopentyloxy) PGI$_2$-methylester and 5,6,7-trinor-4,8-inter-m-phenylene-2,17,18,19,20-pentanor-15-dehydroxy-15-hydroxy-16-(cyclopentyloxy) PGI$_2$ methylester

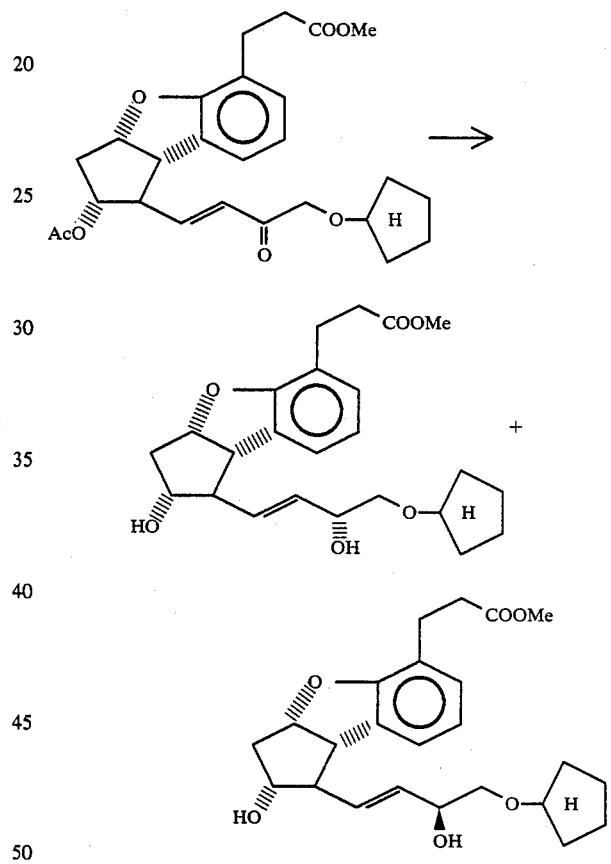

To a solution of 1.57 gr. (3.44 mmol) of 5,6,7-trinor-4,8-inter-m-phenylene-2,17,18,19,20-pentanor-11,15-dideoxy-11-acetoxy-15-oxo-16-(cyclopentyloxy) PGI$_2$ methylester in 50 ml of methanol was added 1.67 gr. (4.47 mmol) of cerium chloride (7H$_2$O) at 0° C. and 156 mg (4.13 mmol) sodium borohydride was added. After the resultant reaction mixture was stirred at 0° C. for 10 min, 15 ml of the saturated aqueous sodium bicarbonate was added, the resultant reaction mixture was concentrated. Ethyl acetate was added to the residue and the resultant mixture was filtered. The filtrate was washed with water and saturated sodium chloride solution, dried and concentrated to give 1.40 gr. of an oily material. The oil was dissolved in 20 ml of anhydrous methanol. To the resultant solution was added 0.16 ml (0.84 mmol) of the sodium methoxide (5.22N), and the resultant mixture was stirred at room temperature for 2 hours. The resultant reaction solution was adjusted to pH7 with acetic acid and concentrated. The residue was dissolved in ethyl acetate. The resultant solution was washed with water and saturated sodium chloride solution, dried over magnesium sulfate and concentrated to give 1.23 gr. of oily material, which was separated by column chromatography (Merk Robar column ethyl acetate: cyclohexane=5:1) to give 591 mg (yield 41%) of 5,6,7-trinor-4,8-inter-m-phenylene-2,17,18,19,20-pentanor-15-dehydroxy-15-β-hydroxy-16-(cyclopentyloxy) PGI$_2$ methylester (less polar material) and 509 mg (yield 36%) of 5,6,7-trinor-4,8-inter-m-phenylene-2,17,18,19,20-pentanor-16-(cyclopentyloxy) PGI$_2$ methylester.

15-α isomer

Melting point: 71.5°–72.5° C. (ethyl acetate-n-hexane).

IR (KBr): cm$^{-1}$ 3425, 2950, 2860, 1730, 1590, 1450, 1360, 1300, 1250, 1190, 1120, 1100, 1070, 1030, 1000, 980, 945, 900, 885, 860, 830, 780, 740, 620, 600, 550, 530, 500, 400, 330.

NMR (400 MHz, CDCl$_3$)δ: 1.5–1.85 (8H, m), 2.00 (1H, ddd, J=5.3, 8.7, 13.8 Hz), 2.21 (1H, d, J=4.9 Hz), 2.47 (1H, q, J=8.2 Hz), 2.6–2.7 (3H, m), 2.72 (1H, d, J=2.9 Hz), 2.85–3.0 (2H, m), 3.27 (1H, dd, J=8.2, 9.2 Hz), 3.4–3.55 (2H, m), 3.66 (3H, S), 3.9–4.0 (2H, m), 4.3–4.4 (1H, m), 5.14 (1H, ddd, J=5.3, 7.2, 9.2 Hz) 5.59 (1H, dd, J=6.1, 15.4 Hz), 5.78 (1H, dd, J=8.2, 15.4 Hz), 6.76 (1H, t, J=7.3 Hz), 6.972 (1H, d, J=7.3 Hz), 6.982(1H, d, J=7.3 Hz).

Mass (m/e): 416 (M+) 398 (M+—H$_2$O) 317 (M+—CH$_2$O$_5$H$_9$).

Anal. calcd. for C (%) H (%) C$_{24}$H$_{32}$O$_6$: 69.21 7.74 Found: 69.21 7.76

15-β isomer

Melting point: 106°–107° C. (ethyl acetate-n-hexane).

IR (KBr): cm$^{-1}$ 3530, 2960, 1730, 1600, 1450, 1370, 1350, 1300, 1270, 1250, 1200, 1180, 1130, 1090, 1050, 1010, 980, 950, 900, 890, 860, 700, 600, 520, 480.

NMR (400 MHz, CDCl$_3$)δ: 1.5–1.9 (8H, m), 1.85 (1H, d, J=4.9 Hz) 2.01 (1H, ddd, J=5.1, 8.5, 13.7 Hz) 2.49 (1H, q, J=8.1 Hz), 2.6–2.75 (4H, m) 2.85–3.0(2H, m), 3.28 (1H, dd, J=8.1, 9.2 Hz), 3.45–3.55 (2H, m), 3.66 (3H, S) 3.9–4.0 (2H, m), 4.25–4.35 (1H, m) 5.15 (1H, ddd, J=5.1, 7.2, 9.2 Hz) 5.62 (1H, dd, J=5.6, 15.6 Hz) 5.81 (1H, ddd, J=1.4, 8.1, 15.6 Hz) 6.77 (1H, t, J=7.6 Hz) 6.97 (1H, d, J=7.6 Hz), 7.01 (1H, d, J=7.6 Hz).

Mass (m/e): 416 (M+) 398 (M+—H$_2$O) 317 (M+—CH$_2$OC$_5$H$_9$).

Anal. calcd. for C$_{24}$H$_{32}$O$_6$: C(%); 69.21 H(%); 7.74 Found: C(%); 69.16 H(%); 7.78.

EXAMPLE 232

5,6,7-trinor-4,8-inter-m-phenylene-2,17,18,19,20-pentanor-16-(cyclopentyloxy) PGI$_2$

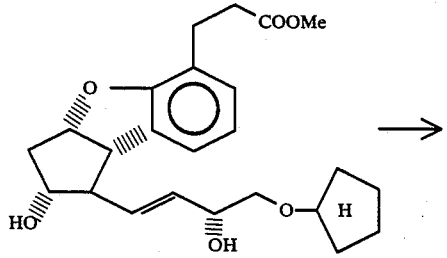

-continued

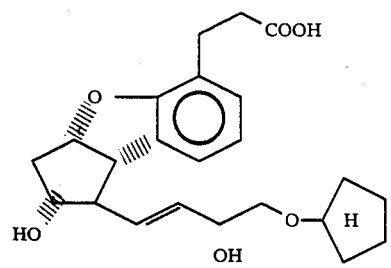

To a solution of 250 mg (0.60 mmol) of 5,6,7-trinor-4,8-inter-m-phenylene-2,17,18,19,20-pentanor-16-(cyclopentyloxy) PGI$_2$ methylester in 15 ml of methanol was added a solution of 3 ml of sodium hydroxide (1N). The solution was stirred at room temperature for 24 hours. The resultant reaction mixture was concentrated. Water was added to the residue, and the resultant mixture was adjusted to pH4 with hydrochloric acid (1N) and the resultant mixture was extracted with ethyl acetate. The organic layer was washed with saturated sodium chloride solution, dried and concentrated to give 244 mg. of a crude crystal, which was recrystallized from ethanol to give 185 mg (yield 77%) of 5,6,7-trinor-4,8-inter-m-phenylene-2,17,18,19,20-pentanor-16-(cyclopentyloxy) PGI$_2$.

Melting point: 147°–147.5° C.

IR (KBr): cm$^{-1}$ 3400, 2950, 2870, 1695, 1600, 1450, 1435, 1410, 1380, 1350, 1310, 1250, 1210, 1190, 1110, 1100, 1080, 1050, 1030, 1000, 980, 950, 900, 860, 790, 765, 740, 690, 600, 555, 510, 400.

NMR (400 MHz, DMSO-d$_6$)δ: 1.4–1.8 (9H, m), 2.14 (1H, q, J=8.3 Hz) 2.4–2.6 (3H, m), 2.65–2.80 (2H, m), 3.2–3.5 (3H, m), 3.7–3.8 (1H, m), 4.9–4.0 (1H, m), 4.05–4.15 (1H, m), 4.7–4.9 (1H, m), 5.05 (1H, q, J=7.5 Hz), 5.50 (1H, dd, J=6.3, 15.2 Hz), 5.71 (1H, dd, J;32 8.3, 15.2 Hz); 6.70 (1H, t, J=7.3 Hz), 6.95 (1H, br.d, J=7 Hz), 6.97 (1H, br.d, J=7 Hz).

Mass 402 (M+) 384 (M+—H$_2$O). Anal. calcd. for C$_{23}$H$_{30}$O$_6$: C(%); 68.63 H(%); 7.51 Found: C(%); 68.28 H(%); 7.57.

EXAMPLE 233

5,6,7-trinor-4,8-inter-m-phenylene-2,17,18,19,20-pentanor-15-dehydroxy-15-β-hydroxy-16-(cyclopentyloxy) PGI$_2$

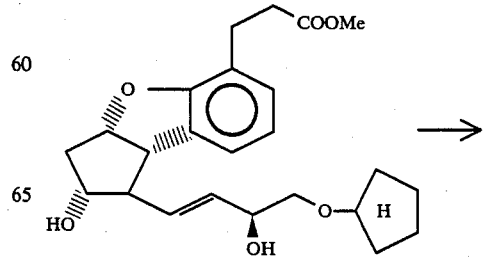

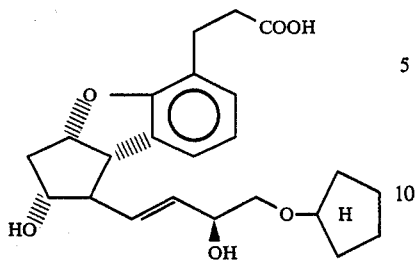

To a solution of 300 mg (0.72 mmol) of 5,6,7-trinor-4,8-inter-m-phenylene-2,17,18,19,20-pentanor-15-dehydroxy-15-β-hydroxy-16-(cyclopentyloxy) PGI2 methylester in 15 ml of methanol was added a solution of 4 ml of sodium hydroxide (1N) and the solution was stirred at room temperature for 24 hours. The resultant reaction mixture was concentrated, water was added to the residue, and the resultant solution was adjusted to pH4 with hydrochloric acid (1N) and the resultant product was extracted with ethyl acetate. The organic layer was washed with saturated sodium chloride solution, dried and concentrated to give 261 mg. of a crude crystal, which was recrystallized from ethanol-ethyl acetate-cyclohexane to give 174 mg (yield 60%) of 5,6,7-trinor-4,8-inter-m-phenylene-2,17,18,19,20-pentanor-15-dehydroxy-15-β-hydroxy-16-(cyclopentyloxy) PGI2.

Melting point: 143°–144° C.

IR (KBr): cm$^{-1}$ 3530, 3270, 2960, 1730, 1600, 1455, 1370, 1345, 1330, 1310, 1280, 1250, 1180, 1155, 1090, 1040, 1015, 970, 940, 900, 870, 840, 790, 770, 750, 720, 600, 490, 450, 400.

NMR (400 MHz, DMSO-d$_6$)δ: 1.4–1.8 (9H, m), 2.15 (1H, q, J=8.5 Hz) 2.45–2.6 (3H, m), 2.7–2.8 (2H, m) 3.27 (2H, d, J=5.9 Hz), 3.39 (1H, t, J=8.5 Hz), 3.7–3.8 (1H, m), 3.9–4.0 (1H, m), 4.05–4.15 (1H, m), 4.8–4.9 (1H, m), 5.05 (1H, q, J=8.5 Hz), 5.53 (1H, dd, J=5.4, 15.5 Hz), 5.74 (1H, dd, J=8.5, 15.5 Hz), 6.70 (1H, t, J=7.8 Hz), 6.95 (1H, d, J=7.8 Hz), 6.97 (1H, d, J=7.8 Hz).

Mass (m/e): 402 (M+) 384 (M+—H$_2$O). Anal. calcd. for C$_{23}$H$_{30}$O$_6$: C(%); 68.63 H(%); 7.51 Found: C(%); 68.43 H(%); 7.55.

EXAMPLE 234

5,6,7-trinor-4,8-inter-m-phenylene-1-decarbohydroxy-2-hydroxy-16,16-dimethyl PGI2

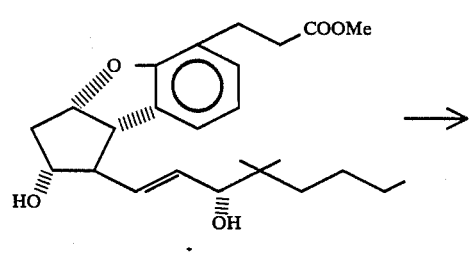

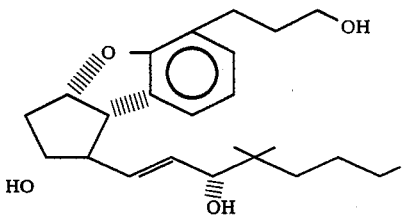

To a solution of 62 mg of 5,6,7-trinor-4,8-inter-m-phenylene-2-nor-16,16-dimethyl PGI2 methylester in 5 ml of anhydrous toluene was added 0.5 ml of diisobutylaluminum hydride (DIBAH) under argon at −78° C., and the resultant mixture was stirred at the same temperature for one hour. To the resultant reaction mixture was added 5 ml of saturated aqueous ammonium chloride solution, the resultant mixture was stirred at room temperature for 10 minutes, 10 ml of water was added and the resultant mixture was extracted with 10 ml of ethyl acetate 3 times. The combined organic layers were washed with 30 ml of water and saturated sodium chloride solution, and dried over anhydrous sodium sulfate. The solvent of the resultant mixture was removed to give an oily material, which was purified by a Robar column (Merk Type B, eluate-ethyl acetate:cyclohexane=3:1) give 38.1 mg (yield 66%) of 5,6,7-trinor-4,8-inter-m-phenylene-1-decarboxyhydroxy-2-hydroxy-16,16-dimethyl PGI2.

Melting point: 113°–113.5° C.

IR (liquid film): 3350, 2950, 2925, 2852, 1598, 1444, 1379, 1359, 1340, 1295, 1254, 1190, 1060, 1021, 964, 882, 860, 830, 739, cm$^{-1}$.

MS (m/e): 388 (M+) 57 (b.P.).

HRMS: obsd. 388 2636 calcd. 388 2613.

PMR (CDcl$_3$): 0.82–0.95 (3H, m), 0.87 (3H, S), 0.90 (3H, S), 1.15–1.38 (6H, m), 1.69–1.93 (3H, m), 1.93–2.02 (1H, m), 2.08–2.37 (1H, m), 2.40–2.48 (1H, m), 2.62–2.75 (3H, m), 2.76–2.96 (1H, m), 3.42–3.48 (1H, m), 3.52–3.63 (2H, m), 3.81–3.86 (1H, m), 3.88–3.96 (1H, m), 5.11–5.15 (1H, m), 5.58–6.70 (2H, m), 6.79 (1H, t, J=7.33 Hz), 6.94–6.98 (2H, m).

REFERENCE EXAMPLE 96 d-2-endo-tetrahydropyranyloxy-1-exo-tetrahydropyranyloxymethyl-3a,8b-cis-2,3,3a-8b-tetrahydro-1H-5-cyclopenta[b] benzofuran carboxylic acid, methyl ester

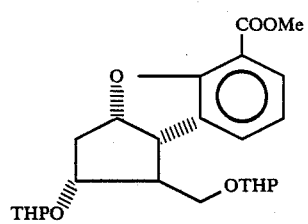

To a mixture of d-7-bromo-3a,8b-cis-3a,8b-dihydro-3H-5-cyclopenta[b] benzofuran carboxylic acid (25.0 g, 89.0 mmol), trioxane (16.0 g, 178 mmol) and acetic acid (102 ml, 1.78 mol), concentrated sulfuric acid was added slowly, and the mixture was stirred for 5 hours at 70° C. The reaction mixture was concentrated and methanol (300 ml), water (50 ml) and 10N aqueous solution of sodium hydroxide (90 ml) were added to the residue, and the resulting mixture was heated to reflux for 2 hours. After stirring the reaction mixture at room temperature for another 10 hours, the mixture was filtered. The resulting precipitate was washed with methanol (70 ml×3). To the combined filtrate, 1N of hydrochloric acid (100 ml) was added, and then the mixture was concentrated. Ethyl acetate (400 ml) was added to the residue and the mixture was washed with water (100 ml). The aqueous layer was re-extracted with ethyl acetate (150 ml×6), and the combined organic layers were washed with saturated aqueous sodium chloride (300 ml) and then dried over anhydrous magnesium sulphate. By concentrating the resulting extracts, 35.4 g of a concentrate was obtained. Then this concentrate was dissolved in methanol (300 ml), and 10% palladium on carbon (5.00 g) was added thereto. The resulting mixture was stirred for 3 hours at room temperature under hydrogen atmosphere. To this reaction mixture, methanol (500 ml) was added under nitrogen atmosphere and the resulting mixture was heated to reflux for 1 hour. The resulting solution was stirred for another 12 hours at room temperature, and sodium hydrogen carbonate (7.50 g, 89.3 mmol) was added. The obtained mixture was stirred for 30 minutes at room temperature and was filtered. The filtrate was concentrated, and the residue was dissolved in THF (250 ml). To this mixture, p-toluene sulfonic acid (846 mg, 4.45 mmol) and 3,4-dihydro-2H-pyrane (29.9 g, 356 mmol) were added, and the resulting mixture was stirred for three hours at room temperature. To the obtained mixture, was added pyridine (352 mg, 4.45 mg, 4.45 mmol), and the mixture was concentrated. To the thus obtained residue, ethyl acetate (400 ml) was added, and the mixture was washed with water (150 ml) and saturated aqueous sodium chloride solution (150 ml), then dried over anhydrous magnesium sulfate, and filtered. By concentrating the obtained filtrate, an oily product of 38.7 g was obtained. By purifying the oily product by means of a column chromatography (silica gel; ethyl acetate/cyclohexane=½), d-2-endo-tetrahydropyranyloxy-1-exo-tetrahydropyranyloxymethyl-3a,8b-cis-2,3,3a,8b-tetrahydro-1H-5-cyclopenta[b]benzofuran carboxylic acid, methyl ester (23.7 g, 54.8 mmol) was obtained with a yield of 61.6%. The structure was confirmed by the following data.

$[\alpha]_d^{25}$: +85.3 (c=0.788, EtOH).

IR (Liquid Membrane Method): 3000, 2930, 2850, 1710, 1610, 1440, 1340, 1280, 1260, 1200, 1170, 1120, 1050, 1010, 960, 890, 850, 800, 740 cm$^{-1}$.

NMR (270 MHz, CDCl$_3$): 1.1–2.0 (12H, m), 2.05–2.6 (3H, m), 3.3–4.3 (11H, m), 4.5–4.7 (2H, m), 5.3–5.45 (1H, m), 6.8–6.9 (1H, m), 7.3–7.5 (1H, m), 7.65–7.8 (1H, m)

Mass (EI method, m/e): 432 (M+).

High Resolution Mass Spectrum: Calcd.: (C$_{24}$H$_{32}$C$_7$, M+) 432.2148 Found: (M+) 432.2166.

REFERENCE EXAMPLE 97 d-7-bromo-2-endo-hydroxy-1-exo-hydroxymethyl-3a,8b-cis-2,3,3a,8b-tetrahydro-1H-5-cyclopenta[b]benzofuran carboxylic acid

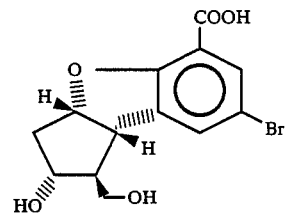

dl-7-bromo-2-endo-hydroxy-1-exo-hydroxymethyl-3a,8b-cis-2,3,3a,8b-tetrahydro-1H-5-cyclopenta[b] benzofuran carboxylic acid (32.5 g, 99 mmol) and d-cis-N-benzyl-2-hydroxymethylcyclohexyl amine (21.7 g, 99 mmol) were dissolved in 70 ml of methanol under heating, and the solution was allowed to cool to room tempeature. A seed of a salt of d-carboxylic acid.d-amine was inoculated to the solution and the solution was left to stand for 3 days. The thus obtained crystalline was recrystallized from 70 ml of ethanol, and then from 10 ml of 50% aqueous solution of methanol to obtain 5.30 g of d-7-bromo-2-endo-hydroxy-1-exo-hydroxymethyl-3a,8b-cis-2,3,3a,8b-tetrahydro-1H-5-cyclopenta[b]benzofuran carboxylic acid,d-cis-N-benzyl-2-hydroxymethylcyclohexyl amine salt (yeild: 9.8%). The crystals were dispersed in 40 ml of distilled water, and 6 ml of 6N sulfuric acid was added. The mixture was stirred for 30 minutes to precipitate d-carboxylic acid. After filtration, the crystals were washed with 10 ml of acetone and then dried to obtain d-7-bromo-2-endo-hydroxy-1-exo-hydroxymethyl-3a,8b-cis-2,3,3a,8b-tetrahydro-1H-5-cyclopenta[b] benzofuran carboxylic acid.

Weight: 3.00 g; Yield: 9.3%. The optical purity was determined by liquid chromatography after converting the carboxylic acid to methyl ester with diazomethane.

Optical Purity: not less than 99%.

Column: YMC-pack A-K03, 4.6 mm diameter×250 mm.

Mobile Phase: n-hexane/ethanol/methylene chloride=85/10/5.

Flow Rate: 1 ml/min.

Oven Temperature: room temperature.

Specific Rotation: $[\alpha]_D^{25}$=+15.2° (c=0.92, methanol) m.p.: 115.5°–116.5° C.

IR (KBr Method): 3640, 3500, 3400–2500, 3110, 2980, 2850, 1695, 1650, 1605, 1450, 1390, 1370, 1350, 1335, 1305, 1300, 1260, 1240, 1220, 1170, 1120, 1075, 1020, 995, 950, 915, 885, 870, 840, 795, 790, 690, 655, 620, 560, 525 cm$^{-1}$.

NMR (400 MHz, CDCl$_3$DMSO-d$_6$ δ): 2.02–2.10 (2H, m), 2.50–2.57 (1H, m), 2.80–3.20 (3H, bs), 3.60 (1H, t, J=7.8 Hz), 3.66 (1H, dd, J=5.4, 10.5 Hz), 3.78 (1H, dd J=5.4, 10.4 Hz), 4.01 (1H, q, J=6.5 Hz), 5.31 (1H, ddd, J=5.4, 7.8, 9.3 Hz), 7.52 (1H, m), 7.81 (1H, d, J=2.4 Hz).

Mass (EI Method; m/e): 328, 330 (M+).

High Resolution Mass Spectrum: Calcd.: (C$_{13}$H$_{13}$O$_5$Br M+) 327.9909 Found: (M+) 327.9928.

REFERENCE EXAMPLE 98 d-2-endo-hydroxy-1-exo-hydroxymethyl-3a,8b-cis-2,3,3a,8b-tetrahydro-1H-5-cyclopenta[b] benzofuran carboxylic acid, methyl ester

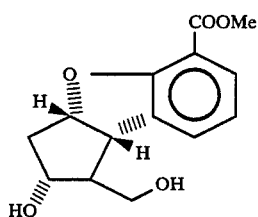

d-7-bromo-2-endo-hydroxy-1-exo-hydroxymethyl-3a,8b-cis-2,3,3a,8b-tetrahydro-1H-5-cyclopenta[b] benzofuran carboxylic acid (29.18 g, 88.4 mmol) was dissolved in methanol (15 litters), and 3 g of 10% palladium on charcoal was added thereto, and the mixture was stirred for 2 hours at room temperature under hydrogen atmosphere. The hydrogen atmosphere was replaced with argon, and the reaction mixture was heated to reflux for 3 hours, and then filtered. The filtrate was concentrated, and 200 ml of water was added thereto. The resulting mixture was extracted with chloroform (300 ml×3) and the organic layers were washed with saturated aqueous solution of sodium chloride (100 ml), dried over anhydrous magnesium sulfate, and concentrated to obtain 22.3 g of crude crystals. The obtained crystals were recrystallized from ethyl acetate to obtain prism crystals of d-2-endo-hydroxy-1-exo-hydroxymethyl-3a,8b-cis-2,3,3a,8b-tetrahydro-1H-5-cyclopenta[b]benzofuran carboxylic acid, methyl ester (20.87 g, 79.1 mmol).

Yield: 89.4%.

The structure was confirmed by the following data:

Specific Rotation: $[\alpha]_D^{20} = +109.6°$ (c=1.028, methanol) m.p.: 154°–155° C.

IR (KBr Method): 3280, 3170, 3030, 2990, 2950, 2900, 1720, 1605, 1445, 1430, 1370, 1355, 1315, 1275, 1250, 1220, 1190, 1170, 1140, 1105, 1075, 1065, 1055, 1040, 1115, 995, 965, 930, 905, 880, 855, 840, 765, 710, 625 cm$^{-1}$.

NMR (400 MHz, CDCl$_3$-DMSO-d$_6$, δ): 2.01–2.08 (2H, m), 2.56 2.63 (1H, m), 3.54 (1H, t, J=8.3 Hz), 3.78 (2H, t, J=5.4 Hz), 3.88 (3H, s), 4.05 (1H, d, J=4.9 Hz), 4.01–4.08 (1H, m), 4.14 (1H, t, J=5.3 Hz), 5.26 (1H, ddd, J=5.3, 8.3, 9.3 Hz), 6.86 (1H, t, J=7.3 Hz), 7.41 (1H, m), 7.70 (1H, dd, J=1.0, 7.3 Hz)

Mass (EI Method, m/e): 264 (M+).

High Resolution Mass Spectrum: Calcd.: (C$_{14}$H$_{16}$O$_5$ M+) 264.0962 Found: M+) 264.0980.

REFERENCE EXAMPLE 99 d-3-[2-endo-hydroxy-1-exo-hydroxymethyl-3a,8b-cis-2,3,3a,8b-tetrahydro-1H-5-cyclopenta[b]benzofuranyl]-propionic acid, methyl ester

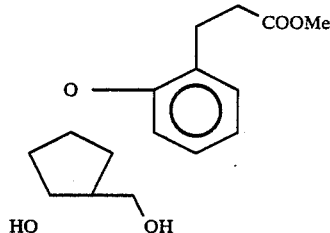

d-2-endo-hydroxy-1-exo-hydroxymethyl-3a,8b-cis-2,3,3a,8b-tetrahydro-1H-5-cyclopenta[b]benzofuran carboxylic acid, methyl ester (47.20 g, 187.30 mmol) was dissolved in 250 ml of anhydrous THF, and dihydropyran (47.60 ml, 515.80 mmol) was added thereto. Then 150 ml of p-toluene sulfonic acid solution in THF (3.363 g of p-toluene sulfonic acid was dissolved in 180 ml of THF, and dried over molecular sieves 4A1/16) was added under cooling in an ice bath, and the resulting mixture was stirred for 3 hours at room temperature. To the reaction mixture, was added 20 g of sodium hydrogen carbonate, and the mixture was stirred for 10 minutes at room temperature. The resulting mixture was filtered with suction through Cellite, and the obtained filtrate was concentrated. To the obtained residue, was added 200 ml of water, and the mixture was extracted with ethyl acetate (200 ml×2). The combined organic layers were washed with 300 ml of saturated aqueous solution of sodium chloride, dried over anhydrous sodium sulfate (80 g), and concentrated to obtain an oil of 114.58 g.

To a stirred solution of lithium aluminum hydride (5.331 g, 140.47 mmol) in 250 ml of THF, precooled in an ice bath, under argon stream, was added dropwise a solution of the oil in 150 ml of anhydrous THF, and the resulting mixture was stirred for 15 minutes. While cooling in an ice bath, 100 ml of ethyl acetate, and then 15 ml of saturated aqueous solution of sodium sulfate were added to the reaction mixture, and the resulting mixture was filtered with suction through Celite. The obtained filtrate was concentrated to obtain an oily product (91.2 g).

Then the thus obtained oily product was dissolved in 350 ml of dichloromethane, and 350 g of active manganese dioxide was added to the mixture while cooling in an ice bath, and the resulting mixture was stirred overnight at room temperature. The reaction mixture was filtered with suction using Celite. The obtained filtrate was concentrated to obtain 81.21 g of an oil product.

The oily product was dissolved in 1000 ml of benzen, and carboxymethylene triphenylphosphorane (93.8 g, 280.95 mmol) was added thereto, and the resulting mixture was stirred for 2 days at room temperature, and then concentrated. The by-product triphenylphosphine oxide was removed by a chromatography (silica gel; ethyl acetate/cyclohexane=1/4) to obtain 82.58 g of an oily product.

The thus obtained oily product (82.58 g) was dissolved in 400 ml of methanol, and 10 g of palladium on carbon was added thereto under an argon stream. The argon was replaced with hydrogen, and the resulting mixture was stirred overnight at room temperature. The reaction mixture was then filtered with suction using Celite. The obtained filtrate was concentrated to obtain 79.14 g of an oily product.

Finally, the thus obtained 79.14 g of oily product was dissolved in 400 ml of methanol, and 2.4 g of p-toluene sulfonic acid was added thereto while cooling the mixture in an ice bath, and the resulting mixture was stirred overnight. To the reaction mixture, was added 20 g of sodium hydrogen carbonate, and the resulting mixture was stirred for 20 minutes at room temperature. The resulting mixture was filtered with suction using Celite, and the filtrate was concentrated. To the residue, 100 ml of water was added, and the mixture was extracted with ethyl acetate (100 ml×2). The combined layers were washed with 100 ml of saturated aqueous solution of sodium chloride, dried over 30 g of anhydrous sodium sulfate, and concentrated. The residue was recrystallized from ethyl acetate/cyclohexane (6/1) to obtain colorless crystals of d-3-[2-endo-hydroxy-1-exo-hydroxymethyl-3a,8b-cis-2,3,3a,8b-tetrahydro-1H-5-cyclopenta[b]benzofuranyl propionic acid, methyl ester (32.51 g, 111,34 mmol) with a yield of 59.4%.

The structure was confirmed by the following data: m.p.: 110°–110.5° C. $[\alpha]_D^{20}$: +30.52 (c=0.868, MeOH).

IR (KBr Method): 3400, 2950, 2905, 2855, 1700, 1591, 1456, 1442, 1359, 1321, 1293, 1279, 1243, 1213, 1181, 1155, 1102, 1059, 1010, 968, 950, 919, 899, 843, 833, 802, 766, 742, 620, 580, 542, 521, 500, 443 cm$^{-1}$.

NMR (400 MHz, CDCl$_3$, δ): 1.8–1.9 (1H, broad S), 2.01–2.08 (1H, m), 2.12–2.20 (1H, m), 2.2–2.3 (1H, broad S), 2.55–2.72 (3H, m), 2.84–2.97 (2H, m), 3.39–3.45 (1H, m), 3.66 (3H, s), 3.76–3.83 (1H, m), 3.94–4.00 (1H, m), 4.10–4.18 (1H, m), 5.10–5.19 (1H, m), 6.79 (1H, t, J=7.32), 6.97 (1H, d, T=7.32), 7.04 (1H, d, J=7.32)

Mass (EI Method, m/e): 292 (M+).

REFERENCE EXAMPLE 100

5,6,7-trinor-4,8-inter-m-phenylene-2,18,19,20-tetranor-11,15-didehydroxy-11-acetoxy-15-oxo-16,16-dimethyl-17-ethoxy PGI$_2$ methyl ester

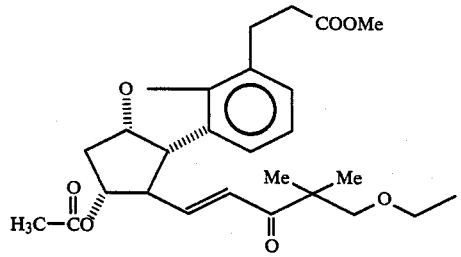

Under argon atmosphere, 3-[2-endo-hydroxy-1-exo-hydroxymethyl-3a,8b-cis-2,3,3a,8b-tetrahydro-1H-5-cyclopenta[b]benzofuranyl]propionic acid, methyl ester (1.0 g, 2.99 mmol) was dissolved in 6 ml of anhydrous THF. To the mixture, were added pyridine (0.073 ml, 0.9 mmol) and trifluoro acetic acid (0.068 ml, 0.88 mmol) under stirring, and then DMSO (2.11 ml, 29.7 mmol) and D.C.C. (0.82 g, 3.97 mmol) were added, and the mixture was stirred for 2.5 hours at room temperature. On the other hand, sodium hydride (60% mineral oil dispersion, 192 mg, 4.8 mmol) was suspended in 6 ml of anhydrous THF under argon atmosphere and 3,3-dimethyl-2-oxo-5-oxa-heptyl phosphonic acid, dimethyl ester (1.21 g, 4.8 mmol) in 3 ml of anhydrous THF was added dropwise thereto under cooling in an ice bath, and the resulting mixture was stirred for 30 minutes. To this reaction mixture, was added above-synthesized aldehyde ester under cooling in an ice bath, and the resulting mixture was stirred for 30 minutes under the same conditions. The mixture was neutralized with acetic acid, and the resulting mixture was filtered. The obtained filtrate was concentrated. To the residue, 10 ml of water was added and the mixture was extracted with ethyl acetate (50 ml×2). The ethyl acetate layers were washed with water (20 ml×1) and then with saturated aqueous solution of sodium chloride (10 ml×1), dried over anhydrous sodium sulfate, and concentrated. The residue was purified by a column chromatography (silica gel, 50 g: ethyl acetate/cyclohexane=1/6), and then further purified by Robar column manufactured by Merck & Co. Inc. (silica gel, ethyl acetate/cyclohexane=1/6) to obtain 5,6,7-trinor-4,8-inter-m-phenylene-2,18,19,20-tetranor-11,15-didehydroxy-11-acetoxy-15-oxo-16,16-dimethyl-17-ethoxy PGI$_2$ methyl ester as a colorless transparent oil (Amount: 1.05 g, 2.29 mmol, Yield: 76.6%). The structure was confirmed by the following data:

IR (Liquid Film): 2970, 2920, 2860, 1730, 1680, 1620, 1590, 1445, 1360, 1320, 1290, 1230, 1190, 1110, 1065, 975, 940, 890, 850, 740 cm$^{-1}$.

NMR (400 MHz, CDCl$_3$, δ): 1.16 (3H, t, J=6.8 Hz), 1.17 (6H, s), 1.76 (3H, s), 2.1–2.2 (1H, m), 2.5–2.8 (3H, m), 2.8–3.0 (3H, m), 3.4–3.5 (4H, m), 3.68 (3H, s), 3.6–3.7 (1H, m), 4.98 (1H, q J=5.86 Hz), 5.2–5.3 (1H, m), 6.62 (1H, d,d, J=15.1, 0.97 Hz), 6.7–6.9 (2H, m), 6.9–7.0 (1H, m).

Mass (EI Method, m/e): 458 (M+).

REFERENCE EXAMPLE 101

5,6,7-trinor-4,8-inter-m-phenylene-11,15-didehydroxy-11-acetoxy-15-oxo-2-nor-w-homo-16,16-dimethyl-17-propoxy PGI$_2$ methyl ester

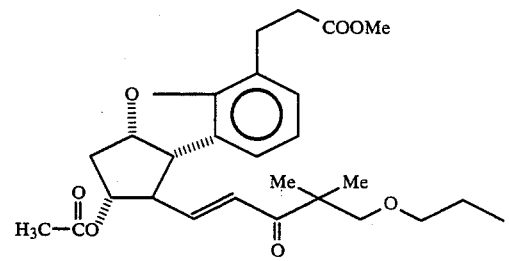

Under an argon stream, 3-[2-endo-acetoxy-1-exo-hydroxymethyl-3a,8b-cis-2,3,3a,8b-tetrahydro-1H-5-cyclopenta[b]benzofuranyl]propionic acid, methyl ester (1.0613 g, 3.18 mmol) was dissolved in 15 ml of THF, an anhydrous pyridine (0.26 ml, 3.18 mmol), 5 ml of anhydrous DMSO, and trifluoro acetic acid (0.12 ml, 1.59 mmol) were added to the solution, and further DCC (994.1 mg, 4.77 mmol) was added thereto. The resulting mixture was stirred for 2 hours and 40 minutes at room temperature. To the reaction mixture, calcium carbonate (1.034 g, 10.34 mmol) was added, and the resulting mixture was stirred for 15 minutes, and left to stand.

On the other hand, sodium hydride (60% mineral oil dispersion, 190.8 mg, 4.77 mmol) was suspended in 20 ml of anhydrous THF, and 3,3-dimethyl-2-oxo-4-oxa-octyl phosphonic acid, dimethyl ester (1.35 g, 4.77 mmol) in 5 ml of anhydrous THF was added dropwise thereto under cooling in an ice bath, and the resulting mixture was stirred for 30 minutes under argon atmosphere. To the reaction mixture, was added the supernatant of the above-prepared reaction mixture of the aldehyde ester by means of a syringe under cooling in an ice bath. The residue was washed with anhydrous THF (10 ml, 5 ml×2), and the supernatant was combined, and the resulting mixture was stirred for 10 minutes at room temperature. To this mixture, was added 50 ml of aquous solution of saturated ammonium chloride, and extracted with ethyl acetate (30 ml×3). The combined layers were washed with 70 ml of water and 70 ml of saturated aqueous sodium chloride solution, dried over anhydrous sodium sulfate (30 g), and concentrated. By purifying this residue by means of a column chromtography (silica gel: ethyl acetate/cyclohexane=⅓), 5,6,7-trinor-4,8-inter-m-phenylene-11,15-didehydroxy-11-acetoxy-15-oxo-2-nor-w-homo-16,16-dimethyl-17-propoxy $PGI_2$ methyl ester (1.4194 g, 3.01 mmol) in the form of a colorless oil was obtained with a yield of 95%. The structure was confirmed by the following data:

IR (Liquid Film Method): 2951, 2855, 1730, 1682, 1621, 1591, 1443, 1361, 1321, 1296, 1230, 1189, 1104, 1060, 1004, 980, 950, 889, 848, 743 $cm^{-1}$.

NMR (400 MHz, $CDCl_3$, δ): 0.88 (3H, t, J=7.3), 1.16 (6H, s), 1.51–1.57 (2H, m), 1.75 (3H, s), 2.10–2.17 (1h, m), 2.57–2.71 (3H, m), 2.87–2.93 (2H, m), 2.93–2.99 (1H, m), 3.36 (2H, t, J=6.3), 3.44 (2H, br s), 3.67 (3H, s), 3.65–3.69 (1H, m), 4.95–5.01 (1H, m), 5.22–5.28 (1H, m), 6.62 (1H, d, J=15.1), 6.76 (1H, t, J=7.3), 6.81 (1H, dd, J=8.3, 15.1), 6.96–7.01 (2H, m).

Mass (EI Method, m/e): 472 (M+).

REFERENCE EXAMPLE 102

5,6,7-trinor-4,8-inter-m-phenylene-2,17,18,19,20-pentanor-11,15-didehydroxy-11-acetoxy-15-oxo-16,16-dimethyl-16-phenoxy $PGI_2$ methyl ester

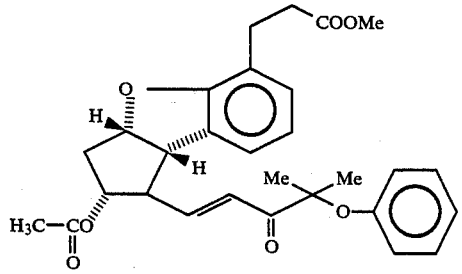

Under argon atmosphere, 3-[2-endo-acetoxy-1-exo-hydroxymethyl-3a,8b-cis-2,3,3a,8b-tetrahydro-1H-5-cyclopenta[b]benzofuranyl propionic acid, methyl ester (1.5 g, 4.49 mmol) was dissolved in 9 ml of anhydrous THF. To this solution, pyridine (0.11 ml, 1.36 mmol) and trifluoro acetic acid (0.102 ml, 1.32 mmol) were added under stirring, and then DMSO (3.17 ml, 44.6 mmol) and D.C.C. (1.23 g, 5.96 mmol) were added thereto, and the resulting mixture was stirred for 2.5 hours at room temperature. On the other hand, under argon atmosphere, sodium hydride (60% mineral oil dispersion, 270 mg, 6.74 mmol) was dissolved in 10 ml of anhydrous THF. To this suspension, was added dropwise under cooling in an ice bath, 3,3-dimethyl-3-phenoxy-2-oxo-propylphosphonic acid dimethyl ester (1.92 g, 6.74 mmol) in 5 ml of anhydrous THF and the mixture was stirred for 30 minutes. To this reaction mixture, the above-prepared aldehyde ester was added under cooling in an ice bath, and the resulting mixture was stirred for 30 minutes in the same conditions. The mixture was neutralized, then filtered and the filtrate was concentrated. To the residue, 20 ml of water was added and extracted with ethyl acetate (50 ml×2), and the ethyl acetate layers were washed with water (20 ml×1) and saturated aqueous solution of sodium chloride (10 ml×1), dried over anhydrous sodium sulfate, and concentrated. The residue was purified by a column chromatography (silica gel 60 g, ethyl acetate/cyclohexane=1/5), and was further purified by Rober column manufactured by Merck & Co., Inc. (silica gel, ethyl acetate/cyclohexane=1/6) to obtain 5,6,7-trinor-4,8-inter-m-phenylene-2,17,18,19,20-pentanor-11,15-didehydroxy-11-acetoxy-15-oxo-16,16-dimethyl-16-phenoxy $PGI_2$ methyl ester in the form of a colorless transparent oil (Amount: 1.88 g, 3.82 mmol, Yield: 85.1%). The structure was confirmed by the following data:

IR (Liquid Film Method): 2970, 2920, 1725, 1690, 1620, 1590, 1480, 1440, 1370, 1230, 1150, 1060, 950, 880, 750, 690 $cm^{-1}$.

NMR (100 MHz, $CDCl_3$, δ): 1.4–1.7 (6H, m), 1.71 (3H, s), 1.8–2.2 (1H, m), 2.2–3.1 (6H, m), 3.65 (3H, s), 3.4–3.8 (1H, m), 5.7–6.3 (2H, m), 7.5–8.4 (10H, m).

Mass (EI Method, m/e): 492 (M+).

REFERENCE EXAMPLE 103 d-5,6,7-trinor-4,8-inter-m-phenylene-2,17,18,19,20-pentanor-11,15-didehydroxy-11-acetoxy-15-oxo-16-(S)-methyl-16-phenoxy $PGI_2$ methyl ester

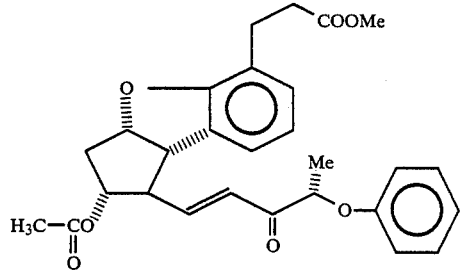

Under argon atmosphere, d-3-(2-endo-hydroxy-1-exo-hydroxymethyl-3a,8b-cis-2,3,3a,8b-tetrahydro-1H-5-cyclopenta[b]benzofuranyl) propionic acid, methyl ester (1.0 g, 2.99 mmol) was dissolved in 8 ml of anhydrous THF. While stirring this soluton, pyridine (0.073 ml, 0.9 mmol) and trifluoro acetic acid (0.067 ml, 0.87 mmol) were added to the solution, and then DMSO (2.12 ml, 29.9 mmol) and D.C.C (0.8 g, 3.9 mmol) was added thereto, and the resulting mixture was stirred for 3 hours at room temperature. On the other hand, under argon atmosphere, sodium hydride (60% mineral oil dispersion, 192 mg, 5.0 mmol) was suspended in 7 ml of anhydrous THF. To this suspension, was added dropwise 3-(S)-methyl-3-phenoxy-2-oxo-propyl phosphonic acid, dimethyl ester (1.36 g, 5 mmol) while cooling the mixture in an ice bath, and the resulting mixture was stirred for 30 minutes. To this reaction mixture, the above-prepared aldehyde ester was added while cooling the mixture in an ice bath and the resultant mixture was stirred for 1 hour at room temperature. The mixture was neutralized with acetic acid, and filtered. The obtained inorganic substance was washed with ethyl acetate (10 ml×5), and the combined filtrates were concentrated. To the residue, 30 ml of water was added, and the mixture was extracted with ethyl acetate (70 ml×1), and the extract was washed with water (30 ml×1), and then with saturated aqueous soluton of sodium chloride (30 ml×1), dried over anhydrous sodium sulfate, and concentrated. The residue was separated from solid contents by a column chromatography (silica gel, ethyl acetate/cyclohexane=1/5), and was further purified by Rober column manufactured by Merck & Co., Inc. (silicagel, ethyl acetate/cyclohexane=1/5) to obtain d-5,6,7-trinor-4,8-inter-m-phenylene-2,17,18,19,20-pentanor-11,15-didehydroxy-11-acetoxy-15-oxo-16-(S)-methyl-16-phenoxy PGI$_2$ methyl ester (Amount: 885 mg, 1.85 mmol, Yield: 61.8%) in the form of an oil. The structure was confirmed by the following data:

Specific Rotation $[\alpha]_D^{20}$= +83.84 (c=0.78, MeOH)
IR (Liquid film Method): 2930, 1730, 1620, 1595, 1485, 1450, 1365, 1230, 1190, 1170, 1060, 980, 845, 800, 750, 690 cm$^{-1}$.
NMR (400 MHz, CDCl$_3$, γ): 1.57 (3H, d, J=6.8 Hz), 1.68 (3H, s), 2.0–2.2 (1H, m), 2.5–2.7 (3H, m), 2.7–3.0 (3H, m), 3.61 (1H, t, J=7.6 Hz), 3.67 (3H, s), 4.76 (1H, q, 6.8 Hz), 4.92 (1H, q, J=6.5 Hz), 5.1–5.3 (1H, m), 6.7–6.8 (2H, m), 6.84 (2H, d, J=7.8 Hz), 6.9–7.1 (3H, m), 7.2–7.4 (2H, m).
Mass (EI Method); 478 (M+).

REFERENCE EXAMPLE 104 d-5,6,7-trinor-4,8-inter-m-phenylene-2,17,18,19,20-pentanor-11,15-didehydroxy-11-acetoxy-15-oxo-16-(R)-methyl-16-phenoxy PGI$_2$ methyl ester

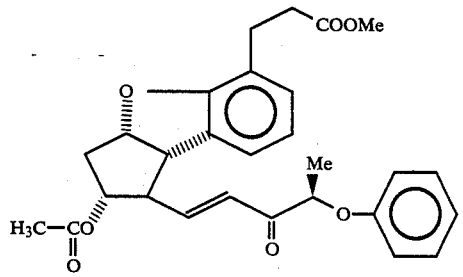

Under argon atmosphere, d-3-(2-endo-hydroxy-1-exo-hydroxymethyl-3a,8b-cis-2,3,3a,8b-tetrahydro-1H-5-cyclopenta[b]benzofuranyl propionic acid, methyl ester (874 mg, 2.62 mmol) was dissolved in 7 ml of anhydrous THF. While stirring this solution, pyridine (0.065 ml, 0.81 mmol) and trifluoro acetic acid (0.06 ml, 0.79 mmol) were added to the solution, and then DMSO (2.33 ml, 32.8 mmol) and D.C.C (0.82 g, 3.97 mmol) was added thereto, and the resulting mixture was stirred for 3 hours at room temperature. Onthe other hand, under argon atmosphere, sodium hydride (60% mineral oil dispersion, 188 mg, 4.7 mmol) was suspended in 6 ml of anhydrous THF. To this suspension, was added dropwise 3-(R)-metyl-3-phenoxy-2-oxo-propyl phosphonic acid, dimethyl ester (1.28 g, 4.7 mmol) while cooling the mixture in an ice bath, and the resulting mixture was stirred for 30 minutes. To this reaction mixture, above-prepared aldehyde ester was added while cooling the mixture in an ice bath, and the resulting mixture was stirred for 1 hour at room temperature. The reaction mixture was neutralized with acetic acid and filtered. The obtained filtrate was concentrated. To the residue, was added 30 ml of water, and the mixture was extracted with ethyl acetate (100 ml×1) and the extract was washed with water (30 ml×1), and then with saturated aqueous solution of sodium chloride (30 ml×1), dried over anhydrous sodium sulfate, and concentrated. The concentration residue was purified by a column chromatography (silica gel 40 g, ethyl acetate/cyclohexane=1/7), and the resultant was further purified by Rober column manufactured by Merck & Co., Inc. (silica gel, ethyl acetate/cyclohexane=⅓) to obtain d-5,6,7-trinor-4,8-iner-m-phenylene-2,17,18,19,20-pentanor-11,15-didehydroxy-11-acetoxy-15-oxo-16-(R)-methyl-16-phenoxy PGI$_2$ *methyl ester* (Amount: 806 mg, 1.69 mmol, Yield: 64.5%) in the form of an oil. The structure was confirmed by the following data:

Specific Rotation $[\alpha]_D^{20}$= +219.4 (c=0.84, MeOH)
IR (Liquid Film Method): 3020, 2970, 2925, 1720, 1690, 1615, 1590, 1480, 1440, 1360, 1315, 1230, 1165, 1120, 1060, 980, 880, 860, 840, 790, 745, 690 cm$^{-1}$.
NMR (400 MHz, CDCl$_3$, γ): 1.55 (3H, d, J=6.7 Hz), 1.76 (3H, s), 1.9–2.1 (1H, m), 2.4–2.7 (3H, m), 2.8–3.0 (3H, m), 3.5–3.6 (1H, m), 3.66 (3H, s), 4.75 (1H, q, J=7.0 Hz), 4.93 (1H, q, J=6.7 Hz), 5.1–5.2 (1H, m), 6.5–6.7 (3H, m), 6.8–6.9 (2H, m), 6.9–7.1 (3H, m), 7.2–7.4 (2H, m)
Mass (EI Method, m/e): 478 (M+).

REFERENCE EXAMPLE 105 d-5,6,7-trinor-4,8-inter-m-phenylene-11,15-didehydroxy-11-acetoxy-15-oxo-2,18,19,20-tetranor-16-methyl-16-phenoxy PGI$_2$ methyl ester

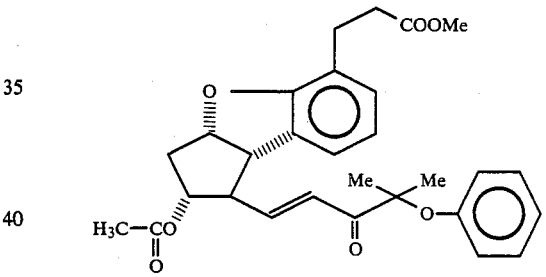

Under argon stream, d-3-[2-endo-acetoxy-1-exo-hydrolxymethyl-3a,8b-cis-2,3,3a,8b-tetrahydro-1H-5-cyclopenta[b]benzofuranyl]propionic acid, methyl ester (14.01 g, 41.95 mmol) was dissolved in 80 ml of anhydrous THF, and anhydrous pyridine (3.39 ml, 41.95 mmol), 40 ml of anhydrous DMSO, and trifluoro acetic acid (1.62 ml, 20.98 mmol) were added to the solution, and further DCC (12.98 mg, 62.92 mmol) was added thereto. The resulting mixture was stirred for 2.5 hours at room temperature. To the reaction mixture, was added calcium carbonate (13.65 g, 136.34 mmol), and the resulting mixture was stirred for 30 minutes, and left to stand.

On the other hand, sodium hydride (60% mineral oil dispersion, 2.52 g, 62.92 mmol) was suspended in 150 ml of anhydrous THF, and 3-methyl-3-phenoxy-2-oxo-butyl phosphonic acid, dimethyl ester (18.0 g, 62.92 mmol) in 20 ml of anhydrous THF was added dropwise thereto under cooling in an ice bath under argon atmosphere, and the resulting mixture was stirred for 30 minutes at room temperature. To the reaction mixture, was added the supernatant of the above-prepared reaction mixture of the aldehyde ester by means of a syringe under cooling in an ice bath. The residue was washed with anhydrous THF (50 ml×4), and the supernatant was combined, and the resulting mixture was stirred for 40 minutes at room temperature. After stirring, 4.5 ml of acetic acid was added thereto and the mixture was concentrated. To the obtained residue, 200 ml of water was added and the mixture was extracted with ethyl acetate (200 ml×2, 100 ml×1), and the combined organic layers were washed with 400 ml of saturated aqueous solution of sodium hydroxide, dried over anhydrous sodium sulfate (40 g), and concentrated. By purifying the residue by means of a column chromatography (silica gel: ethyl acetate/cyclohexane=1/5), d-5,6,7-trinor-4,8-inter-m-phenylene-11,15-didehydroxy-11-acetoxy-15-oxo-2,18,19,20-tetranor-16-methyl-16-phenoxy PGI$_2$ methyl ester in the form of a colorless oil was obtained (17.90 g, 36.38 mmol) in a yield of 86.7%. The structure was confirmed by the following data:

$[\alpha]_D^{20}$: +99.38° (c=0.974, MeOH).

IR (Liquid Film Method): 2980, 2940, 1730, 1693, 1622, 1592, 1484, 1444, 1370, 1321, 1294, 1235, 1193, 1150, 1060, 983, 950, 885, 860, 748, 694 cm$^{-1}$.

NMR (400 MHz, CDCl$_3$, δ): 1.52 (3H, s), 1.55 (3H, s), 1.71 (3H, s), 1.95-2.03 (1H, m), 2.50-2.67 (3H, m), 2.82-2.92 (3H, m), 3.53-3.58 (1H, m), 3.66 (3H, s), 4.90-4.97 (1H, m), 5.10-5.15 (1H, m), 6.60-6.64 (2H, m), 6.72-6.80 (3H, m), 6.91-7.05 (3H, m), 7.20-7.28 (2H, m).

Mass (EI Method, m/e): 492 (M+).

EXAMPLE 235

5,6,7-trinor-4,8-inter-m-phenylene-2,18,19,20-tetranor-16,16-dimethyl-17-ethoxy PGI$_2$ methyl ester, and 5,6,7-trinor-4,8-inter-m-phenylene--15-epi-2,18,19,20-tetranor-16,16-dimethyl-17-ethoxy PGI$_2$ methyl ester

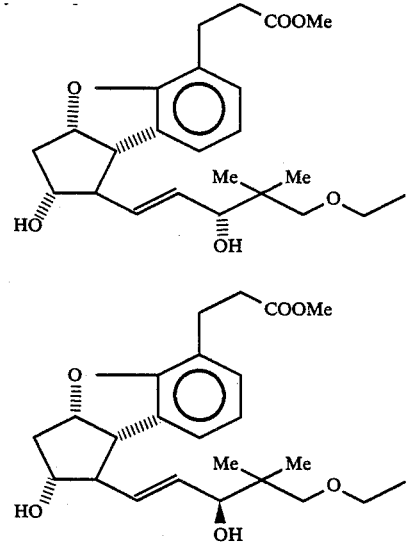

To a solution of 5,6,7-trinor-4,8-inter-m-phenylene-2,18,19,20-tetranor-11,15-didehydroxy-11-acetoxy-15-oxo-16,16-dimethyl-17-ethoxy PGI$_2$ methyl ester (1.05 g, 2.29 mmol) in 50 ml of methanol, was added cerous chloride heptahydrate (915 mg, 2.46 mmol), and then slowly sodium borohydride (138 mg, 3.64 mmol) under cooling in an ice bath. After 10 minutes stirring, saturated aqeuous sodium hydrogen carbonate solution was added to the mixture, and the resulting mixture was filtered. The obtained filtrate was concentrated. To the residue, 30 ml of water was added, and the mixture was extracted with ethyl acetate (100 ml×1). The obtained ethyl acetate layer was washed with water (20 ml×1) and then with saturated aqueous sodium chloride solution (20 ml×1), dried over anhydrous sodium sulfate, and concentrated to afford an oily product (1.03 g). The oily product was dissolved in 30 ml of anhydrous methanol under argon atmosphere, and sodium methoxide (5.22N, 0.115 ml, 0.6 mmol) was added thereto under stirring. The resulting mixture was stirred for 14 hours at room temperature. The mixture was neutralized with acetic acid and then concentrated. To the obtained residue, 20 ml of water was added and the resulting mixture was extracted with ethyl acetate (100 ml×2) and the ethyl acetate layers were washed with water (20 ml×1) and saturated aqueous sodium chloride solution (20 ml×1), dried over anhydrous sodium sulfate, and concentrated. The residue was purified using Rober column manufactured by Merck & Co., Inc. (silica gel, ethyl acetate/cyclohexane=2/1) to obtain 5,6,7-trinor-4,8-inter-m-phenylene-15-epi-2,18,19,20-tetranor-16,16-dimethyl-17-ethoxy PGI$_2$ methyl ester from first eluted fraction (low polar fraction) (Amount: 449 mg, 1.07 mmol, Yield: 48%) and 5,6,7-trinor-4,8-inter-m-phenylene-2,18,19,20-tetranor-16,16-dimethyl-17-ethoxy PGI$_2$ methyl ester from secondly eluted fraction (high polar fraction) (Amount: 445 mg, 1.06 mmol, Yield: 47.5%). The structures of these were confirmed by the following data. 5,6,7-trinor-4,8-inter-m-phenylene-2,18,19,20-tetranor-16,16-dimethyl-17-ethoxy PGI$_2$ methyl ester.

IR (Liquid Film Method): 3410, 2970, 2870, 1730, 1595, 1450, 1360, 1250, 1190, 1100, 1065, 1030, 1000, 965, 880, 855, 830, 750 cm$^{-1}$.

NMR (400 MHz, CDCl$_3$, γ): 0.92 (3H, s), 0.947 (3H, s), 1.20 (3H, t, J=7.1 Hz), 1.9-2.1 (1H, m), 2.4-2.6 (2H, m), 2.8-3.0 (2H, m), 3.29 (1H, d, J=8.8 Hz), 3.37 (1H, d, J=8.8 Hz), 3.4-3.6 (3H, m), 3.66 (3H, s), 3.9-4.1 (3H, m), 5.0-5.2 (1H, m), 5.6-5.8 (2H, m), 6.76 (1H, t, J=7.3 Hz), 6.97 (2H, d, J=7.3 Hz)

Mass (EI Method, m/e): 418 (M+)

High Resolution Mass Spectrum: Calcd.: (M+, C$_{24}$H$_{34}$O$_6$) 418.2355 Found: (M+) 418.2341.

5,6,7-trinor-4,8-inter-m-phenylene-15-epi-2,18,19,20-tetranor-16,16-dimethyl-17-ethoxy PGI$_2$ methyl ester IR (Liquid Film Method): 3400, 2960, 2860, 1720, 1590, 1440, 1360, 1250, 1190, 1095, 1020, 970, 880, 860, 830, 750 cm$^{-1}$.

NMR (400 MHz, CDCl$_3$, γ): 0.928 (3H, s), 0.933 (3H, s), 1.23 (3H, t, J=7.1 Hz), 1.8-2.1 (1H, m), 1.9-2.1 (1H, m), 2.53 (1H, q, J=7.3 Hz), 2.5-2.8 (3H, m), 2.8-3.0 (2H, m), 3.3 (1H, d, J=8.8 Hz), 3.4 (1H, d, J=8.8 Hz), 3.4-3.6 (3H, m), 3.66 (3H, s), 3.8-4.1 (3H, m), 5.1-5.2 (1H, m), 5.6-5.8 (2H, m), 6.77 (1H, t, J=7.2 Hz), 6.97 (1H, d, J=7.2 Hz), 7.03 (1H, d, J=7.2 Hz).

Mass (EI Method, m/e): 418 (M+).

High Resolution Mass Spectrum: Calcd.: (M+, C$_{24}$H$_{34}$O$_6$) 418.2355 Found: (M+) 418.2340.

EXAMPLE 236

5,6,7-trinor-4,8-inter-m-phenylene-2,18,19,20-tetranor-16,16-dimethyl-17-ethoxy PGI₂

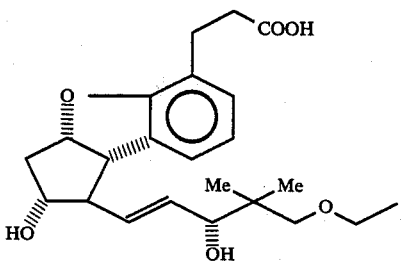

5,6,7-trinor-4,8-inter-m-phenylene-2,18,19,20-tetranor-16,16-dimethyl-17-ethoxy PGI₂ methyl ester (275 mg, 0.66 mmol) was dissolved in 20 ml of methanol. To this solution, 1N aqueous sodium hydroxide solution (5.3 ml, 5.3 mmol) was added under stirring while cooling the solution in an ice bath, and the resulting mixture was stirred for 14 hours at room temperature. The reaction mixture was neutralized with 1N hydrochloric acid, and was concentrated. To the residue, 10 ml of water was added and the resulting mixture was extracted with ethyl acetate (60 ml×2), and the obtained ethyl acetate layers were washed with water (10 ml×1), saturated aqueous sodium chloride solution (10 ml×1), dried over anhydrous sodium sulfate and concentrated. The residue was recrystallized from a mixed solvent of 3 ml of ethyl acetate and 4 ml of n-hexane to obtain 5,6,7-trinor-4,8-inter-m-phenylene-2,18,19,20-tetranor-16,16-dimethyl-17-ethoxy PGI₂ in the form of white crystals. Its structure was confirmed by the following data:

m.p.: 119.2°–120.9° C. (Recrystallization Solvent: ethyl acetate/n-hexane ⅔).

IR (KBr Method): 3400, 2960, 2920, 2850, 1695, 1590, 1450, 1410, 1280, 1260, 1240, 1200, 1085, 1065, 1010, 995, 965, 915, 850, 820, 800, 780, 740 cm⁻¹.

NMR (400 MHz, CDCl₃, δ): 0.92 (3H, s), 0.95 (3H, s), 1.21 (3H, t, J=7.1 Hz), 1.9–2.1 (1H, m), 2.4–2.6 (1H, m), 2.6–2.8 (3H, m), 2.8–3.0 (2H, m), 3.29 (1H, d, J=9.0 Hz), 3.37 (1H, d, J=9.0 Hz), 2.0–3.3 (3H, br s), 3.4–3.6 (3H, m), 3.9–4.0 (2H, m), 5.1–5.2 (1H, m), 5.6–5.8 (2H, m), 6.76 (1H, t, J=7.6 Hz), 6.9–7.1 (2H, m).

Mass (EI Method, m/e): 404 (M+)

High Resolution Mass Spectrum: Calcd.: (M+, C₂₃H₃₂O₆) 404.2199 Found: (M+) 404.2191.

EXAMPLE 237

5,6,7-trinor-4,8-inter-m-phenylene-15-epi-2,18,19,20-tetranor-16,16-dimethyl-17-ethoxy PGI₂

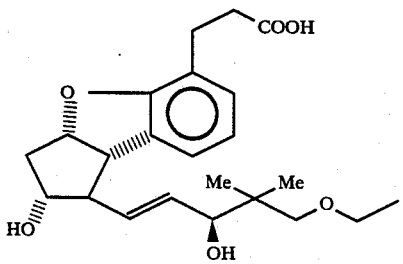

5,6,7-trinor-4,8-inter-m-phenylene-15-epi-2,18,19,20-tetranor-16,16-dimethyl-17-ethoxy PGI₂ methyl ester (280 mg, 0.67 mmol) was dissolved in 25 ml of methanol. To this solution was added 1N aqueous sodium hydroxide solutin (5.4 ml, 5.4 mmol) under cooling in an ice bath, and the resulting mixture was stirred for 4 hours at room temperature. The reaction mixture was concentrated, and 15 ml of water was added to the concentrated residue. After neutralizing the mixture with 1N hydrochloric acid, the mixture was extracted with ethyl acetate (50 ml×2) and the extracts were washed with water (15 ml×1) and then with saturated aqueous sodium chloride solution (15 ml×1), dried over anhydrous sodium sulfate, and concentrated to obtain 5,6,7-trinor-4,8-inter-m-phenylene-15-epi-2,18,19,20-tetranor-16,16-dimethyl-17-ethoxy PGI₂ as a transparent oil (Amount: 271 mg, 0.67 mmol, Yield: 100%). Its structure was confirmed by the following data:

IR (Liquid Film Method): 3400, 2960, 2870, 1705, 1590, 1440, 1250, 1210, 1190, 1090, 1060, 1030, 970, 860, 750 cm⁻¹.

NMR (400 MHz, CDCl₃, γ): 0.923 (3H, s), 0.932 (3H, s), 1.22 (3H, t, J=7.1 Hz), 1.9–2.1 (1H, m), 2.52 (1H, q, J=7.3 Hz), 2.5–2.8 (3H, m), 2.8–3.0 (2H, m), 3.30 (1H, d, J=8.8 Hz), 3.38 (1H, d, J=8.8 Hz), 3.4–3.6 (3H, m), 3.9–4.0 (1H, m), 3.0–5.0 (2H, m), 4.0 (1H, d, J=4.9 Hz), 5.1–5.2 (1H, m), 5.6–5.8 (2H, m), 6.77 (1H, t, J=7.4 Hz), 6.98 (1H, d, J=7.4 Hz), 7.03 (1H, d, J=7.4 Hz)

Mass (EI Method, m/e): 404 (M+)

High Resolution Mass Spectrum: Calcd.: (M+, C₂₃H₃₂O₆) 404.2199 Found: (M+) 404.2199.

EXAMPLE 238

5,6,7-trinor-4,8-inter-m-phenylene-2-nor-w-homo-16,16-dimethyl-17-propoxy PGI₂ methyl ester and 5,6,7-trinor-4,8-inter-m-phenylene-15-epi-2-nor-w-homo-16,16-dimethyl-17-propoxy PGI₂ methyl ester

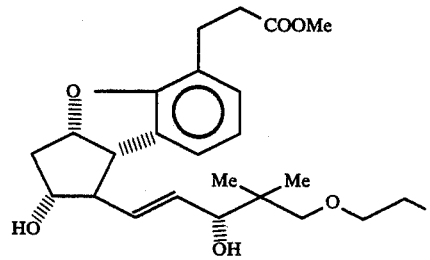

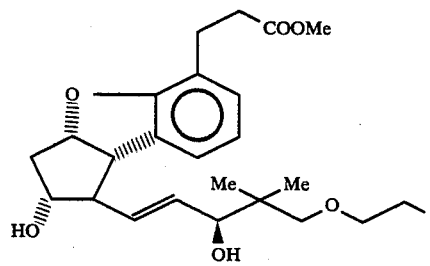

To a precooled, stirred solution of 5,6,7-trinor-4,8-inter-m-phenylene-11,15-didehydroxy-11-acetoxy-15-oxo-2-nor-w-homo-16,16-dimethyl-17-propoxy PGI₂ methyl ester (1.3624 g, 2.89 mmol) in 20 ml of methanol, was added cerium trichloride heptahydrate (1.6131 g, 4.33 mmol) and sodium borohydride (107.1 mg, 3.46 mmol), and the resulting mixture was stirred for 10 minutes. To the mixture, 20 ml of saturated aqueous sodium hydrogen carbonate solution was added and the mixture was stirred for 10 minutes at room temperature. The reaction mixture was suction-filtered through a pad of Celite, and the solid was washed with 150 ml of ethyl acetate. The solution was concentrated, and the residue was extracted with ethyl acetate (30 ml×3). The combined organic layers were washed with 70 ml of saturated aqueous sodium chloride solution, dried over anhydrous sodium sulfate (30 g), and concentrated to obtain 1.26 g of an oily product.

The thus obtained oil was subjected to azeotropic distillation with benzene (15 ml×3), and was dissolved in 20 ml of anhydrous methanol. To the mixture, was added 5.22N of sodium methoxide (0.06 ml, 0.29 ml), and the resulting mixture was stirred for 3 hours at room temperature under argon stream. To the reaction mixture, 0.1 ml of acetic acid was added, and the resulting mixture was concentrated. To the obtained residue, 10 ml of waer was added and the resulting mixture was extracted with ethyl acetate (10 ml×3). The combined organic layers were washed with 30 ml of saturated aqueous sodium chloride solution, dried over anhydrous sodium sulfate (15 g), and concentrated to obtain an oily product of 1.2112 g. By purifying the thus obtained oily product with a column chromatography (silica gel; ethyl acetate/cyclohexane=3/1), 5,6,7-trinor-4,8-inter-m-phenylene-15-epi-2-nor-w-homo-16,16-dimethyl-17-propoxy PGI$_2$ methyl ester (547.1 mg, 1.27 mmol) of less polarity was obtained firstly in a yield of 44%. Subsequently, from the secondly eluted fraction containing more polar material, 5,6,7-trinor-4,8-inter-m-phenylene-2-nor-w-homo-16,16-dimethyl-17-propoxy PGI$_2$ methyl ester (492.3 mg, 1.14 mmol) was obtained in a 40% yeild. Their structures were confirmed by the following data: 5,6,7-trinor-4,8-inter-m-phenylene-2-nor-w-homo-16,16-dimethyl-17-propoxy PGI$_2$ methyl ester IR (Liquid Film Method): 3380, 2951, 2860, 1728, 1595, 1445, 1360, 1296, 1254, 1191, 1095, 1032, 1002, 968, 885, 861, 835, 743 cm$^{-1}$.

NMR (400 MHz, CDCl$_3$, δ): 0.91–0.97 (3H, m), 0.93 (3H, s), 0.95 (3H, s), 1.55–1.64 (2H, m), 1.96–2.03 (1H, m), 2.45–2.51 (2H, m), 2.61–2.67 (3H, m), 2.87–2.91 (2H, m), 3.29–3.43 (4H, m), 3.48 (1H, t, J=8.3), 3.66 (3H, s), 3.92–3.98 (2H, m), 4.01–4.03 (1H, m), 5.11–5.16 (1H, m), 5.62–5.77 (2H, m), 6.75 (1H, t, J=7.3), 6.97 (2H, d, J=7.3).

Mass (EI Method, m/e): 432 (M+).

High Resolution Mass Spectrum: Calcd.: (C$_{25}$H$_{36}$O$_6$, M+) 432.2512 Found: (M+) 432.2519.

5,6,7-trinor-4,8-inter-m-phenylene-15-epi-2-nor-w-homo-16,16-dimethyl-17-propoxy PGI$_2$ methyl ester IR (Liquid Film Method): 3400, 2951, 2860, 1725, 1593, 1444, 1362, 1297, 1251, 1190, 1146, 1093, 1031, 972, 884, 862, 835, 743 cm$^{-1}$.

NMR (400 MHz, CDCl$_3$, δ): 0.91–0.97 (3H, m), 0.94 (6H, s), 1.56–1.65 (2H, m), 1.88 (1H, br s), 1.98–2.04 (1H, m), 2.50–2.56 (1H, m), 2.59–2.68 (3H, m), 2.87–2.92 (2H, m), 3.29–3.42 (4H, m), 3.52 (1H, t, J=8.3), 3.66 (3H, s), 3.93–4.02 (3H, m), 5.13–5.18 (1H, m), 5.62–5.76 (2H, m), 6.77 (1H, t, J=7.3), 6.97 (1H, d, J=7.3), 7.03 (1H, d, J=7.3)

Mass (EI Method, m/e): 432 (M+).

High Resolution Mass Spectrum: Calcd.: (C$_{25}$H$_{36}$O$_6$, M+) 432.2512 Found: (M+) 432.2508.

EXAMPLE 239

5,6,7-trinor-4,8-inter-m-phenylene-2-nor-w-homo-16,16-dimethyl-17-propoxy PGI$_2$

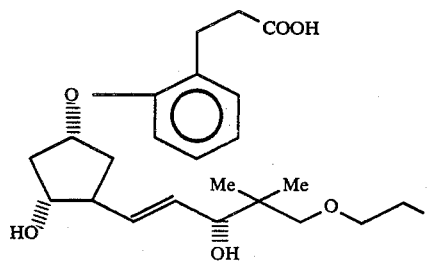

To a solution of 5,6,7-trinor-4,8-inter-m-phenylene-2-nor-w-homo-16,16-dimethyl-17-propoxy PGI$_2$ methyl ester (309.9 mg, 0.72 mmol) in 12 ml of methanol, was added 0.92N aqueous sodium hydroxide solution (2.3 ml, 2.16 mmol) was added, and the mixture was stirred overnight at room temperature under argon atmosphere. To the reaction mixture, was added 2.6 ml of 1N hydrochloric acid and then 15 ml of water, and the resulting mixture was extracted with ethyl acetate (15 ml×3). The combined organic layers were, washed with 40 ml of saturated aqueous sodium chloride solution, dried over anhydrous sodium sulfate (15 g), and concentrated to quantitatively obtain 5,6,7-trinor-4,8-inter-m-phenylene-2-nor-w-homo-16,16-dimethyl-17-propoxy PGI$_2$ (299.1 mg, 0.72 mmol) as a sole product. By recrystallizing the thus obtained product from ethyl acetate/cyclohexane (1/1), a colorless needle-like crystals were obtained. Its structure was confirmed by the following data:

m.p.: 107.5°–108.5° C.

IR (KBr Method): 3375 (3625–2250), 2956, 2928, 2853, 1697, 1595, 1447, 1417, 1382, 1354, 1285, 1255, 1201, 1157, 1139, 1102, 1063, 1040, 1017, 983, 964, 921, 902, 850, 822, 802, 782, 762, 742, 642, 603 cm$^{-1}$.

NMR (400 MHz, CDCl$_3$, δ): 0.90–0.97 (3H, m), 0.92 (3H, s), 0.94 (3H, s), 1.55–1.64 (2H, m), 1.96–2.04 (1H, m), 2.44–2.52 (1H, m), 2.59–2.74 (3H, m), 2.83–2.98 (2H, m), 3.28–3.43 (4H, m), 3.47 (1H, t, J=8.3), 3.91–4.00 (2H, m), 2.8–4.6 (3H, br s), 5.12–5.17 (1H, m), 5.61–5.72 (2H, m), 6.75 (1H, t, J=7.3), 6.95–6.99 (2H, m).

Mass (EI Method, m/e): 418.

High Resolution Mass Spectrum: Calcd.: (C$_{24}$H$_{34}$O$_6$, M+) 418.2356 Found: (M+) 418.2385.

EXAMPLE 240

5,6,7-trinor-4,8-inter-m-phenylene-15-epi-2-nor-w-homo-16,16-dimethyl-17-propoxy PGI$_2$

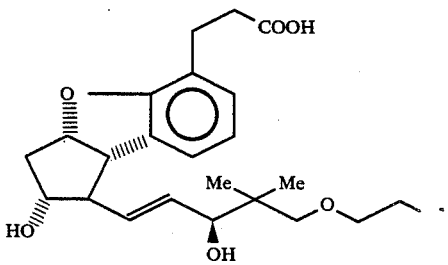

To a solution of 5,6,7-trinor-4,8-inter-m-phenylene-15-epi-2-nor-w-homo-16,16-dimethyl-17-propoxy PGI$_2$ methyl ester (346.3 mg, 0.81 mmol) in 12 ml of methanol, was added 0.92N aqueous sodium hydroxide solution (2.64 ml, 2.43 mmol) was added, and the mixture was stirred overnight at room temperature under argon atmosphere. To the reaction mixture, was added 3 ml of 1N hydrochloric acid and then 15 ml of water, and the resulting mixture was extracted with ethyl acetate (15 ml×3). The combined organic layers were washed with 40 ml of saturated aqueous sodium chloride solution, dried over anhydrous sodium sulfate (15 g), and concentrated to quantitatively obtain 5,6,7-trinor-4,8-inter-m-phenylene-15-epi-2-nor-w-homo-16,16-dimethyl-17-propoxy PGI$_2$ (299.1 mg, 0.72 mmol) as a sole product. Its structure was confirmed by the following data:

IR (Liquid Film Method): 3380 (3675–2250), 2951, 2860, 1702, 1592, 1444, 1404, 1381, 1257, 1187, 1149, 1092, 1024, 1000, 965, 944, 884, 861, 834, 741 cm$^{-1}$.

NMR (400 MHz, CDCl$_3$, δ): 0.91–0.96 (3H, m), 0.94 (6H, s), 1.56–1.65 (2H, m), 1.98–2.06 (1H, m), 2.50–2.73 (4H, m), 2.83–2.86 (2H, m), 3.30–3.45 (4H, m), 3.52 (1H, t, J=8.3), 3.93–4.01 (2H, m), 2.8–4.6 (3H, br S), 5.13–5.19 (1H, m), 5.64–5.76 (2H, m), 6.77 (1H, t, J=7.3), 6.98 (1H, d, J=7.3), 7.01 (1H, d, J=7.3)

Mass (EI Method, m/e): 418 (M+).

High Resolution Mass Spectrum: Calc.: (C$_{24}$H$_{34}$O$_6$, M+) 418.2356 Found: (M+) 418.2337.

EXAMPLE 241

5,6,7-trinor-4,8-inter-m-phenylene-2,17,18,19,20-pentanor-16,16-dimethyl-16-phenoxy PGI$_2$ methyl ester
and
5,6,7-trinor-4,8-inter-m-phenylene-15-epi-2,17,18,19,20-pentanor-16,16-dimethyl-16-phenoxy PGI$_2$ methyl ester

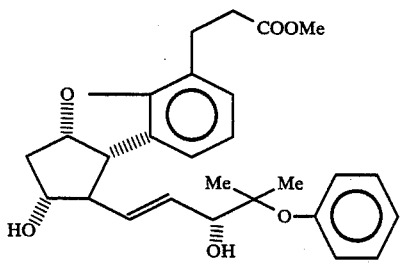

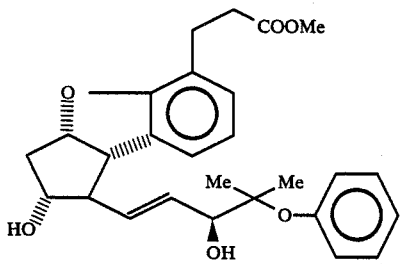

5,6,7-trinor-4,8-inter-m-phenylene-2,17,18,19,20-pentanor-11,15-didehydroxy-15-acetoxy-16,16,-dimethyl-16-phenoxy PGI$_2$ methyl ester (1.88 g, 3.82 mmol) was dissolved in 85 ml of methanol. To this solution, cerium trichloride haptahydrate (1.39 g, 3.72 mmol) was added and then sodium borohydride (0.21 g, 5.58 mmol) was added slowly while cooling the mixture in an ice bath. The mixture was kept stirred in the same conditions for 20 minutes. To the reaction mixture, 20 ml of saturated sodium hydrogen carbonate was added, and the resulting mixture was filtered and the filtrate was concentrated. To the concentration residue, 10 ml of water was added and the resulting mixture was extracted with ethyl acetate (60 ml×1), and the ethyl acetate layer was washed with water (10 ml×1) and then with saturated aqueous sodium chloride solution (10 ml×1), dried over anhydrous sodium sulfate, and concentrated to obtained an oily product (1.84 g). The thus obtained oily product was dissolved in 50 ml of anhydrous methanol under argon atmosphere, and then a solution of sodium methoxide in methanol (5.22N, 0.173 ml, 0.906 mmol) was added to the resulting mixture under stirring, and the mixture was stirred for 14 hours at room temperature. The mixture was neutralized with acetic acid and concentrated. To the residue, 10 ml of water was added, and the resulting mixture was extracted with ethyl acetate (50 ml×2) and the ethyl acetate layer were washed with water (10ml×1) and with saturated aqueous sodium chloride solution (10 ml×1), dried over anhydrous sodium sulfate, and concentrated. The separation of isomers was accomplished by column chromatography using Rober column manufactured by Merck & Co., Inc. (silica gel, ethyl acetate/cyclohexane 2/1) 5,6,7-trinor-4,8-inter-m-phenylene-15-epi-2,17,18,19,20-pentanor-16,16-dimethyl-16-phenoxy PGI$_2$ methyl ester from first eluted fraction containing less polar material (Amount: 647 mg, 1.43 mmol, Yield: 37.5%) and 5,6,7-trinor-4,8-inter-m-phenylene-2,17,18,19,20-pentanor-16,16-dimethyl-16-phenoxy PGI$_2$ methyl ester from secondly eluted fraction containing more polar material (Amount: 618 mg, 1.37 mmol, Yield: 35.7%) were obtained. Their structures were confirmed by the following data: 5,6,7-trinor-4,8-inter-m-phenylene-2,17,18,19,20-pentanor-16,16-dimethyl-16-phenoxy PGI$_2$ methyl ester m.p.: 124.5°–126.1° C. (Recrystallization Solvent: ethyl acetate/n-hexane (4/3)).

IR (KBr Method): 3500, 3400, 2960, 1710, 1590, 1480, 1440, 1360, 1320, 1280, 1260, 1215, 1190, 1145, 1090, 1065, 1020, 975, 950, 880, 860, 830, 780, 740, 690 cm$^{-1}$.

NMR (400 MHz, CDCl$_3$, γ): 1.25 (3H, s), 1.26 (3H, s), 1.9–2.1 (1H, m), 2.3–2.5 (1H, m), 2.52 (1H, q, J=8.3 Hz), 2.6–2.7 (3H, m), 2.8–3.0 (2H, m), 3.0–3.2 (1H, m), 3.49 (1H, t, J=H, t, J=8.3 Hz), 3.66 (3H, s), 3.9–4.1 (1H, m), 4.1–4.3 (1H, m), 5.1–5.2 (1H, m), 5.72 (1H, dd, J=15.4 Hz, 6.8 Hz), 5.83 (1H, dd, J=15.4 Hz, 8.3 Hz), 6.75 (1H, t, J=7.3 Hz), 6.9–7.0 (4H, m), 7.05–7.15 (1H, m), 7.2–7.4 (2H, m).

Mass (EI Method): 452 (M+).

Elemental Analysis: Calcd.: (as C$_{27}$H$_{32}$O$_6$) C (%); 71.66 H (%); 7.13 Found: C (%); 71.47 H (%); 7.15.

5,6,7-trinor-4,8-inter-m-phenylene-15-epi-2,17,18,19,20-pentanor-16,16-dimethyl-16-phenoxy PGI$_2$ methyl ester m.p.: 95.3°–96.1° C. (Recrystallizatin Solvent: ethyl acetate/cyclohexane (1/1))

IR (KBr Method): 3370, 2970, 2850, 1730, 1590, 1480, 1420, 1370, 1360, 1290, 1250, 1225, 1190, 1125, 1100, 1070, 1030, 970, 950, 880, 860, 830, 780, 740, 695 cm$^{-1}$.

NMR (400 MHz, CDCl$_3$, γ): 1.24 (3H, s), 1.27 (3H, s), 1.9–2.3 (1H, m), 2.54 (1H, q, J=8.2 Hz), 2.5–2.7 (4H, m), 2.8–3.0 (3H, m), 3.53 (1H, t, J=8.2 Hz), 3.66 (3H, s), 3.9–4.1 (1H, m), 4.2–4.3 (1H, m), 5.1–5.2. (1H, m), 5.73 (1H, dd, J=15.4 Hz, 5.9 Hz), 5.86 (1H, ddd, J=15.4 Hz, 8.2 Hz, 1.0 Hz), 6.76 (1H, t, J=7.6 Hz), 6.9–7.0 (4H, m), 7.1–7.2 (1H, m), 7.2–7.4 (2H, m).

Mass (EI Method, m/e): 452 (M+).

Elemental Analysis: Calcd.: (as $C_{27}H_{32}O_6$) C (%); 71.66 H (%); 7.13 Found: C (%); 71.43 H (%); 7.19.

EXAMPLE 242

5,6,7-trinor-4,8-inter-m-phenylene-2,17,18,19,20-pentanor-16,16-dimethyl-16-phenoxy $PGI_2$

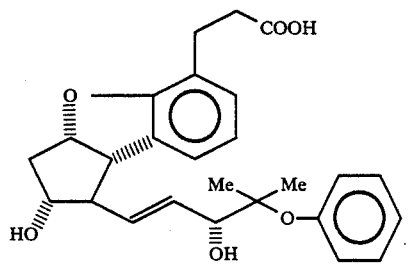

To a stirred solution of 5,6,7-trinor-4,8-inter-m-phenylene-2,17,18,19,20-pentanor-16,16-dimethyl-16-phenoxy $PGI_2$ methyl ester (300 mg, 0.66 mmol) in 30 ml of methanol, was added 1N aqueous sodium hydroxide solution was added while cooling the solution in an ice bath, and the resulting mixture was stirred for 14 hours at room temperature. The reaction mixture was concentrated, and 10 ml of water was added to the residue. The resulting mixture was then neutralized with 1N hydrochloric acid, and extracted with ethyl acetate (50 ml×2). The ethyl acetate layers were washed with water (10 ml×1), and with saturated aqueous sodium chloride solution (10 ml×1), dried over anhydrous sodium sulfate, and concentrated. The residue was recrystallized from 2 ml of ethyl acetate and 1.5 ml of n-hexane to obtain 5,6,7-trinor-4,8-inter-m-phenylene-2,17,18,19,20-pentanor-16,16-dimethyl-16-phenoxy $PGI_2$ (Amount: 274 mg, 0.626 ml. Yield: 94.3%) in the form of white crystals. Its structure was confirmed by the following data: m.p.: 154.5°–155.6° C. (Recrystallization Solvent: ethyl aceate/n-hexane=4/3).

IR (KBr Method): 3360, 2970, 2870, 1700, 1590, 1480, 1470, 1375, 1210, 1220, 1190, 1150, 1120, 1090, 1065, 1030, 1000, 960, 910, 880, 860, 830, 780, 740, 695 cm$^{-1}$.

NMR (400 MHz, DMSO, γ): 1.17 (3H, s), 1.24 (3H, s), 1.6–1.8 (1H, m), 2.1–2.3 (1H, m), 2.4–2.6 (3H, m), 2.71 (2H, t, J=7.6 Hz), 3.42 (1H, t, J=9.0 Hz), 3.7–3.8 (1H, m), 4.0–4.1 (1H, m), 4.8–4.9 (1H, m), 5.0–5.1 (2H, m), 5.6–5.9 (2H, m), 6.69 (1H, t, J=7.3 Hz), 6.9–7.1 (5H, m), 7.29 (2H, t, J=7.8 Hz)

Mass (EI Method, m/e): 438 (M+).

High Resolution Mass Spectrum: Calcd.: (M+, $C_{26}H_{30}O_6$) 438.2042 Found: (M+) 438.2028.

EXAMPLE 243

5,6,7-trinor-4,8-inter-m-phenylene-15-epi-2,17,18,19,20-pentanor-16,16-dimethyl-16-phenoxy $PGI_2$

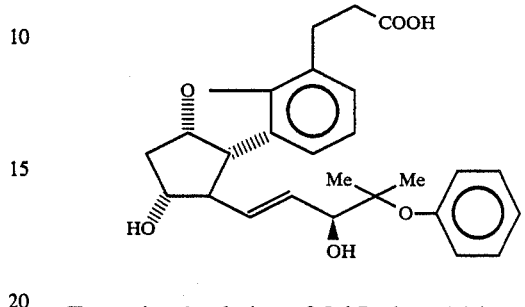

To a stirred solution of 5,6,7-trinor-4,8-inter-m-phenylene-15-epi-2,17,18,19,20-pentanor-16,16-dimethyl-16-phenoxy $PGI_2$ methyl ester (300 mg, 0.664 mmol) in 30 ml of methanol, was added 1N aqueous sodium hydroxide solution (5.15 ml, 5.15 mmol) while cooling the solution in an ice bath, and the resulting mixture was stirred for 14 hours at room temperature. The reaction mixture was concentrated, and 10 ml of water was added to the residue. The resulting mixture was extracted with ethyl acetate (50 ml×2). The ethyl acetate layers were washed with water (10 ml×1), and with saturated aqueous sodium chloride solution (10 ml×1), dried over anhydrous sodium sulfate, and concentrated. The concentration residue was recrystallized from 2 ml of ethyl acetate and 1.5 ml of n-hexane to obtain 5,6,7-trinor-4,8-inter-m-phenylene-15-epi-2,17,18,19,20-pentanor-16,16-dimethyl-16-phenoxy $PGI_2$ (Amount: 241 mg, 0.55 ml, Yield: 82.9%) in the form of white crystals. Its structure was confirmed by the following data: m.p.: 103.5°–105.0° C. (Recrystallization Solvent: ethyl acetate/n-hexane=4/3).

IR (KBr Method): 3400, 2970, 2920, 1695, 1590, 1480, 1445, 1360, 1250, 1220, 1190, 1060, 1030, 980, 950, 870, 850, 770, 740, 695 cm$^{-1}$.

NMR (400 MHz, DMSO, γ): 1.15 (3H, s), 1.24 (3H, s), 1.6–1.8 (1H, m), 2.1–2.3 (1H, m), 2.4–2.6 (3H, m), 2.72 (2H, t, J=7.8 Hz), 3.43 (1H, t, J=9 Hz), 3.7–3.8 (1H, m), 4.0–4.1 (1H, m), 4.8–4.9 (1H, m), 5.0–5.2 (2H, m), 5.6–5.9 (2H, m), 6.70 (1H, t, J=7.6 Hz), 6.9–7.1 (5H, m), 7.2–7.4 (2H, m)

Mass (EI Method, m/e): 438 (M+).

Elemental Analysis: Calcd.: (as $C_{26}H_{30}O_6$) C(%): 71.21 H(%): 6.90 Found: C(%): 71.20 H(%): 6.89.

EXAMPLE 244 d-5,6,7-trinor-4,8-inter-m-phenylene-2,17,18,19,20-pentanor-16-(S)-methyl-16-phenoxy PGI₂ methyl ester and d-5,6,7-trinor-4,8-inter-m-phenylene-15-epi-2,17,18,19,20-pentanor-16-(S)-methyl-16-phenoxy PGI₂ methyl ester

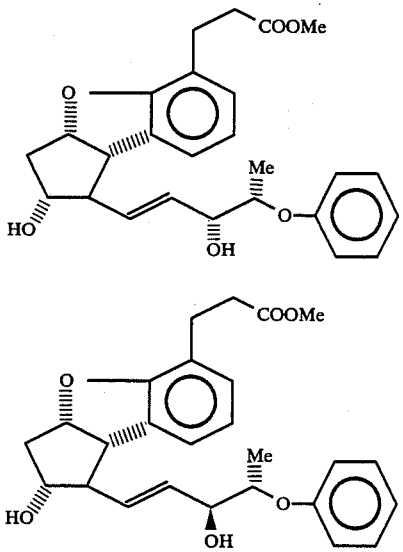

To a stirred solution of d-5,6,7-trinor-4,8-inter-m-phenylene-2,17,18,19,20-pentanor-11,15-didehydroxy-11-acetoxy-15-oxo-16-(S)-methyl-16-phenoxy PGI₂ methyl ester (850 mg, 1.78 mmol) in 40 ml of methanol, was added cerium (III) trichloride heptahydrate (663 mg, 1.78 mmol), and then sodium borohydride (67.3 mg, 1.78 mmol) was added slowly to the mixture while cooling the mixture in an ice bath. The resulting mixture was kept stirred for 20 minutes. To this reaction mixture, was added 10 ml of saturated aqueous sodium hydrogen carbonate solution, and the mixture was filtered. The solids were washed with ethyl acetate (10 ml×5), and the filtrates were combined and concentrated. To the residue, 30 ml of water was added, and the resulting mixture was extracted with ethyl acetate (100 ml×1), washed with water (30 ml×1) and saturated aqueous sodium chloride solution (30 ml×1), dried over anhydrous sodium sulfate, and concentrated. The residue was subjected to azeotropic distillation with benzene (10 ml×2) to obtain an oily product (843 mg). This oily product was dissolved in anhydrous methanol under argon atmosphere. To this solution, a solution of sodium methoxide in methanol (5.22N, 0.05 ml, 0.264 mmol) was added under stirring, and the mixture was stirred for 2 hours at room temperature, neutralized with acetic acid and concentrated. The residue was mixed with 20 ml of water, and the extracted with ethyl acetate (50 ml×2). The ethyl acetate layers were washed with water (20 ml×1) and with saturated aqueous sodium chloride solution (30 ml×1), dried over anhydrous sodium sulfate, and concentrated. Separation of isomers was accomplished by column chromatography using Rober column manufactured by Merck & Co., Inc. (silica gel:ethyl acetate/cyclohexane=2/1), to obtain, as a first eluted fraction containing less polar material, d-5,6,7-trinor-4,8-inter-m-phenylene-15-epi-2,17,18,19,20-pentanor-16-(S)-methyl-16-phenoxy PGI₂ methyl ester as an oil (Amount: 555 mg, 1.27 mmol, Yield: 72%) and, as a secondly eluted fraction containing more polar one, d-5,6,7-trinor-4,8-inter-m-phenylene-2,17,18,19,20-pentanor-16-(S)-methyl-16-phenoxy PGI₂ methyl ester as white crystals (49.5 mg). Then the obtained d-5,6,7-trinor-4,8-inter-m-phenylene-15-epi-2,17,18,19,20-pentanor-16-(S)-methyl-16-phenoxy PGI₂ methyl ester (555 mg, 1.27 mmol) was dissolved in 10 ml of methylene chloride. To the resulting mixture, was added manganese dioxide (4.96 g, 57 mmol) under stirring, and the mixture was stirred overnight at room temperature. This reaction mixture was filtered through a pad of Hyflo Super-Cel. The obtained solids were washed with ethyl acetate (20 ml×8), and the filtrates were combined and concentrated. The residue was purified by Rober column manufactured by Merck & Co., Inc. (silica gel, ethyl acetate/cyclohexane=1/1) to obtain an oily product (425 mg). The obtained oily product (375 mg, 0.86 mmol) was dissolved in 20 ml of methanol, and cerium (III) chloride heptahydrate (318 mg, 0.86 mmol) was added to the solution under stirring. To the resulting mixture, sodium borohydride (25.9 mg, 0.69 mmol) was added slowly under cooling in an ice bath, and the mixture was stirred for 20 minutes. To this reaction mixture, 10 ml of saturated aqueous sodium hydrogen carbonate was added and the mixture was filtered. The solids were washed with ethyl acetate (10 ml×5), and the filtrates were combined and concentrated. To the concentration residue, 30 ml of water was added and the resulting mixture was extracted with ethyl acetate (100 ml×1). The ethyl acetate layer was washed with water (3 ml×1) and saturated aqueous sodium chloride solution (30 ml×1), dried over anhydrous sodium sulfate, and concentrated. The concentration residue was separated and purified by using Rober column manufactured by Merck & Co., Inc. (silica gel, ethyl acetate/cyclohexane=2/1)to obtain a crystal (44.6 mg). The thus obtained crystal was combined with the above-obtained d-5,6,7-trinor-4,8-inter-m-phenylene-2,17,18,19,20-pentanor-16-(S)-methyl-16-phenoxy PGI₂ methyl ester (49.5 mg), and the combined mass was recrystallized from 2 ml of ethyl acetate and 4 ml of n-hexane to obtain d-5,6,7-trinor-4,8-inter-m-phenylene-2,5,6,7-pentanor-16(S)-methyl-16-phenoxy PGI₂ methyl ester in the form of white crystals (Amount: 47.6 mg, 0.11 mmol, Yield: 6.2%). Their structures were confirmed by the following data.

d-5,6,7-trinor-4,8-inter-m-phenylene-2,17,18,19,20-pentanor-16-(S)-methyl-16-phenoxy PGI₂ methyl ester.

Specific Rotation: $[\alpha]_D^{20} = +108.73$ (c=0.882, MeOH) m.p.: 122.0°–123.0° C. (Recrystallization Solvent: ethyl acetate/n-hexane=½).

IR (KBr Method): 3430, 3030, 2920, 2880, 1725, 1700, 1590, 1485, 1445, 1365, 1335, 1295, 1265, 1240, 1180, 1135, 1080, 1010, 960, 940, 870, 850, 825, 735, 690 cm⁻¹.

NMR (400 MHz, CDCl₃, γ): 1.30 (3H, d, J=6.4 Hz), 1.9–2.1 (2H, m), 2.3–2.4 (1H, m), 2.53 (1H, q, J=8.1 Hz), 2.6–2.7 (3H, m), 2.8–3.0 (2H, m), 3.50 (1H, t, J=8.1 Hz), 3.66 (3H, s), 3.9–4.1 (1H, m), 4.3–4.5 (2H, m), 5.1–5.2 (1H, m), 5.73 (1H, dd, J=15.4, 6.1 Hz), 5.82 (1H, dd, J=15.4, 8.1 Hz), 6.72 (1H, t, J=8.1 Hz), 6.9–7.0 (5H, m), 7.2–7.4 (2H, m)

Mass (EI Method, m/e): 438 (M⁺).

High Resolution Mass Spectrum: Calcd.: (M⁺, $C_{26}H_{30}O_6$) 438.2042 Found: (M⁺) 438.2063.

d-5,6,7-trinor-4,8-inter-m-phenylene-15-epi-2,17,18,19,20-pentanor-16-(S)-methyl-16-phenoxy PGI₂ methyl ester Specific Rotation $[\alpha]_D^{20} = +77.99$ (C=0.868, MeOH).

IR (Liquid Film Method): 3400, 2970, 2920, 1715, 1590, 1485, 1445, 1370, 1230, 1190, 1170, 1060, 970, 920, 880, 855, 750, 690 cm$^{-1}$.

NMR (400 MHz, CDCl$_3$, γ): 1.30 (3H, d, J=5.9 Hz), 1.7–1.8 (1H, m), 1.9–2.1 (1H, m), 2.55 (1H, q, J=7.6 Hz), 2.6–2.7 (4H, m), 2.8–3.0 (2H, m), 3.53 (1H, t, J=8.3 Hz), 3.66 (3H, s), 3.96 (3H, s), 3.9–4.1 (1H, m), 4.2–4.4 (2H, m), 5.1–5.2 (1H, m), 5.71 (1H, dd, J=14.9, 5.9 Hz), 5.88 (1H, dd, J=14.9, 7.6 Hz), 6.71 (1H, t, J=7.3 Hz), 6.9–7.1 (5H, m), 7.2–7.4 (2H, m)

Mass (EI Method, m/e): 438 (M+).

High Resolution Mass Spectrum: Calcd.: (M+, C$_{26}$H$_{30}$O$_6$) 438.2042 Found: (M+) 438.2022.

EXAMPLE 245 d-5,6,7-trinor-4,8-inter-m-phenylene-2,17,18,19,20-pentanor-16-(S)-methyl-16-phenoxy PGI$_2$

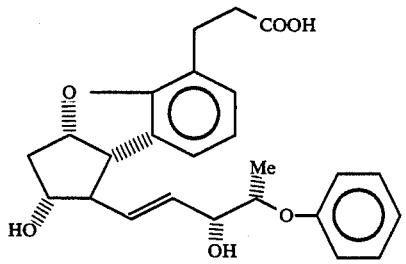

To a stirred solution of d-5,6,7-trinor-4,8-inter-m-phenylene-2,17,18,19,20-pentanor-16-(S)-methyl-phenoxy PGI$_2$ methyl ester (44 mg, 0.1 mmol) in 6 ml of methanol, was added 1N aqueous sodium hydroxide solution (1 ml, 1 mmol) while cooling the mixture in an ice bath, and the mixture was stirred for 14 hours at room temperature. This reaction mixture was concentrated and 5 ml of water was added to the concentrate. The mixture was neutralized with 1N hydrochloric acid, extracted with ethyl acetate (50 ml×2), and the ethyl acetate layers were washed with water (20 ml×1) and saturated aqueous sodium chloride solution (20 ml×1), dried over anhydrous sodium sulfate, and concentrated to obtain d-5,6,7-trinor-4,8-inter-m-phenylene-2,17,18,19,20-pentanor-16-(S)-methyl-16-phenoxy PGI$_2$ as an oily product (Amount: 41.3 mg, 0.097 mmol, Yield: 97.4%). Its structure was confirmed by the following data:

Specific Rotation: $[\alpha]_D^{20} = +115.37$ (C=0.826, MeOH).

IR (Liquid Film Method): 3420, 2970, 2920, 1700, 1590, 1490, 1450, 1370, 1240, 1075, 1060, 1020, 1000, 965, 940, 880, 860, 740, 690 cm$^{-1}$.

NMR (400 MHz, CDCl$_3$, γ): 1.30 (3H, d, J=5.9 Hz), 1.8–3.3 (2H, m), 1.9–2.1 (1H, m), 2.49 (1H, q, J=8.1 Hz), 2.5–2.8 (3H, m), 2.8–3.0 (2H, m), 3.47 (1H, t, J=8.1 Hz), 3.3–4.8 (1H, m), 3.9–4.0 (1H, m), 4.35 (1H, dd, J=6.5, 3.4 Hz), 4.4–4.5 (1H, m), 5.0–5.2 (1H, m), 5.71 (1H, dd, J=15.5, 6.5 Hz), 5.8 (1H, dd, J=15.5, 8.1 Hz), 6.71 (1H, t, J=7.3 Hz), 6.9–7.1 (5H, m), 7.2–7.4 (2H, m).

Mass (EI Method, m/e): 424 (M+)

High Resolution Mass Spectrum: Calcd.: (M+, C$_{25}$H$_{28}$O$_6$) 424.1886 Found: (M+) 424.1884.

EXAMPLE 246 d-5,6,7-trinor-4,8-inter-m-phenylene-15-epi-2,17,18,19,20-pentanor-16-(S)-methyl-16-phenoxy PGI$_2$

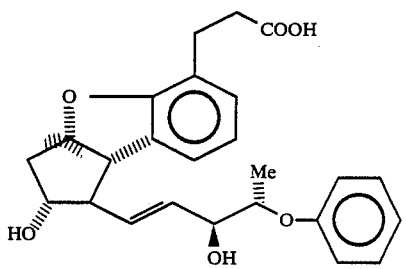

d-5,6,7-trinor-4,8-inter-m-phenylene-15-epi-2,17,18,19,20-pentanor-16-(S)-methyl-phenoxy PGI$_2$ methyl ester (381 mg, 0.87 mmol) was dissolved in 40 ml of methanol and the solution was cooled in an ice bath. To this stirred solution, was added 1N aqueous sodium hydroxide solution (8.7 ml, 8.7 mmol) and the mixture was stirred for 5 hours at room temperature. This reaction mixture was concentrated and 30 ml of water was added to the concentrate. The mixture was neutralized with 1N hydrochloric acid, extracted with ethyl acetate (50 ml×2), and the ethyl acetate layers were washed with water (30 ml×1) and saturated aqueous sodium chloride solution (30 ml×1), dried over anhydrous sodium sulfate, and concentrated to obtain d-5,6,7-trinor-4,8-inter-m-phenylene-15-epi-2,17,18,19,20-pentanor-16-(S)-methyl-phenoxy PGI$_2$ as an oily product (Amount: 341 mg, 0.8 mmol, Yield: 92.4%). Its structure was confirmed by the following data:

Specific Rotation: $[\alpha]_D^{20} = +75.39$ (c=0.89, MeOH).

IR (Liquid Film Method): 3370, 3010, 2970, 2925, 1700, 1590, 1405, 1445, 1370, 1230, 1060, 970, 920, 880, 855, 750, 690, 660 cm$^{-1}$.

NMR (400 MHz, CDCl$_3$, γ): 1.30 (3H, d, J=5.9 Hz), 1.9–2.1 (1H, m), 2.1–3.6 (3H, m), 2.53 (1H, q, J=7.6 Hz), 2.5–2.8 (3H, m), 2.8–3.0 (2H, m), 3.52 (1H, t, J=8.3 Hz), 3.9–4.1 (1H, m), 4.2–4.4 (2H, m), 5.1–5.2 (1H, m), 5.70 (1H, dd, J=15.3, 5.9 Hz), 5.87 (1H, dd, J=15.3, 8.3 Hz), 6.71 (1H, t, J=7.6 Hz), 6.9–7.1 (5H, m), 7.2–7.4 (2H, m).

Mass (EI Method, m/e): 424 (M+).

High Resolution Mass Spectrum: Calc.: (M+, C$_{25}$H$_{28}$O$_6$) 424.1886 Found: (M+) 424.1913.

EXAMPLE 247 d-5,6,7-trinor-4,8-inter-m-phenylene-2,17,18,19,20-pentanor-16-(R)-methyl-16-phenoxy PGI$_2$ methyl ester and d-5,6,7-trinor-4,8-inter-m-phenylene-15-epi-2,17,18,19,20-pentanor-16-(R)-methyl-16-phenoxy PGI$_2$ methyl ester

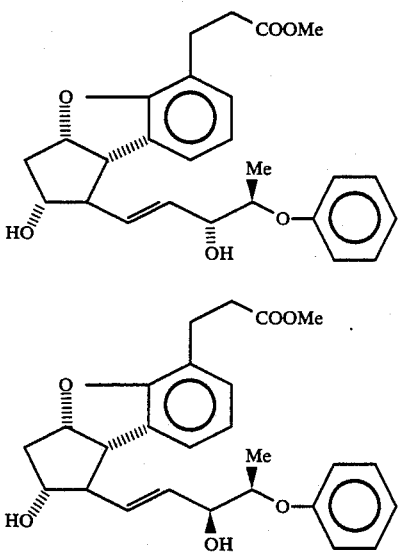

d-5,6,7-trinor-4,8-inter-m-phenylene-2,17,18,19,20-pentanor-11,15-didehydroxy-11-acetoxy-15-oxo-16-(R)-methyl-16-phenoxy PGI$_2$ methyl ester (763 mg, 1.6 mmol) was dissolved in 40 ml of methanol. The solution was cooled in an ice bath. To this stirred solution, was added cerium (III) trichloride heptahydrate (662 mg, 1.77 mmol), followed by the slow addition of sodium borohydride (74 mg, 1.95 mmol). The resulting mixture was kept stirred for 20 minutes under the same conditions. To this reaction mixture, 9 ml of saturated sodium hydrogen carbonate was added, and the mixture was filtered. The obtained precipitate was washed with ethyl acetate (20 ml×3), and the filtrates were combined and concentrated. To the residue, 100 ml of ethyl acetate was added, and the resulting mixture was washed with with water (30 ml×1) and saturated aqueous sodium chloride solution (30 ml×1), dried over anhydrous sodium sulfate, and concentrated. The obtained concentrate was subjected to azeotropic distillation with benzene (10 ml×2) to obtain an oily product (752 mg). This oily product was dissolved in anhydrous methanol under argon atmosphere. To this solution, a solution of sodium methoxide in methanol (5.22N, 0.083 ml, 0.44 mmol) was added under stirring, and the mixture was stirred for 2.5 hours at room temperature. The mixture was neutralized with acetic acid, concentrated, diluted with 20 ml of water, and extracted with ethyl acetate (50 ml×2). The ethyl acetate layers were washed with water (20 ml×1) and with saturated aqueous sodium chloride solution (30 ml×1), dried over anhydrous sodium sulfate, and concentrated. Separation of isomers was accomplished by column chromatography using Rober column manufactured by Merck & Co., Inc. (silica gel:ethyl acetate/cyclohexane=2/1), to obtain, as a first eluted fraction containing of less polar material, d-5,6,7-trinor-4,8-inter-m-phenylene-15-epi-2,17,18,19,20-pentanor-16-(R)-methyl-16-phenoxy PGI$_2$ methyl ester (Amount: 95.5 mg, 0.22 mmol, Yield: 13.6%) and, as a secondly eluted fraction containing more polar material, d-5,6,7-trinor-4,8-inter-m-phenylene-2,17,18,19,20-pentanor-16-(S)-methyl-16-phenoxy PGI$_2$ methyl ester (Amount: 437 mg, 1 mmol, Yield: 62.5%). Their structures were confirmed by the following data:

d-5,6,7-trinor-4,8-inter-m-phenylene-2,17,18,19,20-pentanor-16-(R)-methyl-16-phenoxy PGI$_2$ methyl ester.

Specific Rotation: $[\alpha]_D^{20} = +96.47$ (c=1.306, methanol) m.p.: 88.5°–90.1° C. (Recrystallization Solvent: ethyl acetate/n-hexane=½).

IR (KBr Method): 3380, 2960, 2925, 2860, 1715, 1590, 1485, 1445, 1360, 1230, 1180, 1090, 1065, 1050, 1010, 970, 950, 920, 860, 740, 690 cm$^{-1}$.

NMR (400 MHz, CDCl$_3$, γ): 1.30 (3H, d, J=6.4 Hz), 1.9–2.1 (1H, m), 2.4–2.6 (2H, m), 2.5–2.7 (3H, m), 2.8–3.0 (3H, m), 3.47 (1H, t, J=8.6 Hz), 3.66 (3H, s), 3.9–4.1 (1H, m), 4.1–4.4 (2H, m), 5.0–5.2 (1H, m), 5.65 (1H, dd, J=15.2, 6.8 Hz), 5.84 (1H, dd, J=15.2; 8.6 (Hz), 6.73 (1H, t, J=7.3 Hz), 6.8–7.0 (5H, m), 7.2–7.4 (2H, m).

Mass (EI Method, m/e): 438 (M+).

High Resolution Mass Spectrum: Calcd.: (M+, C$_{26}$H$_{30}$O$_6$) 438.2042 Found: (M+) 438.2031.

d-5,6,7-trinor-4,8-inter-m-phenylene-15-epi-2,17,18,19,20-pentanor-16-(R)-methyl-16-phenoxy PGI$_2$ methyl ester.

Specific Rotation: $[\alpha]_D^{20} = +70.15$ (c=1.91, MeOH).

IR (Liquid Film Method): 3370, 2920, 1715, 1590, 1480, 1460, 1360, 1230, 1190, 1055, 1020, 965, 880, 850, 745, 690 cm$^{-1}$.

NMR (400 MHz, CDCl$_3$, γ): 1.31 (3H, d, J=6.35 Hz), 1.7–1.8 (1H, m), 1.9–2.1 (1H, m), 2.25 (1H, d, J=4.9 Hz), 2.54 (1H, q, J=8.0 Hz), 2.5–2.7 (3H, m), 2.8–3.0 (2H, m), 3.52 (1H, t, J=8.0 Hz), 3.66 (3H, s), 3.9–4.1 (1H, m), 4.1–4.5 (2H, m), 5.1–5.2 (1H, m), 5.73 (1H, dd, J=14.8, 5.7 Hz), 5.85 (1H, dd, J=14.8, 8.0 Hz), 6.75 (1H, d, J=7.6 Hz), 6.8–7.1 (5H, m), 7.2–7.4 (2H, m).

Mass (EI Method, m/e): 438 (M+).

High Resolution Mass Spectrum: Calcd.: (M+, C$_{26}$H$_{30}$O$_6$) 438.2042 Found: (M+) 438.2033.

EXAMPLE 248 d-5,6,7-trinor-4,8-inter-m-phenylene-2,17,18,19,20-pentanor-16-(R)-methyl-16-phenoxy PGI$_2$

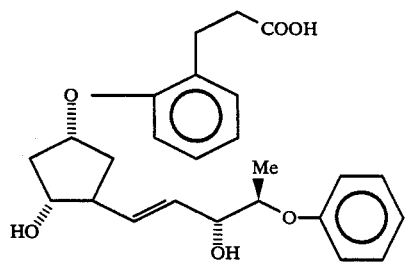

d-5,6,7-trinor-4,8-inter-m-phenylene-2,17,18,19,20-pentanor-16-(R)-methyl-16-phenoxy PGI$_2$ methyl ester (373 mg, 0.85 mmol) was dissolved in 50 ml of methanol and the solution was cooled in an ice bath. To this stirred solution, was added 1N aqueous sodium hydroxide solution (8.5 ml, 8.5 mmol), and the mixture was stirred for 3 hours at room temperature. This reaction mixture was concentrated and 30 ml of water was added to the concentrate. The mixture was neutralized with 1N hydrochloric acid, extracted with ethyl acetate (50 ml×2), and the ethyl acetate layers were washed with water (30 ml×1) and with saturated aqueous sodium chloride solution (20 ml×1), dried over anhydrous sodium sulfate, and concentrated. The residue was recrystallized from 4 ml of ethyl acetate and 8 ml of n-hexane to obtain d-5,6,7-trinor-4,8-inter-m-phenylene-2,17,18,19,20-pentanor-16-(R)-methyl-16-phenoxy PGI$_2$ as white crystals (Amount: 307 mg, 0.72 mmol, Yield: 85.2%). Its structure was confirmed by the following data:

Specific Rotation: $[\alpha]_D^{20} = +96.15$ (c=0.624, MeOH).

m.p.: 94.8°–96.5° C. (Recrystallization Solvent: ethyl acetate/n-hexane=½).

IR (KBr Method): 3380, 2970, 2920, 1700, 1590, 1485, 1445, 1230, 1170, 1060, 965, 910, 855, 745, 690 cm$^{-1}$.

NMR (400 MHz, CDCl$_3$, δ): 1.30 (3H, d, J=6.7 Hz), 1.9–2.1 (1H, m), 2.3–3.4 (3H, m), 2.47 (1H, q, J=8.3 Hz), 2.5–3.0 (5H, m), 3.47 (1H, t, J=8.3 Hz), 3.9–4.0 (1H, m), 4.21 (1H, t, J=6.7 Hz), 4.2–4.4 (1H, m), 5.0–5.2 (1H, m), 5.64 (1H, dd, J=15.1, 6.7 Hz), 5.83 (1H, dd, J=15.1, 8.3 Hz), 6.74 (1H, t, J=7.3 Hz), 6.9–7.0 (5H, m), 7.2–7.4 (2H, m).

Mass (EI Method, m/e): 424 (M+).

High Resolution Mass Spectrum: Calcd.: (M+, C$_{25}$H$_{28}$O$_6$) 424.1886 Found: (M+) 424.1893.

EXAMPLE 249 d-5,6,7-trinor-4,8-inter-m-phenylene-15-epi-2,17,18,19,20-pentanor-16-(R)-methyl-16-phenoxy PGI$_2$

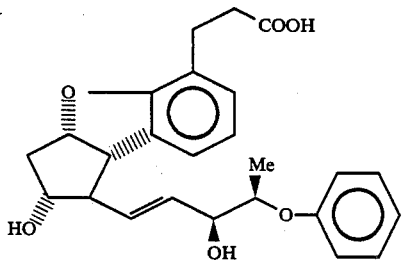

d-5,6,7-trinor-4,8-inter-m-phenylene-15-epi-2,17,18,19,20-pentanor-16-(R)-methyl-16-phenoxy PGI$_2$ methyl ester (90.0 mg, 0.205 mmol) was dissolved in 10 ml of methanol and the solution was cooled in an ice bath. To this stirred solution, was added 1N aqueous sodium hydroxide solution (2.05 ml, 2.05 mmol), and the mixture was stirred for 4 hours at room temperature. This reaction mixture was concentrated and 10 ml of water was added to the concentrate. The mixture mixture was neutralized with 1N hydrochloric acid, extracted with ethyl acetate (50 ml×2), and the ethyl acetate layers were washed with water (20 ml×1) and with saturated aqueous sodium chloride solution (20 ml×1), dried over anhydrous sodium sulfate, and concentrated to obtain d-5,6,7-trinor-4,8-inter-m-phenylene-15-epi-2,17,18,19,20-pentanor-16-(R)-methyl-16-phenoxy PGI$_2$ as a colorless transparent liquid (Amount: 83.1 mg, 0.196 mmol, Yield: 92.6%). Its structure was confirmed by the following data:

Specific Rotation: $[\alpha]_D^{20} = +71.47$ (c=0.61, MeOH).

IR (Liquid Film Method): 3350, 2970, 2920, 1700, 1590, 1480, 1440, 1370, 1230, 1060, 960, 880, 855, 825, 790, 750, 690 cm$^{-1}$.

NMR (400 MHz, CDCl$_3$, δ): 1.30 (3H, d, J=6.7 Hz), 1.9–2.1 (1H, m), 2.3–3.4 (3H, m), 2.47 (1H, q, J=8.3 Hz), 2.5–3.0 (5H, m), 3.47 (1H, t, J=8.3 Hz), 3.9–4.0 (1H, m), 4.21 (1H, t, J=6.7 Hz), 4.2–4.4 (1H, m), 5.0–5.2 (1H, m), 5.64 (1H, dd, J=15.1, 6.7 Hz), 5.83 (1H, dd, J=15.1, 8.3 Hz), 6.74 (1H, t, J=7.3 Hz), 6.9–7.0 (5H, m), 7.2–7.4 (2H, m).

Mass (EI Method, m/e): 424 (M+).

High Resolution Mass Spectrum: Calcd.: (M+, C$_{25}$H$_{28}$O$_6$) 424.1886 Found: (M+) 424.1899.

EXAMPLE 250 d-5,6,7-trinor-4,8-inter-m-phenylene-2,18,19,20-tetranor-16-methyl-16-phenoxy PGI$_2$ methyl ester and d-5,6,7-trinor-4,8-inter-m-phenylene-15-epi-2,18,19,20-tetranor-16-methyl-16-phenoxy PGI$_2$ methyl ester

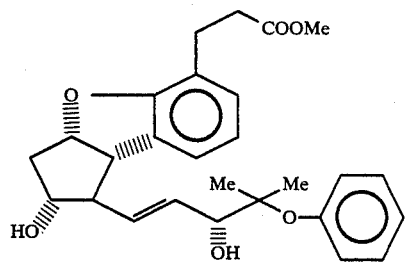

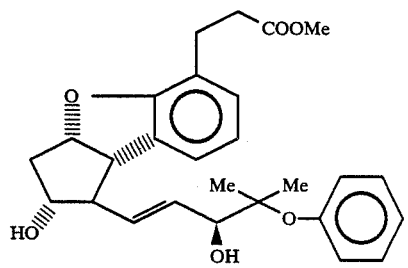

d-5,6,7-trinor-4,8-inter-m-phenylene-11,15-didehydroxy-11-acetoxy-15-oxo-2,18,19,20-tetranor-16-methyl-16-phenoxy PGI$_2$ methyl ester (17.52 g, 35.61 mmol) was dissolved in 250 ml of methanol. The solution was cooled in an ice bath. To this stirred solution, cerium (III) trichloride heptahydrate (19.9 g, 53.41 mmol) was added and dissolved, followed by the slow addtion of sodium borohydride (1.35 g, 35.61 mmol). After stirring the resulting mixture for 10 minutes, 150 ml of saturated sodium hydrogen carbonate solution was added thereto, and the mixture was stirred for 20 minutes. The reaction mixture was suction-filtered through a pad of Celite. The filtrate was concentrated and the obtained residue was extracted with ethyl acetate (150 ml×3). The combined organic were washed with 300 ml of saturated aqueous sodium chloride solution, dried over anhydrous sodium sulfate (30 g), and concentrated to obtain 18.42 g of an oil.

Then the oil was subjected to azeotropic distillation with benzen (20 ml×3), and 125 ml of anhydrous methanol was added thereto to dissolve the same. To the resulting mixture, 5.22N of sodium methoxide (0.68 ml, 3.56 mmol) was added and the resulting mixture was stirred for 1.5 hours at room temperature under argon atmosphere. To the reaction mixture, 0.8 ml of acetic acid was added and the mixture was concentrated. To the obtained concentration residue, 100 ml of water was added and the resulting mixture was extracted with ethyl acetate (100 ml×3). The organic phases were combined, washed with 250 ml of saturated aqueous sodium chloride solution, dried over anhydrous sodium sulfate (30 g), and concentrated to obtain 17.82 g of an oily product. The separation of isomers was accomplished by column chromatography (silica gel: ethyl acetate/cyclohexane=2/1) to obtain, as a first eluted fraction containing less polar material, d-5,6,7-trinor-4,8-inter-m-phenylene-15-epi-2,18,19,20-tetranor-16-methyl-16-phenoxy PGI₂ methyl ester (7.7173 g, 17.07 mmol) in a yield of 47.9%, and as a secondly eluted fraction containing more polar one, d-5,6,7-trinor-4,8-inter-m-phenylene-2,18,19,20-tetranor-16-methyl-16-phenoxy PGI₂ methyl ester (6.9805 g, 15.44 mmol) with a yeild of 43.4%. This was recrystallized from ethyl acetate to obtain colorless needle-like crystals. Their structures were confirmed by the following data:

d-5,6,7-trinor-4,8-inter-m-phenylene-2,18,19,20-tetranor-16-methyl-16-phenoxy PGI₂ methyl ester m.p.: 104°–105° C.

Specific Rotation: $[\alpha]_D^{20} = +118.21$ (c=0.906, MeOH). IR (KBr Method): 3510, 3405, 2920, 2905, 1714, 1667, 1584, 1482, 1442, 1380, 1362, 1342, 1322, 1283, 1262, 1227, 1184, 1174, 1144, 1125, 1105, 1088, 1065, 1030, 1015, 977, 952, 915, 883, 865, 838, 823, 785, 746, 699, 625, 605, 585, 548, 538, 520, 474, 439 cm⁻¹.

NMR (400 MHz, CDCl₃, δ): 1.25 (3H, s), 1.26 (3H, s), 1.95, 2.06 (1H, m), 2.30–2.41 (1H, broad s), 2.48–2.58 (1H, m), 2.59–2.70 (3H, m), 2.83–2.97 (2H, m), 3.03–3.12 (1H, broad s), 3.49 (1H, t, J=8.24 Hz), 3.66 (3H, s), 3.92–4.02 (1H, m), 4.17–4.24 (1H, m), 5.11–5.19 (1H, m), 5.71 (1H, dd, J=15.26, 7.02 Hz), 5.83 (1H, dd, J=15.62, 8.24 Hz), 6.75 (1H, t, J=7.32), 6.92–7.02 (4H, m), 7.10–7.14 (1H, m), 7.24–7.34 (2H, m).

Mass EI Method, m/e): 452 (M⁺).

High Resolution Mass Spectrum:

Calcd.: (C₂₇H₃₂O₆, M⁺) 452.2199 Found: (M⁺) 452.2190.

d-5,6,7-trinor-4,8-inter-m-phenylene-15-epi-2,18,19,20-tetranor-16-methyl-16-phenoxy PGI₂ methyl ester.

Specific Rotation: $[\alpha]_D^{20} = +64.64$ (C=1.072, MeOH).

IR (Liquid Film Method): 3400, 2970, 2930, 1722, 1587, 1482, 1444, 1362, 1250, 1222, 1193, 1124, 1045, 1024, 970, 881, 861, 834, 783, 744, 701 cm⁻¹.

NMR (400 MHz, CDCl₃, δ): 1.24 (3H, s), 1.26 (3H, s), 1.5–1.8 (1H, broad s), 1.98–2.08 (1H, m), 2.51–2.71 (4H, m), 2.84–2.95 (2H, m), 2.9–3.1 (1H, broad s), 3.51–3.58 (1H, m), 3.66 (3H, s), 3.97–4.03 (1H, m), 4.20–4.23 (1H, m), 5.13–5.20 (1H, m), 5.72–5.79 (1H, m), 5.83–5.92 (1H, m), 6.76 (1H, t, J=7.32), 6.93–7.04 (4H, m), 7.10–7.16 (1H, m), 7.25–7.33 (2H, m).

Mass (EI Method, m/e): 452 (M⁺).

High Resolution Mass Spectrum: Calcd.: (C₂₇H₃₂O₆, M⁺) 452.2199 Found: (M⁺) 452.2204.

EXAMPLE 251 d-5,6,7-trinor-4,8-inter-m-phenylene-2,18,19,20-tetranor-16-methyl-16-phenoxy PGI₂

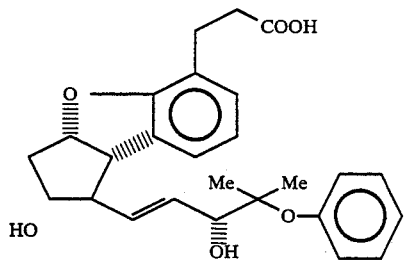

d-5,6,7-trinor-4,8-inter-m-phenylene-2,18,19,20-tetranor-16-methyl-16-phenoxy PGI₂ methyl ester (5.01 g, 11.08 mmol) was dissolved in 200 ml of methanol. To this solution, 1N aqueous sodium hydroxide solution (33.25 ml, 33.25 mmol) was added, and the mixture was stirred overnight at room temperature under argon atmosphere. The reaction mixture was concentrated and 34.5 ml of 1N hydrochloric acid was added thereto under cooling in an ice bath. The mixture was extracted with ethyl acetate (70 ml×3). The combined organic layers were washed with 150 ml of saturated aqueous sodium chloride solution, dried over anhydrous sodium sulfate (40 g), and concentrated to quantitatively obtain d-5,6,7-trinor-4,8-inter-m-phenylene-2,18,19,20-tetranor-16-methyl-16-phenoxy PGI₂ as a sole product (4.8528 g, 11.08 mmol). This was recrystallized from ethyl acetate/n-hexane (5/1) to obtain colorless needle-like crystals. Its structure was confirmed by the following data:

m.p.: 125°–125.5° C.

Specific Rotation: $[\alpha]_D^{20} = 122.84$ (c=0.998, MeOH).

IR (KBr Method): 3375 (3650–2200), 3050, 2975, 2916, 1703, 1590, 1481, 1442, 1380, 1361, 1323, 1300, 1287, 1267, 1248, 1229, 1207, 1150, 1129, 1068, 1038, 1020, 980, 958, 907, 886, 868, 839, 824, 786, 766, 744, 702, 584, 486, 446 cm⁻¹.

PMR (400 MHz, CDCl₃, δ): 1.24 (3H, s), 1.25 (3H, s), 1.98–2.08 (1H, m), 2–4.5 (3H, broad s), 2.46–2.53 (1H, m), 2.62–2.77 (3H, m), 2.85–3.00 (2H, m), 3.47 (1H, t, J=8.3 Hz), 3.93–3.99 (1H, m), 5.10–5.18 (1H, m), 5.69 (1H, dd, J=15.63, 6.83 Hz), 5.81 (1H, dd, J=15.63, 8.3 Hz), 6.75 (1H, t, J=7.33), 6.92–7.03 (4H, m), 7.10–7.15 (1H, m), 7.26–7.34 (2H, m)

Mass (EI Method, m/e): 438 (M⁺).

High Resolution Mass Spectrum:

Calcd.: (C₂₆H₃₀O₆, M⁺) 438.2043 Found: (M⁺) 438.2021.

EXAMPLE 252 d-5,6,7-trinor-4,8-inter-m-phenylene-15-epi-2,18,19,20-tetranor-16-methyl-16-phenoxy PGI$_2$

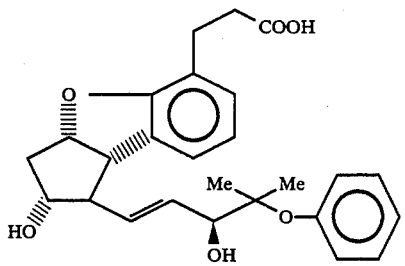

d-5,6,7-trinor-4,8-inter-m-phenylene-15-epi-2,18,19,20-tetranor-16-methyl-16-phenoxy PGI$_2$ methyl ester (241.8 mg, 0.535 mmol) was dissolved in 8 ml of methanol. To this solution, 1N aqueous sodium hydroxide solution (1.6 ml, 1.60 mmol) was added, and the mixture was stirred for 4 hours at room temperature under argon atmosphere. To the reaction mixture, 2 ml of 1N hydrochloric acid was added thereto, and 15 ml of water was added to the mixture. The mixture was extracted with ethyl acetate (15 ml×3). The combined organic layers were washed with 40 ml of saturated aqueous sodium chloride solution, dried over anhydrous sodium sulfate (10 g), and concentrated to obtain stoichiometrical amount of d-5,6,7-trinor-4,8-inter-m-phenylene-15-epi-2,18,19,20-tetranor-16-methyl-16-phenoxy PGI$_2$ as a sole product (234.2 mg, 0.353 mmol). Its structure was confirmed by the following data:

Specific Rotation: $[\alpha]_D^{20} = +66.73$ (C=0.920, MeOH).

IR (Liquid Film Method): 3400 (3650–2100), 2975, 2930, 1705, 1590, 1483, 1444, 1364, 1222, 1190, 1127, 1064, 1039, 965, 945, 910, 880, 860, 830, 780, 741, 700 cm$^{-1}$.

PMR (400 MHz, CDCl$_3$): 1.24 (3H, s), 1.25 (3H, s), 1.98–2.09 (1H, m), 2.2–4.5 (3H, broad s), 2.50–2.78 (4H, m), 2.82–2.97 (2H, m), 3.50–3.57 (1H, m), 3.93–4.03 (1H, m), 4.19–4.24 (1H, m), 5.10–5.21 (1H, m), 5.73 (1H, dd, J=6.11, 15.38 Hz), 5.85 (1H, dd, J=8.55, 15.38), 6.75 (1H, t, J=7.32), 6.93–7.07 (4H, m), 7.09–7.18 (1H, m), 7.23–7.35 (2H, m).

Mass (EI Method, m/e): 438 (M$^+$).

High Resolution Mass Spectrum: Calcd.: (C$_{26}$H$_{30}$O$_6$, M$^+$) 438.2043 Found: (M$^+$) 438.2057.

EXAMPLE 253 d-5,6,7-trinor-4,8-inter-m-phenylene-2,18,19,20-tetranor-16-methyl-16-phenoxy PGI$_2$ sodium salt

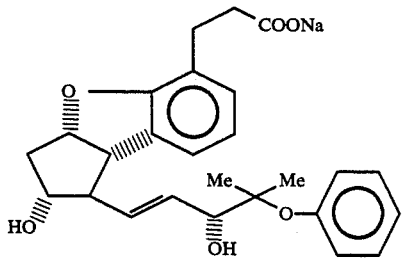

d-5,6,7-tinor-4,8-inter-m-phenylene-2,18,19,20-tetranor-16-methyl-16-phenoxy PGI$_2$ methyl ester (2.9897 g, 6.8176 mmol) was dissolved in 70% aqueous ethanol solution (30 ml). To this solution, aqueous sodium hydroxide solution (0.1017N, 60.312 ml) was first added, and then aqueous sodium hydrogen carbonate solution (0.1007N, 6.7696 ml) was added. To this reaction mixture, 100 ml of anhydrous ethanol was added and the mixture was left to stand overnight in a refrigerator.

The reaction mixture was then filtered by using a membrane filter (regenerated cellulose, type TM-4P, 0.2 um) at 0°–5° C. under reduced pressure, and the filtrate was concentrated to 5 g. To this residue, 10 ml of distilled water was added to dissolve the residue, and this solution was freeze-dried for 4 hours and 20 minutes. Also, 12 ml of distilled water was added to the residue to dissolve the residue, and the solution was freeze-dried for 5 hours. The obtained salt was pulverized under argon atmosphere and was dried under reduced pressure to obtain d-5,6,7-trinor-4,8-inter-m-phenylene-2,18,19,20-tetranor-16-methyl-16-phenoxy PGI$_2$ sodium salt (3.0915 g, 6.7132 mmol) with a yield of 98.5%. Its structure was determined by the following data:

Specific Rotation: $[\alpha]_D^{20} = +120.0$ (c=0.992, MeOH).

IR (KBr Method): 3375 (3700–2000), 2960, 2920, 1552, 1480, 1441, 1400, 1334, 1282, 1220, 1182, 1150, 1124, 1090, 1062, 1022, 1000, 963, 855, 828, 777, 740, 699 cm$^{-1}$.

NMR (400 MHz, D$_2$O, δ): 1.22 (3H, s), 1.24 (3H, s), 1.81–1.94 (1H, m), 2.28–2.37 (1H, m), 2.37–2.51 (2H, m), 2.64–2.75 (1H, m), 2.75–2.88 (2H, m), 3.23–3.38 (1H, m), 3.89–3.99 (1H, m), 4.12—4.22 (1H, m), 5.02–5.11 (1H, m), 5.61–5.70 (2H, m), 6.67–6.79 (1H, m), 6.86–6.95 (1H, m), 6.99–7.12 (3H, m), 7.12–7.22 (1H, m), 7.27–7.42 (2H, m)

Mass (CI Method, m/e): 461 (M$^+$ +1).

High Resolution Mass Spectrum:
Calcd.: (C$_{26}$H$_{29}$O$_6$Na, M$^+$-Na) 437.1964 Found: (M$^+$-Na) 437.1968.

EXAMPLE 254 d-3-decarboxy-3-hydroxymethyl-5,6,7-trinor-4,8-inter-m-phenylene-2,18,19,20p-tetranor-16-methyl-16-phenoxy PGI$_2$

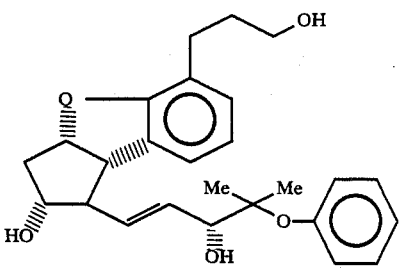

d-5,6,7-trinor-4,8-inter-m-phenylene-2,18,19,20-tetranor-16-methyl-16-phenoxy PGI$_2$ methyl ester (140 mg, 0.31 mmol) was dissolved in 3 ml of anhydrous toluene. To this solution, was added diisobutyl aluminum hydride (1.03 ml, 1.56 mmol) was added at −78° C. under argon atmosphere and the resulting mixture was stirred for 20 minutes at the same temperature. The mixture was warmed to 0° C., and stirred for 10 minutes at this temperature. To the reaction mixture, were added 5 ml of saturated aqueous ammonium chloride solution and then 5 ml of 1N hydrochloric acid, and the mixture was extracted with ethyl acetate (10 ml×3). The combined organic layers were washed with 25 ml of saturated aqueous sodium chloride solution, dried over anhydrous sodium sulfate (10 g), and concentrated to obtain 142.9 mg of an oily product. This oily product was purified by column chromatography (silica gel: acetonitrile) to obtain d-3-decarboxy-3-hydroxymethyl-5,6,7-trinor-4,8-inter-m-phenylene-2,18,19,20-tetranor-16-methyl-16-phenoxy PGI$_2$ as of a colorless oil (128.6 mg, 0.3 mmol) with a yield of 97.8%. Its structure was confirmed by the following data:

Specific Rotation: $[\alpha]_D^{20} - +103.11$ (c=0.418, MeOH).

IR (Liquid Film Method): 3350, 2970, 2930, 1691, 1586, 1481, 1443, 1362, 1250, 1220, 1184, 1152, 1125, 1063, 1023, 968, 910, 882, 861, 831, 781, 740, 700 cm$^{-1}$.

NMR (400 MHz, CDCl$_3$, δ): 1.25 (3H, s), 1.26 (3H, s), 1.4–2.3 (3H, broad s), 1.76–1.93 (2H, m), 1.96–2.07 (1H, m), 2.50–2.58 (1H, m), 2.60–2.76 (3H, m), 3.50–3.63 (3H, m), 3.98–4.05 (1H, m), 4.18–4.23 81H, m), 5.10–5.18 (1H, m), 5.72 (1H, dd, J=8.55, 15.62 Hz), 5.72 (1H, dd, J=6.84, 15.62 Hz), 6.78 (1H, t, J=7.33 Hz), 6.93–7.02 (4H, m), 7.11–7.18 (1H, m), 7.24–7.34 (2H, m).

Mass (EI Method, m/e): 424 (M+)

High Resolution Mass Spectrum: Calcd.: (C$_{26}$H$_{32}$O$_5$, M+) 424.2250 Found: (M+) 424.2269.

EXAMPLE 255

5,6,7-trinor-4,8-inter-m-phenylene-2,18,19,20-tetranor-13,14-dihydro-16-phenoxy PGI$_2$ methyl ester

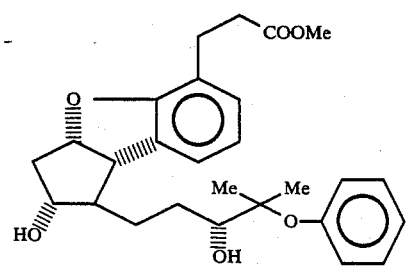

5,6,7-trinor-4,8-inter-m-phenylene-2,18,19,20-tetranor-16-methyl-16-phenoxy PGI$_2$ methyl ester (118.2 mg, 0.262 mmol) was dissolved in 10 ml of ethyl acetate and was hydrogenated using 35 mg of 10% palladium on carbon catalyst at room temperature under atmospheric pressure. The palladium on carbon was removed by filtration through Celite, and the ethyl acetate was removed off under reduced pressure. The obtained colorless oily product was purified by column chromatography (Rober column A type, manufactured by Merck & Co., Inc.,; cyclohexane/ethyl acetate=1/3) to obtain 5,6,7-trinor-4,8-inter-m-phenylene-2,18,19,20-tetranor-13,14-dihydro-16-methyl-16-phenoxy PGI$_2$ methyl ester (102.9 mg, 0.227 mmol) with a yield of 87%. Its structure was confirmed by the following data:

IR (Liquid Film Method): 3430, 3090, 3050, 2990, 2970, 2940, 2890, 1745, 1600, 1490, 1455, 1385, 1370, 1300, 1265, 1360, 1230, 1190, 1155, 1145, 1095, 1075, 1055, 1030, 990, 965, 915, 885, 870, 840, 790, 750, 705 cm$^{-1}$.

NMR (400 MHz, CDCl$_3$, δ): 1.23 (6H, s), 1.59–1.85 (6H, m), 2.04–2.16 (2H, m), 2.43–2.50 (1H, m), 2.59–2.70 (2H, m), 2.82–2.93 (2H, m), 3.42–3.49 (1H, m), 3.65–3.70 (4H, m), 4.02–4.07 (1H, m), 5.19–5.24 (1H, m), 6.76–6.80 (1H, m), 6.95–7.00 (3H, m), 7.08–7.15 (2H, m), 7.26–7.31 (3H, m).

Mass (EI Method, m/e): 454 (M+).

High Resolution Mass Spectrum: Calcd.: (C$_{27}$H$_{34}$O$_6$, M+) 454.2355 Found: (M+) 454.2364.

EXAMPLE 256

5,6,7-trinor-4,8-inter-m-phenylene-2,18,19,20-tetranor-13,14-dihydro-16-methyl-16-phenoxy PGI$_2$

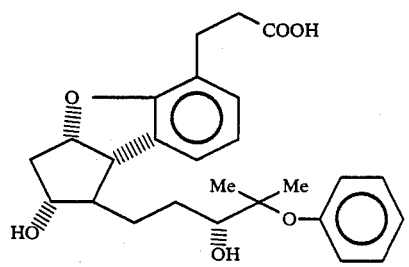

5,6,7-trinor-4,8-inter-m-phenylene-2,18,19,20-tetranor-13,14-dihydro-16-methyl-16-phenoxy PGI$_2$ methyl ester (70 mg, 0.154 mmol) was dissolved in 20 ml of methanol and 0.46 ml of 1N aqueous sodium hydroxide solution was added to the solution under argon atmosphere, and the mixture was left to stand overnight. The methanol was moved off under reduced pressure and 10 ml of water was added thereto. The mixture was extracted with ethyl acetate, and 1N aqueous hydrochloric acid solution was added to the aqueous layer phase to adjust its pH to 2. The mixture was then extracted with ethyl acetate, and the extract was washed with saturated aqueous sodium chloride solution, dried over anhydrous sodium sulfate. Then the solvent was removed off under reduced pressure to obtain 5,6,7-trinor-4,8-inter-m-phenylene-2,18,19,20-tetranor-13,14-dihydro-16-methyl-16-phenoxy PGI$_2$ 57.1 mg, 0.130 mmol) with a yield of 84%. This was recrystallized from n-hexane/ethyl acetate to obtain white crystals. Its structure was confirmed by the following data: m.p.: 131.5°–132.5° C.

IR (KBr Method): 3425, 3070, 3045, 2990, 2955, 2940, 2870, 1704, 1603, 1598, 1495, 1455, 1450, 1420, 1405, 1385, 1375 1365, 1350, 1325, 1315, 1280, 1235, 1210, 1155, 1138, 1110, 1075, 1045, 1035, 970, 955, 940, 918, 883, 855, 835, 822, 802, 790, 770, 750, 732, 700, 610, 580, 538, 477 cm$^{-1}$.

NMR: (400 MHz, CDCl$_3$, δ): 1.23 (6H, s), 1.61–1.82 (5H, m), 2.08–2.17 (3H, m), 2.41–2.48 (1H, m), 2.62–2.76 (2H, m), 2.84–2.96 (2H, m), 3.42–3.46 (1H, m), 3.67–3.69 (1H, m), 4.04–4.08 (1H, m), 5.20–5.25 (1H, m), 6.77–6.81 (1H, m), 6.96–6.99 (3H, m), 7.07–7.14 (2H, m), 7.25–7.31 (3H, m)

Mass (EI Method, m/e): 440 (M+).

High Resolution Mass Spectrum: Calcd.: (C$_{26}$H$_{32}$O$_6$, M+) 440.2198 Found: (M+) 440.2169.

We claim:

1. A 5,6,7-trinor-4,8-inter-m-phenylene PGI$_2$ derivative represented by the formula

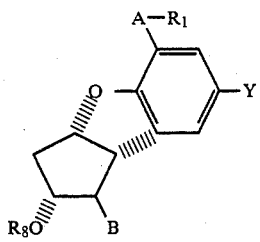 (I)

wherein
$R_1$ is a group selected from the class consisting of:
(a) a $COOR_2$, wherein $R_2$ denotes
(i) hydrogen or a pharmacologically acceptable cation,
(ii) a straight chain alkyl having 1-12 carbon atoms or a branched alkyl having 3-12 carbon atoms,
(iii)

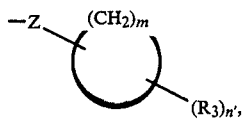

wherein Z denotes valence bond, or straight chain or branched alkylene which may be represented by $C_tH_{2t}$, wherein t denotes an integer of 1-5, further, m denotes an integer of 5-12, $R_3$ denotes hydrogen or alkyl having 1-5 carbon atoms, and n' denotes an integer of 1-3,
(iv) $-(CH_2CH_2O)_lCH_3$ wherein $l$ is an integer of 1-5,
(v) $-Z-Ar_1$, wherein Z is the same as defined above, $Ar_1$ denotes phenyl, α-naphthyl, β-naphthyl, 2-pyridyl, 3-pyridyl, 4-pyridyl, α-furyl, β-furyl, αthienyl, β-thienyl or substituted phenyl (wherein the substituent is at least one chlorine, bromine, fluorine, trifluoromethyl, alkyl having 1-4 carbon atoms, nitro, methoxy, phenyl, phenoxy,

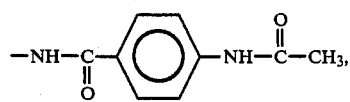

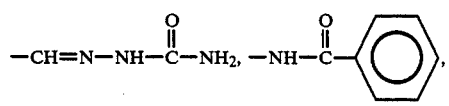

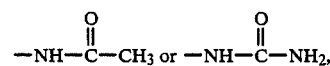

(vi) $-C_lH_{2l}COOR_3$
(vii) $-CH_2CH_lH_{2l}M(R_3)_2$ wherein l and $R_3$ are the same as defined above),
(viii)

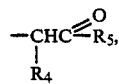

wherein $R_4$ denotes hydrogen or benzoyl and $R_5$ denotes phenyl, p-bromophenyl, p-biphenyl, p-benzamidophenyl or 2-naphthyl,
(ix) $-C_pH_{2p}-B'$, wherein B' is

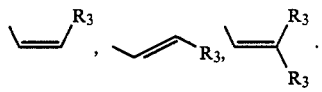

or $-C\equiv C-R_6$, wherein $R_3$ is the same as defined above, $R_6$ denotes straight chain or branched alkyl having 1-30 carbon atoms, and p is an integer of 1-5, or
(x)

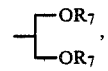

wherein $R_7$ denotes alkyl or acyl having 1-30 carbon atoms,
(b) $-CH_2OH$,
(c)

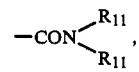

wherein $R_{11}$ denotes hydrogen, alkyl having 1-10 carbon atoms, cycloalkyl having 3-12 carbon atoms, phenyl, substituted phenyl, aralkyl having 7-12 carbon atoms or $-SO_2R_{12}$, wherein $R_{12}$ denotes alkyl having 1-10 carbon atoms, cycloalkyl having 3-12 carbon atoms, phenyl, substituted phenyl or aralkyl having 7-12 carbon atoms, the two $R_{11}$ may be the same or different, however, when one denotes $-SO_2R_{12}$, the other is not $-SO_2R_{12}$, and
(d)

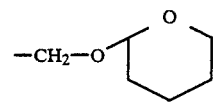

A denotes $-(CH_2)_n-$,

Y denotes hydrogen, chlorine, fluorine, bromine, formyl, methoxy or nitro,
B denotes to all A and Y
(i)

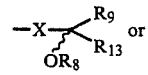

(ii)

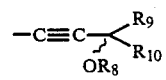

further, when Y is chlorine, fluorine, bromine, formyl, methoxy or nitro, B further denotes
(iii)

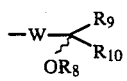

wherein $R_9$ denotes hydrogen or alkyl group having 1-4 carbon atoms, $R_8$ denotes hydrogen, acyl having 1-12 carbon atoms, aroyl having 6-15 carbon atoms, tetrahydropyranyl, tetrahydrofurayl, 1-ethoxy ethyl or t-butyl, X denotes
(i) —CH$_2$ZCH$_2$—,
(ii) —CH=CH— (trans) or
(iii) —C≡C—

$R_{10}$ denotes
(i) straight chain alkyl having 4-10 carbon atoms, or
(ii)

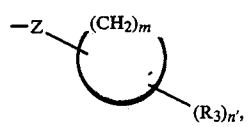

wherein Z, m, $R_3$ and n' are the same as defined above, or
(iii) —Z—AR$_2$, wherein Z is the same as defined above, and Ar$_2$ denotes phenyl, α-naphthyl, β-naphthyl or at least one chlorine, bromine, fluorine, trifluoromethyl, alkyl having 1-4 carbon atoms, nitro, methoxy, phenyl or phenoxysubstituted phenyl, $R_{13}$ denotes
(i) branched alkyl having 5-10 carbon atoms, or
(ii) —C$_t$H$_{2t}$OR$_{14}$, wherein C$_t$H$_{2t}$ is the same as defined above, and $R_{14}$ denotes straight chain or branched alkyl having 1-5 carbon atoms,

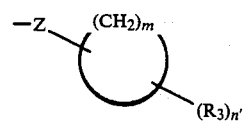

or —Z—Ar$_2$, wherein Z, m, $R_3$, n' and Ar$_2$ are the same as defined above, or
(iii)

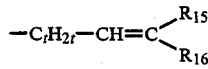

wherein C$_t$H$_{2t}$ is the same as defined above, $R_{15}$ and $R_{16}$ denote hydrogen, methyl, ethyl, propyl or butyl group, W denotes
(i) —CH$_2$CH$_2$— or
(ii) —CH=CH— (trans) and the formula (I) denotes d form, l form or dl form.

2. A PGI$_2$ derivative of claim 1 wherein $R_2$ is a group selected from the class consisting of hydrogen, pharmacologically acceptable cation and —CH$_3$.

3. A PGI$_2$ derivative of claim 1 wherein B is a group selected from the class consisting of
(i)

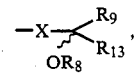

and
(ii)

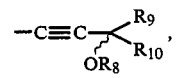

wherein $R_8$, $R_9$, $R_{10}$, $R_{13}$ and X are the same as defined in claim 1.

4. A PGI$_2$ derivative of claim 3 wherein X is a group selected from the class consisting of —CH=CH—(trans) and —C≡C—.

5. A PGI$_2$ derivative of claim 3 wherein X is a group selected from the class consisting of —C=CH—(trans) and —C≡C—, and $R_{13}$ is a group selected from the class consisting of
(i) branched alkyl having 5-10 carbon atoms, and
(ii)

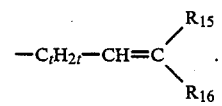

6. A PGI$_2$ derivative of claim 3 wherein $R_{10}$ is a group selected from the class consisting of
(i) straight chain alkyl having 4-10 carbon atoms, and
(ii)

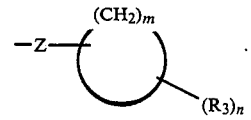

7. A PGI$_2$ derivative of claim 3 wherein $R_8$ is hydrogen and $R_9$ is hydrogen.

8. A PGI$_2$ derivative of claim 5 wherein t is 3 or 4, $R_{15}$ is hydrogen or methyl and $R_{16}$ is methyl or ethyl.

9. A PGI$_2$ derivative of claim 3 wherein B is

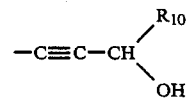

wherein $R_{10}$ is

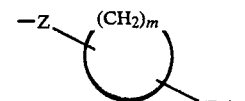

wherein m is 5 or 6 $R_3$ is hydrogen, methyl or ethyl and n' is 1 or 2.

10. A PGI$_2$ derivative of claim 1 wherein B is

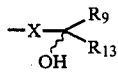

and

Y is hydrogen, wherein
X is —CH=CH— or —C≡—,
$R_9$ is hydrogen or alkyl group having 1–4 carbon atoms, and $R_{13}$ is a group selected from the class consisting of
(i) branched alkyl having 5–10 carbon atoms, and
(ii)

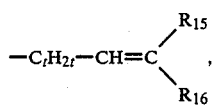

wherein t, $R_{15}$, and $R_{16}$ are the same as defined in claim 1.

11. A $PGI_2$ derivative of claim 10 wherein t is 3 or 4 $R_{15}$ is hydrogen or methyl, and $R_{16}$ is methyl or ethyl.

12. A $PGI_2$ derivative of claim 1 wherein B is

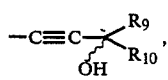

wherein $R_{10}$ is a group selected from the class consisting of
(i) straight chain alkyl having 4–10 carbon atoms, and
(ii)

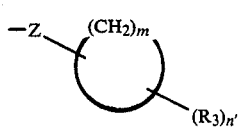

Y is hydrogen, wherein n', $R_9$, Z, m and $R_3$ are the same as in claim 1.

13. A $PGI_2$ derivative of claim 12 wherein $R_9$ is hydrogen, m is 5 or 6, $R_3$ is hydrogen, methyl or ethyl and n' is 1 or 2.

14. A $PGI_2$ derivative of claim 1 wherein B is

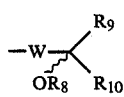

wherein $R_8$, $R_9$, $R_{10}$ and W are the same as defined in claim 1.

15. A $PGI_2$ derivative of claim 14 wherein W is —CH=CH—(trans).

16. A $PGI_2$ derivative of claim 14 wherein W is —CH=CH—(trans) and $R_{10}$ is a group selected from the class consisting of
(i) straight chain alkyl having 4–10 carbon atoms, and
(ii)

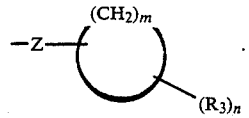

17. A $PGI_2$ derivative of claim 14 wherein W is —CH=CH—(trans), $R_9$ is hydrogen and $R_{10}$ is

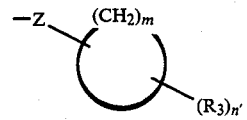

wherein m is 5 or 6, $R_3$ is hydrogen, methyl, ethyl or propyl and n' is 1 or 2.

18. A $PGI_2$ derivative of any one of claims 3, 4, 5, 6, 7, 8, 9, 10, 11, 12, 13, 14, 15, 16, 17, wherein $R_1$ is $COOR_2$ wherein $R_2$ is a group selected from the class consisting of hydrogen, pharmacologically acceptable cations and —$CH_3$.

19. 5,6,7-trinor-4,8-inter-m-phenylene-2-nor-16,16-dimethyl $PGI_2$ or its methyl ester.

20. 5,6,7-trinor-4,8-inter-m-phenylene-2-nor-17(S)-methyl $PGI_2$ or its methyl ester.

21. 5,6,7-trinor-4,8-inter-m-phenylene-2-nor-17(R)-methyl $PGI_2$ or its methyl ester.

22. 5,6,7-trinor-4,8-inter-m-phenylene-2-nor-16,16-dimethyl-ω-homo $PGI_2$ or its methyl ester.

23. 5,6,7-trinor-4,8-inter-m-phenylene-2-nor-17(S)-methyl-ω-homo $PGI_2$ or its methyl ester.

24. 5,6,7-trinor-4,8-inter-m-phenylene-2-nor-17(R)-methyl-ω-homo $PGI_2$ or its methyl ester.

25. 5,6,7-trinor-4,8-inter-m-phenylene-2,17,18,19,20-pentanor-16,16-dimethyl-16-propoxy $PGI_2$ or its methyl ester.

26. 5,6,7-trinor-4,8-inter-m-phenylene-2,18,19,20-tetranor-16,16-dimethyl-17-ethoxy $PGI_2$ or its methyl ester.

27. 5,6,7-trinor-4,8-inter-m-phenylene-2,18,19,20-tetranor-16,16-dimethyl-17-propoxy $PGI_2$ or its methyl ester.

28. 5,6,7-trinor-4,8-inter-m-phenylene-2,17,18,19,20-pentanor-16-phenoxy $PGI_2$ or its methyl ester.

29. 5,6,7-trinor-4,8-inter-m-phenylene-2,17,18,19,20-pentanor-16,16-dimethyl-16-phenoxy $PGI_2$ or its methyl ester.

30. 5,6,7-trinor-4,8-inter-m-phenylene-2,17,18,19,20-pentanor-16-methyl-16-phenoxy $PGI_2$ or its methyl ester.

31. A pharmaceutical composition for use as an anti-ulcer agent comprising a pharmaceutically acceptable carrier and a $PGI_2$ derivative of claim 1 in sufficient amount to provide from about 0.001 to about 100 mg of said $PGI_2$ derivative per dose.

32. A pharmaceutical composition for use as an anti-thrombotic agent comprising a pharmaceutically acceptable carrier and a $PGI_2$ derivative of claim 1 in sufficient amount to provide from about 0.001 to about 50 mg of said $PGI_2$ derivative per dose.

33. A pharmaceutical composition for use as an anti-hypertensive agent comprising a pharmaceutically acceptable carrier and a $PGI_2$ derivative of claim 1 in sufficient amount to provide from about 0.001 to about 5.0 mg of said $PGI_2$ derivative per dose.

34. A method for treatment of Buerger's disease comprising injecting intravenously a mixture of a pharmaceutically acceptable carrier and a $PGI_2$ derivative of claim 1, wherein the rate of delivery of said $PGI_2$ derivative is from about 0.001 to about 100 ng/kg/minute.

* * * * *